(12) United States Patent
Wong et al.

(10) Patent No.: US 9,879,042 B2
(45) Date of Patent: Jan. 30, 2018

(54) HUMAN INKT CELL ACTIVATION USING GLYCOLIPIDS

(71) Applicant: Academia Sinica, Taipei (TW)

(72) Inventors: Chi-Huey Wong, La Jolla, CA (US); Alice L. Yu, Taipei (TW); Kun-Hsien Lin, New Taipei (TW); Tai-Na Wu, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/847,835

(22) Filed: Sep. 8, 2015

(65) Prior Publication Data

US 2016/0102116 A1    Apr. 14, 2016

Related U.S. Application Data

(60) Provisional application No. 62/047,602, filed on Sep. 8, 2014.

(51) Int. Cl.
| | |
|---|---|
| *C07H 17/02* | (2006.01) |
| *C07H 15/18* | (2006.01) |
| *A61K 39/39* | (2006.01) |
| *C07H 15/04* | (2006.01) |
| *A61K 39/00* | (2006.01) |

(52) U.S. Cl.
CPC ............ *C07H 15/18* (2013.01); *A61K 39/39* (2013.01); *C07H 15/04* (2013.01); *A61K 2039/55511* (2013.01); *A61K 2039/585* (2013.01); *C07H 17/02* (2013.01)

(58) Field of Classification Search
CPC .................................................. C07H 17/02
USPC ........................................... 514/25; 536/17.9
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Toba et al. "Synthesis and biological . . . " Bioorg. Med. Chem. 20, p. 2850-59 (2012).*
Dhodapkar et al. "Galactosyl . . . " CA145:254715 (2006).*
Fujio et al. "Structure based . . . " CA145:240945 (2006).*
Klein et al. "Isomaltamines . . . " CA110:95711 (1989).*
Porcelli et al. "Preparation of . . . " CA147:440317 (2007).*
Tsuji et al. "Glycolipies . . . " CA147:425477 (2007).*
Wong et al. "Galactowyl . . . " CA152:166997 (2010).*
Zhang et al. "New cerebrosides . . . " CA156:225776 (2011).*
Immunogenicity, Wikipedia p. 1-3 (2016).*
Boost immune, Healthy Living p. 1 (2016).*
Fujio, M., et al. "Structure-Based Discovery of Glycolipids for CD1d-Mediated NKT Cell Activation: Tuning the Adjuvant versus Immunosuppression Activity." J. Am. Chem. Soc. (2006), vol. 128, pp. 9022-9023.*

(Continued)

*Primary Examiner* — Noble E Jarrell
*Assistant Examiner* — John S Kenyon
(74) *Attorney, Agent, or Firm* — Duane Morris LLP; Vicki G. Norton

(57) ABSTRACT

Glycosphingolipids (GSLs) compositions and methods for iNKT-independent induction of chemokines are disclosed.

38 Claims, 33 Drawing Sheets

(56) References Cited

U.S. PATENT DOCUMENTS

| | | | |
|---|---|---|---|
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A * | 12/1998 | Akimoto .............. C07H 15/10 424/520 |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 * | 4/2011 | Tsuji .................... C07H 15/10 424/184.1 |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 * | 9/2011 | Porcelli ................ A61K 39/39 514/25 |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,815,941 B2 | 8/2014 | Withers |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |

(56) References Cited

U.S. PATENT DOCUMENTS

| | | |
|---|---|---|
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Theng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2015/0087814 A1 | 3/2015 | Wang |
| 2015/0160217 A1 | 6/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/044859 | 5/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |

(56) References Cited

FOREIGN PATENT DOCUMENTS

| WO | WO 2011/145957 A1 | 11/2011 | | |
|---|---|---|---|---|
| WO | WO 2012094540 A2 | * | 7/2012 | ............. A61K 39/39 |
| WO | WO 2013/011347 A1 | 1/2013 | | |
| WO | WO 2013/012066 | 1/2013 | | |
| WO | WO 2013/024895 A1 | 2/2013 | | |
| WO | WO 2013/088395 A1 | 6/2013 | | |
| WO | WO 2013/120066 A1 | 8/2013 | | |
| WO | WO 2013/130603 A1 | 9/2013 | | |
| WO | WO 2013/152034 A1 | 10/2013 | | |
| WO | WO 2013/155375 A1 | 10/2013 | | |
| WO | WO 2013/181585 A2 | 12/2013 | | |
| WO | WO 2014/031498 | 2/2014 | | |
| WO | WO 2014/031762 A1 | 2/2014 | | |
| WO | WO 2014/078373 A1 | 5/2014 | | |
| WO | WO 2014/210397 A1 | 12/2014 | | |
| WO | WO 2014/210564 | 12/2014 | | |
| WO | WO 2015/026484 A1 | 2/2015 | | |
| WO | WO 2015/035337 A1 | 3/2015 | | |
| WO | WO 2015/038963 A1 | 3/2015 | | |
| WO | WO 2015/184008 | 12/2015 | | |
| WO | WO 2016/040369 A2 | 3/2016 | | |

OTHER PUBLICATIONS

U.S. Appl. No. 15/011,543, filed Jan. 30, 2016, Chi-Huey Wong, et al.
U.S. Appl. No. 15/173,496, filed Jun. 3, 2016, Chi-Huey Wong, et al.
U.S. Appl. No. 15/005,930, filed Jan. 25, 2016, Chi-Huey Wong, et al.
U.S. Appl. No. 15/011,544, filed Jan. 30, 2016, Chi-Huey Wong, et al.
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool",*J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli,*" *Mol. Microbiol.*, Jan. 2001, 39(1):199-210.
Bachmann, *Cellular and Molecular Biology, vol. 2, Chapter 72: Derivations and Genotypes of Some Mutant Derivatives of Escherichia coli K-12*, Neidhardt et al., eds., 1987, pp. 1190-1219, American Society for Microbiology, Washington, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Barnes et al., "Methods for growth of cultured cells in serum-five medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Bass et al., "Hormone phage: an enrichment method for variant proteins with altered binding properties," *Proteins*, 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.
Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin $G_1$ fragments," *Science*, Jul. 5, 1985, 229(4708):81-83.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods*. Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9. 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Caner Res.* 1989;52:81-149.
Clynes R, et al., "Fc receptors are required in passive and active immunity to melanoma" *Proc Natl Acad Sci U S A.* Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
de Almeida et al., "Thiacycloalkynes for copper-free click chemistry," *Angew. Chem. Int. Ed. Engl.*, Mar. 5, 2012, 51(10):2443-2447.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.

(56) References Cited

OTHER PUBLICATIONS

Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.

Engels et al., "Gene synthesis [new synthetic methods (77)]," *Angew. Chem. Int. Ed. Engl.*, Jun. 1989, 28(6):716-734.

Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.

Fishwild et al., "High-avidity human IgGκ monoclonal antibodies from a novel strain of minilocus transgenic mice," *Nature Biotechnol.*, Jul. 1996, 14(7):845-851.

Fredman et al., "Expression of gangliosides GD3 and 3'-isoLM1 in autopsy brains from patients with malignant tumors," *J. Neurochem.*, Jan. 1993, 60(1):99-105.

Fredman et al., "Potential anglioside antigens associated with human gliomas," *Neurol. Res.*, Jun. 1986, 8(2):123-126.

Fredman et al., "Sialyllactotetraosylceramide, a ganglioside marker for human malignant gliomas," *J. Neurochem.*, Mar. 1988, 50(3):912-919.

Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.

Fujita M et al., "A novel disaccharide substrate having 1,2-oxazoline moiety for detection of transglycosylating activity of endoglycosidases" *Biochim Biophys Acta.* Sep. 3, 2001;1528(1):9-14.

Galfrè et al., "Preparation of monoclonal antibodies: strategies and procedures," *Methods Enzymol.*, 1981, 73(Pt B):3-46.

Gazzano-Santoro et al., "A non-radioactive complement-dependent cytotoxicity assay for anti-CD20 nonclonal antibody," *J. Immunol. Methods*, Mar. 28, 1997, 202(2):163-171.

GenBank accession No. AAA24922.1, "endoglycosidase F [Elizabethkingia meningoseptica]," May 27, 2008.

GenBank accession No. AAA24923.1, "endoglycosidase, partial [Elizabethkingia meningoseptica]," Jun. 8, 1993.

GenBank accession No. AAA24924.1.1, "endoglycosidase, partial [Elizabethkingia meningoseptica]," Jun. 7, 1993.

GenBank accession No. AAA26738.1, "endo-beta-N-acetylglucosaminidase H [Streptomyces plicatus]," Apr. 26, 1993.

GenBank accession No. J05449.1, "F.meningosepticum peptide-N-4-(N-acetyl-beta-D-glucosaminyl) asparagine amidase (PNGase F) mRNA, complete cds," Jan. 16, 1996.

GenBank accession No. YP_212855.1, "Putative exported alpha-L-fucosidase protein [Bacteroides fragilis NCTC 9343]," Mar. 2, 2014.

Gerson et al., "ESR. Spectra and Structures of Radical Anions in the Dibenzo[a, e]cyclooctene Series," *Helvetica Chinica Acta*, Jan. 1, 1976, 59(6): 2038-2048.

Gill et al., "Direct brain infusion of glial cell line-derived neurotrophic factor in Parkinson disease," *Nature Med.*, May 2003, 9(5):589-595 and Addendum from Apr. 2006, 12(4):479.

Goding, *Monoclonal Antibodies: Principles and Practice* $2^{nd}$ ed., Chapter 3: *Production of Monoclonal Antibodies*, 1986, pp. 59-103, Academic Press, London.

Golkowski et al., "Strategy for catch and release of azide-tagged biomolecules utilizing a photolabile strained alkyne construct," *Organic and Biomolecular Chemistry*, Jan. 1, 2012, 10(23):4496.

Goochee CF et al., "The oligosaccharides of glycoproteins: bioprocess factors affecting oligosaccharide structure and their effect on glycoprotein properties", *Biotechnology* (N Y). Dec. 1991;9(12):1347-55.

Gordon et al., "Reactivity of biarylazacyclooctynones in copper-free click chemistry," *J. Am. Chem. Soc.*, Jun. 6, 2012, 134(22): 9199-9208.

Gottschling et al., "Stage-specific embryonic antigen-4 is expressed in basaloid lung cancer and associated with poor prognosis," *Eur. Respir. J.*, Mar. 2013, 41(3):656-663.

Graham et al., "Characteristics of a human cell line transformed by DNA from human adenovirus type 5," *J. Gen. Virol.*, Jul. 1977, 36(1):59-72.

Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.

Green, "Targeting targeted therapy," *N. Engl. J. Med.*, May 20, 2004, 350(21):2191-2193

Griffiths et al., "Human anti-self antibodies with high specificity from phage display libraries," *EMBO J.*, Feb. 1993, 12(2):725-734.

Gruber et al., "Efficient tumor cell lysis mediated by a bispecific single chain antibody expressed in *Escherichia coli*," *J. Immunol.*, Jun. 1, 1994, 152(11):5368-5374.

Guss et al., "Structure of the IgG-binding regions of streptococcal protein G," *EMBO J.*, Jul. 1986, 5(7):1567-1575.

Guyer et al., "Immunoglobulin binding by mouse intestinal epithelial cell receptors," *J. Immunol.*, Aug. 1976, 117(2):587-593.

Hakomori et al., "Glycosphingolipid antigens and cancer therapy," *Chem. Biol.*, Feb. 1997, 4(2):97-104.

Hakomori, "Glycosylation defining cancer malignancy: new wine in an old bottle," *Proc. Natl. Acad. Sci. U.S.A.*, Aug. 6, 2002, 99(16):10231-10233.

Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.

Harris, "Production of humanized monoclonal antibodies for in vivo imaging and therapy," *Biochem. Soc. Transactions*, Nov. 1995, 23(4):1035-1038.

Hawkins et al., "Selection of phage antibodies by binding affinity. Mimicking affinity maturation," *J. Mol. Biol.*, 1992, 226(3):889-896.

Heyman, "Complement and Fc-receptors in regulation of the antibody response," *Immunol. Lett.*, Dec. 1996, 54(2-3):195-199.

Hinman et al., "Preparation and characterization of monoclonal antibody conjugates of the calicheamicins: a novel and potent family of antitumor antibiotics," *Cancer Res.*, Jul. 15, 1993, 53(14):3336-3342.

Hogrefe et al., "A bacteriophage lambda vector for the cloning and expression of immunoglobulin Fab fragments on the surface of filamentous phage," *Gene*, Jun. 15, 1993, 128(1):119-126.

Holliger et al., "'Diabodies': small bivalent and bispecific antibody fragments," *Proc. Natl. Acad. Sci. U.S.A.*, Jul. 15, 1993, 90(14):6444-6448.

Honegger et al., "Yet another numbering scheme for immunoglobulin variable domains. an automatic modeling and analysis tool," *J. Mol. Biol.*, Jun. 8, 2001, 309:657-670.

Hoogenboom et al., "By-passing immunisation. Human antibodies from synthetic repertoires of germline $V_H$ gene segments rearranged in vitro," *J. Mol. Biol.*, Sep. 20, 1992, 227(2):381-388.

Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.

Huang et al., "Carbohydrate-based vaccines with a glycolipid adjuvant for breast cancer," *Proc. Natl. Acad. Sci. U.S.A.*, Feb. 12, 2013, 110(7):2517-2522.

Hung et al., "Investigation of SSEA-4 binding protein in breast cancer cells," *J. Am. Chem. Soc.*, Apr. 24, 2013, 135(16):5934-5937.

Hurle et al., "Protein engineering techniques for antibody humanization," *Curr. Opin. Biotechnol.*, Aug. 1994, 5(4):428-433.

Inouye et al., "Single-step purification of $F(ab')_{2 \mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.

Jackson et al., "In vitro antibody maturation: Improvement of a high affinity, neutralizing antibody against IL-1β," *J. Immunol.*, Apr. 1, 1995, 154(7):3310-3319.

Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.

(56) References Cited

OTHER PUBLICATIONS

Jakobovits et al., "Germ-line transmission and expression of a human-derived yeast artificial chromosome," *Nature*, Mar. 18, 1993, 362(6417):255-258.

Jenkins N, Curling EM., "Glycosylation of recombinant proteins: problems and prospects", *Enzyme Microb Technol.* May 1994;16(5):354-64.

Jewett et al., "Synthesis of a fluorogenic cyclooctyne activate by Cu-free click chemistry," *Org. Lett.*, Nov. 18, 2011, 13(22):5937-5939.

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (SSEA-3 and -4) are epitopes of a unique globo-series ganglioside isolated from human teratocarcinoma cells," *EMBO J.*, 1983, 2 (12):2355-2361.

Karlin S. et al., "Methods for assessing the statistical significance of molecular sequence features by using general scoring schemes", *Proc Natl Acad Sci U S A*. Mar. 1990;87(6):2264-8.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.

Kim et al., "Localization of the site of the murine IgG1 molecule that is involved in binding to the murine intestinal Fc receptor," *Eur. J. Immunol.*, 1994, 24:2429-2434.

Köhler et al., "Continuous cultures of fused cells secreting antibody of predefined specificity," *Nature*, Aug. 7, 1975, 256(5517):495-497.

Kontermann, "Intrabodies as therapeutic agents," *Methods*, Oct. 2004, 34(2):163-170.

Kostelny et al., "Formation of a bispecific antibody by the use of leucine zippers," *J. Immunol.*, Mar. 1, 1992, 148(5):1547-1553.

Kozbor, "A human hybrid myeloma for production of human monoclonal antibodies," *J. Immunol.*, Dec. 1984, 133(6):3001-3005.

Kriegler M et al., "A novel form of NF/cachectin is a cell surface cytotoxic transmembrane protein: ramifications for the complex physiology of TNF" *Cell.* Apr. 8, 1988;53(1):45-53.

Kudo et al., "Up-regulation of a set of glycosyltransferase genes in human colorectal cancer," *Lab. Invest.*, Jul. 1998, 78(7):797-811.

Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, 2$^{nd}$ ed., 1975, pp. 73-75, Worth Publishers, New York.

Leung et al., "A method for random mutagenesis of a defined DNA segment using a modified polymerase chain reaction," *Technique—A Journal of Methods in Cell and Molecular Biology*, Aug. 1989, 1(1):11-15.

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood*. May 15, 2007;109(10):4336-42. Epub Jan. 23, 2007.

Liu et al., "Eradication of large colon tumor xenografts by targeted delivery of maytansinoids," *Proc. Natl., Acad. Sci. U.S.A.*, Aug. 6, 1996, 93(16):8618-8623.

LoBuglio et al., "Mouse/human chimeric monoclonal antibody in man: kinetics and.immune response," *Proc. Natl. Acad. Sci. U.S.A.*, Jun. 1989, 86(11):4220-4224.

Lode et al., "Targeted therapy with a novel enediyne antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Louis et al., "The 2007 WHO classification of tumours of the central nervous system," *Acta. Neuropathol.*, Aug. 2007, 114(2):97-109.

Lu et al., "Single chain anti-c-Met antibody conjugated nanoparticles for in vivo tumor-targeted imaging and drug delivery," *Biomaterials*, Apr. 2011, 32(12):3265-3274.

MacFarlane GT, et al., "Formation of glycoprotein degrading enzymes by Bacteroides fragilis" *FEMS Microbiol Lett*. Jan. 15, 1991;61(2-3):289-93.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Mather et al., "Culture of testicular cells in hormone-supplemented serum-five medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

Meezan et al., "Comparative studies on the carbohydrate-containing membrane components of normal and virus-transformed mouse

(56) References Cited

OTHER PUBLICATIONS fibroblasts: II: Separation of glycoproteins and glycopeptides by Sephadex chromatography," *Biochemistry*, Jun. 1969, 8(6):2518-2524.
Meyer, "Malignant gliomas in adults," *N. Engl. J. Med.*, Oct. 23, 2008, 359(17):1850.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Morelle, W. et al., "The Mass Spectrometric Analysis of Glycoproteins and their Glycan Sturctures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')₂ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Nicolaou et al., "Calicheamicin $\Theta_1^I$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Noto et al., "CD44 and SSEA-4 positive cells in an oral cancer cell line HSC-4 possess cancer stem-like cell characteristics," *Oral Oncol.*, Aug. 2013, 49(8):787-795.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.
Pearlman et al., *Peptide and Protein Drug Delivery, Chapter 6: Analysis of Protein Drugs*, Lee, ed., 1991, pp. 247-301, Marcel Dekker Publishing, New York.
Peipp et al., "Antibody fucosylation differentially impacts cytotoxicity mediated by NK and PMN effector cells," *Blood*, 2008, 112(6):2390-2399.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies, Chapter 11: Antibodies from Escherichia coli*, Rosenberg et.al., eds., 1994, pp. 269-315, Springer-Verlag, Berlin.

Pouloukhtine et al., "Selective labeling of living cells by a photo-triggered click reaction," *J. Am. Chem. Soc.*, Nov. 4, 2009, 131(43):15769-15776.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigbò P, Guzmán E, Romeu A, Garcia-Vallvé S. Optimizer: a web server for.optimizing the codon usage of DNA sequences. *Nucleic Acids Res.* Jul. 2007;35(Web Server issue):W126-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.

(56) References Cited

OTHER PUBLICATIONS

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Skerra, "Bacterial expression of immunoglobulin fragments," *Curr. Opinion in Immunol.*, Apr. 1993, 5(2):256-262.

Slamon DJ, et al., "Human breast cancer: correlation of relapse and survival with amplification of the HER-2/neu oncogene" *Science.* Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem.* May 25, 1987;262(15):6951-4.

Smyth MJ, et al., "CD4+CD25+ T regulatory cells suppress NK cell-mediated immunotherapy of cancer" *J Immunol.* Feb. 1, 2006;176(3):1582-7.

Suresh et al., "Bispecific monoclonal antibodies from hybrid hybridomas," *Methods in Enzymology*, 1986, 121:210-228.

Suzuki E, et al., "A nonfucosylated anti-HER2 antibody augments antibody-dependent cellular cytotoxicity in breast cancer patients" *Clin Cancer Res.* Mar. 15, 2007;13(6):1875-82.

Svennerholm et al., "Human brain gangliosides: Developmental changes from early fetal stage to advanced age," *Biochim. Biophys. Acta*, Sep. 25, 1989, 1005(2): 109-117.

Syrigos et al., "Antibody directed enzyme prodrug therapy (ADEPT): a review of the experimental and clinical considerations," *Anticancer Research*, Jan.-Feb. 1999, 19(1A):605-614.

Takeda et al., "Construction of chimaeric processed immunoglobulin genes containing mouse variable and human constant region sequences," *Nature*, Apr. 4-10, 1985, 314(6010):452-454.

Taylor-Papadimitriou et al., "Exploiting altered glycosylation patterns in cancer: Progress and challenges in diagnosis and therapy," *Trends Biotechnol.*, Jun. 1994, 12(6):227-233.

Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.

Tomlinson et al., "The repertoire of human germline $V_H$ sequences reveals about fifty groups of $V_H$ segments with different hypervariable loops," *J. Mol. Biol.*, Oct. 5, 1992, 227(3):776-798.

Traunecker et al., "Bispecific single chain molecules (Janusins) target cytotoxic lymphocytes on HIV infected cells," *EMBO J.*, Dec. 1991, 10(12):3655-3659.

Traylor et al., "Gangliosides of human cerebral astrocytomas," *J. Neurochem.*, Jan. 1980m 34(1):126-131.

Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.

Tutt et al., "Trispecific F(ab')$_3$ derivatives that use cooperative signaling via the TCR/CD3 complex and CD2 to activate and redirect resting cytotoxic T cells," *J. Immunol.*, Jul. 1, 1991, 147(1):60-69.

Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.

Urlaub et al., "Isolation of Chinese hamster cell mutants deficient in dihydrofolate reductase activity." *Proc. Natl. Acad. Sci. U.S.A.*, Jul. 1980, 77(7):4216-4220.

Valentine MA, et al., "Phosphorylation of the CD20 phosphoprotein in resting B lymphocytes. Regulation by protein kinase C" *J Biol Chem.* Jul. 5, 1989;264(19):11282-7.

van Beek et al., "Increased sialic acid density in surface glycoprotein of transformed and malignant cells—a general phenomenon?" *Cancer Res.*, Nov. 1973, 33(11):2913-2922.

Van Meir et al., "Exciting new advances in neuro-oncology: the avenue to a cure for malignant glioma," *CA Cancer J. Clin.*, May-Jun. 2010, 60(3):166-193.

Van Slambrouck et al., "Clustering of monosialyl-Gb5 initiates downstream signalling events leading to invasion of MCF-7 breast cancer cells," *Biochem. J.*, Feb. 1, 2007, 401(3):689-699.

Vaswani et al., "Humanized antibodies as potential therapeutic drugs," *Ann. Allergy, Asthma Immunol.*, Aug. 1998, 81(2):105-116, 119.

Verhoeyen et al., "Reshaping human antibodies: grafting an antilysozyme activity," *Science*, Mar. 25, 1988, 239(4847):1534-1536.

Vermeer AW et al., "The thermal stability of immunoglobulin: unfolding and aggregation of a multi-domain protein" *Biophys J.* Jan. 2000;78(1):394-404.

Wang et al., "Glycan microarray of Globo H and related structures for quantitative analysis of breast cancer," *Proc. Natl. Acad. Sci. U.S.A.*, Aug. 19, 2008, 105(33):11661-11666.

Ward et al., "Binding activities of a repertoire of single immunoglobulin variable domains secreted from *Escherichia coli*," *Nature*, Oct. 12, 1989, 341(6242):544-546.

Waterhouse et al., "Combinatorial infection and in vivo recombination: a strategy for making large phage antibody repertoires," *Nuc. Acids Res.*, May 11, 1993, 21(9):2265-2266.

Wikstrand et al., "Monoclonal antibody therapy of human gliomas: Current status and future approaches," *Cancer Metastasis Rev.*, 1999, 18(4):451-464.

Williams et al., "Cloning and sequencing of human immunoglobulin V lambda gene segments." *Eur. J. Immunol.*, Jul. 1993, 23(7):1456-1461.

Winter et al., "Making antibodies by phage display technology," *Annu. Rev. Immunol.*, 1994, 12:433-455.

Woof et al., "Human antibody-Fc receptor interactions illuminated by crystal structures," *Nat. Rev. Immunol.*, Feb. 2004, 4(2):89-99.

Yansura et al., "Nucleotide sequence selection for increased expression of heterologous genes in *Escherichia coli*," *Methods: A Companion to Methods in Enzymol.*, Aug. 1992, 4(2):151-158.

Ye et al., "Stage-specific embryonic antigen 4 expression in epithelial ovarian carcinoma," *Int. J. Gynecol. Cancer*, Aug. 2010, 20(6):958-964.

Yelton et al., "Affinity maturation of the BR96 anti-carcinoma antibody by codon-based mutagenesis." *J. Immunol.*, Aug. 15, 1995, 155(4):1994-2004.

Yu et al., "Anti-GD2 antibody with GM-CSF, interleukin-2, and isotretinoin for neuroblastoma," *N. Engl. J. Med.*, Sep. 30, 2010, 363(14):1324-1334.

Zapata et al., "Engineering linear F(ab')$_2$ fragments for efficient production in *Escherichia coli* and enhanced antiproliferative activity," *Protein Eng.*, Oct. 1995, 8(10):1057-1062.

Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.

Zhang et al., "Selection of tumor antigens as targets for immune attack using immunohistochemistry: I. Focus on gangliosides," *Int. J. Cancer*, Sep. 26, 1997, 73(1):42-49.

International Search Report and Written Opinion issued for International application No. PCT/US2015/032738, dated Oct. 20, 2015, 15 pages.

International Search Report and Written Opinion issued for International application No. PCT/US2015/032744, dated Oct. 2, 2015, 12 pages.

(56) References Cited

OTHER PUBLICATIONS

International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
European Search Report issued in connection with corresponding European Patent Application No. 15181446.4, dated Dec. 7, 2015, 10 pages.
Abbas et al., "Functional diversity of helper T lymphocytes," Nature, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013).
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1+ CD4+ CD8− thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.

Barouch, D. H. Challenges in the development of an HIV-I vaccine. Nature 455, 613-619, (2008).
Barry, C.S. et al., 'Naked' and Hydrated Conformers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R. "In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," Nature, Jul. 5, 2007, 448(7149):44-49.
Bosmann et al., "Enzyme activity in invasive tumors of human breast and colon," Proc. Natl. Acad. Sci. USA, May 1974, 71(5):1833-1837.
Bost, Kenneth et al., Antibodies Against A Peptide Sequence Within The HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Bricard et al., "Enrichment of human CD4+ Vα24/Vβ11 invariant NKT cells in intrahepatic malignant tumors," J. Immunol., Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.

(56) References Cited

OTHER PUBLICATIONS

Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasens tive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of Bodipy dye through Cu(I) catalyzed azide-alkyne cycloaddition (CuAAC) reaction." Sci. China Chemistry 2012, 55, 125-130.
Chari, Ravi et al., Immunoconjugates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir-and Amantadine-resistant Influenza Viruses A (H1N1), Emerg. Infect. Dis., Jun. 2009, 15(6): 966-968.
Cheung et al., Stage-specific embryonic antigen-3 (SSEA-3) and beta3Ga1T5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," *J. Mol. Biol.*, Dec. 5, 1985, 186(3):651-663.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2. 6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," *J. Immunol.*, Jun. 15, 1997, 158(12):5603-5611.
Debets, M. F. et al., Bioconjugation with Strained Alkenes and Alkynes, Acc. Chem. Res. 2011, 44, 805-815.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant V$\alpha$24-J$\alpha$Q/V$\beta$11 T cell receptor is expressed in all individuals by clonally expanded CD4$^-$8$^-$ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).

(56) References Cited

OTHER PUBLICATIONS

Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4[30] and CD8[+] T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prelusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and.immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Friscourt, F. et al., A Fluorogenic Probe for the Catalyst-Free Detection of Azide-Tagged Molecules, J. Am. Chem. Soc. 2012, 134, 18809-18815.
Fujimore, Kenji et al., A Modeling Analysis of Monoclonal Antibody Percolation Through Tumors: A Binding-Site Barrier, J Nuc Med. 31: 1191-1198 (1990).
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Giaccone, Giuseppe et al., "A phase I study of the natural killer T-cell ligand α-galactosylceramide (KRN7000) in patients with solid tumors," Clin. Cancer Res., Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 824-557, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goldenthal et al., "Safety Evaluation of Vaccine Adjuvants: National Cooperative Vaccine Development Working Group," AIDS Res. Hum. Retroviruses, 1993, 9(Supp.1):S47-S51.
Govorkova et al, Combination chemotherapy for influenza. Viruses. Aug. 2010;2(8):1510-29.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.
Greenbaum et al., "Chemical approaches for functionally probing the proteome," Mol. Cell. Proteomics, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen.genetically coupled to cholera toxin A2/B subunits," J. Immuol., May 1, 1995, 154(9):4322-4332.
Ham, Richard et al., Media and Growth Requirements, Meth. Enz 58, 44 (1979).
Hammerling et al., In: Monoclonal Antibodies and T-Cell Hybridomas 563-587, 1981.

(56) References Cited

OTHER PUBLICATIONS

Han, Junyan et al., 3- and 5-Functionalized BODIPYs via the Liebeskind-Srogl Reaction, Organic & Biomolecular Chemistry (2009), 7(1), 34-36.

Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).

Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).

Hasegawa, Akira, et al., Synthesis of Sialyl Lewis X Ganglioside Analogues Containing Modified L-Fucose Residues, Carbohydr. Res. 1995, 274, 165-181.

Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.

Henglein, A. et al., Absorption Spectrum and Some Chemical Reactions of Colloidal Platinum in Aqueous Solution, J. Phys. Chem., 99, 14129 (1995).

Heiner, A et al., A new family of bioorthogonally applicable fluorogenic labelst, Org. Biomol. Chem. 2013, 11, 3297-3306.

Hey, Thomas et al., Artificial, non-antibody binding proteins for pharmaceutical and industrial application, Trends in Biotechnology 23(10) 514-522 (2005).

Hirabayashi, J. et al., Oligosaccharide Microarrays for Glycomics, Trends in Biotechnology 21 (4): 141-143, 2003.

Holmskov, Uffe et al., Collectins: Collagenous C-Type Lectins of the Innate Immune Defense System, 1994, Immunol. Today, 15: 67.

Honda et al., Synthesis and anti-influenza virus activity of 7-0-alkylated derivatives related to zanamivir. Bioorg Med Chem Lett. Aug. 5, 2002;12(15):1925-8.

Hotha, Srinivas et al., "Click Chemistry" Inspired Synthesis of Pseudo-Oligosaccharides and Amino Acid Glycoconjugates, J Org Chem 2006, 71, 364-367.

Horiya, S. et al., Recent strategies targeting HIV glycans in vaccine design. Nat. Chem. Biol. 10, 990-999, (2014).

Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.

Howard et al., "Biological properties of interleukin 10," Immunol. Today, Jun. 1992, 13(6):198-200.

Hsu et al., "Alkynyl sugar analogs for the labeling and visualization of glycoconjugates in cells," Proc. Natl. Acad. Sci. USA, Feb. 20, 2007, 104(8), 2614-2619.

Hsu, C, H. et al. Highly alpha-selective sialyl phosphate donors for efficient preparation of natural sialosides. Chem. Eur. J 16-6, 1754-1760, (2010).

Huang, Lijun et al., Iterative One-Pot Syntheses of Chitotetroses, Carbohydr. Res. 2006, 341, 1669-1679.

Huang et al., Recombinant immunotherpaeutics: current state and perspectives regarding the feasibility and market, Appl Microbiol Biotechnol, 87: 401-410. 2010.

International Search Report and Written Opinion issued for International application No. PCT/US2015/011748, dated Aug. 21, 2015, 17 pages.

International Search Report dated Jan. 13, 2012, from corresponding International Patent Application No. PCT/US2011/035982, 17 pages.

International Search Report dated Nov. 13, 2014, from corresponding International Patent Application No. PCT/US2014/054617, 10 pages.

International Search Report and Written Opinion in International Application No. PCT/US16/15858, dated Jun. 27, 2016, in 8 pages.

International Search Report issued for International application No. PCT/US15/22977, dated Jun. 22, 2015, 3 pages.

International Search Report issued for International application No. PCT/US15/40199, dated Mar. 2, 2016, 6 pages.

International Search Report issued for International application No. PCT/US2009/050754, dated Feb. 24, 2010, 10 pages.

International Search Report and Written Opinion in International Application No. PCT/US2017/021454, dated Jul. 31, 2017, 8 pages.

Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.

Ito, Akihero et al., A Novel Ganglioside Isolated From Renal Cell Carcinoma, Biol Chem 2001, 276, 16695.

Jacobs et al., "Metabolic labeling of glycoproteins with chemical tags through unnatural sialic acid biosynthesis," Methods Enzymol., 2000, 327:260-275.

Japanese Office Action dated Apr. 21, 2015, from Related Japanese Patent Application No. 2013-510261, 6 Pages.

Jayasena, Sumedha, Aptamers: An Emerging Class of Molecules That Rival Antibodies in Diagnostics, Clin. Chem. (1999), 45, 1628-1650.

Jewett, J.C.; Bertozzi, C.R., Cu-Free Click Cycloaddition Reactions in Chemical Biology, Chem. Soc. Rev. 2010, 39, 1272-1279.

Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.

Jin, R. C. et al., Photoinduced Conversion of Silver Nanospheres to Nanoprisms, Science (2001), 294, 1901-1903.

Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.

John, F. & Hendrickson, T. L. Synthesis of Truncated Analogues for Studying the Process of Glycosyl Phosphatidylinositol Modification. Org. Lett. 12, 2080-2083, (2010).

Jonges, M. et al., Dynamics of Antiviral-Resistant Influenza Viruses in the Netherlands, 2005-2008, Antiviral Res., Sep. 2009, 83(3): 290-297.

Jorgensen, Trond et al., Up-Regulation of the Oligosaccharide Sialyl Lewisx: A New Prognostic Parameter in Metastatic Prostate Cancer, Cancer Res. 55, 1817-1819, 1995.

Jose, Tiney et al., Energy transfer dyads based on Nile Red, Tetrahedron Letters (2009), 50(47), 6442-6445.

Joshi, Shantaran et al., Cell Surface Properties Associated with Malignancy of Metastatic Large Cell Lymphoma Cells, (1987) Cancer Res. 47, 3551-3557.

Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.

Kale et al., Detection of intact influenza viruses using biotinylated biantennary S-sialosides. J Am Chem Soc. Jul. 2, 2008;130(26):8169-71.

Kalesh et al., "Peptide-based activity-based probes (ABPs) for target-specific profiling of protein tyrosine phosphatases (PTPs)," Chem. Commun., Jan. 28, 2010, 46(4):589-591.

Kamkaew, a. et al., "BODIPY dyes in photodynamic therapy." Chem. Soc. Rev. 2013, 42, 77-88.

Kawakami et al., "Critical role of V$\alpha$14$^+$ natural killer T cells in the innate phase of host protection against Streptococcus pneumoniae infection," Eur. J. Immunol., Dec. 2003, 33(12):3322-3330.

Kawano et al., "CD1d-restricted and TCR-mediated activation of $v_\alpha$14 NKT cells by glycosylceramides," Science, Nov. 28, 1997, 278(5343):1626-1629.

Kanie, Osmau et al., Orthogonal glycosylation strategy in synthesis of extended blood group B determinant. Tetrahedron Lett. 37, 4551-4554 (1996).

Kannappan, Ramaswamy et al., "Photoaffinity labeling of sialidase with a biotin-conjugated phenylaminodizairine derivative of 2,3-didehydro-2-deoxy-N-acetylneuraminic acid," Biol. Pharm. Bull., Mar. 2008, 31(3):352-356.

(56) References Cited

OTHER PUBLICATIONS

Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kotteas et al., Immunotherapy for pancreatic cancer, J cancer Res Clin Oncol, 142(8): 1795-1805, 2016.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.

Lantz et al., "An invariant T cell receptor α chain is used by a unique subset of major histocompatibility complex class I-specific CD4+ and CD4−8− T cells in mice and humans," J. Exp. Med., Sep. 1, 1994, 180(3):1097-1106.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected αω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lemieux, R. U. et al., Halide ion catalyzed glycosidation reactions. Syntheses of a-linked disaccharides. J Am. Chem. Soc. 97(14), 4056-62, (1975).
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/ PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chinsica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, P. H., Wang, S. K. & Wong, C.-H. Quantitative analysis of carbohydrate-protein interactions using glycan microarrays: Determination of surface and solution dissociation constants. J. Am. Chem. Soc. 129, 11177-11184, (2007).
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Lin et al., A common glycan structure on immunoglobulin G for enhancement of effector functions, PNAS, Aug. 25, 2015, vol. 112, No. 34, p. 10611-10616.
Liu et al., "Activity-based protein profiling: the serine hydrolases," *Proc. Natl. Acad. Sci. USA*, Dec. 21, 1999, 96(26):14694-14699.

(56) References Cited

OTHER PUBLICATIONS

Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Nad Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," Angew. Chem. Int. Ed. Engl., Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR α chain in $NK1.1^+$ T cell populations, Int. Immunol., Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," Nat. Biotechnol., Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," Glycobiology, Jul. 2012, 22(7):880-896.
Miyagi et al., "Plasma membrane-associated sialidase as a crucial regulator of transmembrane signalling," J. Biochem., Sep. 2008, 144(3):279-285.

Miyagi et al., "Sialidase and malignancy: a minireview," Glycoconj. J., 2004, 20(3):189-198.
Miyagi, "Aberrant expression of sialidase and cancer progression," Proc. Jpn. Acad. Ser. B. Phys. Biol. Sci., 2008(10), 84:407-418.
Miyaji, E. N. et al., Induction of Neutralizing Antibodies Against Diphtheria Toxin by Priming with Recombinant Mycobacterium Bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," Nature, Oct. 4, 2001, 413(6855):531-534.
Monti et al., "Sialidases in vertebrates: a family of enzymes tailored for several cell functions," Adv. Carbohydr. Chem. Biochem., 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," Immunol. Today, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.
Nieuwenhuis et al., "CD1d-dependent macrophage-mediated clearance of Pseudomonas aeruginosa from lung," Nat. Med., Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," Proc. Natl. Acad. Sci. USA, Jul. 1985, 82(14):4592-4596.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," Immunity, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.

(56) References Cited

OTHER PUBLICATIONS

Okamura et al., "Interleukin-18: a novel cytokine that augments both innate and acquired immunity," *Adv. Immunol.*, 1998, 70:281-312.

Olden, Kenneth et al., Carbohydrate Moieties of Glycoproteins: A Re-Evaluation of Their Function, Biochem et Biophys Acta 650:209-232 (1982).

Otsubo N, et al., An Efficient and Straightforward Synthesis of Sialyl Lex Glycolipid as a Potent Selectin Blocker [[1]], Carbohydr. Res. 1998, 306, 517-530.

Ottolini et al., Combination anti- inflammatory and antiviral therapy of influenza in a cotton rat model. Pediatr. Pulmonol. 2003:36;290-4.

Oyelaran, 0. & Gildersleeve, J. C. Glycan arrays: recent advances and future challenges. Curr. Opin. Chem. Biol. 13, 406-413, (2009).

Pabst, M. et al., Glycan profiles of the 27 Nglycosylation sites of the HIV envelope protein CN54gp140. Biol. Chem. 393, 719-730, (2012).

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).

Pancera, M. et al. Structural basis for diverse N-glycan recognition by HIV-I-neutralizing V1-V2-directed antibody PG16. Nat. Struct. Mol. Biol. 20, 804-813, (2013).

Parker, C. A.; Rees, W. T., Correction of Fluorescence Spectra and Measurement of Fluorescence Quantum Efficiency, Analyst 1960, 85, 587-600.

Parrish, M. L. et al., A Microarray Platform Comparison for Neuroscience Applications, J. Neurosci. Methods, 2004, 132, 57-68.

Patricelli et al., "Functional interrogation of the kinome using nucleotide acyl phosphates," *Biochemistry*, Jan. 16, 2007, 46(2):350-358.

Paulson, J. C., Blixt, 0. & Collins, B. E. Sweet spots in functional glycomics. Nat. Chem. Biol. 2, 238-248, (2006).

Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.

Peiris et al., Re-emergence of fatal human influenza A subtype H5N1disease. Lancet. Feb. 21, 2004 ;363(9409):617-9.

Pejchal, R. et al. A potent and broad neutralizing antibody recognizes and penetrates the HIV glycan shield. Science 334, 1097-1103, (2011).

Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.

Perlmutter, R.M. et al., Subclass Restriction of Murine Anti-Carbohydrate Antibodies, Journal of Immunology 1978, 121, 566-572.

Pettit, George et al., Antineoplastic Agents. Part 189. The Absolute Configuration and Synthesis of Natural (−)-Dolastatin 10, J Am Chem Soc. 111:5463-5465 (1989).

Pettit, George et al., Dolastatins 23: Stereospecific Synthesis of Dolaisoleuine, J Chem Soc Perkin Trans. 15:853-585 (1996).

Pettit, George et al., Antineoplastic Agents 365. Dolastatin 10 SAR Probes, Anti-Cancer Drug Design 13:243-277 (1998).

Pettit, Robin et al., Specific Activities of Dolastatin 10 and Peptide Derivatives Against Cryptococcus Neoformans, Antimicrob Agents Chemother. 42:2961-2965 (1998).

Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.

Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.

Pratt, M. R. & Bertozzi, C. R. Chemoselective ligation applied to the synthesis of a biantennary N-linked glycoform of CD52. J. Am. Chem. Soc. 125, 6149-6159, (2003).

Prescher, J. A.; Bertozzi, C.R. "Chemistry in living systems." Nat. Chem. Biol. 2005, 1, 13-21.

Pritchard, L. K. et al. Structural Constraints Determine the Glycosylation of HIV-I Envelope Trimers. Cell Rep. 11, 1604-13, (2015).

Pritchard, Laura et al., Cell- and Protein-Directed Glycosylation of Native Cleaved HIV-I Envelope. J. Virol. 89, 8932-44, (2015).

Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.

Qi, Jianjun et al., Developing visible fluorogenic 'clickon' dyes for cellular imaging, Bioconjugate Chem. 2011, 22, 1758-1762.

Rabbani, Said et al., Glycosyltransferases: An efficient tool for the enzymatic synthesis of oligosaccharides and derivatives as well as mimetics thereof Chimia 60, 23-27, (2006).

Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.

Rana, G. Kucukayan-Dogu, E. Bengu "Growth of vertically aligned carbon nanotubes over self-ordered nano-porous alumina films and their surface properties" Applied Surface Science, 2012, 258 7112-7117.

Raska, M. et al. Glycosylation patterns of HIV-I gp120 depend on the type of expressing cells and affect antibody recognition. J. Biol. Chem. 285, 20860-20869, (2010).

Rillahan, C. D. & Paulson, J. C. Glycan microarrays for decoding the glycome. Annu. Rev. Biochem. 80, 797-823, (2011).

Ritamo, Ilja al., Comparison of the Glycosylation of in Vitro Generated Polyclonal Human lgG and Therapeutic Immunoglins, Mol Immunol. Feb. 2014; 57(2): 255-62.

Rogers, GN et al., Single Amino Acid Substitutions in Influenza Haemagglutinin Change Receptor Binding Specificity. Nature, 304:76, 1983.

Rogers, GN et al., Receptor Determinants of Human and Animal Influenza Virus Isolates: Differences in Receptor Specificity of the H3 Hemagglutinin Based on Species of Origin. Virology, 127:361, 1983.

Romagnani, "Induction of $T_H1$ and $T_H2$ responses: a key role for the 'natural' immune response?" *Immunol. Today*, Oct. 1992, 13(10):379-381.

Rosenstein, N.E. et al, Meningococcal Disease, N Engl J Med 2001, 344, 1378-1388.

Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.

Roth, Jurgen et al., Reexpression of Poly(sialic Acid) Units of the Neural Cell Adhesion Molecule in Wilms Tumor, Proc. Natl. Acad. Sci. 85, 2999-3000, 1988.

Rudnick et al., Affinity and Avidity in Antibody-Based Tumor Targeting, Can Biotherp & Radoipharm, 24, 155-162 (2009).

Russell et al., "The structure of H5N1 avian influenza neuraminidase suggests new opportunities for drug design," Nature, Sep. 7, 2006, 443(7107):45-49.

Saito, Seiichi et al., Haptoglobin-β Chain Defined by Monoclonal Antibody RM2 as a Novel Serum Marker for Prostate Cancer, Int. J Cancer, 2008, 123(3), 633-640.

Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.

Salisbury et al., "Activity-based probes for proteomic profiling of histone deacetylase complexes," *Proc. Natl. Acad. Sci. USA*, Jan. 23, 2007, 104(4):1171-1176.

Salomon et al., Inhibition of the cytokine response does not protect against lethal H5N1 nfluenza infection. Proc Natl Acad Sci U S A Jul. 24, 2007;104(30): 12479-81.

(56) References Cited

OTHER PUBLICATIONS

Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," Proc. Natl. Acad. Sci. USA, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. USA., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem*., Aug. 27, 2004, 279(35):37021-37029.
Sheu et al., "Surveillance for neuraminidase inhibitor resistance among human influenza A and B viruses circulating worldwide from 2004 to 2008," *Antimicrob. Agents Chemother*., Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).

Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et at, "Proteomic profiling of metalloprotease activities with cocktails of active-site probes," *Nat. Chem. Biol*., May 2006, 2(5):274-281.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced By 6) Dextran J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of *Pseudomonas aeruginosa* NagZ," *J. Am. Chem. Soc*., Jan. 9, 2008, 130(1):327-335.
Su, G. Hahner, W. Thou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

(56) References Cited

OTHER PUBLICATIONS

Supplementary European Search Report in European Application No. EP 13775664.9, dated Oct. 27, 2015, in 7 pages.
Sutton, VR et al., Bcl-2 Prevents Apoptosis Induced by Perforin and Granzyme B, But Not That Mediated by Whole Cytotoxic Lymphocytes, J of Immunology 1997, 158(12), 5783.
Tahir et al., "Loss of IFN-γ production by invariant NK T cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from *Vibrio* sp. JT-FAJ-16. J. Biochem. 142, 403-412, (2007).
Takano, Rya et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.

Ulrich, G.; Ziessel, R.; Harriman, A. "The chemistry of fluorescent bodipy dyes: Versatility unsurpassed." Angew. Chem. Int. Ed. 2008, 47, 1184-1201.
van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphonic acid analogue of N-Acetyl-2,3-didehydro-2-deoxyneuraniinic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mot. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Then et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol. 20, 275-281, (2002).

(56) References Cited

OTHER PUBLICATIONS

Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).

Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Brockman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.

\* cited by examiner $R^1, R^2, R^3, R^4, R^5, R^6$ = Various protecting groups

Reagents and conditions: (a) $C_{13}H_{27}PPh_3Br$, LHMDS, THF; (b) $H_2$, Pd(OH)$_2$, EtOAc; (c) Tf$_2$O, 2,6-lutidine, TMGA, CH$_2$Cl$_2$; (d) Staudinger reaction; (e) EDC, HBTU, Et$_3$N, CH$_2$Cl$_2$.

R¹, R², R³, R⁴, R⁵, R⁶ = Various protecting groups

Reagents and conditions: (a) C₁₃H₂₇PPh₃Br, LHMDS, THF; (b) H₂, Pd(OH)₂, EtOAc; (c) Tf₂O, 2,6-lutidine, TMGA, CH₂Cl₂; (d) Staudinger reaction; (e) EDC, HBTU, Et₃N, CH₂Cl₂.

R$^1$, R$^2$, R$^3$, R$^4$, R$^5$, R$^6$, R$^7$, R$^8$ = Various protecting groups Reagents and conditions: (a) C$_{15}$H$_{31}$PPh$_3$Br, n-BuLi, THF; (b) OsO$_4$, NMO, t-BuOH, H$_2$O; (c) EDC, HBTU, Et$_3$N, CH$_2$Cl$_2$.

$R^1, R^2, R^3, R^4, R^5, R^6, R^7$ = Various protecting groups

Reagents and conditions: (a) $C_{16}H_{33}PPh_3Br$, $n$-BuLi, THF; (b) $OsO_4$, NMO, $t$-BuOH, $H_2O$; (c) EDC, HBTU, $Et_3N$, $CH_2Cl_2$.

$R^1, R^2, R^3, R^4, R^5, R^6, R^7, R^8$ = Various protecting groups

Reagents and conditions: (a) $C_{12}H_{25}PPh_3Br$, n-BuLi, THF; (b) Staudinger reaction; (c) EDC, HBTU, $Et_3N$, $CH_2Cl_2$.

$R^1, R^2, R^3, R^4, R^5, R^6, R^7$ = Various protecting groups

Reagents and conditions: (a) $C_{19}H_{27}PPh_3Br$, LHMDS, THF; (b) $H_2$, Pd/C, EtOAc; (c) MsCl, pyridine; (d) $NaBH_4$, MeOH; (e) Staudinger reaction; (f) EDU, HBTU, $Et_3N$, $CH_2Cl_2$.

$R^1, R^2, R^3, R^4, R^5, R^6, R^7, R^8$ = Various protecting groups

Reagents and conditions: (a) $C_{13}H_{27}PPh_3Br$, LHMDS, THF; (b) $H_2$, Pd/C, EtOAc; (c) MsCl, pyridine; (d) $NaBH_4$, MeOH; (e) Staudinger reaction; (f) EDU, HBTU, $Et_3N$, $CH_2Cl_2$.

$R^1, R^2, R^3, R^4, R^5, R^6, R^7, R^8, R^9, R^{10}$ = Various protecting groups Reagents and conditions: (a) NaIO$_4$; (b) C$_{13}$H$_{27}$PPh$_3$Br, LHMDS, THF; (c) Staudinger reaction; (d) EDC, HBTU, Et$_3$N, CH$_2$Cl$_2$.

$R^1, R^2, R^3, R^4, R^5, R^6, R^7, R^8, R^9, R^{10}, R^{11}$ = Various protecting groups Reagents and conditions: (a) NaIO$_4$; (b) C$_{13}$H$_{27}$PPh$_3$Br, LHMDS, THF; (c) Staudinger reaction; (d) EDC, HBTU, Et$_3$N, CH$_2$Cl$_2$.

$R^1, R^2, R^3, R^4, R^5, R^6, R^7, R^8$ = Various protecting groups

Reagents and conditions: (a) NaIO$_4$, PBS; (b) C$_{14}$H$_{29}$MgCl, THF; (c) Staudinger reaction; (d) EDC, HBTU, Et$_3$N, CH$_2$Cl$_2$.

R¹, R², R³, R⁴, R⁵, R⁶ = Various protecting groups

Reagents and conditions: (a) CH₃PPh₃Br, LHMDS, THF; (b) Grubbs catalyst second generation; (c) Staudinger reaction; (d) EDC, HBTU, Et₃N, CH₂Cl₂.

R[1], R[2], R[3], R[4], R[5], R[6] = Various protecting groups

Reagents and conditions: (a) CH$_3$PPh$_3$Br, LHMDS, THF; (b) Grubbs catalyst second generation; (c) Staudinger reaction; (d) EDC, HBTU, Et$_3$N, CH$_2$Cl$_2$.

R1, R2, R3, R4, R5, R6 = Various protecting groups

Reagents and conditions: (a) CH3PPh3Br, LHMDS, THF; (b) acryloyl chloride, Et3N, DMAP, CH2Cl2; (c) Grubbs catalyst second generation; (d) 1-dodecene, Grubbs catalyst second generation; (e) Staudinger reaction; (f) EDC, HBTU, Et3N, CH2Cl2.

R1, R2, R3, R4, R5, R6 = Various protecting groups

Reagents and conditions: (a) CH3PPh3Br, LHMDS, THF; (b) acryloyl chloride, Et3N, DMAP, CH2Cl2; (c) Grubbs catalyst second generation; (d) 1-dodecene, Grubbs catalyst second generation; (e) Staudinger reaction; (f) EDC, HBTU, Et3N, CH2Cl2.

R[1], R[2], R[3], R[4], R[5], R[6] = Various protecting groups

Reagents and conditions: (a) CH$_3$PPh$_3$Br, LHMDS, THF; (b) acryloyl chloride, Et$_3$N, DMAP, CH$_2$Cl$_2$; (c) Grubbs catalyst second generation; (d) 1-dodecene, Grubbs catalyst second generation; (e) Staudinger reaction; (f) EDC, HBTU, Et$_3$N, CH$_2$Cl$_2$.

$R^1, R^2, R^3, R^4, R^5, R^6, R^7, R^8$ = Various protecting groups

Reagents and conditions: (a) 1-tetradecyne, BuLi, THF; (b) Staudinger reaction; (c) EDC, HBTU, Et$_3$N, CH$_2$Cl$_2$.

| mCD1d-GSL | KD (nM) |
|---|---|
| C1 | 1.240 ± 0.003 |
| C1-Glc | 5.137 ± 0.110 |
| C34 | 0.735 ± 0.010 |
| C34-Glc | 7.960 ± 1.269 |
| 7DW8-5 | 0.755 ± 0.018 |
| 7DW8-5-Glc | 7.540 ± 1.813 |

| hCD1d-GSL | KD (nM) |
|---|---|
| C1 | 16.410 ± 4.200 |
| C1-Glc | 8.550 ± 0.617 |
| C34 | 0.498 ± 0.005 |
| C34-Glc | 0.378 ± 0.019 |
| 7DW8-5 | 0.777 ± 0.022 |
| 7DW8-5-Glc | 0.481 ± 0.008 |

B

| mCD1d:GSL | KD (nM) with L363 |
|---|---|
| C1 | 4.56 ± 0.50 |
| 7DW8-5 | 2.36 ± 0.01 |
| 7DW8-5-Glc | 2.26 ± 0.21 |

D

| glycolipid | KD (nM) of binary complex |
|---|---|
| C1 | 160.20 ± 17.46 |
| 7DW8-5 | 7.40 ± 0.72** |
| 7DW8-5-Glc | 5.36 ± 1.56** | n.s. between 7DW8-5 & 7DW8-5-Glc

A

B

C

D

Statistical evaluation was performed using one-way ANOVA. * P < 0.05 compared with C1. #, P=0.002 compared with C34, using Student's T test.

HUMAN INKT CELL ACTIVATION USING GLYCOLIPIDS

RELATED APPLICATION

This application claims the benefit of priority to U.S. Provisional Patent Application No. 62/047,602, entitled "Human iNKT Cell Activation Using Glycolipids", filed on Sep. 8, 2014, the entirety of which is incorporated herein.

FIELD OF THE INVENTION

This invention relates generally to the field of immune therapeutics. In particular, the instant disclosure relates to glycolipids and variants thereof that modulate invariant natural killer T (iNKT) cells in humans and stimulate cytokine and/or chemokine production and thus transactivate downstream immune cells thereby bridging the innate and adaptive immunity.

BACKGROUND OF THE INVENTION

Natural killer-like T (NKT) cells are a distinct population of T lymphocytes with enormous therapeutic potential in the treatment of diseases such as cancer and autoimmune disorders. Invariant natural killer T (iNKT) cells form a subset of regulatory T cells with features of both innate and adaptive immunity. In contrast to conventional T cells that are activated by a peptide presented by an MHC class I or II molecule, iNKT cells recognize lipid derivatives present in the context of CD1d, a non-classical MHC I molecule expressed on antigen presenting cells (APCs).

Certain glycolipids with alpha linkages with glucose or galactose have been found to exhibit antitumor activity in vitro and in vivo and shown to be the most potent ligand yet known for both mouse and human invariant natural killer T cells (iNKT cells).

Invariant NKT cells (iNKT cells) carry the invariant TCR-α chain (Vα14/Jα18 in mice and Vα24/Jα18 in humans) and co-express CD161 antigen (NK cell marker NK1.1 in mice and NKR-P1A in humans). (1) Lantz, O.; Bendelac, A. J. Exp. Med. 1994, 180, 1097; (2) Dellabona, P.; Padovan, E.; Casorati, G.; Brockhaus, M.; Lanzavecchia, A. J. Exp. Med. 1994, 180, 1171; (3) Makino, Y.; Kanno, R.; Ito, T.; Higashino, K.; Taniguchi, M. Int. Immunol. 1995, 7, 1157; and (4) Davodeau, F.; Peyrat, M. A.; Necker, A.; Dominici, R.; Blanchard, F.; Leget, C.; Gaschet, J.; Costa, P.; Jacques, Y.; Godard, A.; Vie, H.; Poggi, A.; Romagne, F.; Bonneville, M. J. Immunol. 1997, 158, 5603. They secrete large amounts of Th1 (e.g., IFN-γ, IL-2) and Th2 (e.g., IL-4, IL-6) cytokines in response to αGalCer presented by the CD1d molecule on the antigen-presenting cells.[5-9] (5) Kawano, T.; Cui, J.; Koezuka, Y.; Toura, I.; Kaneko, Y.; Motoki, K.; Ueno, H.; Nakagawa, R.; Sato, H.; Kondo, E.; Koseki, H.; Taniguchi, M. Science 1997, 278, 1626; (6) Yoshimoto, T.; Paul, W. E. J. Exp. Med. 1994, 179, 1285; (7) Arase, H.; Arase, N.; Nakagawa, K.; Good, R. A.; Onoe, K. Eur. J. Immunol. 1993, 23, 307; (8) Kawakami, K.; Yamamoto, N.; Kinjo, Y.; Miyagi, K.; Nakasone, C.; Uezu, K.; Kinjo, T.; Nakayama, T.; Taniguchi, M.; Saito, A. Eur. J. Immunol. 2003, 33, 3322; and (9) Nieuwenhuis, E. E.; Matsumoto, T.; Exley, M.; Schleipman, R. A.; Glickman, J.; Bailey, D. T.; Corazza, N.; Colgan, S. P.; Onderdonk, A. B.; Blumberg, R. S. Nat. Med. 2002, 8, 588. These secreted cytokines could then transactivate downstream immune cells, including dendritic cells (DC), natural killer cells (NK), B cells, $CD4^+$ T and $CD8^+$ T cells, and thereby bridging the innate and adaptive immunity.[10-12] (10) Eberl, G.; MacDonald, H. R. Eur. J. Immunol. 2000, 30, 985; (11) Eberl, G.; Brawand, P.; MacDonald, H. R. J. Immunol. 2000, 165, 4305; and (12) Kitamura, H.; Ohta, A.; Sekimoto, M.; Sato, M.; Iwakabe, K.; Nakui, M.; Yahata, T.; Meng, H.; Koda, T.; Nishimura, S.; Kawano, T.; Taniguchi, M.; Nishimura, T. Cell. Immunol. 2000, 199, 37.

However, the counterbalance of Th1 and Th2 cytokines may limit the clinical application of aGalCer for the treatment of a variety of disorders.[13-16] (13) Tahir, S. M.; Cheng, O.; Shaulov, A.; Koezuka, Y.; Bubley, G. J.; Wilson, S. B.; Balk, S. P.; Exley, M. A. J. Immunol. 2001, 167, 4046; (14) Dhodapkar, M. V.; Geller, M. D.; Chang, D. H.; Shimizu, K.; Fujii, S.; Dhodapkar, K. M.; Krasovsky, J. J. Exp. Med. 2003, 197, 1667; (15) Giaccone, G.; Punt, C. J.; Ando, Y.; Ruijter, R.; Nishi, N.; Peters, M.; von Blomberg, B. M.; Scheper, R. J.; van der Vliet, H. J.; van den Eertwegh, A. J.; Roelvink, M.; Beijnen, J.; Zwierzina, H.; Pinedo, H. M. Clin. Cancer Res. 2002, 8, 3702; and (16) Bricard, G.; Cesson, V.; Devevre, E.; Bouzourene, H.; Barbey, C.; Rufer, N.; Im, J. S.; Alves, P. M.; Martinet, O.; Halkic, N.; Cerottini, J. C.; Romero, P.; Porcelli, S. A.; Macdonald, H. R.; Speiser, D. E. J. Immunol. 2009, 182, 5140.

SUMMARY OF THE INVENTION

Accordingly, many analogues were designed to stimulate selective Th1 or Th2 cytokine responses of iNKT cells. Glycolipids with marked Th1 bias in both mice and men, leading to superior tumour protection in vivo. For example, glycosphingolipids (GSLs) with the truncated sphingosine tail could drive immune responses into Th2 direction and prevented autoimmune encephalomyelitis. Miyamoto, K.; Miyake, S.; Yamamura, T. Nature 2001, 413, 531. On the other hand, GSL with phenyl ring on the acyl chain induced Th1-biased cytokines in mice and humans and displayed more potent anticancer activities against breast, lung and melanoma tumors in mice. (Chang, Y. J.; Huang, J. R.; Tsai, Y. C.; Hung, J. T.; Wu, D.; Fujio, M.; Wong, C. H.; Yu, A. L. Proc. Natl. Acad. Sci. U.S.A. 2007, 104, 10299 and Wu, T. N.; Lin, K. H.; Chang, Y. J.; Huang, J. R.; Cheng, J. Y.; Yu, A. L.; Wong, C. H. Proc. Natl. Acad. Sci. U.S.A. 2011, 108, 17275.

Examination of the binary interaction between CD1d and glycolipids, as well as the ternary interaction between iNKT TCR and CD1d-glycolipid complex elucidated the mechanisms underlying their structure-activity relationships (SAR). As compared to aGalCer, phenyl GSLs with the same glycosyl group exhibited stronger binary and ternary interactions, leading to more Th1-biased responses, and the biological responses had a significant correlation with the binding avidities of the ternary complex both in mice and humans. 19-21 Wu, T. N.; Lin, K. H.; Chang, Y. J.; Huang, J. R.; Cheng, J. Y.; Yu, A. L.; Wong, C. H. Proc. Natl. Acad. Sci. U.S.A. 2011, 108, 17275; Liang, P. H.; Imamura, M.; Li, X.; Wu, D.; Fujio, M.; Guy, R. T.; Wu, B. C.; Tsuji, M.; Wong, C. H. J. Am. Chem. Soc. 2008, 130, 12348; and Li, X.; Fujio, M.; Imamura, M.; Wu, D.; Vasan, S.; Wong, C. H.; Ho, D. D.; Tsuji, M. Proc. Natl. Acad. Sci. U.S.A. 2010, 107, 13010.

Invariant natural killer T (iNKT) cells are known to have marked immunomodulatory capacity due to their ability to produce copious amounts of effector cytokines. There is a need for improved glycosphingolipids that stimulate human invariant NKT (iNKT) cells and modulate cytokine and chemokine production in humans.

Accordingly, the present disclosure is based on the unexpected discovery that glycosphingolipids (GSLs) have surprising efficacy in immune stimulation. Methods for iNKT-independent induction of chemokines by these exemplary GSL are disclosed. Methods for immune stimulation in humans using GSLs are also provided.

The present disclosure provides a method for augmenting an immunogenicity of an antigen in a subject in need thereof, comprising combined administration said antigen as coadministration or coformulation with an adjuvant composition comprising a GSLs of the general Formula 1.

According to the present invention, the use of GSLs as an immune adjuvant results in an enhancement and/or extension of the duration of the protective immunity induced by the antigen and is attributed at least in part to the enhancement and/or extension of antigen specific Th1-type responses.

The GSLs-containing adjuvant of the invention can be conjointly administered with any antigen, in particular, with antigens derived from infectious agents or tumors. Preferably, the adjuvant and antigen are administered simultaneously, most preferably in a single dosage form.

In a further embodiment, the invention provides a prophylactic and/or therapeutic method for treating a disease in a subject comprising administering to said subject an immunoprotective antigen together with an adjuvant composition that includes GSLs. As specified herein, this method can be useful for preventing and/or treating various infectious or neoplastic diseases.

In conjunction with the methods of the present invention, also provided are pharmaceutical and vaccine compositions comprising an immunogenically effective amount of an antigen and an immunogenically effective amount of an adjuvant selected from GSLs within Formula 1 as well as, optionally, a pharmaceutically acceptable carrier or excipient.

Accordingly, in one aspect, the present disclosure relates to structural and functional exemplars of immune adjuvant compounds of Formula (I):

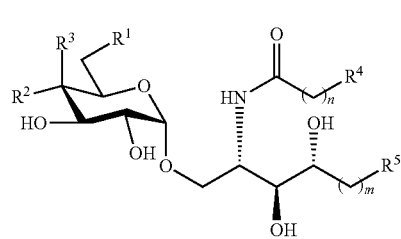

(I)

or pharmaceutically acceptable salt thereof; wherein $R^1$, $R^2$, $R^3$, $R^4$, $R^5$, n and m are as described herein.

In some embodiments, $R^4$ is of Formula (II):

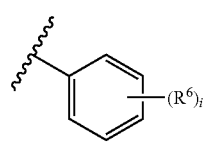

(II)

wherein i and $R^6$ are as described herein.

In some embodiments, $R^4$ is of Formula (III):

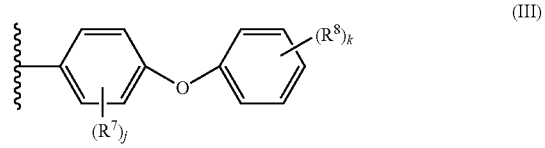

(III)

wherein j, k, $R^7$ and $R^8$ are as described herein.

In certain aspects, embodiments of the present disclosure can include or exclude (e.g. proviso out) any members or exemplars listed herein, including members of the exemplars listed in FIG. 1. In certain embodiments, the exemplars can include or exclude any one or more of compounds C34, II-1 to II-12, III-1 to III-24, and compounds 43 and 53.

In certain embodiments, the following compounds are provided:

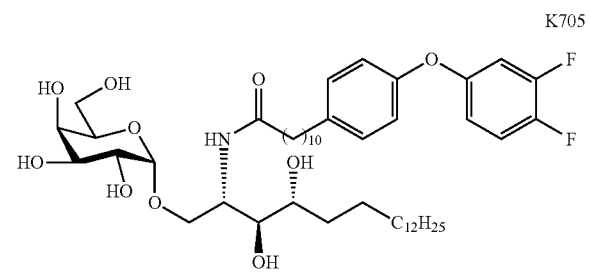

K705

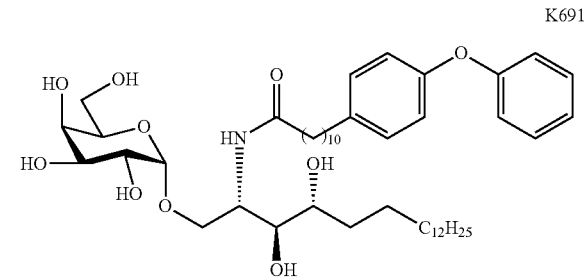

K691

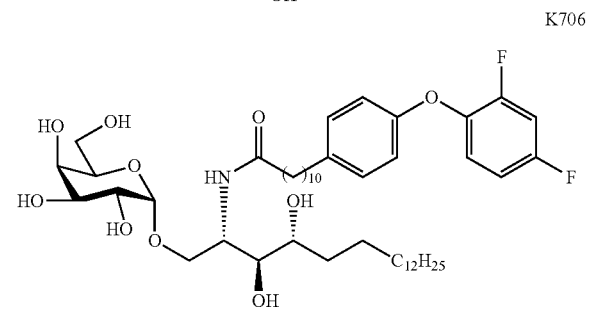

K706

Aspects of the disclosure also relates to pharmaceutical compositions comprising (i) a compound disclosed herein in an amount sufficient to stimulate an immune response when administered to a subject, including humans, and (ii) a pharmaceutically acceptable excipient.

In some embodiments, the pharmaceutical composition comprises an antigen and a vaccine adjuvant. In certain embodiments, the antigen is a tumor antigen.

In some embodiments, the pharmaceutical composition comprises an anti-cancer therapeutic.

In some embodiments of the pharmaceutical composition, $R^4$ in the compound is selected from substituted or unsubstituted aryl, and substituted or unsubstituted heteroaryl, and wherein the compound is capable of increasing Th1 cytokines in humans with minimum accompanying increase in Th2 cytokines.

Aspects of the invention relates to methods for stimulating an immune response in a human subject in need thereof, the method comprising: administering to the subject a therapeutically effective amount of a composition disclosed herein.

In some aspects, the compound is administered in amount capable of elevating invariant Natural Killer T (iNKT) cells in humans.

In some aspects, administration of the compound increases cytokine and/or chemokine production in humans. In some embodiments, the cytokine production is sufficient to transactivate downstream immune cells. In some embodiments, the downstream immune cells comprise one or more of dendritic cells (DC), natural killer cells (NK), B cells, CD4$^+$ T and CD8$^+$ T cells.

In some aspects, the cytokines comprise Th1 cytokines. In some embodiments, the Th1 cytokines are selected from: interferon-gamma (IFN-γ), GM-CSF, TNFα, interleukin 2, interleukin 12.

In some aspects, the chemokines are selected from: RANTES, MIP-1α, KC, MCP-1, IP-10 and MIG.

In some aspects, administration of the composition has an anti-cancer effect. In some embodiments, the cancer is selected from the group consisting of lung cancer, breast cancer, hepatoma, leukemia, solid tumor and carcinoma.

In some embodiments, R$^4$ in the compound is selected from substituted or unsubstituted aryl, and substituted or unsubstituted heteroaryl, and wherein increase in Th1 cytokines in humans exceeds any increase in Th2 cytokines.

Aspects of the invention relates to methods for elevating invariant Natural Killer T (iNKT) cells production in a human subject in need thereof, the method comprising: administering to the subject a therapeutically effective amount of a composition, wherein the composition comprises a compound disclosed herein. In some embodiments, the elevation of iNKT levels is greater when compared to the elevation resulting from administration of an equivalent amount of a glycolipid analogue comprising alpha-galactose (αGal) as the glycosyl head group.

Aspects of the invention relates to methods for stimulating cytokine and/or chemokine production in a human subject in need thereof, the method comprising: administering to the subject a therapeutically effective amount of a composition, wherein the composition comprises an amount sufficient to increase cytokine/chemokine production, of a compound disclosed herein.

In some aspects, cytokine production is sufficient to transactivate downstream immune cells. In some embodiments, the downstream immune cells comprise one or more of dendritic cells (DC), natural killer cells (NK), B cells, CD4$^+$ T and CD8$^+$ T cells.

In some aspects, the cytokines comprise Th1 cytokines. In some embodiments, the cytokines are selected from: interferon-gamma (IFN-γ), GM-CSF, TNFα, interleukin 2, and interleukin 12.

In some aspects, the chemokines are selected from: RANTES, MIP-1α, KC, MCP-1, IP-10 and MIG.

In some aspects, this disclosure relates to an article of manufacture comprising the GSLs of Formula I.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 2B-1 to 2B-19 Synthesis scheme of Exemplary C34 derivatives.

FIG. 3 shows: The ternary interaction of CD1d-glycolipid complex with iNKT cells. (3A) DN3A4-1.2 Vα14+ iNKT hybridoma cells and (3B) 7DW8-5-expanded Vα24+ iNKT cells were incubated with various concentrations of the indicated dimeric mCD1d-glycolipid and hCD1d-glycolipid complexes for 30 min at 4° C., respectively. The level of bound complexes at the indicated concentration was detected by anti-mIgG1 secondary antibody and analyzed by flow cytometry. The relationship between the binding percentage and the concentration of CD1ddi-glycolipids complex was plotted in mice (3A) and humans (3B). KD values in mice (3C) and humans (3D) were calculated from Scatchard transformation of the plot (3A) and (3B), respectively. Assay was performed in duplicates.

FIG. 4 shows: mCD1d vs. hCD1d swapping assay. (4A) Murine DN3A4-1.2 Vα14+ iNKT hybridoma cells or (4B) C1-expanded Vα24+ iNKT cells were pulsed with the indicated glycolipid presented by either mCD1d (A20-CD1d cells) or hCD1d (HeLa-CD1d cells) at 1, 0.1, and 0.01 μg/ml. After 18 hr, the supernatants were harvested to measure IL-2 secretion by an ELISA assay (4A) or using Beadlyte® Human Cytokine kit and Luminex® 200™ reading system (4B). Assays were performed in triplicates. 8-5 was the abbreviation of 7DW8-5.

FIG. 5 shows: Computer modeling of the ternary complex of CD1d-GSL-iNKT TCR. (5A)/(5B) hydrogen bonds within the CD1d-C1-iNKT TCR complex of mice (5A) and humans (5B) were shown. Formation of hydrogen bonds was noted in the conserved residues, including human Asp80 (mouse Asp80), human Thr154 (mouse Thr156), human Asp151 (mouse Asp 153) of CD1d and human Gly96 (mouse Gly96) of iNKT TCR. Besides, mouse Asn30 as well as human Phe29 and Ser30 of iNKT TCR were the key residues forming H-bond interactions with 3'- and/or 4'-OHs of C1. (5C) the equatorial 4'-OH of glucose could compensate for the loss of Phe29 interaction by a stronger interaction with a crystal water, which was trapped by human iNKT TCR-Phe51 and hCD1d-Trp153. (5D) the higher energy from aromatic interactions could drive the acyl chain of C34 or C34-Glc to a lower position (near Cys12) of the A' channel within CD1d, leading to a subtle perturbation to the orientation of the head group. (5E) The computed free energy of the ternary complex using Autodock4.2.

FIG. 6 shows: Dose-dependent chemokine secretions triggered by 7DW8-5-Glc. B6 wild type mice were i.v. injected with 7DW8-5-Glc at 0.1 or 1 µg/mouse. Sera collected at 2 h and 18 h post-injection were analyzed for chemokine secretions such as IP-10 (6A), KC (6B), MCP-1 (6C), and MIP-1α (6D). These chemokines peaked at 2 hr post-injection.

FIG. 7 shows: iNKT-dependent productions of cytokines and chemokines. B6 wild type and Jα18 knockout mice were i.v. injected with the indicated glycolipids (1 µg/mouse) or vehicle. Sera collected at 2 h and 18 h post-injection were analyzed for cytokines like IL-2 (7A), IL-6 (7B), GM-CSF (7C) and TNFα (7D) as well as chemokines such as IP-10 (7E), MIG (7F), KC (7G) and MCP-1 (7H). Only MIG peaked at 18 hr post-injection, while the others peaked at 2 hr post-injection.

FIG. 8 shows: FACS analyses of WT mouse immune cells after the indicated glycolipid stimulation. B6 WT mice treated with the indicated glycolipid (1 µg/mouse) or vehicle (1% DMSO in PBS) were sacrificed at 72 hr post-injection and their splenocytes were subjected to FACS analysis. (8A) The total splenocytes, (8B) total CD11Chi cells, (8C) CD11Chi/CD80+ cells, (8D) CD11Chi/CD86+ cells, (8E) CD4+ T cells and (8F) CD8+ T cells.

FIG. 9 shows: FACS analyses of Jα18 KO mouse immune cells after the indicated glycolipid stimulation. B6 Jα18 KO mice treated with the indicated glycolipid (1 µg/mouse) or vehicle (% DMSO in PBS) were sacrificed at 72 hr post-injection and their splenocytes were subjected to FACS analysis. (9A) The total splenocytes, (9B) total CD11Chi cells, (9C) CD11Chi/CD80+ cells, (9D) CD11Chi/CD86+ cells, (9E) CD4+ T cells and (9F) CD8+ T cells (student t test: *, p<0.05, as compared to D).

FIG. 10 shows: Binding strengths of the binary complex between mCD1d and glycolipid. (10A, 10B) Different concentrations of mCD1d-glycolipid complexes coated on the ELISA plate were incubated with the saturated amount of L363 antibody conjugated with biotin, followed by streptavidin-HRP detection and ELISA measurement. (10A) The relationship between OD values reflecting L363 antibody binding and the concentration of CD1ddi-glycolipids complex was plotted. (10B) The dissociation constant (KD) between L363 antibody and the indicated mCD1d-glycolipid complex was calculated as described in Materials and methods. (10C) The relationship between OD values reflecting L363 antibody binding and the concentration of glycolipids was plotted. (10D) KD values of the binary complex were calculated from the linear regression of the Scatchard transformation of the L363 antibody binding curve (10C).

FIG. 11 shows: CD1d dimer staining of in vivo C1-pulsed splenocytes. B6 WT splenocytes (n=3) were harvested 3 days after injection with C1 (1 µg/mouse) and stained with CD3, CD45R and the indicated dimer complex conjugated with RPE for 1 hr at 4 degrees Celsius. (11A) CD3+/CD45R− cells were gated to analyze the dimer staining. (11B) unloaded dimer was used as the control. (11C) mCD1d dimer loaded with 7DW8-5-Glc stained 17.1±0.8% of C1-pulsed splenocytes. (11D) mCD1d dimer loaded with 7DW8-5 stained 36.2±5.0% of C1-pulsed splenocytes.

FIG. 12 shows: mCD1d vs. hCD1d swapping assay. C1-expanded Vα24+ iNKT cells were pulsed with the indicated glycolipid antigen presented by either mCD1d (A20-CD1d cells) or hCD1d (HeLa-CD1d cells) at 1, 0.1, and 0.01 µg/ml. After 18 hr, the supernatants were harvested for the measurement of IFN-γ (12A) and IL-4 (12B) secretions. (12C) The ratio of IFN-γ over IL-4 was calculated at different concentrations of glycolipids. The ratio of IFN-γ over IL-4 from different glycolipids were compared to that from C1 at the indicated concentrations by student t test (*, p<0.05; , p<0.01; *, p<0.001). Assays were performed in triplicates.

FIG. 13 shows: cytokine production upon stimulation of human iNKT cells by K691, K706 and C34. Human Vα24-restricted NKT cells were isolated from PBMC by magnetic beads, and iNKT cells were cultured with 50 µg/mL recombinant human IL-2. Two days later, iNKT cells were co-cultured with autologous monocyte-derived DCs and different glycolipids at 1 µg/mL in 96 wells. At 72 hrs, the supernatant were collected to determine the cytokines profiles by Luminex. (A) Secretion of IFN-γ and IL-4 was similar among all glycolipids. (B) Ratio of IFN-γ/IL-4 in C34, K691, and K706 was significantly higher than C1. (C) Secretion of GM-CSF did not show statistically significant differences among these glycolipids, suggesting that F-series analogs of C34 have similar activity as C34 to activate the myeloid cells. (D) No statistical significance was observed in the induction of IL-10 and IL-13 among these glycolipids, indicating that the F-series analogs of C34 showed comparable activity as C34 in inducing Th2 suppressive cytokines. One-way ANOVA was used for statistic analysis. *** P<0.001 compared with C1. #, P<0.05 compared to C34.

DETAILED DESCRIPTIONS

Figure 1:
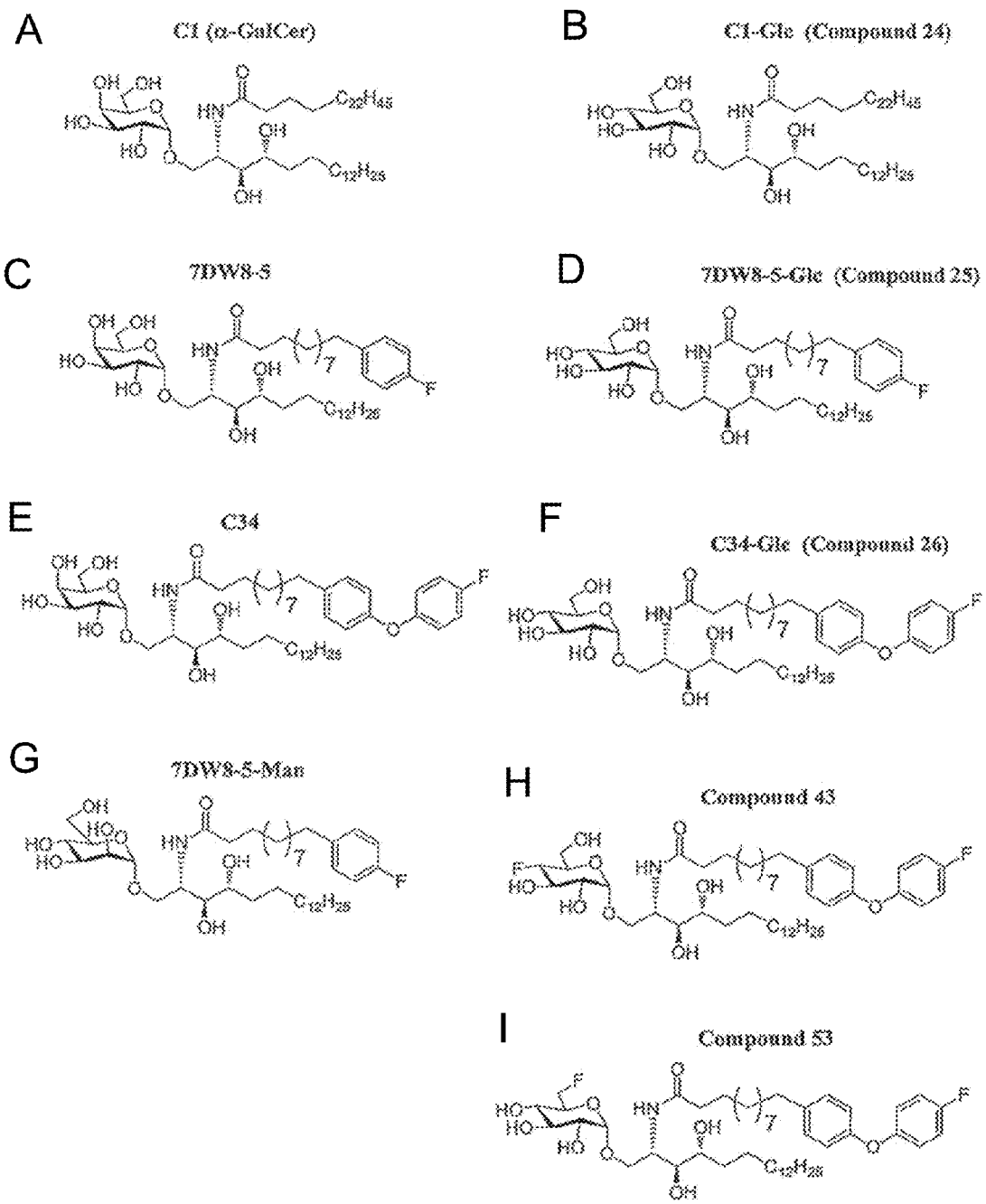
FIG. 1 shows: The structures of glycolipids with αGal or αGlc. Glycolipids C1 (α-GalCer) (1A), C1-Glc (Compound 24) (1B), 7DW8-5 (1C), 7DW8-5-Glc (Compound 25) (1D), C34 (1E), C34-Glc (Compound 26) (1F), 7DW8-5-Man (1G), Compound 43 (1H), and Compound 53 (1I) are shown. 7DW8-5-Man is the only compound with αMan. In certain aspects, embodiments of the present disclosure can include or exclude (e.g. proviso out) any members or exemplars listed herein.
Figure 1J:
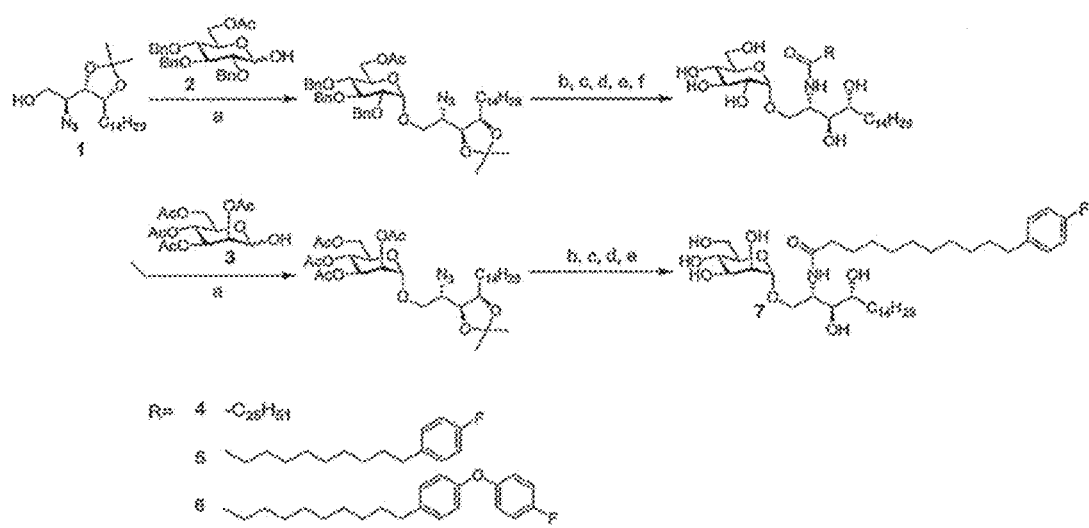
FIG. 1J. Exemplary representative synthetic scheme.

Natural killer T cells (NKTs) represent a subset of T lymphocytes with unique properties, including reactivity for natural or synthetic glycolipids presented by CD1d and expression of an invariant T cell antigen receptor (TCR) alpha chain. NKTs are different from functionally differentiated conventional αβ T cells in that they share properties of both natural killer cells and T cells are can rapidly produce both TH1-type and TH2-type responses upon stimulation with their ligands (innate immunity). The activation of NKTs paradoxically can lead either to suppression or stimulation of immune responses. For example, the production of TH1 cytokines is thought to promote cellular immunity with antitumor, antiviral/antibacterial, and adjuvant activities, whereas TH2 cytokine production is thought to subdue autoimmune diseases and promote antibody production. Because NKTs play a regulatory role in the immune system, they are attractive targets for immunotherapy.

Accordingly, methods and compositions comprising exemplary GSLs are provided herein.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986). In addition, the methods of making and using immune adjuvants are described in U.S. Pat. Nos. 7,488,491 and 7,928,077, the relevant disclosures of which are incorporated by reference herein.

As used herein, the term "lipid" refers to any fat-soluble (lipophilic) molecule that participates in cell signaling pathways. As used herein, the term "glycolipid" refers to a carbohydrate-attached lipid that serves as a marker for cellular recognition.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except proline.

As used herein, the term "glycoprotein" refers to a protein covalently modified with glycan(s). There are four types of glycoproteins: 1) N-linked glycoproteins, 2) O-linked glycoproteins (mucins), 3) glucosaminoglycans (GAGs, which are also called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "analog" refers to a compound, e.g., a drug, whose structure is related to that of another compound but whose chemical and biological properties may be quite different.

As used herein, the term "antigen" is defined as any substance capable of eliciting an immune response.

As used herein, the term "pathogen" is a biological agent that causes disease or illness to its host. The body contains many natural defenses against some of the common pathogens (such as *Pneumocystis*) in the form of the human immune system.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

Other Definitions

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. Unless otherwise indicated herein, either explicitly or by implication, if the term "treatment" (or "treating") is used without reference to possible prevention, it is intended that prevention be encompassed as well.

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-12, IL-18, IL-2, IFN-γ, TNF, IL-4, IL-10, IL-13, IL-21 and TGF-β. "Cytokine" is a generic term for a group of proteins released by one cell population which act on another cell population as intercellular mediators. Examples of such cytokines are lymphokines, monokines, and traditional polypeptide hormones. Included among the cytokines are interferons (IFN, notably IFN-γ), interleukins (IL, notably IL-1, IL-2, IL-4, IL-10, IL-12), colony stimulating factors (CSF), thrombopoietin (TPO), erythropoietin (EPO), leukemia inhibitory factor (LIF), kit-ligand, growth hormones (GH), insulin-like growth factors (IGF), parathyroid hormone, thyroxine, insulin, relaxin, follicle stimulating hormone (FSH), thyroid stimulating hormone (TSH), leutinizing hormone (LH), hematopoietic growth factor, hepatic growth factor, fibroblast growth factors (FGF), prolactin, placental lactogen, tumor necrosis factors (TNF), mullerian-inhibiting substance, mouse gonadotropin-associated peptide, inhibin, activin, vascular endothelial growth factor (VEGF), integrin, nerve growth factors (NGF), platelet growth factor, transforming growth factors (TGF), osteoinductive factors, etc.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C—C chemokines (RANTES, MCP-1, MIP-1α, and MIP-1β), C—X—C chemokines (IL-8), C chemokines (Lymphotactin), and CXXXC chemokines (Fractalkine).

As used herein, the term "epitope" is defined as the parts of an antigen molecule which contact the antigen binding site of an antibody or a T cell receptor.

To further explain differential binding avidities of the ternary complex in mice and men, computer modeling was performed based on the x-ray structures of murine and human CD1d-αGalCer-iNKT TCR complexes, respectively (PDB access code 3HUJ, 3QUX, 3QUY, 3QUZ, and 3HE6).[27-29] (27) Borg, N. A.; Wun, K. S.; Kjer-Nielsen, L.; Wilce, M. C.; Pellicci, D. G.; Koh, R.; Besra, G. S.; Bharadwaj, M.; Godfrey, D. I.; McCluskey, J.; Rossjohn, J. Nature 2007, 448, 44; (28) Pellicci, D. G.; Patel, O.; Kjer-Nielsen, L.; Pang, S. S.; Sullivan, L. C.; Kyparissoudis, K.; Brooks, A. G.; Reid, H. H.; Gras, S.; Lucet, I. S.; Koh, R.; Smyth, M. J.; Mallevaey, T.; Matsuda, J. L.; Gapin, L.; McCluskey, J.; Godfrey, D. I.; Rossjohn, J. Immunity 2009, 31, 47; and (29) Aspeslagh, S.; Li, Y.; Yu, E. D.; Pauwels, N.; Trappeniers, M.; Girardi, E.; Decruy, T.; Van Beneden, K.; Venken, K.; Drennan, M.; Leybaert, L.; Wang, J.; Franck, R. W.; Van Calenbergh, S.; Zajonc, D. M.; Elewaut, D. EMBO J. 2011, 30, 2294.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the terms "immunologic adjuvant" refers to a substance used in conjunction with an immunogen which enhances or modifies the immune response to the immunogen. Specifically, the terms "adjuvant" and "immunoadjuvant" are used interchangeably in the present invention and refer to a compound or mixture that may be non-immunogenic when administered to a host alone, but that augments the host's immune response to another antigen when administered conjointly with that antigen. Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more Type I cytokines.

Exemplary adjuvants of the invention comprise compounds which can be represented by a general Formula 1.

Preferably, the exemplary adjuvant of the invention is pharmaceutically acceptable for use in humans.

The adjuvant of the invention can be administered as part of a pharmaceutical or vaccine composition comprising an antigen or as a separate formulation, which is administered conjointly with a second composition containing an antigen. In any of these compositions glycosphingolipids (GSLs) can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutamine, [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

Within the meaning of the present invention, the term "conjoint administration or coadministration" is used to refer to administration of an immune adjuvant and an antigen simultaneously in one composition, or simultaneously in different compositions, or sequentially. For the sequential administration to be considered "conjoint", however, the antigen and adjuvant must be administered separated by a time interval that still permits the adjuvant to augment the immune response to the antigen. For example, when the antigen is a polypeptide, the antigen and adjuvant are administered on the same day, preferably within an hour of each other, and most preferably simultaneously. However, when nucleic acid is delivered to the subject and the polypeptide antigen is expressed in the subject's cells, the adjuvant is administered within 24 hours of nucleic acid administration, preferably within 6 hours.

As used herein, the term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system.

The term "antigen" refers to any agent (e.g., protein, peptide, polysaccharide, glycoprotein, glycolipid, nucleic acid, or combination thereof) that, when introduced into a host, animal or human, having an immune system (directly or upon expression as in, e.g., DNA vaccines), is recognized by the immune system of the host and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR). Within the meaning of the present invention, the antigens are preferably "surface antigens", i.e., expressed naturally on the surface of a pathogen, or the surface of an infected cell, or the surface of a tumor cell. A molecule that is antigenic need not be itself immunogenic, i.e., capable of eliciting an immune response without an adjuvant or carrier. As used herein, the term "antigen specific" refers to a property of a cell population such that supply of a particular antigen, or a fragment of the antigen, results in specific cell characteristic.

The term "epitope" or "antigenic determinant" refers to any portion of an antigen recognized either by B cells, or T cells, or both. Preferably, interaction of such epitope with an antigen recognition site of an immunoglobulin (antibody) or T cell antigen receptor (TCR) leads to the induction of antigen-specific immune response. T cells recognize proteins only when they have been cleaved into smaller peptides and are presented in a complex called the "major histocompatability complex (MHC)" located on another cell's surface. There are two classes of MHC complexes- class I and class II, and each class is made up of many different alleles. Class I MHC complexes are found on virtually every cell and present peptides from proteins produced inside the cell. Thus, class I MHC complexes are useful for killing cells infected by viruses or cells which have become cancerous as the result of expression of an oncogene. T cells which have a protein called CD8 on their surface, bind specifically to the MHC class I/peptide complexes via the T cell receptor (TCR). This leads to cytolytic effector activities. Class II MHC complexes are found only on antigen-presenting cells (APC) and are used to present peptides from circulating pathogens which have been endocytosed by APCs. T cells which have a protein called CD4 bind to the MHC class II/peptide complexes via TCR. This leads to the synthesis of specific cytokines which stimulate an immune response. To be effectively recognized by the immune system via MHC class I presentation, an antigenic polypeptide has to contain an epitope of at least about 8 to 10 amino acids, while to be effectively recognized by the immune system via MHC class II presentation, an antigenic polypeptide has to contain an epitope of at least about 13 to 25 amino acids. See, e.g., Fundamental Immunology, 3$^{rd}$ Edition, W. E. Paul ed., 1999, Lippincott-Raven Publ.

The term "species-specific" antigen refers to an antigen that is only present in or derived from a particular species. Thus, the term "malaria-derived" or "malaria-specific" antigen refers to a natural (e.g., irradiated sporozoites) or synthetic (e.g., chemically produced multiple antigen peptide [MAP] or recombinantly synthesized polypeptide) antigen comprising at least one epitope (B cell and/or T cell) derived from any one of the proteins constituting *plasmodium* (said *plasmodium* being without limitation *P. falciparum, P. vivax, P. malariae, P. ovale, P. reichenowi, P. knowlesi, P. cynomolgi, P. brasilianum, P. yoelii, P. berghei,* or *P. chabaudi*) and comprising at least 5-10 amino acid residues. A preferred plasmodial protein for antigen generation is circumsporozoite (CS) protein, however, other proteins can be also used, e.g., Thrombospondin Related Adhesion (Anonymous) protein (TRAP), also called Sporozoite Surface Protein 2 (SSP2), LSA I, hsp70, SALSA, STARP, Hep17, MSA, RAP-1, RAP-2, etc.

The term "vaccine" refers to a composition (e.g., protein or vector such as, e.g., an adenoviral vector, Sindbis virus vector, or pox virus vector) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs, e.g., to prevent organ rejection or suppress an autoimmune condition). Vaccine efficacy can be established in animal models.

The term "DNA vaccine" is an informal term of art, and is used herein to refer to a vaccine delivered by means of a recombinant vector. An alternative, and more descriptive term used herein is "vector vaccine" (since some potential vectors, such as retroviruses and lentiviruses are RNA viruses, and since in some instances non-viral RNA instead of DNA is delivered to cells through the vector). Generally, the vector is administered in vivo, but ex vivo transduction of appropriate antigen presenting cells, such as dendritic cells (DC), with administration of the transduced cells in vivo, is also contemplated.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. Preferably, the disease is either infectious disease (e.g., viral, bacterial, parasitic, or fungal) or malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.).

The term "protect" is used herein to mean prevent or treat, or both, as appropriate, development or continuance of a disease in a subject. Within the meaning of the present invention, the disease can be selected from the group consisting of infection (e.g., viral, bacterial, parasitic, or fungal) and/or malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.). For example, according to the present invention, a therapeutic administration of a tumor-specific antigen conjointly with an adjuvant comprising exemplary agents of Formula 1 can enhance an anti-tumor immune response leading to slow-down in tumor growth and metastasis or even tumor regression.

The term "protective immunity" refers to an immune response in a host animal (either active/acquired or passive/innate, or both) which leads to inactivation and/or reduction in the load of said antigen and to generation of long-lasting immunity (that is acquired, e.g., through production of antibodies), which prevents or delays the development of a disease upon repeated exposure to the same or a related antigen. A "protective immune response" comprises a humoral (antibody) immunity or cellular immunity, or both, effective to, e.g., eliminate or reduce the load of a pathogen or infected cell (or produce any other measurable alleviation of the infection), or to reduce a tumor burden in an immunized (vaccinated) subject. Within the meaning of the present invention, protective immunity may be partial.

Immune systems are classified into two general systems, the "innate" or "natural" immune system and the "acquired" or "adaptive" immune system. It is thought that the innate immune system initially keeps the infection under control, allowing time for the adaptive immune system to develop an appropriate response. Recent studies have suggested that the various components of the innate immune system trigger and augment the components of the adaptive immune system, including antigen-specific B and T lymphocytes (Fearon and Locksley, supra; Kos, 1998, Immunol. Res., 17: 303; Romagnani, 1992, Immunol. Today, 13: 379; Banchereau and Steinman, 1988, Nature, 392: 245).

The term "innate immunity" or "natural immunity" refers to innate immune responses that are not affected by prior contact with the antigen. Cells of the innate immune system, including macrophages and dendritic cells (DC), take up foreign antigens through pattern recognition receptors, combine peptide fragments of these antigens with MHC class I and class II molecules, and stimulate naive $CD8^+$ and $CD4^+$ T cells respectively (Banchereau and Steinman, supra; Holmskov et al., 1994, Immunol. Today, 15: 67; Ulevitch and Tobias, 1995, Annu. Rev. Immunol., 13: 437). Professional antigen-presenting cells (APC) communicate with these T cells leading to the differentiation of naive $CD4^+$ T cells into T-helper 1 (Th1) or T-helper 2 (Th2) lymphocytes that mediate cellular and humoral immunity, respectively (Trinchieri, 1995, Annu. Rev. Immunol., 13: 251; Howard and O'Garra, 1992, Immunol. Today, 13: 198; Abbas et al., 1996, Nature, 383: 787; Okamura et al., 1998, Adv. Immunol., 70: 281; Mosmann and Sad, 1996, Immunol. Today, 17: 138; O'Garra, 1998, Immunity, 8: 275).

The term "acquired immunity" or "adaptive immunity" is used herein to mean active or passive, humoral or cellular immunity that is established during the life of an animal, is specific for the inducing antigen, and is marked by an enhanced response on repeated encounters with said antigen. A key feature of the T lymphocytes of the adaptive immune system is their ability to detect minute concentrations of pathogen-derived peptides presented by MHC molecules on the cell surface.

As used herein, the term "augment the immune response" means enhancing or extending the duration of the immune response, or both. When referred to a property of an agent (e.g., adjuvant), the term "[able to] augment the immunogenicity" refers to the ability to enhance the immunogenicity of an antigen or the ability to extend the duration of the immune response to an antigen, or both.

The phrase "enhance immune response" within the meaning of the present invention refers to the property or process of increasing the scale and/or efficiency of immunoreactivity to a given antigen, said immunoreactivity being either humoral or cellular immunity, or both. An immune response is believed to be enhanced, if any measurable parameter of antigen-specific immunoreactivity (e.g., antibody titer, T cell production) is increased at least two-fold, preferably ten-fold, most preferably thirty-fold.

The term "therapeutically effective" applied to dose or amount refers to that quantity of a compound or pharmaceutical composition or vaccine that is sufficient to result in a desired activity upon administration to a mammal in need thereof. As used herein with respect to adjuvant—and antigen-containing compositions or vaccines, the term "therapeutically effective amount/dose" is used interchangeably with the term "immunogenically effective amount/dose" and refers to the amount/dose of a compound (e.g., an antigen and/or an adjuvant comprising glycosphingolipids (GSLs) or pharmaceutical composition or vaccine that is sufficient to produce an effective immune response upon administration to a mammal.

The phrase "pharmaceutically acceptable", as used in connection with compositions of the invention, refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical or vaccine compositions of the invention refers to a diluent, excipient, or vehicle with which a compound (e.g., an antigen and/or an adjuvant comprising glycosphingolipids (GSLs) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, $18^{th}$ Edition.

The term "native antibodies" or "immunoglobulins" refers to usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain (VL) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J Mol. Biol., 186: 651-663, 1985; Novotny and Haber, Proc. Natl. Acad. Sci. USA, 82: 4592-4596, 1985).

The term "antibody" or "Ab" is used in the broadest sense and specifically covers not only native antibodies but also single monoclonal antibodies (including agonist and antagonist antibodies), antibody compositions with polyepitopic specificity, as well as antibody fragments (e.g., Fab, F(ab')2, scFv and Fv), so long as they exhibit the desired biological activity.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids.

As used herein, the term "adaptive immune system" refers to highly specialized, systemic cells and processes that eliminate pathogenic challenges. The cells of the adaptive immune system are a type of leukocyte, called a lymphocyte. B cells and T cells are the major types of lymphocytes.

As used herein, the term "T cells" and "Ts" refer to a group of white blood cells known as lymphocytes, which play a central role in cell-mediated immunity. T cells can be distinguished from other lymphocyte types, such as B cells and NKs by the presence of a special receptor on their cell surface called the T cell receptor (TCR). Several different subsets of T cells have been described, each with a distinct function. Helper T ($T_H$) Cells are the "middlemen" of the adaptive immune system. Once activated, they divide rapidly and secrete small proteins called cytokines that regulate or "help" the immune response. Depending on the cytokine signals received, these cells differentiate into $T_H1$, $T_H2$, $T_H17$, or one of other subsets, which secrete different cytokines.

As used herein, the term "antigen-presenting cell" (APC) refers to a cell that displays foreign antigen complexed with major histocompatibility complex (MHC) on its surface. T-cells may recognize this complex using their TCR. APCs fall into two categories: professional or non-professional. Dendritic cells (DCs) fall under the professional category and are capable of presenting antigen to T cells, in the context of CD1. In an exemplary implementation, the DCs utilized in the methods of this disclosure may be of any of several DC subsets, which differentiate from, in one implementation, lymphoid or, in another implementation, myeloid bone marrow progenitors.

As used herein, the term "naïve cell" refers to an undifferentiated immune system cell, for example, a CD4 T-cell has not yet specialized to recognize a specific pathogen.

As used herein, the term "natural killer cells" and "NKs" refers to a class of lymphoid cells which are activated by interferons to contribute to innate host defense against viruses and other intracellular pathogens.

As used herein, the term "natural killer T cells" (NKTs) refers to a subset of T cells that share characteristics/receptors with both conventional Ts and NKs. Many of these cells recognize the non-polymorphic CD1d molecule, an antigen-presenting molecule that binds self- and foreign lipids and glycolipids. The TCR of the NKTs are able to recognize glycolipid antigens presented (chaperoned) by a CD1d molecule. A major response of NKTs is rapid secretion of cytokines, including IL-4, IFN-γ and IL-10 after stimulation and thus influence diverse immune responses and pathogenic processes. The NKTs may be a homogenous population or a heterogeneous population. In one exemplary implementation, the population may be "non-invariant NKTs", which may comprise human and mouse bone marrow and human liver T cell populations that are, for example, CD1d-reactive noninvariant T cells which express diverse TCRs, and which can also produce a large amount of IL-4 and IFN-γ. The best known subset of CD1d-dependent NKTs expresses an invariant TCR-alpha (TCR-α) chain. These are referred to as type I or invariant NKTs (iNKTs). These cells are conserved between humans (Vα24i NKTs) and mice (Vα14i NKTs) and are implicated in many immunological processes.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-12, IL-18, IL-2, IFN-γ, TNF, IL-4, IL-10, IL-13, IL-21 and TGF-0.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C—C chemokines (RANTES, MCP-1, MIP-1α, and MIP-1β), C—X—C chemokines (IL-8), C chemokines (Lymphotactin), and CXXXC chemokines (Fractalkine).

As used herein, the term "$T_H2$-type response" refers to a pattern of cytokine expression such that certain types of cytokines, interferons, chemokines are produced. Typical $T_H2$ cytokines include, but are not limited to, IL-4, IL-5, IL-6 and IL-10.

As used herein, the term "$T_H1$-type response" refers to a pattern of cytokine expression such that certain types of cytokines, interferons, chemokines are produced. Typical $T_H1$ cytokines include, but are not limited to, IL-2, IFN-γ, GM-CSF and TNF-β.

As used herein, the term "$T_H1$ biased" refers to an immunogenic response in which production of $T_H1$ cytokines and/or chemokines is increased to a greater extent than production of $T_H2$ cytokines and/or chemokines.

As used herein, the term "antimicrobial" refers to a substance that kills or inhibits the growth of microbes such as bacteria, fungi, or viruses.

As used herein, the term "toxoid" refers to a bacterial toxin whose toxicity has been weakened or suppressed either by chemical (formalin) or heat treatment, while other properties, typically immunogenicity, are maintained. Toxoids are used in vaccines as they induce an immune response to the original toxin or increase the response to another antigen. For example, the tetanus toxoid is derived from the tetanospasmin produced by *Clostridium tetani* and causing tetanus. The tetanus toxoid is used by many plasma centers in the United States for the development of plasma rich vaccines.

As used herein, the term "DNA vaccine" refers to a DNA construct that is introduced into cells and subsequently translated into specific antigenic proteins.

As used herein, the term "plasmid" refers to an extrachromosomal circular DNA capable of replicating, which may be used as a cloning vector.

As used herein, the term "microorganism" and "microbe" refers to an organism that is microscopic (too small to be seen by the naked human eye). Microorganisms are incredibly diverse and include, but are not limited to, bacteria and fungi.

As used herein, the term "adjuvant or immunologic adjuvant" refers to a substance used in conjunction with an immunogen which enhances or modifies the immune response to the immunogen. In an exemplary compound/analogs of the present disclosure are used as immunologic adjuvants to modify or augment the effects of a vaccine by stimulating the immune system of a patient who is administered the vaccine to respond to the vaccine more vigorously.

As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "anti-tumor immunotherapy active agent" refers to an exemplary compound/analog of the present disclosure that inhibits, reduces and/or eliminates tumors.

As used herein, the term "granulocyte-macrophage colony-stimulating factor" (GM-CSF) refers to a cytokine which serves as a colony-stimulating factor that stimulates production of white blood cells, particularly granulocytes (neutrophils, basophils, and eosinophils), macrophages, and cells in the bone marrow that are precursors of platelets.

As used herein, the term "antigen specific" refers to a property of a cell population such that supply of a particular antigen, or a fragment of the antigen, results in specific cell proliferation.

As used herein, the term "Flow cytometry" or "FACS" means a technique for examining the physical and chemical properties of particles or cells suspended in a stream of fluid, through optical and electronic detection devices.

Amino acid residues in peptides shall hereinafter be abbreviated as follows: P Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

Mammalian and mycobacterial lipids are known to be presented by human CD1a, CD1b, CD1c, and CD1d. α-Galactosyl ceramide, a lipid found in the marine sponge *Agelas mauritianus*, has been the most extensively studied ligand for CD1d. It has been shown that in vitro stimulation of mouse spleen cells by α-GalCer led to the proliferation of NKTs and production of both IFN-γ and IL-4, a $T_H1$-type and $T_H2$-type response, respectively. Murine studies have shown that cells can be rapidly activated by immature dendritic cells (iDCs) bearing α-GalCer and that the activated iNKTs can in turn induce full maturation of DCs.

Uses of Adjuvants Comprising Glycosphingolipids

In one aspect, the present invention provides a method for augmenting an immunogenicity of an antigen in a mammal, comprising administering said antigen conjointly with an adjuvant composition comprising a glycosphingolipids (GSLs) of Formula 1. According to the present invention, the use of glycosphingolipids (GSLs) as an adjuvant results in an enhancement and/or extension of the duration of the protective immunity induced by the antigen. For example, as disclosed herein, conjoint administration of glycosphingolipids (GSLs) with peptides corresponding to T cell or B cell epitopes of tumor or viral antigens, or DNA constructs expressing these antigens enhances antigen-specific immune responses.

The glycosphingolipids (GSLs)-containing adjuvant of the invention can be conjointly administered with any antigen, in particular, with antigens derived from infectious agents or tumors.

The immunostimulating effects both in mice and humans may depend on the expression of CD1d molecules and are mediated by NKT cells. Indeed, the instant invention demonstrates that adjuvant activity is attributed at least in part to its ability to enhance and/or extend NKT-mediated antigen-specific Th1-type T cell responses and CD8+ T cell (or Tc) responses.

From an immunotherapy view point, glycosphingolipids (GSLs) activation of the NKT cell system appears to have distinct advantages over the other mechanisms for the following reasons: (a) the level of cytotoxicity of activated NKT cells is very high and effective against a wide variety of tumor cells or infected cells; (b) the activation of NKT cells by glycosphingolipids (GSLs) is totally dependent on a CD1d molecule, which is monomorphic among individuals (Porcelli, Adv. Immunol., 59: 1-98, 1995), indicating that glycosphingolipids (GSLs)-containing adjuvants can be utilized by all patients, regardless of MHC haplotype; (c) antigen-presenting functions of DC and NKT activation of human patients can be evaluated before immunotherapy by the in vivo assays in mice using Vα14 NKT cell status as an indicator.

According to the present invention, an adjuvant comprising glycosphingolipids (GSLs) of Formula 1 and antigen can be administered either as two separate formulations or as part of the same composition. If administered separately, the adjuvant and antigen can be administered either sequentially or simultaneously. As disclosed herein, simultaneous administration of glycosphingolipids (GSLs) adjuvant with the antigen is preferred and generally allows to achieve the most efficient immunostimulation.

As the glycosphingolipids (GSLs) adjuvant of the invention exerts its immunostimulatory activity in combination with a plurality of different antigens, it is therefore useful for both preventive and therapeutic applications. Accordingly, in a further aspect, the invention provides a prophylactic and/or therapeutic method for treating a disease in a mammal comprising conjointly administering to said mammal an antigen and an adjuvant comprising a glycosphingolipids (GSLs) of Formula 1. This method can be useful, e.g., for protecting against and/or treating various infections as well as for treating various neoplastic diseases.

Immunogenicity enhancing methods of the invention can be used to combat infections, which include, but are not limited to, parasitic infections (such as those caused by plasmodial species, etc.), viral infections (such as those caused by influenza viruses, leukemia viruses, immunodeficiency viruses such as HIV, papilloma viruses, herpes virus, hepatitis viruses, measles virus, poxviruses, mumps virus, cytomegalovirus [CMV], Epstein-Barr virus, etc.), bacterial infections (such as those caused by *staphylococcus, streptococcus, pneumococcus, Neisseria gonorrhea, Borrelia, pseudomonas*, etc.), and fungal infections (such as those caused by *candida, trichophyton, ptyrosporum*, etc.).

Methods of the invention are also useful in treatment of various cancers, which include without limitation fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

As further disclosed herein, maximal efficiency of the immunogenicity enhancing methods of present invention is attained when an antigen and glycosphingolipids (GSLs) adjuvant are administered simultaneously.

The methods of the invention can be used in conjunction with other treatments. For example, an anti-cancer treatment using tumor-specific antigen and glycosphingolipids (GSLs)-containing adjuvant of the present invention can be used in combination with chemotherapy and/or radiotherapy and/or IL-12 treatment. Anti-viral vaccines comprising glycosphingolipids (GSLs)-containing adjuvant can be used in combination with IFN-α treatment.

Glycosphingolipids (GSLs)-Containing Pharmaceutical and Vaccine Compositions

In conjunction with the methods of the present invention, also provided are pharmaceutical and vaccine compositions comprising an immunogenically effective amount of an antigen and immunogenically effective amount of an adjuvant comprising glycosphingolipids (GSLs) as well as, optionally, an additional immunostimulant, carrier or excipient (preferably all pharmaceutically acceptable). Said antigen and adjuvant can be either formulated as a single composition or as two separate compositions, which can be administered simultaneously or sequentially.

Adjuvants of the invention comprise compounds which belong to the class of sphingoglycolipids, specifically glycosphingolipids (GSLs) which can be represented by a general Formula 1:

The antigens used in immunogenic (e.g., vaccine) compositions of the instant invention can be derived from a eukaryotic cell (e.g., tumor, parasite, fungus), bacterial cell, viral particle, or any portion thereof (e.g. attenuated viral particles or viral components). In the event the material to which the immunogenic response is to be directed is poorly antigenic, it may be additionally conjugated to a carrier molecule such as albumin or hapten, using standard covalent binding techniques, for example, with one of the several commercially available reagent kits.

Examples of preferred tumor antigens of the present invention include tumor-specific proteins such as ErbB receptors, Melan A [MART1], gp100, tyrosinase, TRP-1/gp75, and TRP-2 (in melanoma); MAGE-1 and MAGE-3 (in bladder, head and neck, and non-small cell carcinoma); HPV EG and E7 proteins (in cervical cancer); Mucin [MUC-1](in breast, pancreas, colon, and prostate cancers); prostate-specific antigen [PSA](in prostate cancer); carcinoembryonic antigen [CEA](in colon, breast, and gastrointestinal cancers) and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2. The foregoing lists of antigens are intended as exemplary, as the antigen of interest can be derived from any animal or human pathogen or tumor.

In a specific embodiment, the antigen of the invention may be presented by a recombinant virus expressing said antigen. Preferably, the virus is selected from the group consisting of a recombinant adenovirus, recombinant pox virus, and recombinant Sindbis virus.

In the disclosed compositions, both the antigen and the glycosphingolipids (GSLs) adjuvant are present in immunogenically effective amounts. For each specific antigen, the optimal immunogenically effective amount should be determined experimentally (taking into consideration specific characteristics of a given patient and/or type of treatment). Generally, this amount is in the range of 0.1 g-100 mg of an antigen per kg of the body weight. For the glycosphingolipids (GSLs) adjuvant of the present invention, the optimal immunogenically effective amount is preferably in the range of 10-100 g of the adjuvant per kg of the body weight.

The invention also provides a method for preparing a vaccine composition comprising at least one antigen and an adjuvant comprising glycosphingolipids (GSLs) of Formula 1, said method comprising admixing the adjuvant and the antigen, and optionally one or more physiologically acceptable carriers and/or excipients and/or auxiliary substances.

Formulations and Administration

The invention provides pharmaceutical and vaccine formulations containing therapeutics of the invention (an antigen and glycosphingolipids (GSLs) adjuvant either as a single composition or as two separate compositions which can be administered simultaneously or sequentially), which formulations are suitable for administration to elicit an antigen-specific protective immune response for the treatment and prevention of infectious or neoplastic diseases described above. Compositions of the present invention can be formulated in any conventional manner using one or more physiologically acceptable carriers or excipients. Thus, an antigen and/or an adjuvant comprising a glycosphingolipids (GSLs) of Formula 1, can be formulated for administration by transdermal delivery, or by transmucosal administration, including but not limited to, oral, buccal, intranasal, opthalmic, vaginal, rectal, intracerebral, intradermal, intramuscular, intraperitoneal, intravenous, subcutaneous routes, via scarification (scratching through the top layers of skin, e.g., using a bifurcated needle), by inhalation (pulmonary) or insufflation (either through the mouth or the nose), or by administration to antigen presenting cells ex vivo followed by administration of the cells to the subject, or by any other standard route of immunization.

Preferably, the immunogenic formulations of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

The present invention also contemplates various mucosal vaccination strategies. While the mucosa can be targeted by local delivery of a vaccine, various strategies have been employed to deliver immunogenic compositions to the mucosa. For example, in a specific embodiment, the immunogenic polypeptide or vector vaccine can be administered in an admixture with, or as a conjugate or chimeric fusion protein with, cholera toxin, such as cholera toxin B or a cholera toxin A/B chimera (see, e.g., Hajishengallis, J Immunol., 154: 4322-32, 1995; Jobling and Holmes, Infect Immun., 60: 4915-24, 1992; Lebens and Holmgren, Dev Biol Stand 82:215-27, 1994). In another embodiment, an admixture with heat labile enterotoxin (LT) can be prepared for mucosal vaccination. Other mucosal immunization strategies include encapsulating the immunogen in microcapsules (see, e.g., U.S. Pat. Nos. 5,075,109; 5,820,883, and 5,853,763) and using an immunopotentiating membranous carrier (see, e.g., PCT Application No. WO 98/0558). Immunogenicity of orally administered immunogens can be enhanced by using red blood cells (rbc) or rbc ghosts (see, e.g., U.S. Pat. No. 5,643,577), or by using blue tongue antigen (see, e.g., U.S. Pat. No. 5,690,938). Systemic administration of a targeted immunogen can also produce mucosal immunization (see, U.S. Pat. No. 5,518,725). Various strategies can be also used to deliver genes for expression in mucosal tissues, such as using chimeric rhinoviruses (see, e.g., U.S. Pat. No. 5,714,374), adenoviruses, vaccinia viruses, or specific targeting of a nucleic acid (see, e.g., PCT Application No. WO 97/05267).

For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly-glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Compositions of the present invention can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

As disclosed herein, an antigen and/or glycosphingolipids (GSLs) adjuvant can be mixed with excipients which are pharmaceutically acceptable and compatible with the active ingredients. Suitable excipients are, for example, water, saline, buffered saline, dextrose, glycerol, ethanol, sterile isotonic aqueous buffer or the like and combinations thereof. In addition, if desired, the preparations may also include minor amounts of auxiliary substances such as wetting or emulsifying agents, pH buffering agents, and/or immune stimulators (e.g., adjuvants in addition to glycosphingolipids (GSLs) that enhance the effectiveness of the pharmaceutical composition or vaccine. Non-limiting examples of additional immune stimulators which may enhance the effectiveness of the compositions of the present invention include immunostimulatory, immunopotentiating, or pro-inflammatory cytokines, lymphokines, or chemokines or nucleic acids encoding them (specific examples include interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand, see additional examples of immunostimulatory cytokines in the Section entitled "Definitions"). These additional immunostimulatory molecules can be delivered systemically or locally as proteins or by expression of a vector that codes for expression of the molecule. The techniques described above for delivery of the antigen and glycosphingolipids (GSLs) adjuvant can also be employed for the delivery of additional immunostimulatory molecules.

The invention also provides a pharmaceutical pack or kit comprising one or more containers filled with one or more of the ingredients of the immunogenic formulations of the invention. In a related embodiment, the present invention provides a kit for the preparation of a pharmaceutical or vaccine composition comprising at least one antigen and a glycosphingolipids (GSLs)-containing adjuvant, said kit comprising the antigen in a first container, and the adjuvant in a second container, and optionally instructions for admixing the antigen and the adjuvant and/or for administration of the composition. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient (i.e., an antigen and/or a glycosphingolipids (GSLs)-containing adjuvant). The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

Effective Dose and Safety Evaluations

According to the methods of the present invention, the pharmaceutical and vaccine compositions described herein are administered to a patient at immunogenically effective doses, preferably, with minimal toxicity. As recited in the Section entitled "Definitions", "immunogenically effective dose" or "therapeutically effective dose" of disclosed formulations refers to that amount of an antigen and/or glycosphingolipids (GSLs) adjuvant that is sufficient to produce an effective immune response in the treated subject and therefore sufficient to result in a healthful benefit to said subject.

Following methodologies which are well-established in the art (see, e.g., reports on evaluation of several vaccine formulations containing novel adjuvants in a collaborative effort between the Center for Biological Evaluation and Food and Drug Administration and the National Institute of Allergy and Infectious Diseases [Goldenthal et al., National Cooperative Vaccine Development Working Group. AIDS Res. Hum. Retroviruses, 1993, 9:545-9]), effective doses and toxicity of the compounds and compositions of the instant invention are first determined in preclinical studies using small animal models (e.g., mice) in which both the antigen and glycosphingolipids (GSLs)-containing adjuvant has been found to be immunogenic and that can be reproducibly immunized by the same route proposed for the human clinical trials. Specifically, for any pharmaceutical composition or vaccine used in the methods of the invention, the therapeutically effective dose can be estimated initially from animal models to achieve a circulating plasma concentration range that includes the $IC_{50}$ (i.e., the concentration of the test compound which achieves a half-maximal inhibition of symptoms). Dose-response curves derived from animal systems are then used to determine testing doses for the initial clinical studies in humans. In safety determinations for each composition, the dose and frequency of immunization should meet or exceed those anticipated for use in the clinical trial.

As disclosed herein, the dose of glycosphingolipids (GSLs) with α-glucose (α-Glc), antigen(s) and other components in the compositions of the present invention is determined to ensure that the dose administered continuously or intermittently will not exceed a certain amount in consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices and should be decided according to the judgment of the practitioner and each patient's circumstances according to standard clinical techniques. In this connection, the dose of an antigen is generally in the range of 0.1 g-100 mg per kg of the body weight, and the dose of the glycosphingolipids (GSLs) adjuvant required for augmenting the immune response to the antigen is generally in the range of 10-100 g per kg of the body weight.

Toxicity and therapeutic efficacy of glycosphingolipids (GSLs)-containing immunogenic compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects. As disclosed herein (see also Background Section and Examples), the glycosphingolipids (GSLs) adjuvant of the invention is not only highly immunostimulating at relatively low doses (e.g., 10-100 g of the adjuvant per kg of the body weight) but also possesses low toxicity and does not produce significant side effects.

As specified above, the data obtained from the animal studies can be used in formulating a range of dosage for use in humans. The therapeutically effective dosage of glycosphingolipids (GSLs)-containing compositions of the present invention in humans lies preferably within a range of circulating concentrations that include the $ED_{50}$ with little or no toxicity. The dosage can vary within this range depending upon the dosage form employed and the route of administration utilized. Ideally, a single dose should be used.

Definitions Directed to Chemical Structures

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including for example, chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, NY, 1962); and Wilen, Tables of Resolving Agents and Optical Resolutions p. 268 (E. L. Eliel, Ed., Univ. of Notre Dame Press, Notre Dame, Ind. 1972). The instant disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), 39ydroxy[2.2.1]heptanyl ($C_7$), 39ydroxy[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

Alkyl, alkenyl, alkynyl, carbocyclyl, heterocyclyl, aryl, and heteroaryl groups, as defined herein, which are divalent bridging groups are further referred to using the suffix-ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3{}^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)

$-OR^{aa}$, $-OC(=NR^{bb})R^{aa}$, $-OC(=NR^{bb})OR^{aa}$, $-C(=NR^{bb})N(R^{bb})_2$, $-OC(=NR^{bb})N(R^{bb})_2$, $-NR^{bb}C(=NR^{bb})N(R^{bb})_2$, $-C(=O)NR^{bb}SO_2R^{aa}$, $-NR^{bb}SO_2R^{aa}$, $-SO_2N(R^{bb})_2$, $-SO_2R^{aa}$, $-SO_2OR^{aa}$, $-OSO_2R^{aa}$, $-S(=O)R^{aa}$, $-OS(=O)R^{aa}$, $-Si(R^{aa})_3$, $-Osi(R^{aa})_3$, $-C(=S)N(R^{bb})_2$, $-C(=O)SR^{aa}$, $-C(=S)SR^{aa}$, $-SC(=S)SR^{aa}$, $-SC(=O)SR^{aa}$, $-OC(=O)SR^{aa}$, $-SC(=O)OR^{aa}$, $-SC(=O)R^{aa}$, $-P(=O)_2R^{aa}$, $-OP(=O)_2R^{aa}$, $-P(=O)(R^{aa})_2$, $-OP(=O)(R^{aa})_2$, $-OP(=O)(OR^{cc})_2$, $-P(=O)_2N(R^{bb})_2$, $-OP(=O)_2N(R^{bb})_2$, $-P(=O)(NR^{bb})_2$, $-OP(=O)(NR^{bb})_2$, $-NR^{bb}P(=O)(OR^{cc})_2$, $-NR^{bb}P(=O)(NR^{bb})_2$, $-P(R^{cc})_2$, $-P(R^{cc})_3$, $-OP(R^{cc})_2$, $-OP(R^{cc})_3$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two hydrogens on a carbon atom are replaced with the group =O, =S, =NN($R^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{bb}$ is, independently, selected from hydrogen, $-OH$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R)_2$, $-NR^{ff}C(=O)R^{ee}$, $NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-Osi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two $R^{dd}$ substituents can be joined to form =O or =S; each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl)$_2$, $-N(C_{1-6}$ alkyl)$_2$, alkyl)$_3^+X^-$, $-NH(C_{1-6}$ alkyl)$_2^+X^-$, $-NH_2(C_{1-6}$ alkyl)$^+X^-$, $-NH_3^+X^-$, $-N(OC_{1-6}$ alkyl)($C_{1-6}$ alkyl), $-N(OH)(C_{1-6}$ alkyl), $-NH(OH)$, $-SH$, $-SC_{1-6}$ alkyl, $-SS(C_{1-6}$ alkyl), $-C(=O)(C_{1-6}$ alkyl), $-CO_2H$, $-CO_2(C_{1-6}$ alkyl), $-OC(=O)(C_{1-6}$ alkyl), $-OCO_2(C_{1-6}$ alkyl), $-C(=O)NH_2$, $-C(=O)N(C_{1-6}$ alkyl)$_2$, $-OC(=O)NH(C_{1-6}$ alkyl), $-NHC(=O)(C_{1-6}$ alkyl), $-N(C_{1-6}$ alkyl)C(=O)($C_{1-6}$ alkyl), $-NHCO_2(C_{1-6}$ alkyl), $-NHC(=O)N(C_{1-6}$ alkyl)$_2$, $-NHC(=O)NH(C_{1-6}$ alkyl), $-NHC(=O)NH_2$, $-C(=NH)O(C_{1-6}$ alkyl), $-OC(=NH)(C_{1-6}$ alkyl), $-OC(=NH)OC_{1-6}$ alkyl, $-C(=NH)N(C_{1-6}$ alkyl)$_2$, $-C(=NH)NH(C_{1-6}$ alkyl), $-C(=NH)NH_2$, $-OC(=NH)N(C_{1-6}$ alkyl)$_2$, $-OC(NH)NH(C_{1-6}$ alkyl), $-OC(NH)NH_2$, $-NHC(NH)N(C_{1-6}$ alkyl)$_2$, $-NHC(=NH)NH_2$, $-NHSO_2(C_{1-6}$ alkyl), $-SO_2N(C_{1-6}$ alkyl)$_2$, $-SO_2NH(C_{1-6}$ alkyl), $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl)$_3$, $-Osi(C_{1-6}$ alkyl)$_3$-$C(=S)N(C_{1-6}$ alkyl)$_2$, $C(=S)NH(C_{1-6}$ alkyl), $C(=S)NH_2$, $-C(=O)S(C_{1-6}$ alkyl), $-C(=S)SC_{1-6}$ alkyl, $-SC(=S)SC_{1-6}$ alkyl, $-P(=O)_2(C_{1-6}$ alkyl), $-P(=O)(C_{1-6}$ alkyl)$_2$, $-OP(=O)(C_{1-6}$ alkyl)$_2$, $-OP(=O)(OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two $R^{gg}$ substituents can be joined to form =O or =S; wherein $X^-$ is a counterion.

"Halo" or "halogen" refers to fluorine (fluoro, $-F$), chlorine (chloro, $-Cl$), bromine (bromo, $-Br$), or iodine (iodo, $-I$).

"Acyl" as used herein refers to a moiety selected from the group consisting of $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2-$, $-C(=O)NR^{bb}SO_2R^{aa}$, $-C(=S)N(R^{bb})_2$, $-C(=O)SR^{aa}$, and $-C(=S)SR^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, $-OH$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-Adamantyl)-1-methylethyl (Adpoc), 1, 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N, N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-hydroxyl, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)

phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $R^{aa}$, $N(R^{bb})_2$, $C(=O)SR^{aa}$, $C(=O)R^{aa}$, $CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

Exemplary α-GalCer analogs (GSLs with α-Glc) are used as immunologic adjuvants to accelerate, enhance, prolong, and/or modify or augment the effects of a vaccine by stimulating the immune system of a patient who has been vaccinated. In an exemplary implementation, the analog C34 is used as an adjuvant. As used herein, the term "alum adjuvant" refers to an aluminum salt with immune adjuvant activity, such as, for example, aluminum phosphate and aluminum hydroxide. These exemplary agents can adsorb and precipitates protein antigens in solution; the resulting precipitate improves vaccine immunogenicity by facilitating the slow release of antigen from the vaccine depot formed at the site of inoculation. Additionally, adjuvants contemplated herein can also include suitable organic adjuvants and suitable virosomes. In certain embodiments, exemplary organic adjuvants can include oil-based adjuvants such as squalene, MF59, QS-21 and AS03.

As used herein, the term "anti-tumor immunotherapy active agent" refers to antibody generated by a vaccine of the present disclosure that inhibits, reduces and/or eliminates tumors, either alone and/or in combination with other synergistic agents.

Glycosphingolipids (GSLs) bearing α-galactosyl group (αGal) and phenyl ring on the acyl chain were known to be more potent than α-galactosyl ceramide (αGalCer) to stimulate both murine and human invariant NKT (iNKT) cells. Their activities in mice and humans correlated with the binding avidities of the ternary interaction between iNKT TCR and CD1d-GSL complex.

The instant disclosure relates to the unexpected discovery that GSLs with glucose (αGlc) are stronger than those with αGal for humans but weaker for mice in the induction of cytokines/chemokines and expansion/activation of immune cells. GSLs with glucose (αGlc) and F derivatives of αGlc, and their impact on their immunostimulatory activities in humans are disclosed herein. The immune-stimulatory potencies associated with the strength of ternary interaction for each species are described herein. It is the iNKT TCR rather than CD1d that dictates the species-specific responses, as demonstrated by mCD1d vs. hCD1d swapping assay disclosed herein. Glycosphingolipids (GSLs) with αGlc bear stronger ternary interaction and triggered more Th1-biased immunity as compared to GSLs with αGal in humans. GSLs with αGlc are less stimulatory than GSLs with αGal in mice. The species-specific responses are attributed to the differential binding avidities of ternary complexes between species, reflecting the differences between murine and human iNKT TCR as supported by mCD1d vs. hCD1d swapping assay as described herein.

These novel findings indicate differences in species and provide novel designs of GSL with modifications on the glycosyl group that are more effective for human therapy.

Compounds

The instant disclosure relates to exemplary immune adjuvant compounds of Formula (I):

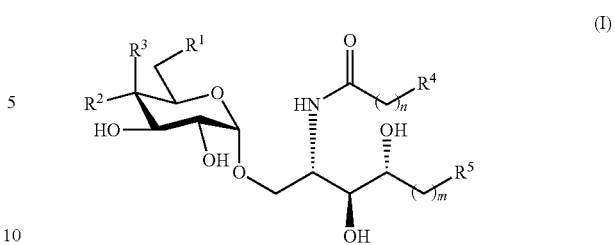

or pharmaceutically acceptable salt thereof; wherein $R^1$ is —OH or halogen; $R^2$ is hydrogen or halogen; $R^3$ is OH, hydrogen or halogen; $R^4$ and $R^5$ are each independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkoxy, an optionally substituted amino group, or optionally substituted acyl; n is an integer of 1 to 15, inclusive; and m is an integer of 1 to 20, inclusive.

In some embodiments of compound (I), $R^2$ is hydrogen. In some embodiments of compound (I), $R^2$ is halogen. In some embodiments of compound (I), $R^2$ is F. In some embodiments of compound (I), $R^2$ is Cl. In some embodiments of compound (I), $R^2$ is Br. In some embodiments of compound (I), $R^2$ is I.

In some embodiments of compound (I), $R^1$ is —OH. In some embodiments of compound (I), $R^1$ is halogen. In some embodiments of compound (I), $R^1$ is F. In some embodiments of compound (I), $R^1$ is Cl. In some embodiments of compound (I), $R^1$ is Br. In some embodiments of compound (I), $R^1$ is I.

In some embodiments of compound (I), $R^3$ is OH. In some embodiments of compound (I), $R^3$ is hydrogen. In some embodiments of compound (I), $R^3$ is halogen. In some embodiments of compound (I), $R^3$ is F. In some embodiments of compound (I), $R^3$ is Cl. In some embodiments of compound (I), $R^3$ is Br. In some embodiments of compound (I), $R^3$ is I.

In some embodiments of compound (I), $R^1$ is —OH; $R^2$ is hydrogen or halogen; and $R^3$ is OH, hydrogen or halogen. In some embodiments of compound (I), $R^1$ is —OH; $R^2$ is hydrogen; and $R^3$ is OH, hydrogen or halogen. In some embodiments of compound (I), $R^1$ is —OH; $R^2$ is hydrogen; and $R^3$ is OH, hydrogen or halogen. In some embodiments of compound (I), $R^1$ is —OH; $R^2$ is halogen; and $R^3$ is OH, hydrogen or halogen. In some embodiments of compound (I), $R^1$ is halogen; $R^2$ is hydrogen or halogen; and $R^3$ is OH, hydrogen or halogen. In some embodiments of compound (I), $R^1$ is halogen; $R^2$ is hydrogen and $R^3$ is OH, hydrogen or halogen. In some embodiments of compound (I), $R^1$ is halogen; $R^2$ is halogen; and $R^3$ is OH, hydrogen or halogen. In some embodiments of compound (I), $R^1$ is halogen; $R^2$ is halogen; and $R^3$ is hydrogen or halogen.

In some embodiments of compound (I), $R^4$ is phenyl. In some embodiments, $R^4$ is optionally substituted phenyl of Formula (II):

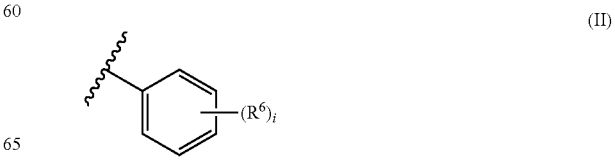

wherein i=0, 1, 2, 3, 4, or 5; each instance of $R^6$ is independently selected from the group consisting of hydrogen, halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl. In certain embodiments, i is 0. In certain embodiments, i is 1. In certain embodiments, i is 2. In certain embodiments, i is 3. In certain embodiments, i is 4. In certain embodiments, i is 5. In certain embodiments, i is 1 and $R^6$ is halogen. In certain embodiments, i is 1 and $R^4$ is one of the formulae:

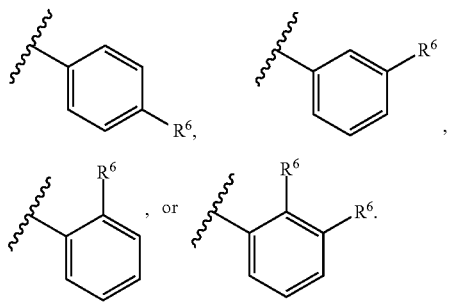

In certain embodiments, i is 2 and $R^4$ is one of the formulae:

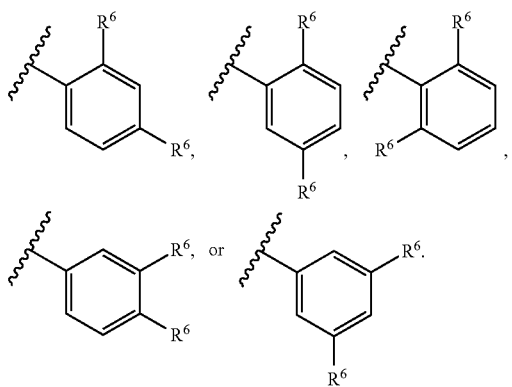

In certain embodiments, i is 3 and $R^4$ is one of the formulae:

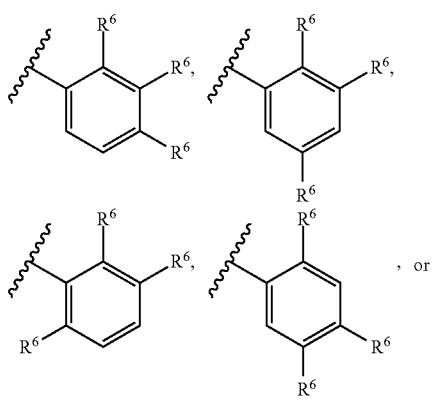

-continued

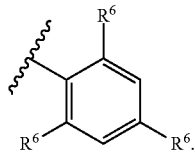

In certain embodiments, i is 4 and $R^4$ is one of the formulae:

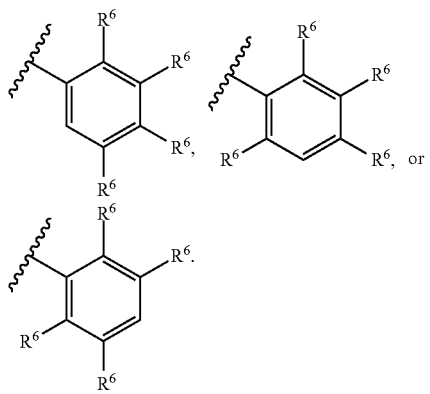

In certain embodiments, i is 5 and $R^4$ is of the formula

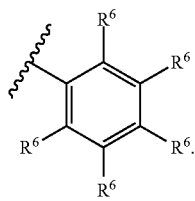

In some embodiments of compound (I), $R^6$ is halogen. In some embodiments of compound (I), $R^6$ is F. In some embodiments of compound (I), $R^6$ is Cl. In some embodiments of compound (I), $R^6$ is Br. In some embodiments of compound (I), $R^6$ is I.

In some embodiments of compound (I), $R^4$ is optionally substituted aryl. In some embodiments of compound (I), $R^4$ is of Formula (III):

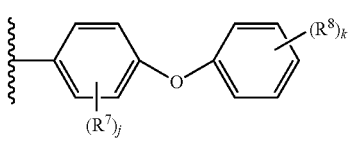

wherein j is 0, 1, 2, 3, or 4; k is 0, 1, 2, 3, 4, or 5; each instance of $R^7$ and $R^8$ is independently selected from the group consisting of hydrogen, halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl. In certain embodiments, k is 0. In certain embodiments, k is 1. In certain embodiments, k is 2. In certain embodiments, k is 3. In certain embodiments, k is 4. In certain embodiments, k is 5. In certain embodiments, k is 1 and $R^8$ is halogen. In certain embodiments, k is 1 and $R^4$ is one of the formulae:

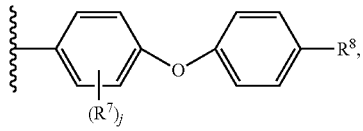

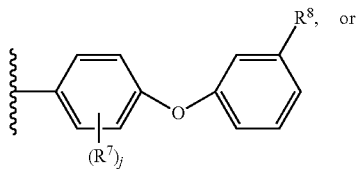

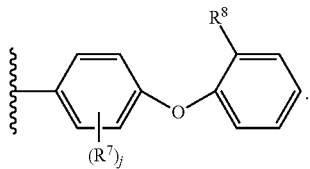

In certain embodiments, k is 2 and $R^4$ is one of the formulae:

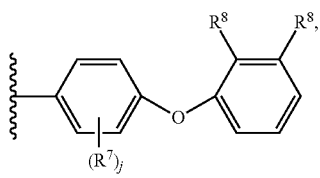

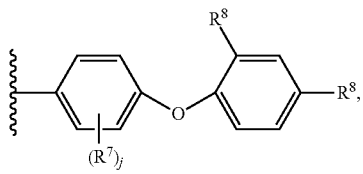

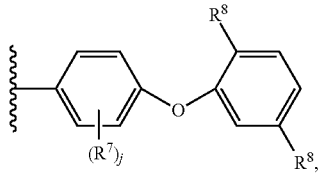

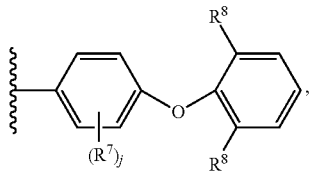

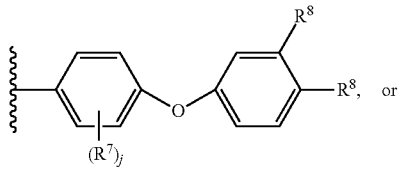

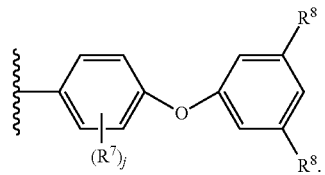

In certain embodiments, k is 3 and $R^4$ is one of the formulae:

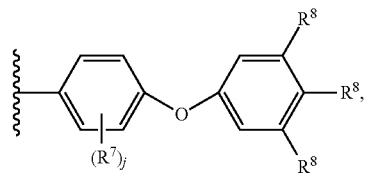

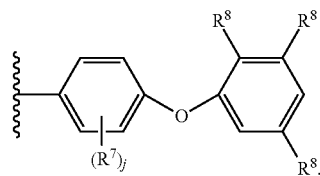

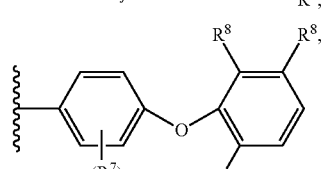

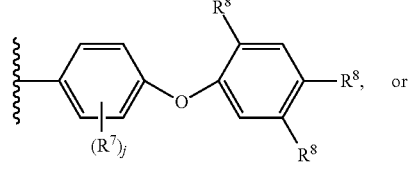

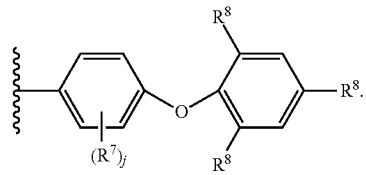

In certain embodiments, k is 4 and $R^4$ is one of the formulae:

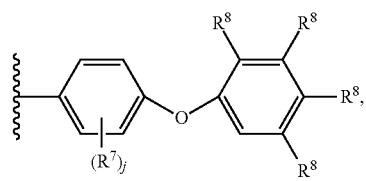

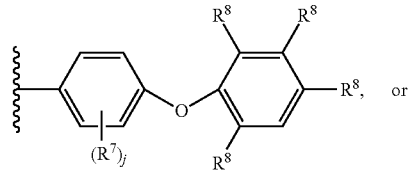

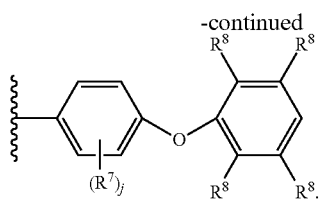

In certain embodiments, k is 5 and $R^4$ is of the formula

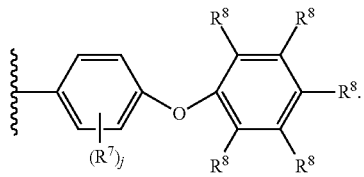

In some embodiments of compound (I), n is an integer of 1 to 15, inclusive. In some embodiments of compound (I), n is an integer of 5 to 15, inclusive. In some embodiments of compound (I), n is an integer of 10 to 15, inclusive. In some embodiments of compound (I), n is 10. In some embodiments of compound (I), n is 11. In some embodiments of compound (I), n is 12. In some embodiments of compound (I), n is 13. In some embodiments of compound (I), n is 14. In some embodiments of compound (I), n is 15.

In some embodiments of compound (I), m is an integer of 1 to 20, inclusive. In some embodiments of compound (I), m is an integer of 5 to 20, inclusive. In some embodiments of compound (I), m is an integer of 5 to 15, inclusive. In some embodiments of compound (I), m is an integer of 10 to 15, inclusive. In some embodiments of compound (I), m is 10. In some embodiments of compound (I), m is 11. In some embodiments of compound (I), m is 12. In some embodiments of compound (I), m is 13. In some embodiments of compound (I), m is 14. In some embodiments of compound (I), m is 15.

The In some embodiments of compound (I), $R^7$ is hydrogen; $R^8$ is F; and k is 1, 2 or 3. In some embodiments of compound (I), $R^7$ is F; $R^8$ is a hydrogen; and j is 1, 2 or 3. In some embodiments of compound (I), $R^7$ and $R^8$ both are F; k is 1, 2 or 3; and j is 1, 2 or 3.

In some embodiments of formula (I), the provided compound may include or exclude (e.g proviso out) one of the following compounds:

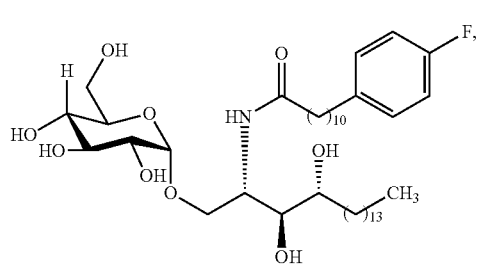

II-1

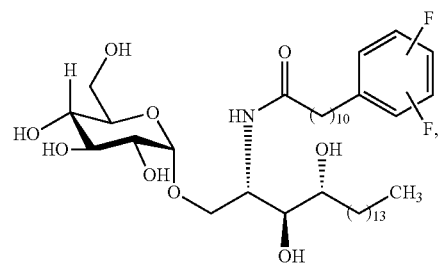

II-2

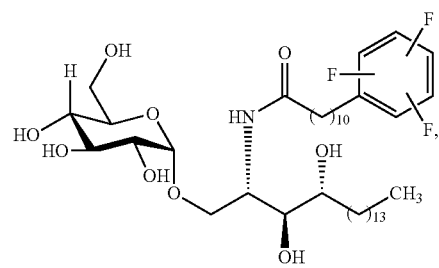

II-3

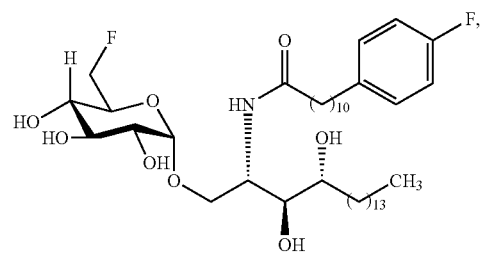

II-4

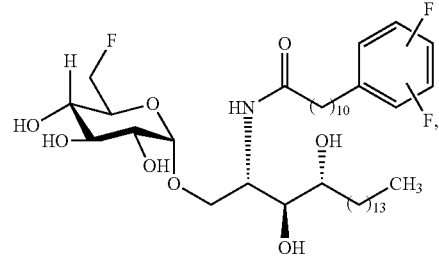

II-5

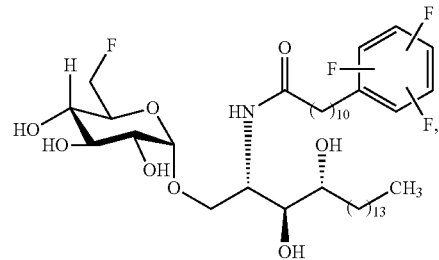

II-6

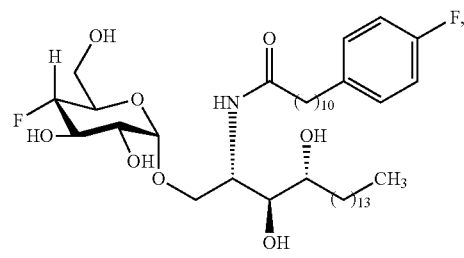

II-7

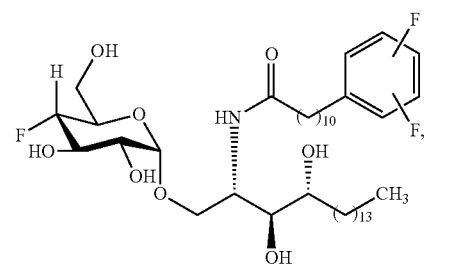
II-8
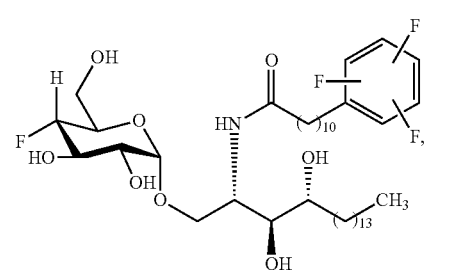
II-9
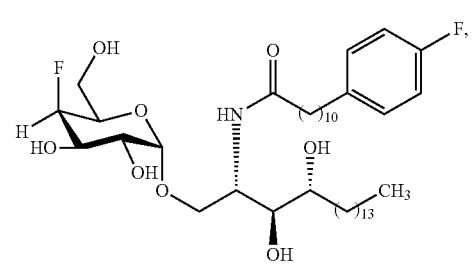
II-10
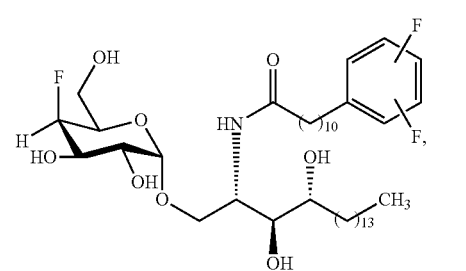
II-11
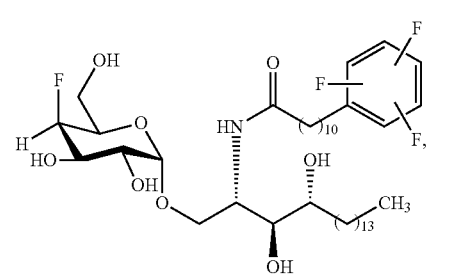
II-12
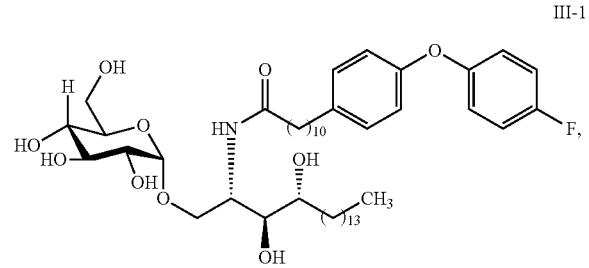
III-1
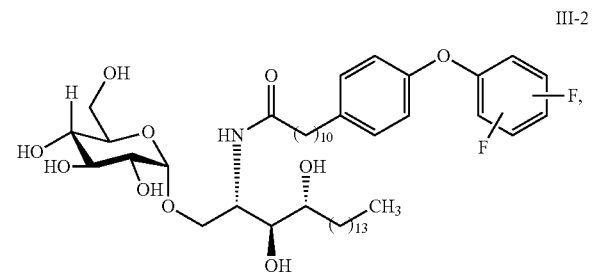
III-2
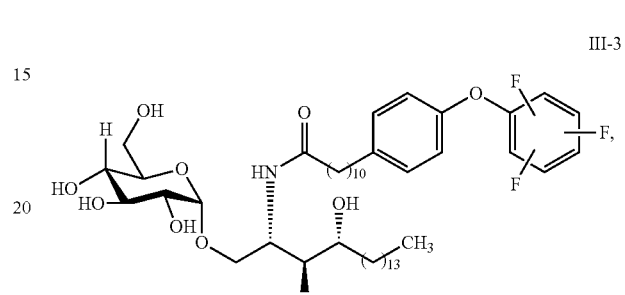
III-3
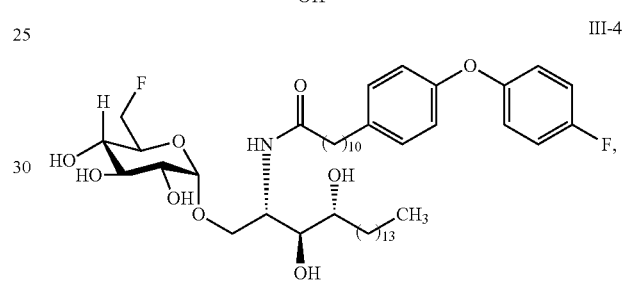
III-4
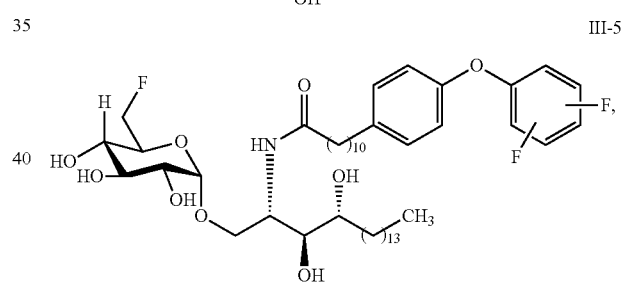
III-5
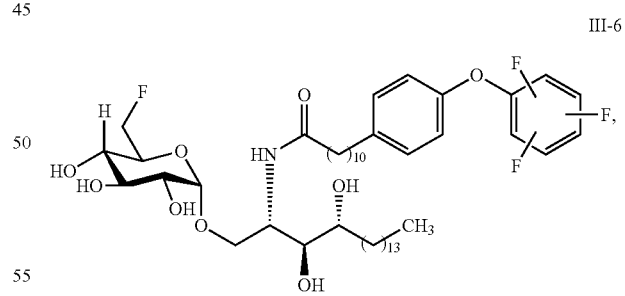
III-6
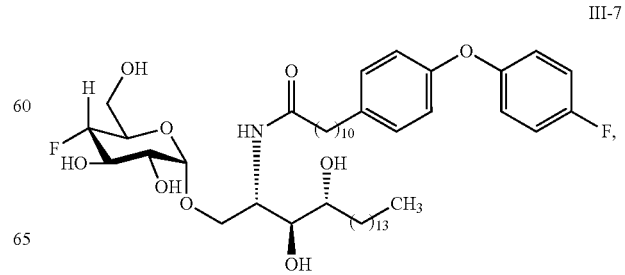
III-7

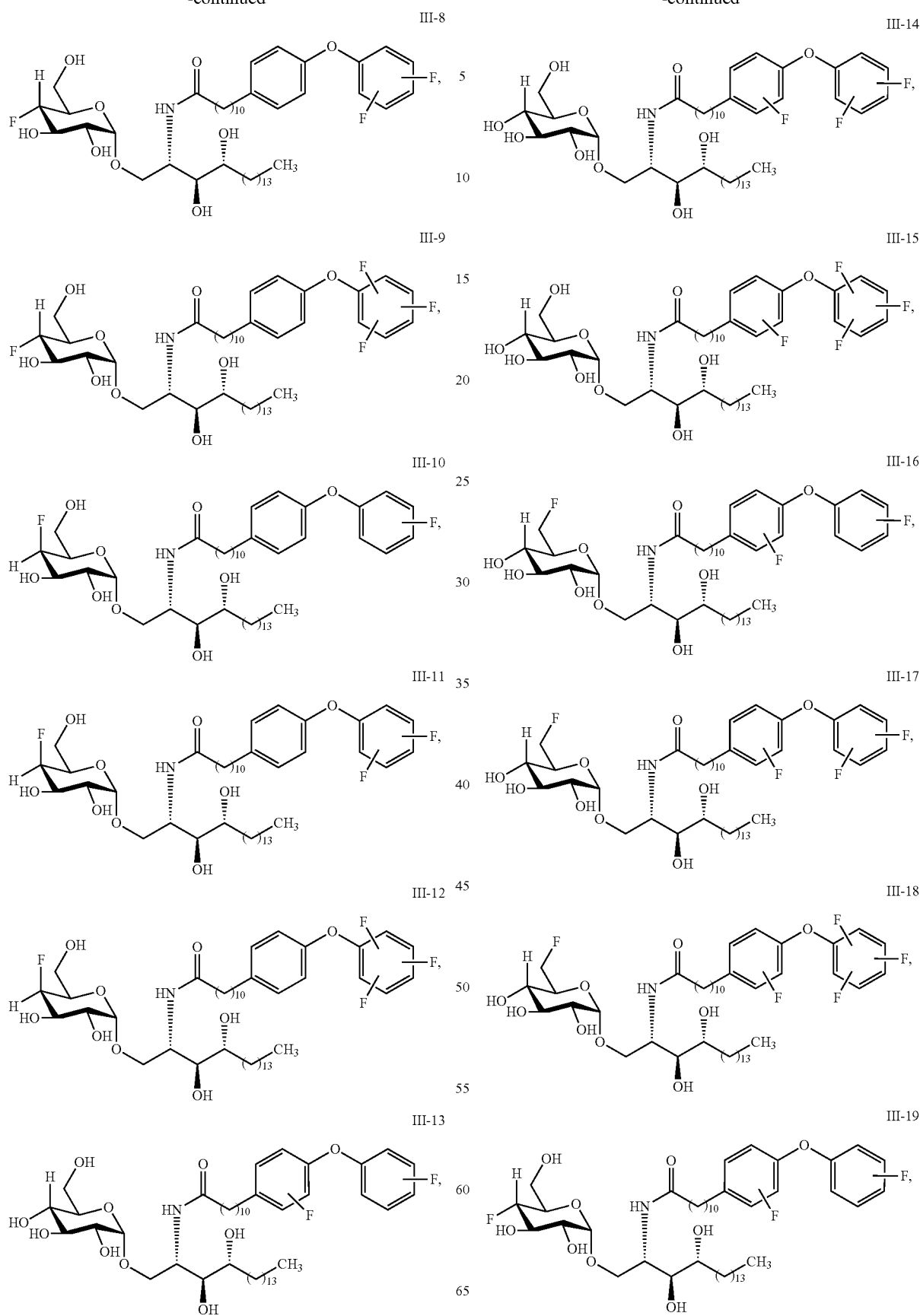

-continued

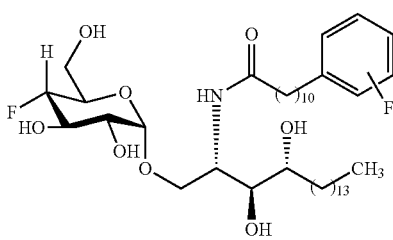
III-20

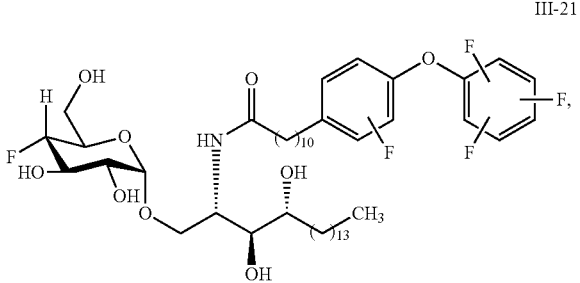
III-21

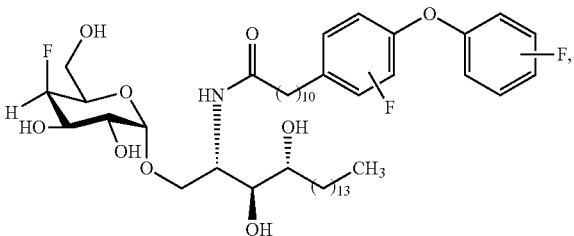
III-22

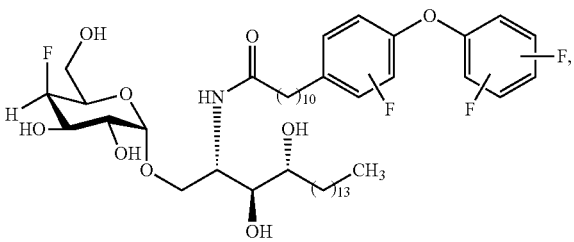
III-23

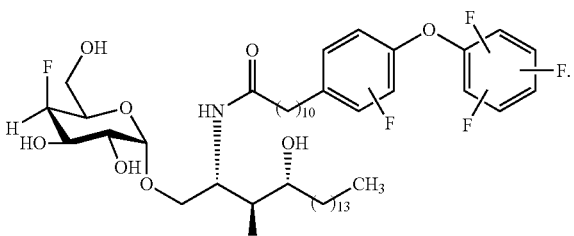
III-24

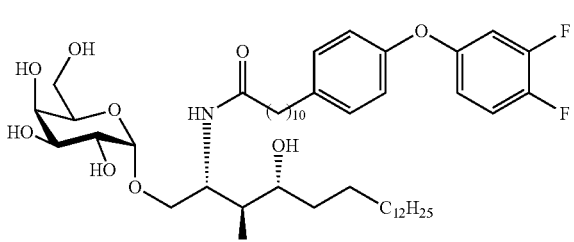
K705

-continued

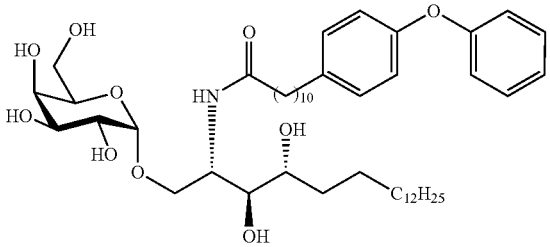
K691

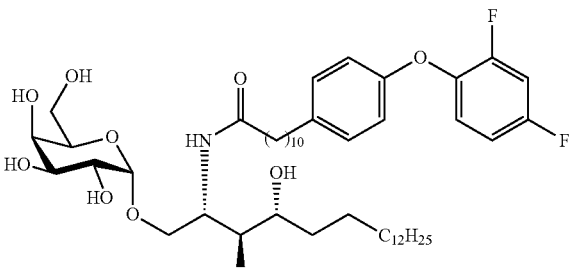
K706

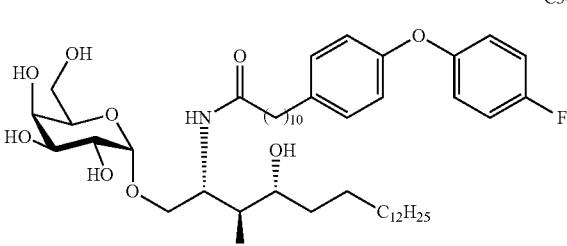
C34

Pharmaceutical Compositions

The present disclosure provides pharmaceutical compositions comprising an exemplary compound described herein and a pharmaceutically acceptable excipient. The compositions disclosed herein can be included in a pharmaceutical or nutraceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringeability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Uses of Compositions Described Herein

The present invention provides compositions useful for stimulating an immune response in a human subject in need thereof, the method comprising: administering to the subject a therapeutically effective amount of a composition disclosed herein.

The compositions described herein can also be used to elevate invariant Natural Killer T (iNKT) cells production in a human subject in need thereof, the method comprising: administering to the subject in need thereof a therapeutically effective amount of a pharmaceutically acceptable composition, wherein the composition comprises an exemplary compound disclosed herein.

The exemplary compositions described herein can also be used to stimulate cytokine and/or chemokine production in a human subject in need thereof, the method comprising: administering to the subject a therapeutically effective amount of a pharmaceutically acceptable composition, wherein the composition comprises an amount sufficient to increase cytokine/chemokine production, of a compound disclosed herein.

By an "effective" amount or a "therapeutically effective" amount of an active agent is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention of an adverse condition and/or the amelioration of an adverse condition, i.e., in addition to an amount effective for the treatment of an adverse condition.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

An adverse condition as that term is used herein may be a "normal" condition that is frequently seen in individuals or a pathologic condition that may or may not be associated with a named disease.

As used herein, the term "lipid" refers to any fat-soluble (lipophilic) molecule that participates in cell signaling pathways.

As used herein, the term "glycolipid" refers to a carbohydrate-attached lipid that serves as a marker for cellular recognition.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of the compositions disclosed herein according to the at least one of the above mentioned methods.

The kits possibly include also compositions comprising active agents, identifiers of a biological event, or other compounds identifiable by a person skilled upon reading of the present disclosure. The kit can also comprise at least one composition comprising an effective amount of the compositions disclosed herein or a cell line. The compositions and the cell line of the kits of parts to be used to perform the at least one method herein disclosed according to procedure identifiable by a person skilled in the art.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

As will be apparent to those of skill in the art upon reading this invention, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

In one aspect, the immune composition described herein can be administered parenterally (e.g., intravenous injection, subcutaneous injection or intramuscular injection). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immune composition described herein.

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immune composition of this invention can also be used to generate antibodies in animals for production of antibodies, which can be used in both cancer treatment and diagnosis. Methods of making monoclonal and polyclonal antibodies and fragments thereof in animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab')$_2$, Fv, scFv (single chain antibody), and dAb (domain antibody; Ward, et. al. (1989) Nature, 341, 544).

Unless otherwise defined, all technical and scientific terms used herein have the same meaning as commonly understood by one of ordinary skill in the art to which this invention pertains. In the case of conflict, the present document, including definitions will control. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included Examples The following examples are put forth so as to provide those skilled in the art with a complete invention and description of how to make and use embodiments in accordance with the invention, and are not intended to limit the scope of what the inventors regard as their discovery. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General:

All reagent chemicals were purchased as reagent grade and used without further purification. Anhydrous solvents such as dichloromethane ($CH_2Cl_2$), tetrahydrofuran (THF), N,N-dimethylformamide (DMF), methanol (MeOH), pyridine were purchased from Acros. HPLC grade solvents chloroform ($CHCl_3$) and methanol were purchased from Merck. Molecular sieves 4 Å (MS 4 Å) for glycosylation was purchased from Acros and activated by flame. Reactions were monitored with analytical thin layer chromatography (TLC) in EM silica gel 60 F254 plates and visualized under UV (254 nm) and/or staining with acidic ceric ammonium molybdate or ninhydrin. Flash column chromatography was performed on silica gel 60 Geduran (40-63 μm, Merck). Biogel LH20 for purification of final products was purchased from Aldrich. $^1$H NMR spectra were recorded on a Bruker Topspin-600 (600 MHz) spectrometer at 20° C. Chemical shifts (δ ppm) were assigned according to the internal standard signal of $CDCl_3$ (δ=7.24 ppm), MeOD (δ=3.31 ppm), and pyridine-d$^5$ (δ=7.58 ppm). $^{13}$C NMR spectra were obtained on a Bruker Topspin-600 (150 MHz) spectrometer and were reported in δ ppm scale using the signal of $CDCl_3$ (δ=77.23 ppm), MeOD (δ=49.15 ppm) for calibration. Coupling constants (J) are reported in Hz. Splitting patterns are described by using the following abbreviations: s, singlet; d, doublet; t, triplet; dd, double doublet; m, multiplet. $^1$H NMR spectra are reported in this order: chemical shift; multiplicity; number(s) of proton; coupling constant(s).

Chemical Syntheses

In certain embodiments of the present disclosure, compositions and methods of use can include or exclude any one or more of the following compounds and methods of making/using the compounds. In certain embodiments, GSLs bearing α-glucose (α-Glc) and derivatives of α-Glc with F at the 4 and/or 6 positions are included or excluded.

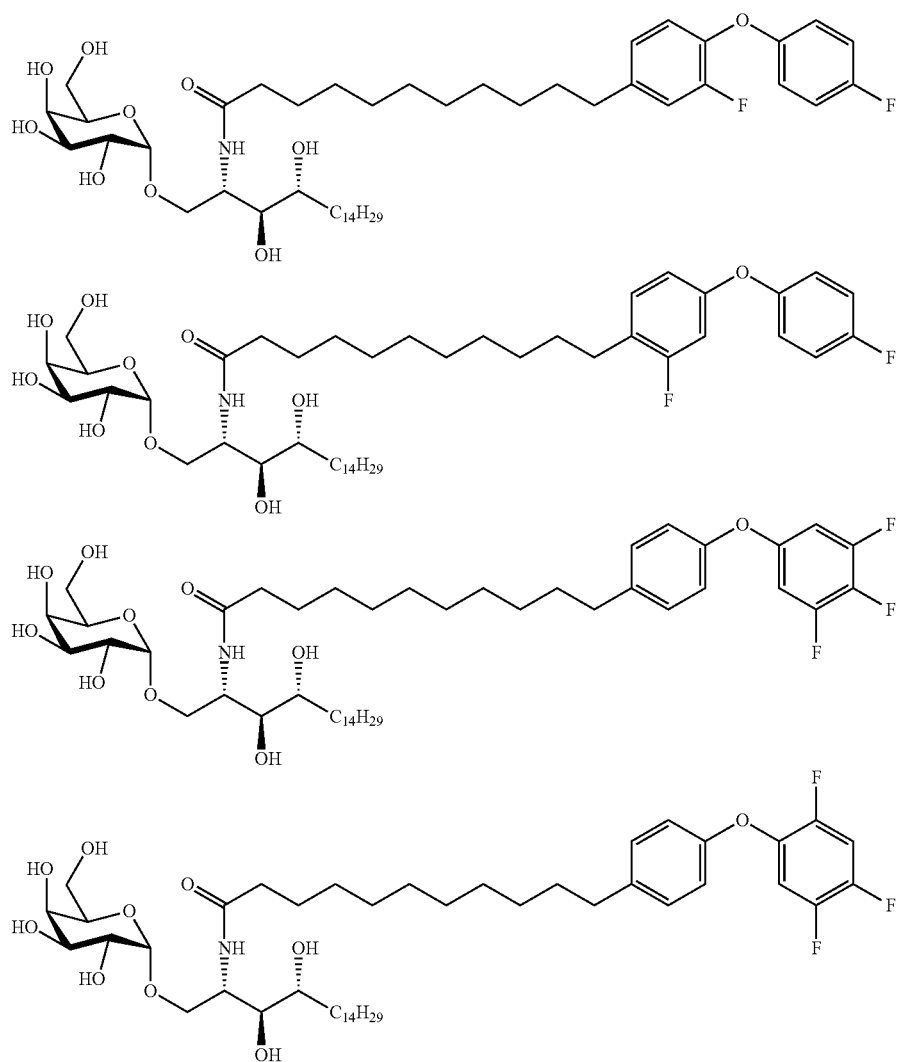
Synthesis of Glucosyl Donor 8
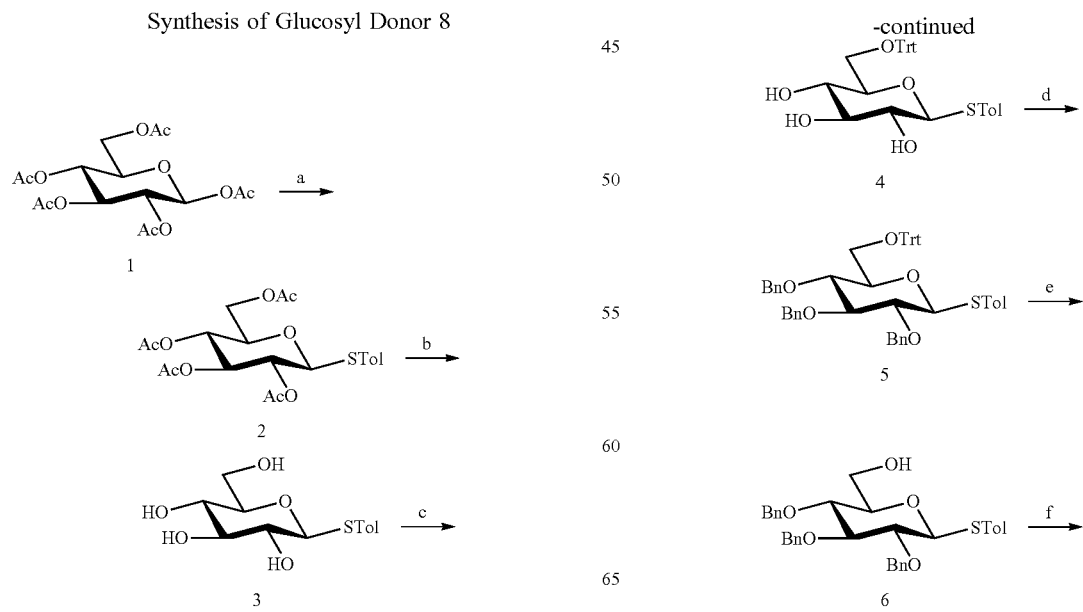

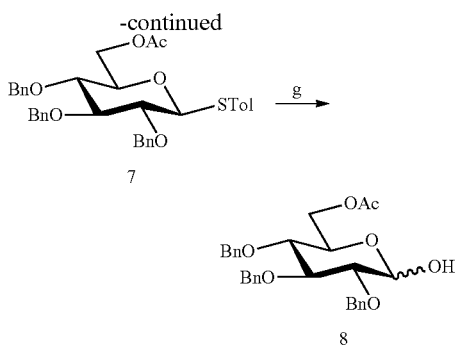

Compound 2

To a solution of 1,2,3,4,6-Penta-O-acetyl-β-D-glucopyranose 1 (40 g, 102.5 mmol) in 200 mL of dry CH$_2$Cl$_2$ was added p-toluenethiol (15.4 g, 123 mmol) and BF$_3$OEt$_2$ (15.4 mL, 123 mmol) at 0° C., the reaction was stirred for 16 h at ambient temperature under argon. The resulting solution was directly extracted with saturated NaHCO$_3$ solution and brine, dried over MgSO$_4$ and evaporated. Followed by recrystallization in a solution of AcOEt-hexanes to give 2 as white solid (32.6 g, 70%). $^1$H NMR (CDCl$_3$, 600 MHz) δ 7.36 (2H, d, J=7.2 Hz), 7.10 (2H, d, J=7.8 Hz), 5.18 (1H, t, J=9.0 Hz), 5.00 (1H, t, J=9.6 Hz), 4.91 (1H, t, J=9.0 Hz), 4.61 (1H, d, J=10.2 Hz), 4.14-4.20 (2H, m), 3.67 (1H, s), 2.33 (3H, s), 2.07 (3H, s), 2.06 (3H, s), 1.99 (3H, s), 1.96 (3H, s). $^{13}$C NMR (CDCl$_3$, 150 MHz) δ 170.78, 170.40, 169.59, 169.45, 139.00, 134.04, 129.88, 127.73, 86.03, 75.94, 74.21, 70.10, 68.38, 62.32, 21.39, 20.97, 20.94, 20.79, 20.78. HRMS (ESI-TOF) for C$_{21}$H$_{26}$O$_9$SNa$^+$ [M+Na]$^+$ calcd 477.1190. found 477.1201.

Compound 3

To a solution of 2 (32.6 g, 71.8 mmol) in 500 mL of dry MeOH was added catalytic amount of sodium methoxide (NaOMe) and stirred for 3 h at ambient temperature. The reaction was neutralized by adding Amberlite IR-120 and filtered, the resulting solution was concentrated to dryness to give 3 (20.3 g, 99%) as white solid, which was directly used for next reaction without further purification. $^1$H NMR (MeOD, 600 MHz) δ 7.46 (2H, d, J=7.8 Hz), 7.12 (2H, d, J=7.8 Hz), 4.50 (1H, d, J=9.6 Hz), 3.85 (1H, d, J=12.6, 1.8 Hz), 3.66 (1H, dd, J=12.0, 5.4 Hz), 3.36 (1H, t, J=9.0 Hz), 3.24-3.28 (2H, m), 3.17 (1H, t, J=9.0 Hz), 2.13 (3H, s). $^{13}$C NMR (MeOD, 150 MHz) δ 138.90, 133.66, 131.33, 130.67, 89.79, 82.16, 79.81, 73.82, 71.50, 63.03, 21.24. HRMS (ESI-TOF) for C$_{13}$H$_{18}$O$_5$SNa$^+$[M+Na]$^+$ calcd 309.0767. found 309.0772.

Compound 4

To a solution of 3 (11.1 g, 38.8 mmol) in 48 mL of dry pyridine was added triphenylmethyl chloride (13.5 g, 46.6 mmol). The reaction was stirred for 16 h at 60° C. under argon. After removal of the solvent, the mixture was purified by flash column chromatography on silica gel (hexanes:AcOEt:MeOH 1:1:0.1) to give 4 (12.3 g, 60%) as white powder. $^1$H NMR (MeOD, 600 MHz) δ 7.56 (1H, d, J=7.8 Hz), 7.47 (6H, d, J=7.8 Hz), 7.27 (6H, t, J=7.2 Hz), 7.22 (3H, t, J=7.2 Hz), 7.05 (2H, d, J=8.4 Hz), 4.58 (1H, d, J=9.6 Hz), 3.40-3.43 (2H, m), 3.31 (1H, m), 3.23-3.27 (3H, m), 2.27 (3H, s). NMR (MeOD, 150 MHz) δ 145.69, 138.71, 133.62, 131.51, 130.77, 130.16, 128.87, 128.13, 89.46, 87.88, 80.98, 80.02, 73.93, 71.85, 65.14, 21.34. HRMS (ESI-TOF) for C$_{32}$H$_{32}$O$_5$SNa$^+$[M+Na]$^+$ calcd 551.1863. found 551.1876.

Compound 5

To a solution of 4 (21.1 g, 39.9 mmol) in 200 mL of dry N,N-dimethylformamide (DMF) was added sodium hydride (60% in mineral oil) (5.8 g, 143.6 mmol) at 0° C. The reaction was stirred for 1 h, followed by the addition of benzyl bromide (17.2 mL, 143.6 mmol) then stirred for 16 h under argon at ambient temperature. The reaction was quenched by MeOH and evaporated to dryness. The residue was diluted with AcOEt, the solution was washed with H$_2$O and brine, dried over MgSO$_4$, and evaporated to dryness. The mixture was purified by flash column chromatography on silica gel (hexanes:AcOEt 9:1) to give 5 (22.3 g, 70%) as white powder. $^1$H NMR (CDCl$_3$, 600 MHz) δ 7.60 (2H, d, J=7.8 Hz), 7.50 (6H, d, J=7.8 Hz), 7.42 (2H, d, J=7.2 Hz), 7.34 (2H, t, J=7.2 Hz), 7.24-7.32 (12H, m), 7.18-7.23 (4H, m), 7.14-7.17 (2H, m), 7.05 (2H, d, J=7.8 Hz), 6.82 (2H, d, J=7.8 Hz), 4.91 (1H, d, J=10.8 Hz), 4.84 (1H, d, J=10.8 Hz), 4.80 (1H, d, J=10.8 Hz), 4.74 (1H, d, J=10.2 Hz), 4.64 (2H, dd, J=9.6, 5.4 Hz), 4.30 (1H, d, J=10.2 Hz), 3.74 (1H, t, J=9.6 Hz), 3.64 (1H, t, J=8.4 Hz), 3.60 (1H, d, J=9.6 Hz), 3.55 (1H, t, J=9.6 Hz), 3.42 (1H, m), 3.25 (1H, dd, J=10.2, 4.2 Hz), 2.30 (3H, s). $^{13}$C NMR (CDCl$_3$, 150 MHz) δ 144.14, 138.57, 138.43, 137.94, 137.90, 133.01, 130.10, 129.96, 129.07, 128.73, 128.67, 128.45, 128.42, 128.31, 128.20, 128.16, 128.15, 128.07, 128.01, 127.89, 127.20, 87.90, 87.07, 86.70, 80.96, 79.04, 78.04, 76.25, 75.61, 75.21, 62.68, 45.18, 21.37. HRMS (ESI-TOF) for C$_{53}$H$_{50}$O$_5$SNa$^+$[M+Na]$^+$ calcd 821.3271. found 821.3310

Compound 6

To a solution of 5 (30.0 g, 37.5 mmol) in 1065 mL of aqueous acetic acid solution (AcOH: H$_2$O 4:1) was stirred for 3 h at 75° C. After removal of the solvent, the residue was purified by flash column chromatography on silica gel (hexanes:AcOEt 2:1) to give 6 (16.7 g, 80%) as white solid. $^1$H NMR (CDCl$_3$, 600 MHz) δ 7.37-7.41 (4H, m), 7.25-7.33 (13H, m), 7.10 (2H, d, J=7.8 Hz), 4.91 (1H, d, J=10.2 Hz), 4.89 (1H, d, J=10.8 Hz), 4.84 (1H, d, J=10.8 Hz), 4.83 (1H, d, J=10.8 Hz), 4.74 (1H, d, J=10.8 Hz), 4.62 (1H, d, J=10.2 Hz), 3.83-3.86 (1H, m), 3.65-3.71 (2H, m), 3.54 (1H, t, J=9.6 Hz), 3.44 (1H, t, J=9.0 Hz), 3.33-3.36 (1H, m), 2.31 (3H, s), 1.87 (1H, t, J=6.6 Hz). $^{13}$C NMR (CDCl$_3$, 150 MHz) δ 138.51, 138.24, 138.14, 138.02, 132.85, 129.99, 129.63, 128.71, 128.66, 128.63, 128.40, 128.22, 128.16, 128.09, 127.98, 127.94, 87.99, 86.75, 81.27, 79.43, 77.81, 76.01, 75.69, 75.30, 62.34, 21.31. HRMS (ESI-TOF) for C$_{34}$H$_{36}$O$_5$SNa$^+$ [M+Na]$^+$ calcd 579.2176. found 579.2188.

Compound 7

To a solution of 6 (5.0 g, 9.0 mmol) in 18 mL of dry pyridine was added acetic anhydride (1.0 mL). The reaction was stirred for 16 h at ambient temperature under argon. After removal of the solvent, the residue was diluted with AcOEt, the solution was washed with H$_2$O and brine, dried over MgSO$_4$ and evaporated to dryness. The mixture was purified by flash column chromatography on silica gel (hexanes:AcOEt 5:1) to give 7 (5.3 g, 99%) as white solid. $^1$H NMR (CDCl$_3$, 600 MHz) δ 7.44 (2H, d, J=7.8 Hz), 7.38 (2H, d, J=7.8 Hz), 7.26-7.34 (11H, m), 7.22-7.24 (2H, m), 7.08 (2H, d, J=7.8 Hz), 4.91 (1H, d, J=10.2 Hz), 4.90 (1H, d, J=11.4 Hz), 4.83 (1H, d, J=10.8 Hz), 4.82 (1H, d, J=10.8 Hz), 4.71 (1H, d, J=10.2 Hz), 4.57 (1H, d, J=9.6 Hz), 4.55 (1H, d, J=10.8 Hz), 4.34 (1H, d, J=12.0 Hz), 4.17-4.20 (1H, m), 3.67-3.70 (1H, m), 3.49-3.50 (2H, m), 3.45 (1H, t, J=9.6 Hz), 2.32 (3H, s), 2.03 (3H, s). $^{13}$C NMR (CDCl$_3$, 150 MHz) δ 170.90, 138.44, 138.16, 138.13, 137.81, 132.98, 129.85, 128.76, 128.72, 128.68, 128.45, 128.30, 128.26, 128.15, 128.02, 88.00, 86.93, 81.07, 77.74, 76.08, 75.68, 75.32, 63.51, 21.35, 21.09. HRMS (ESI-TOF) for C$_{36}$H$_{38}$O$_6$SNa$^+$ [M+Na]$^+$ calcd 621.2281. found 621.2301.

Compound 8

To a solution of 7 (5.5 g, 9.2 mmol) in 129 mL of aqueous acetone solution (acetone: H$_2$O 4:1) was added N-bromosuccinimide (1.7 g, 9.5 mmol). The reaction was stirred for 1 h at ambient temperature. After removal of the solvent, the residue was diluted with AcOEt, extracted with H$_2$O, aqueous sodium thiosulfate (NaS$_2$O$_3$) solution, brine then dried over MgSO$_4$. The mixture was purified by flash column chromatography on silica gel (hexane: AcOEt 2:1) to give 8 (3.1 g, 69%, α/β=1:1) as white solid. NMR (CDCl$_3$, 600 MHz) δ 7.24-7.35 (30H, m), 5.18 (1H, t, J=3.0 Hz), 4.96 (1H, d, J=10.2 Hz), 4.94 (2H, d, J=10.8 Hz), 4.86 (1H, d, J=10.8 Hz), 4.85 (1H, d, J=10.2 Hz), 4.84 (1H, d, J=10.2 Hz), 4.80 (1H, d, J=10.8 Hz), 4.76 (2H, d, J=11.4 Hz), 4.71 (1H, dd, J=7.2, 5.4 Hz), 4.68 (1H, d, J=12.0 Hz), 4.55 (2H, d, J=10.8 Hz), 4.34 (1H, dd, J=12.0, 1.2 Hz), 4.23-4.28 (2H, m), 4.17 (1H, dd, J=12.0, 4.8 Hz), 4.06-4.09 (1H, m), 3.98 (1H, t, J=9.6 Hz), 3.67 (1H, t, J=8.4 Hz), 3.50-3.56 (3H, m), 3.48 (1H, t, J=9.0 Hz), 3.37-3.40 (2H, m), 3.01 (1H, d, J=3.0 Hz), 2.02 (3H, s), 2.01 (3H, s). $^{13}$C NMR (CDCl$_3$, 150 MHz) δ 138.64, 138.49, 138.39, 137.96, 137.89, 137.81, 128.75, 128.70, 128.68, 128.65, 128.63, 128.33, 128.29, 128.27, 128.22, 128.20, 128.14, 128.06, 127.99, 127.93, 97.62, 91.33, 84.71, 83.20, 81.82, 80.18, 77.39, 75.96, 75.92, 75.23, 75.21, 74.98, 73.47, 73.19, 69.02, 63.35, 63.27, 21.06. HRMS (ESI-TOF) for C$_{29}$H$_{32}$O$_7$Na$^+$ [M+Na]$^+$ calcd 515.2040. found 515.2052.

Synthesis of Acceptor 18

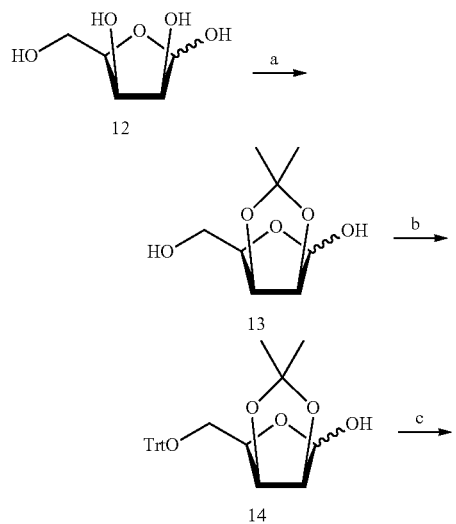

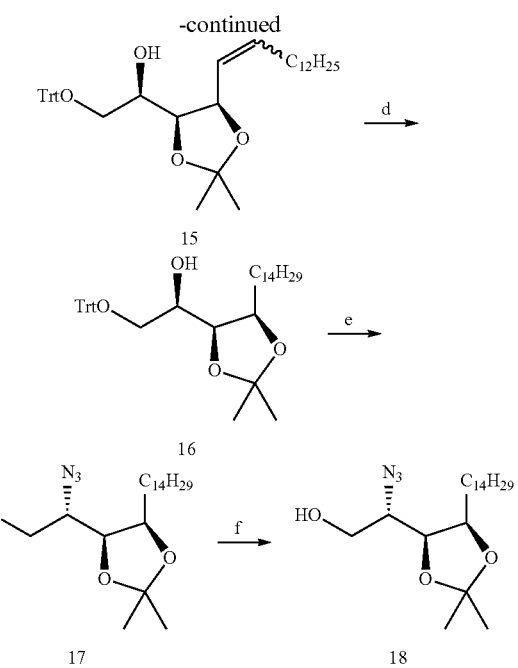

Compound 13

To a solution of D-Lyxose 12 (20 g, 133 mmol) in 200 mL of anhydrous N,N-dimethylformamide (DMF) was added 2-methoxypropene (15 mL, 160 mmol) and camphor-10-sulfonic acid (CSA) (3 g, 13.3 mmol) at 0° C. The reaction was stirred for 16 h at ambient temperature under argon. The solution was quenched with triethylamine (Et$_3$N), evaporated to dryness and directly purified by flash column chromatography on silica gel (hexanes:AcOEt:MeOH 1:1:0.2) to give 13 (21 g, 83%) as white solid. $^1$H NMR (CDCl$_3$, 600 MHz): δ 5.22 (s, 1H), 4.78 (dd, 1H, J=6.0, 3.6 Hz), 4.53 (d, 1H, J=6.0 Hz), 4.17 (m, 1H, J=6.6, 4.8 Hz), 3.82 (dd, 1H, J=11.7, 4.8 Hz), 3.71 (dd, 1H, J=11.7, 6.6 Hz), 1.40 (s, 3H), 1.29 (s, 3H). $^{13}$C NMR (CDCl$_3$, 150 MHz): δ 113.62, 102.27, 87.42, 81.73, 81.35, 61.37, 26.46, 25.02. HRMS (ESI-TOF) for C$_8$H$_{34}$O$_5$Na$^+$ [M+Na]$^+$ calcd 213.0733. found 213.0751.

Compound 14

To a stirred solution of 13 (21 g, 110 mmol) in 140 mL of dry pyridine was added triphenylmethyl chloride (37.8 g, 132 mmol). The reaction was stirred for 16 h at 60° C. under argon. The solution was concentrated to dryness, the residue was dissolved with ethyl acetate (AcOEt), washed with H$_2$O, brine and dried over magnesium sulfate (MgSO$_4$) then evaporated. The mixture was purified by flash column chromatography on silica gel (hexanes:AcOEt 1:2) to give 14 (36.5 g, 77%) as white powder. $^1$H NMR (CDCl$_3$, 600 MHz): δ 7.46 (m, 6H), 7.27 (m, 6H), 7.21 (m, 3H), 5.36 (d, 1H, J=1.8 Hz), 4.73 (dd, 1H, J=6.0, 4.8 Hz), 4.57 (d, 1H, J=6.0 Hz), 4.31 (ddd, 1H, J=4.8, 4.8, 7.8 Hz), 3.41 (dd, 1H, J=9.6, 4.8 Hz), 3.37 (dd, 1H, J=9.6, 7.8 Hz), 2.41 (m, 1H, J=1.8 Hz), 1.27 (s, 3H), 1.25 (s, 3H). $^{13}$C NMR (CDCl$_3$, 150 MHz): δ 143.95, 128.82, 127.75, 126.95, 112.48, 101.22, 86.85, 85.41, 80.11, 79.70, 61.85, 26.02, 25.09. HRMS (ESI-TOF) for C$_{27}$H$_{28}$O$_5$Na$^+$ [M+Na]$^+$ calcd 455.1829. found 455.1833.

Compound 15

To a stirred solution of 14 (8.4 g, 19.4 mmol) in 40 mL of anhydrous tetrahydrofurane (THF) was added lithium bis(trimethylsilyl)amide (LHMDS) (20 mL of 1M solution in THF, 20 mmol) at 0° C., the reaction was stirred for 1 h under argon. To a stirred solution of Wittig reagent $C_{13}H_{27}PPh_3Br$ (20.1 g, 38.2 mmol), prepared from 1-bromotridecane ($C_{13}H_{27}Br$) and triphenylphosphine ($PPh_3$) refluxed in toluene for 5 days, in 83 mL of anhydrous THF was added LHMDS (40 mL of 1M solution in THF, 40 mmol) at 0° C., the reaction was stirred for 1 h under argon to produce the bright orange ylide. The solution of 14 was added dropwise to the ylide at 0° C., and the reaction was allowed to warm to ambient temperature and stirred for 9 h under argon. The resulting solution was quenched with MeOH and evaporated to dryness. The residue was diluted with AcOEt, extracted with $H_2O$ and brine, dried over $MgSO_4$ then concentrated. The mixture was purified by flash column chromatography on silica gel (hexanes:AcOEt 15:1) to give 15 (8.7 g, 75%) as colorless oil. $^1H$ NMR ($CDCl_3$, 600 MHz): δ 7.40-7.45 (m, 9H), 7.25-7.30 (m, 9H), 7.19-7.23 (m, 5H), 5.49-5.57 (m, 3H, J=6.6 Hz), 4.90 (t, 1H, J=6.6 Hz), 4.43 (t, 1.5H, J=6.6 Hz), 4.25 (dd, 0.5H, J=6.6, 4.6 Hz), 4.20 (dd, 1H, J=6.6, 4.5 Hz), 3.74 (m, 1H), 3.68 (m, 0.5H), 3.22 (dd, 0.5H, J=9.6, 5.0 Hz), 3.15 (dd, 1H, J=9.3, 5.1 Hz), 3.10 (m, 1.5H), 2.37 (m, 1.5H), 1.90-2.00 (m, 2H), 1.75 (m, 1H), 1.47 (m, 5H), 1.37 (m, 5H), 1.19-1.33 (m, 35H), 0.86 (t, 5H, J=7.1 Hz). $^{13}C$ NMR ($CDCl_3$, 150 MHz): δ 144.07, 137.58, 135.56, 128.90, 128.02, 127.24, 125.41, 125.15, 108.58, 108.50, 86.90, 86.84, 79.14, 77.86, 77.74, 73.21, 69.51, 69.43, 65.19, 64.84, 32.45, 32.13, 29.89, 29.86, 29.81, 29.71, 29.69, 29.57, 29.50, 29.47, 29.11, 27.80, 27.59, 27.55, 25.26, 22.91, 14.35. HRMS (ESI-TOF) for $C_{40}H_{54}O_4Na^+$ [M+Na]$^+$ calcd 621.3914. found 621.3919.

Compound 16

Compound 16 was prepared from catalytic hydrogenation of 15 (1 g, 1.7 mmol) in 10 mL of anhydrous MeOH containing catalytic amount of palladium hydroxide on carbon (20% Pd). The suspension was stirred for 4 h in an $H_2$ atmosphere. The solution was filtered through Celite 545 to remove the catalyst, evaporated to dryness then purified by flash column chromatography on silica gel (hexane:AcOEt 20:1) to give 16 (903 mg, 90%) as white solid. NMR ($CDCl_3$, 600 MHz): δ 7.43 (m, 6H), 7.27 (m, 6H), 7.21 (m, 3H), 4.12 (dd, 1H, J=6.4, 3.7 Hz), 4.05 (ddd, 1H, J=9.9, 6.4, 3.6 Hz), 3.69 (m, 1H, J=6.0, 6.0, 5.8, 3.7 Hz), 3.18 (m, 2H, J=9.5, 9.5, 6.0, 5.8 Hz), 2.29 (d, 1H, J=6.0 Hz), 1.60-1.67 (m, 1H), 1.45-1.49 (m, 1H), 1.43 (s, 3H), 1.34-1.38 (m, 1H), 1.33 (s, 3H), 1.20-1.30 (m, 23H), 0.86 (t, 3H, J=7.2 Hz). $^{13}C$ NMR ($CDCl_3$, 150 MHz): δ 144.09, 128.91, 128.05, 127.26, 107.95, 87.02, 77.67, 69.15, 65.43, 32.15, 29.92, 29.88, 29.83, 29.77, 29.58, 27.60, 26.99, 25.43, 22.92, 14.36. HRMS (ESI-TOF) for $C_{40}H_{56}O_4Na^+$ [M+Na]$^+$ calcd 623.4071. found 623.4112.

Compound 17

To a solution of 16 (5 g, 8.3 mmol) and 4 Å molecular sieves (1 g) in 39 mL of anhydrous $CH_2Cl_2$ was added 2,6-lutidine (3.5 mL, 30 mmol) at ambient temperature. When the solution was cooled to −45° C., trifluoromethanesulfonic anhydride ($Tf_2O$) (2.67 mL, 15.9 mmol) was added dropwise and the reaction was stirred for 1 h under argon. Followed by the addition of tetramethylguanidinium azide (TMGA) (3.9 g, 25 mmol), the reaction was allowed to warm to ambient temperature and stirred for 16 h under argon. The resulting solution was filtered through Celite 545 to remove 4 Å molecular sieves and the residue was diluted with $CH_2Cl_2$, extracted with $H_2O$ and brine, dried over $MgSO_4$ then evaporated. The mixture was simply purified by flash column chromatography on silica gel (hexanes:AcOEt 20:1) to remove most of the impurities and directly used for the next step.

Compound 18

To a solution of 17 in 20 mL of anhydrous $CH_2Cl_2$ was added tetrafluoroacetic acid/tetrafluoroacetic anhydride (TFA/TFAA 1.8 M/1.8 M in $CH_2Cl_2$) (14 mL, 24.9 mmol) at 4° C. and stirred for 15 min under argon. The reaction was quenched by adding 10 mL of $Et_3N$ then poured into 200 mL of methanol (MeOH) and stirred for another 15 min. After removal of the solvent, the residue was diluted with AcOEt, extracted with $H_2O$, saturated $NaHCO_3$ solution and brine then dried over $MgSO_4$. The organic layer was concentrated in vacuo and the mixture was purified by flash column chromatography on silica gel (hexanes:AcOEt 10:1) to give 18 (2 g, two steps 63%) as yellow oil. $^1H$ NMR ($CDCl_3$, 600 MHz): δ 4.16 (ddd, 1H, J=9.7, 5.6, 3.6 Hz), 3.97 (dd, 1H, J=11.6, 4.2 Hz), 3.94 (dd, 1H, J=9.4, 5.6 Hz), 3.85 (dd, 1H, J=11.6, 5.4 Hz), 3.45 (ddd, 1H, J=9.4, 5.4, 4.2 Hz), 1.50-1.62 (m, 2H, J=9.7, 3.6 Hz), 1.41 (s, 3H), 1.31-1.37 (m, 6H), 1.22-1.30 (m, 22H), 0.86 (t, 3H, J=6.9, 6.9 Hz). $^{13}C$ NMR ($CDCl_3$, 150 MHz): δ 108.66, 77.96, 76.91, 64.18, 61.39, 32.14, 29.90, 29.87, 29.81, 29.80, 29.75, 29.60, 29.58, 28.25, 26.74, 25.77, 22.91, 14.34. HRMS (ESI-TOF) for $C_{23}H_{43}N_3O_3H^+$ [M+H]$^+$ calcd 383.3148. found 356.3157 (—$N_2$).

Synthesis of α-Glucosylceramide Analogues 24-26

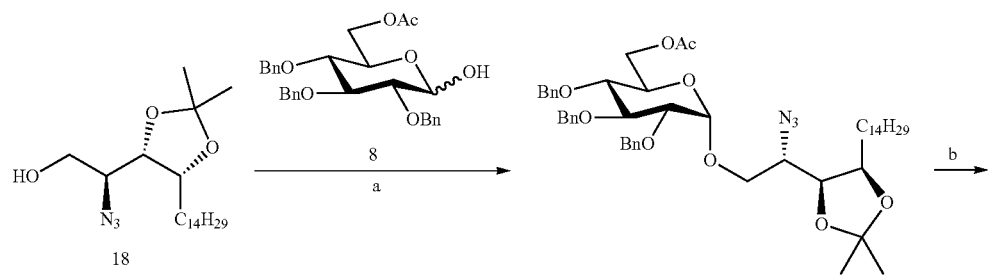

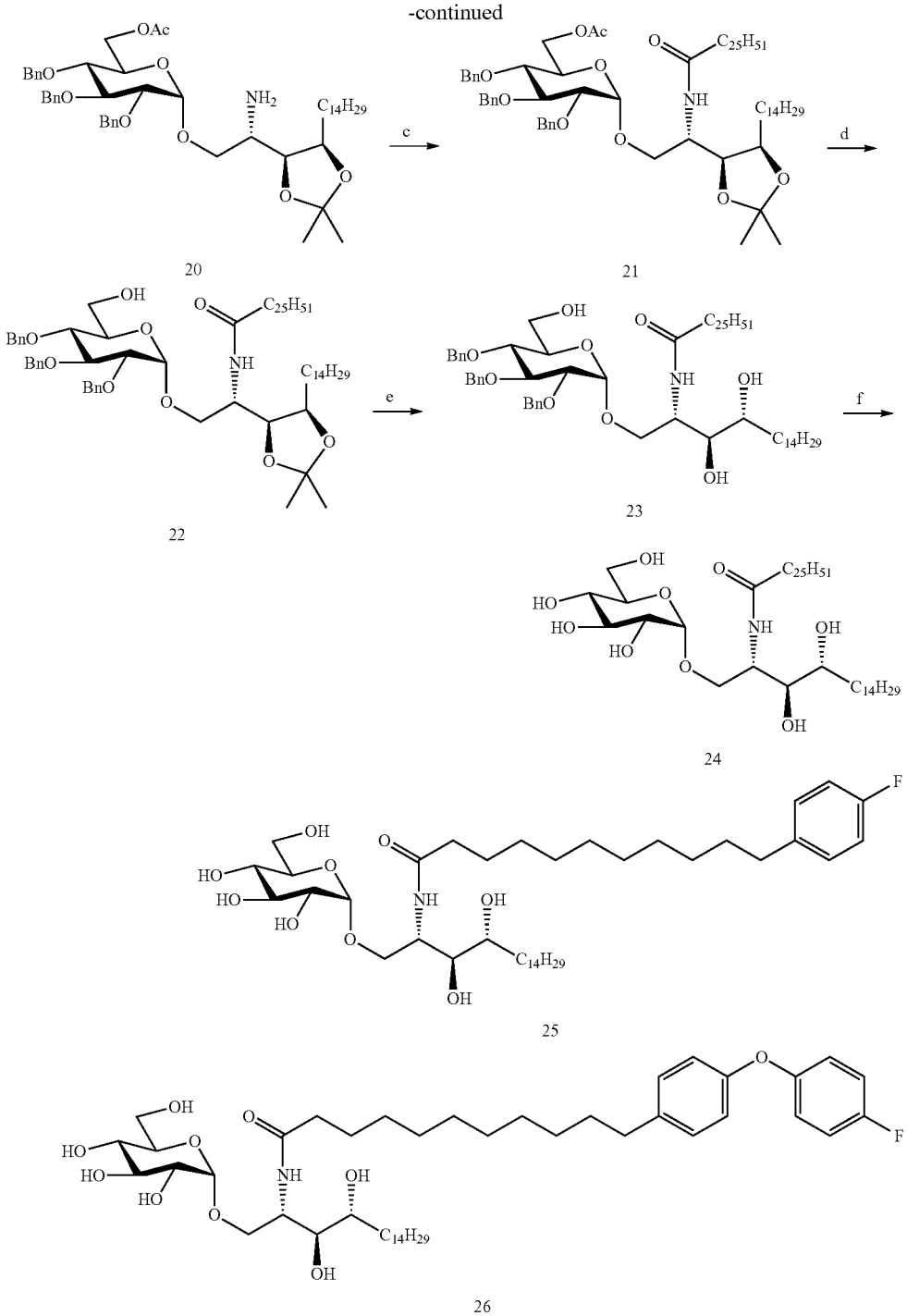

Compound 19

To a solution of glucosyl donor 8 (2.9 g, 5.9 mmol), dimethylsulfide (590 μL, 7.8 mmol), 4 Å molecular sieve (500 mg) and 2-chloropyridine (1.8 mL, 19.5 mmol) in anhydrous $CH_2Cl_2$ (15 mL) was added trifluoromethanesulfonic anhydride (1 mL, 6 mmol) at −45° C. under argon. The reaction was stirred for 20 min at −45° C., 20 min at 0° C. and another 20 min at ambient temperature, followed by the addition of acceptor 18 (1.5 g, 3.9 mmol) in 5 mL of $CH_2Cl_2$. The reaction was stirred for 16 h at ambient temperature under argon. The solution was filtered through Celite 545 to remove molecular sieve. After removal of the solvent, the residue was diluted with AcOEt, the solution was washed with $H_2O$ and brine, dried over $MgSO_4$ and evaporated to dryness. The mixture was purified by flash column chromatography on silica gel (hexanes:AcOEt 10:1) to give 19 as colorless oil (2 g, 60%). $^1H$ NMR ($CDCl_3$, 600 MHz) δ 7.36 (2H, d, J=7.8 Hz), 7.24-7.33 (13H, m), 4.97 (1H, d, J=10.8 Hz), 4.86 (1H, d, J=10.8 Hz), 4.85 (1H, d, J=3.6 Hz), 4.78 (1H, d, J=10.8 Hz), 4.72 (1H, d, J=12.0 Hz), 4.68 (1H, d, J=12.0 Hz), 4.54 (1H, d, J=10.8 Hz), 4.21-4.26 (2H, m), 4.08-4.11 (1H, m), 4.02-4.07 (2H, m), 3.97 (1H, dd, J=9.6, 5.4 Hz), 3.84-3.87 (1H, m), 3.60 (1H, dd, J=10.8, 7.2 Hz), 3.54 (1H, dd, J=9.6, 3.6 Hz), 3.44-3.48 (2H, m), 2.00 (3H, s), 1.57-1.61 (1H, m), 1.50-1.55 (1H, m), 1.37 (3H, s), 1.22-1.35 (27H, m), 0.86 (3H, t, J=7.2 Hz). $^{13}$C NMR (CDCl$_3$, 150 MHz) δ 170.93, 138.82, 138.58, 138.05, 128.68, 128.61, 128.59, 128.34, 128.31, 128.13, 127.90, 127.86, 81.82, 80.26, 77.97, 77.30, 75.93, 75.61, 75.24, 72.92, 69.50, 69.34, 63.26, 59.99, 32.13, 29.90, 29.87, 29.82, 29.77, 29.57, 29.54, 28.42, 26.73, 25.89, 22.90, 21.03, 14.33. HRMS (ESI-TOF) for C$_{30}$H$_{71}$N$_3$O$_9$Na$^+$ [M+Na]$^+$ calcd 880.5083. found 880.5124.

Compound 20

To a solution of 19 (269 mg, 0.31 mmol) in pyridine/H$_2$O (10:1, 12 mL) was added triphenylphosphine (165 mg, 0.63 mmol). The reaction was stirred for 16 h at 45° C. under argon. After removal of the solvent, the residue was diluted with AcOEt, extracted with H$_2$O, brine and dried over MgSO$_4$ then evaporated to dryness. The mixture was used for next step without prior purification.

Compound 21

To a solution of compound 20 in 36 mL of anhydrous CH$_2$Cl$_2$ was added hexacosanoic acid (159 mg, 0.4 mmol), Et$_3$N (88 μL), EDC (90 mg, 0.47 mmol) and HBTu (178 mg, 0.47 mmol). The reaction was stirred for 16 h at ambient temperature under argon. After removal of the solvent, the residue was diluted with AcOEt, extracted with H$_2$O, brine and dried over MgSO$_4$ then evaporated to dryness. The mixture was purified by flash column chromatography on silica gel (hexanes:AcOEt 4:1) to give 21 as white solid (293 mg, 78%, two steps).

Compound 22

To a solution of 21 (293 mg, 0.24 mmol) in 50 mL of co-solvent (MeOH:CH$_2$Cl$_2$ 1:1) was added sodium methoxide (0.024 mmol) and stirred for 6 h under argon at ambient temperature. The reaction was neutralized by Amberlite IR-120 and filtered. After removal of the solvent, the residue was used for next step without prior purification.

Compound 23

The hydrolyzed compound 22 was dissolved in 50 mL of aqueous acetic acid solution (AcOH: H$_2$O 4:1) and stirred for 16 h at 60° C. After removal of the solvent, the mixture was purified by flash column chromatography on silica gel (hexanes:AcOEt:MeOH 1:1:0.1).

Compound 24

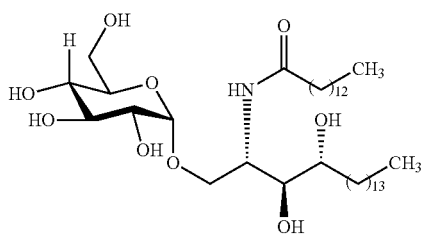

The deacetonide derivative 23 was dissolved in 50 mL of co-solvent (MeOH:CHCl$_3$ 4:1) containing palladium hydroxide on carbon (20% Pd) (cat.) and stirred for 16 h in an H$_2$ atmosphere. The solution was filtered through Celite 545 to remove the catalyst and evaporated to dryness, the mixture was purified by flash column chromatography on silica gel (MeOH:CHCl$_3$ 1:9) and eluted with LH20 (MeOH:CHCl$_3$ 1:1) to give 24 (72 mg, 35% for three steps) as white solid. $^1$H NMR (MeOD-CDCl$_3$ 1:1, 600 MHz) δ: 4.83 (s, 1H), 4.15 (d, J=4.2 Hz, 1H), 3.84 (dd, J=10.8, 4.2 Hz, 1H), 3.76 (d, J=12.0 Hz, 1H), 3.64-3.70 (m, 2H), 3.60 (t, J=9.6 Hz, 1H), 3.51-3.57 (m, 3H), 3.41 (d, J=9.6 Hz, 1H), 3.31 (m, 1H), 2.17 (t, J=7.2 Hz, 2H), 1.50-1.65 (m, 4H), 1.19-1.39 (m, 68H), 0.85 (t, J=6.6 Hz, 6H). $^{13}$C NMR (MeOD-CDCl$_3$ 1:1, 150 MHz) δ: 175.29, 100.06, 75.05, 74.58, 73.03, 72.75, 72.62, 71.01, 67.78, 62.22, 51.11, 37.07, 32.93, 32.62, 30.49, 30.45, 30.40, 30.35, 30.25, 30.13, 30.05, 30.04, 26.61, 26.58, 23.34, 14.47. HRMS (MALDI-TOF) for C$_{50}$H$_{99}$NO$_9$Na$^+$ [M+Na]$^+$ calcd 880.7223. found 880.7212.

Compound 25

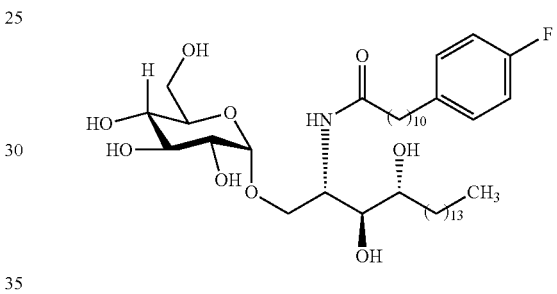

Compound 25 was synthesized using the similar procedure as compound 24. $^1$H NMR (MeOD-CDCl$_3$ 1:1, 600 MHz) δ: 7.09 (dd, J=8.4, 5.4 Hz, 2H), 6.90 (t, J=9.0 Hz, 2H), 4.82 (d, J=3.6 Hz, 1H), 4.14-4.18 (m, 1H), 3.84 (dd, J=10.2, 4.8 Hz, 1H), 3.76 (dd, J=12.0, 2.4 Hz, 1H), 3.64-3.68 (m, 2H), 3.60 (t, J=9.0 Hz, 1H), 3.51-3.56 (m, 3H), 3.41 (dd, J=9.6, 3.6 Hz, 1H), 3.31 (m, 1H), 2.54 (t, J=7.8 Hz, 2H), 2.17 (t, J=7.8 Hz, 2H), 1.51-1.65 (m, 6H), 1.20-1.39 (m, 36H), 0.85 (t, J=6.6 Hz, 3H). $^{13}$C NMR (MeOD-CDCl$_3$ 1:1, 150 MHz) δ: 175.30, 162.67, 161.07, 139.18, 139.16, 130.34, 130.29, 115.46, 115.32, 100.00, 75.03, 74.52, 72.97, 72.68, 72.55, 70.93, 67.71, 62.15, 51.11, 51.03, 37.06, 37.00, 35.72, 32.90, 32.58, 32.32, 30.45, 30.41, 30.35, 30.30, 30.22, 30.15, 30.11, 30.05, 30.00, 29.82, 26.57, 26.53, 23.29, 14.44. HRMS (ESI-TOF) for C$_{41}$H$_{72}$FNO$_9$Na$^+$ [M+Na]$^+$ calcd 764.5083. found 764.5066.

Compound 26

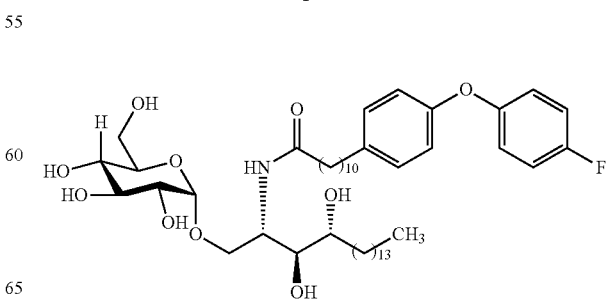

Compound 26 was synthesized using the similar procedure as compound 24. $^1$H NMR (MeOD-CDCl$_3$ 1:1, 600 MHz) δ: 7.10 (d, J=8.4 Hz, 2H), 6.99 (t, J=7.8 Hz, 2H), 6.92 (m, 2H), 6.84 (d, J=7.8 Hz, 2H), 4.83 (d, J=3.0 Hz, 1H), 3.85 (dd, J=10.2, 4.2 Hz, 1H), 3.77 (d, J=11.4 Hz, 1H), 3.67 (m, 2H), 3.61 (t, J=9.6 Hz, 1H), 3.55 (m, 3H), 3.42 (dd, J=9.0, 3.0 Hz, 1H), 3.33 (m, 1H), 2.55 (t, J=7.8 Hz, 2H), 2.18 (t, J=7.8 Hz, 2H), 1.50-1.64 (m, 6H), 1.20-1.40 (m, 36H), 0.85 (t, J=6.6 Hz, 3H). $^{13}$C NMR (MeOD-CDCl$_3$ 1:1, 150 MHz) δ: 175.34, 160.27, 158.67, 156.22, 154.38, 138.73, 130.34, 120.76, 120.71, 119.10, 116.87, 116.72, 100.15, 75.10, 74.66, 73.15, 72.85, 72.65, 71.09, 67.80, 62.26, 51.21, 37.09, 35.90, 32.95, 32.68, 32.44, 30.55, 30.51, 30.47, 30.40, 30.35, 30.28, 30.26, 30.17, 30.11, 30.00, 26.67, 26.63, 23.38, 14.47. HRMS (ESI-TOF) for C$_{47}$H$_{76}$FNO$_{10}$Na$^+$ [M+H]$^+$ calcd 834.5526. found 834.5538.

Synthesis of Fluorinated Donor 38

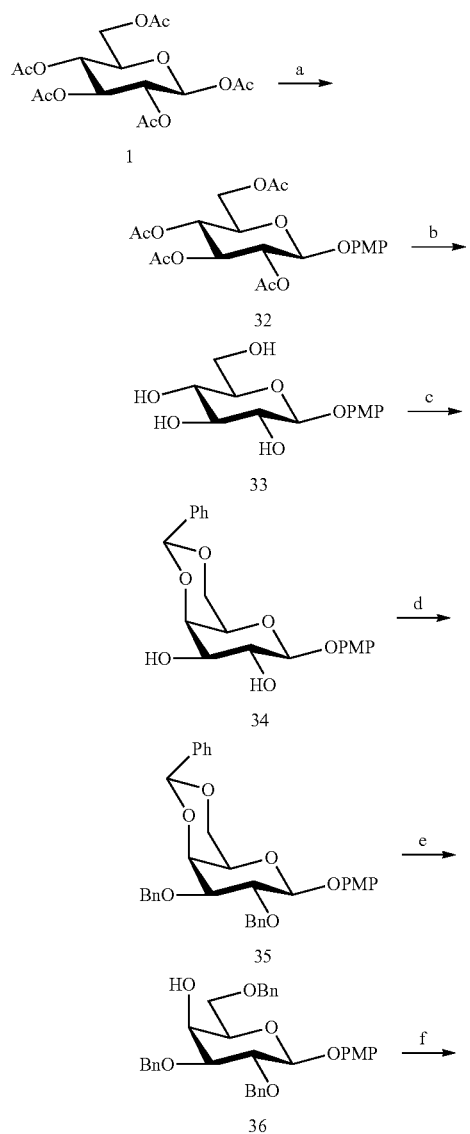

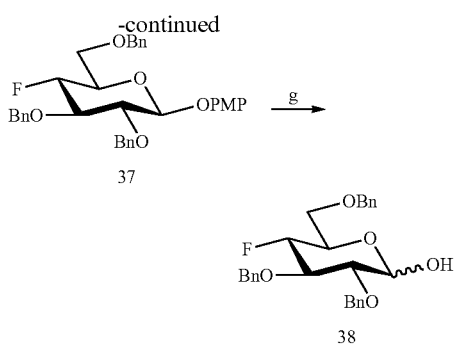

Compound 32

To a solution of 1,2,3,4,6-Penta-O-acetyl-β-D-glucopyranose 1 in dry CH$_2$Cl$_2$ was added 4-methoxyphenol and BF$_3$OEt$_2$ at 0° C., the reaction was stirred for 16 h at ambient temperature under argon. The resulting solution was directly extracted with saturated NaHCO$_3$ solution and brine, dried over MgSO$_4$ and evaporated. The product was recrystallized from a solution of AcOEt-hexanes to give 32 as white solid.

Compound 33

To a solution of 32 in dry MeOH was added catalytic amount of sodium methoxide (NaOMe) and stirred for 3 h at ambient temperature. The reaction was neutralized by adding Amberlite IR-120 and filtered, the resulting solution was concentrated to dryness to give 33 as white solid, which was directly used for next reaction without further purification.

Compound 34

To a solution of 33 in dry co-solvent (DMF and CH$_3$CN) was added benazldehyde dimethylacetal and catalytic amount of sodium methoxide (NaOMe). The reaction was stirred for 16 h at ambient temperature. The solution was neutralized by adding Et$_3$N and concentrated. The mixture was dissolved in ethyl acetate, washed with saturated NaHCO$_3$ solution and brine, dried over MgSO$_4$ and evaporated. The product was recrystallized from a solution of AcOEt-hexanes to give 34 as white solid.

Compound 35

To a solution of 34 in dry N,N-dimethylformamide (DMF) was added sodium hydride (60% in mineral oil) at 0° C. The reaction was stirred for 1 h, followed by the addition of benzyl bromide and the reaction was stirred for 16 h under argon at ambient temperature. The solution was quenched by MeOH and evaporated to dryness. The residue was diluted with AcOEt, the solution was washed with H$_2$O and brine, dried over MgSO$_4$, and evaporated to dryness. The product was recrystallized from a solution of AcOEt-hexanes to give 35 as white solid.

Compound 36

To a solution of 35 in CH$_2$Cl$_2$ was added triethylsilane and trifluoroacetic acid (TFA) at 0° C. The reaction was stirred for 3 h at ambient temperature. The solution was directly washed with H$_2$O, saturated NaHCO$_3$ solution and brine, dried over MgSO$_4$, and evaporated to dryness. The product was recrystallized from a solution of AcOEt-hexanes to give 36 as white solid.

Compound 37

To a solution of 36 in CH$_2$Cl$_2$ was added diethylaminosulfur trifluoride (DAST). The reaction was stirred for 16 h at 45° C. and the solution was directly washed with H$_2$O, saturated NaHCO$_3$ solution and brine, dried over MgSO$_4$, and evaporated to dryness. The residue was purified by flash column chromatography on silica gel to give compound 37 as colorless oil.

Compound 38

To a solution of 37 in dry co-solvent (toluene, H$_2$O and CH$_3$CN) was added ceric ammonium nitrate (CAN). The reaction was stirred for 10 min at ambient temperature. The solution was extracted with ethyl acetate, washed with H$_2$O, saturated NaHCO$_3$ solution and H$_2$O, dried over MgSO$_4$, and evaporated to dryness. The residue was purified by flash column chromatography on silica gel to give compound 38 as colorless oil.

Synthesis of Fluorinated Analogue 43

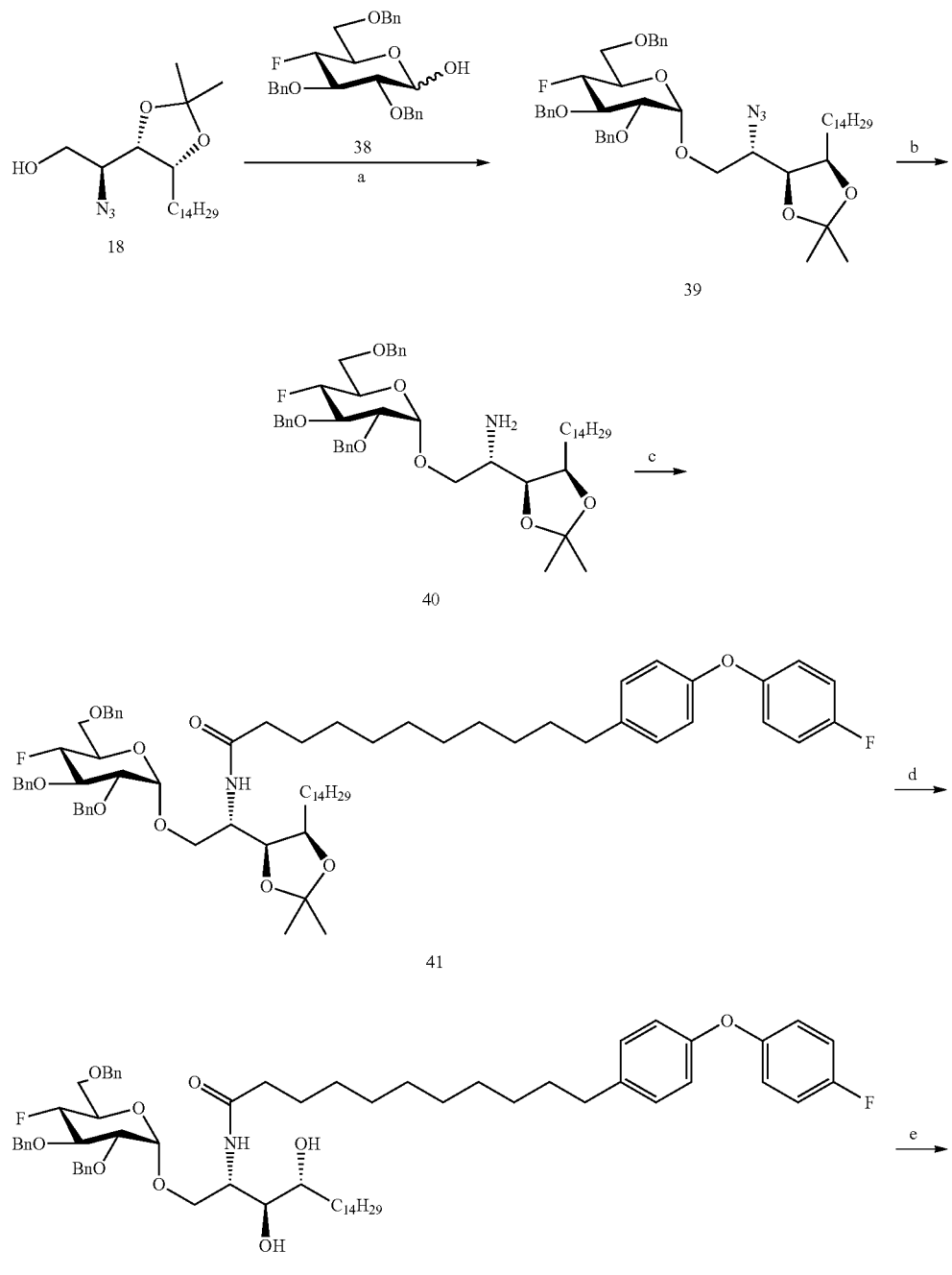

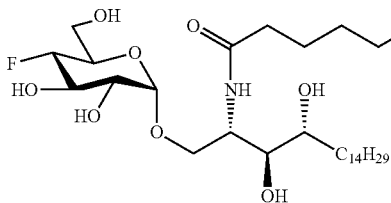

Compound 39

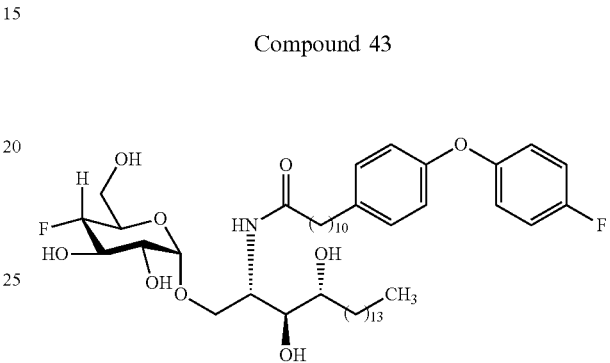

Compound 43

To a solution of donor 38, dimethylsulfide, 4 Å molecular sieve and 2-chloropyridine in anhydrous $CH_2Cl_2$ was added trifluoromethanesulfonic anhydride at −45° C. under argon. The reaction was stirred for 20 min at −45° C., 20 min at 0° C. and another 20 min at ambient temperature, followed by the addition of acceptor 18 in $CH_2Cl_2$. The reaction was stirred for 16 h at ambient temperature under argon. The solution was filtered through Celite 545 to remove molecular sieve. After removal of the solvent, the residue was diluted with AcOEt, the solution was washed with $H_2O$ and brine, dried over $MgSO_4$ and evaporated to dryness. The mixture was purified by flash column chromatography on silica gel to give 39.

Compound 40

To a solution of 39 in pyridine/$H_2O$ (10:1) was added triphenylphosphine. The reaction was stirred for 16 h at 45° C. under argon. After removal of the solvent, the residue was diluted with AcOEt, extracted with $H_2O$, brine and dried over $MgSO_4$ then evaporated to dryness. The mixture was used for next step without prior purification.

Compound 41

To a solution of compound 40 in anhydrous $CH_2Cl_2$ was added 4-(4-fluorophenoxy)phenylundecanoic acid, $Et_3N$, EDC and HBTu. The reaction was stirred for 16 h at ambient temperature under argon. After removal of the solvent, the residue was diluted with AcOEt, extracted with $H_2O$, brine and dried over $MgSO_4$ then evaporated to dryness. The mixture was purified by flash column chromatography on silica gel to give 41.

Compound 42

To a solution of compound 41 in aqueous acetic acid solution (AcOH: $H_2O$ 4:1) and stirred for 16 h at 60° C. After removal of the solvent, the mixture was dissolved in ethyl acetate, washed with saturated $NaHCO_3$ solution and brine, dried over $MgSO_4$ and evaporated. The residue was purified by flash column chromatography on silica gel to give 42.

The deacetonide derivative 42 was dissolved in co-solvent (MeOH:$CHCl_3$ 4:1) containing palladium hydroxide on carbon (20% Pd) (cat.) and stirred for 16 h in an $H_2$ atmosphere. The solution was filtered through Celite 545 to remove the catalyst and evaporated to dryness, the mixture was purified by flash column chromatography on silica gel and eluted with LH20 to give 43. $^1H$ NMR (MeOD-$CDCl_3$ 1:1, 600 MHz) δ: 7.09 (1H, d, J=8.4 Hz), 6.96-6.99 (2H, m), 6.91-6.92 (2H, m), 6.82-6.84 (2H, m), 4.84 (1H, t, J=3.6 Hz), 4.25 (0.5H, t, J=9.0 Hz), 4.15-4.18 (2H, m), 3.82-3.85 (2H, m), 3.75-3.77 (1H, m), 3.69-3.72 (1H, m), 3.64-3.68 (2H, m), 3.50-3.54 (2H, m), 3.44 (1H, dd, J=9.6, 3.6 Hz), 2.54 (2H, t, J=7.2 Hz), 2.17 (2H, t, J=7.8 Hz), 1.50-1.64 (7H, m), 1.22-1.27 (41H, m), 0.84 (3H, t, J=7.2 Hz). $^{13}C$ NMR (MeOD-$CDCl_3$ 1:1, 150 MHz) δ: 175.28, 160.20, 158.61, 156.16, 154.30, 138.67, 130.28, 120.70, 120.64, 119.04, 116.81, 116.66, 99.94, 90.61, 89.41, 75.04, 72.72, 72.59, 72.56, 72.42, 72.37, 70.82, 70.66, 67.82, 61.21, 51.10, 37.05, 35.83, 32.91, 32.61, 32.36, 30.46, 30.43, 30.39, 30.33, 30.27, 30.19, 30.18, 30.09, 30.03, 29.92, 26.63, 26.55, 23.32, 14.41. HRMS (ESI-TOF) for $C_{47}H_{75}F_2NO_9H^+$ $[M+H]^+$ calcd 836.5498. found 836.5483.

Synthesis of Fluorinated Donor 48

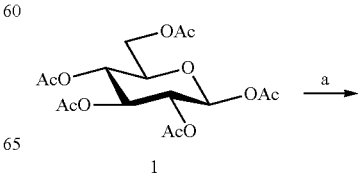

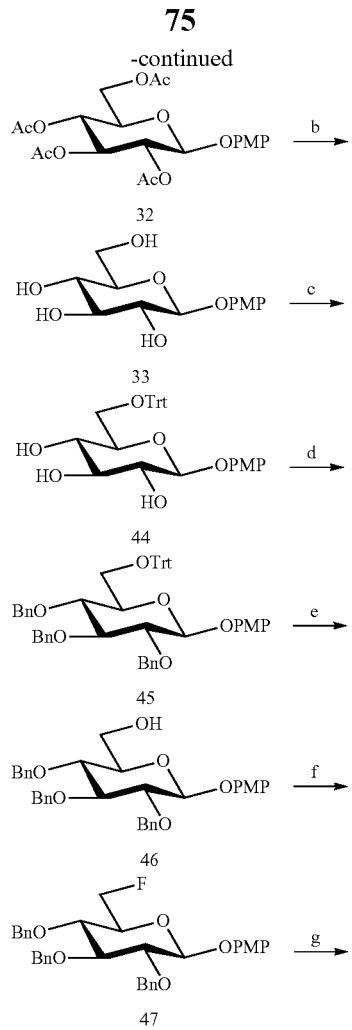

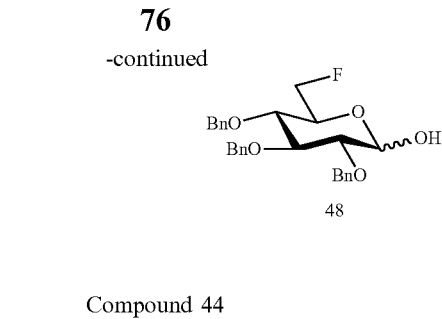

Compound 44

To a solution of 32 in dry pyridine was added triphenylmethyl chloride. The reaction was stirred for 16 h at 60° C. under argon. After removal of the solvent, the mixture was purified by flash column chromatography on silica gel to give 44.

Compound 45

To a solution of 44 in N,N-dimethylformamide (DMF) was added sodium hydride (60% in mineral oil) at 0° C. The reaction was stirred for 1 h, followed by the addition of benzyl bromide and stirred for 16 h under argon at ambient temperature. The reaction was quenched by MeOH and evaporated to dryness. The residue was diluted with AcOEt, the solution was washed with $H_2O$ and brine, dried over $MgSO_4$, and evaporated to dryness. The mixture was purified by flash column chromatography on silica gel to give 45.

Compound 46

To a solution of 45 in aqueous acetic acid solution ($AcOH:H_2O$ 4:1) was stirred for 3 h at 75° C. After removal of the solvent, the mixture was diluted with AcOEt, the solution was washed with $H_2O$ and brine, dried over $MgSO_4$, and evaporated to dryness. The residue was purified by flash column chromatography on silica gel to give 46.

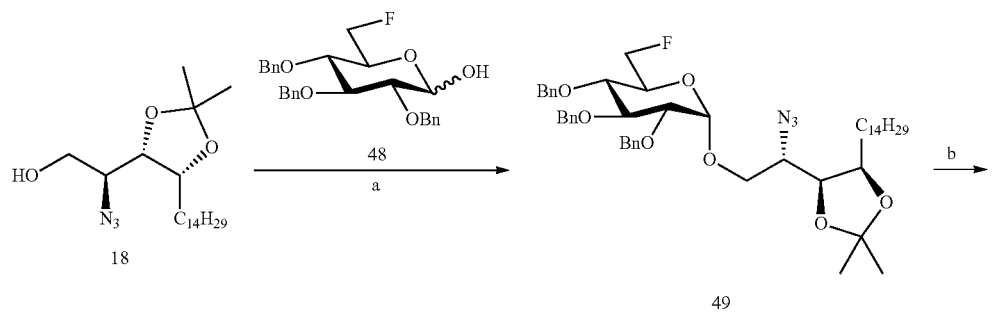

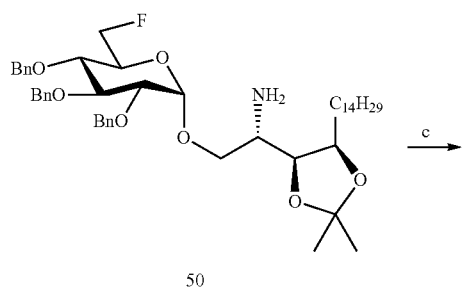

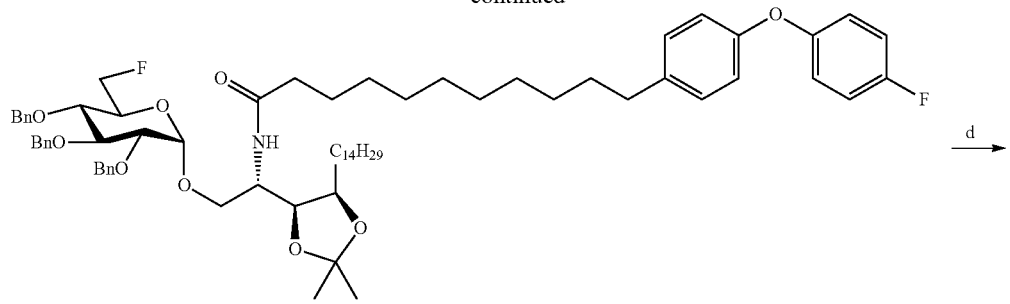

51

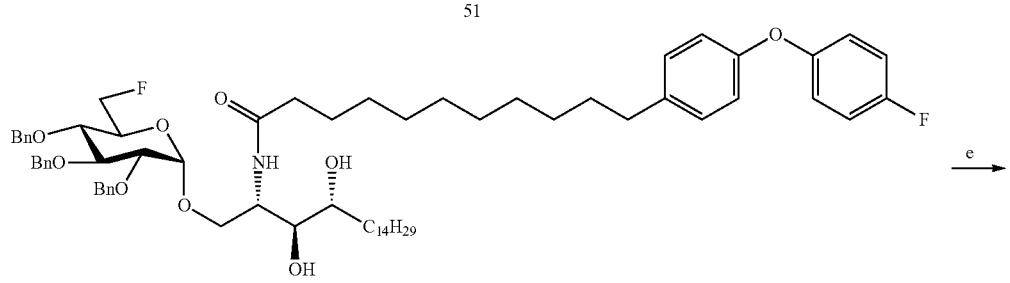

52

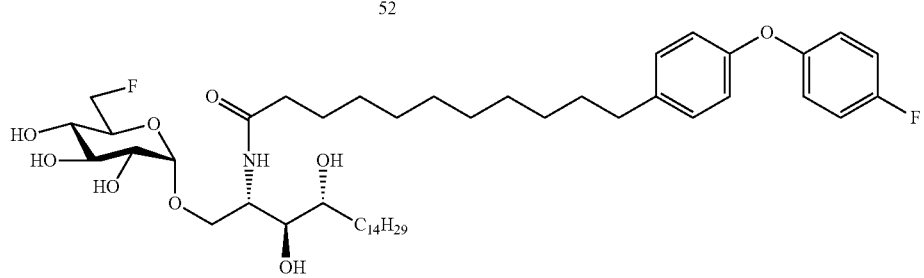

43

Compound 47

To a solution of 46 in CH$_2$Cl$_2$ was added diethylaminosulfur trifluoride (DAST). The reaction was stirred for 16 h at 45° C. and the solution was directly washed with H$_2$O, saturated NaHCO$_3$ solution and brine, dried over MgSO$_4$, and evaporated to dryness. The residue was purified by flash column chromatography on silica gel to give compound 47.

Compound 48

To a solution of 47 in dry co-solvent (toluene, H$_2$O and CH$_3$CN) was added ceric ammonium nitrate (CAN). The reaction was stirred for 10 min at ambient temperature. The solution was extracted with ethyl acetate, washed with H$_2$O, saturated NaHCO$_3$ solution and H$_2$O, dried over MgSO$_4$, and evaporated to dryness. The residue was purified by flash column chromatography on silica gel to give compound 48 as colorless oil.

Synthesis of Fluorinated Analogue 53

Compound 49

To a solution of donor 48, dimethylsulfide, 4 Å molecular sieve and 2-chloropyridine in anhydrous CH$_2$Cl$_2$ was added trifluoromethanesulfonic anhydride at −45° C. under argon. The reaction was stirred for 20 min at −45° C., 20 min at 0° C. and another 20 min at ambient temperature, followed by the addition of acceptor 18 in CH$_2$Cl$_2$. The reaction was stirred for 16 h at ambient temperature under argon. The solution was filtered through Celite 545 to remove molecular sieve. After removal of the solvent, the residue was diluted with AcOEt, the solution was washed with H$_2$O and brine, dried over MgSO$_4$ and evaporated to dryness. The mixture was purified by flash column chromatography on silica gel (hexanes:AcOEt 10:1) to give 49.

Compound 50

To a solution of 49 in pyridine/H$_2$O (10:1) was added triphenylphosphine. The reaction was stirred for 16 h at 45° C. under argon. After removal of the solvent, the residue was diluted with AcOEt, extracted with H$_2$O, brine and dried over MgSO$_4$ then evaporated to dryness. The mixture was used for next step without prior purification.

Compound 51

To a solution of compound 50 in dry CH$_2$Cl$_2$ was added 4-(4-fluorophenoxy)phenylundecanoic acid, Et$_3$N, EDC and HBTu. The reaction was stirred for 16 h at ambient temperature under argon. After removal of the solvent, the mixture was diluted with AcOEt, extracted with H$_2$O, brine and dried over MgSO₄ then evaporated to dryness. The residue was purified by flash column chromatography on silica gel to give 51.

Compound 52

To a solution of compound 51 was dissolved in aqueous acetic acid solution (AcOH: H₂O 4:1) and stirred for 16 h at 60° C. After removal of the solvent, the mixture was diluted with AcOEt, extracted with H₂O, brine and dried over MgSO₄ then evaporated to dryness. The residue was purified by flash column chromatography on silica gel.

Compound 53

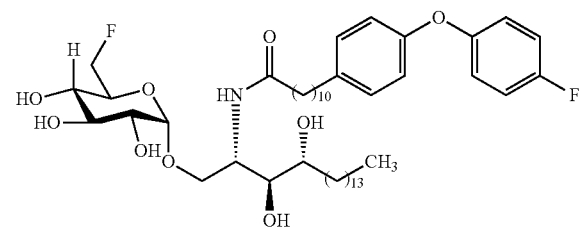

The deacetonide derivative 52 was dissolved co-solvent (MeOH:CHCl₃ 4:1) containing palladium hydroxide on carbon (20% Pd) (cat.) and stirred for 16 h in an H₂ atmosphere. The solution was filtered through Celite 545 to remove the catalyst and evaporated to dryness, the mixture was purified by flash column chromatography on silica gel and eluted with LH20 to give 53. ¹H NMR (MeOD-CDCl₃ 1:1, 600 MHz) δ: 7.51 (0.6H, d, J=8.4 Hz), 7.09-7.11 (2H, m), 6.97-7.00 (2H, m), 6.91-6.94 (2H, m), 6.83-6.85 (2H, m), 4.85 (1H, d, J=3.6 Hz), 4.49-4.59 (2H, m), 4.15-4.18 (1H, m), 3.85 (1H, dd, J=10.8, 4.8 Hz), 3.61-3.71 (3H, m), 3.52-3.58 (2H, m), 3.43 (1H, d, J=9.6, 3.6 Hz), 3.36 (1H, t, J=9.0 Hz), 2.55 (2H, t, J=7.8 Hz), 2.18 (2H, t, J=7.8 Hz), 1.51-1.64 (6H, m), 1.23-1.39 (39H, m), 0.85 (3H, t, J=7.2 Hz). ¹³C NMR (MeOD-CDCl₃ 1:1, 150 MHz) δ: 175.06, 174.98, 159.99, 158.40, 155.94, 154.09, 154.08, 138.48, 130.09, 120.52, 120.46, 118.85, 116.63, 116.47, 100.02, 83.18, 82.04, 74.72, 74.31, 72.44, 72.38, 71.78, 71.67, 69.58, 69.54, 50.88, 50.79, 36.88, 36.83, 35.64, 32.64, 32.42, 32.17, 30.29, 30.24, 30.20, 30.14, 30.08, 30.01, 29.99, 29.91, 29.85, 29.74, 26.42, 26.38, 23.13, 14.26. HRMS (ESI-TOF) for C₄₇H₇₅F₂NO₉H⁺ [M+H]⁺ calcd 836.5483. found 836.5498.

Synthesis of α-Galactosylceramide Analogues

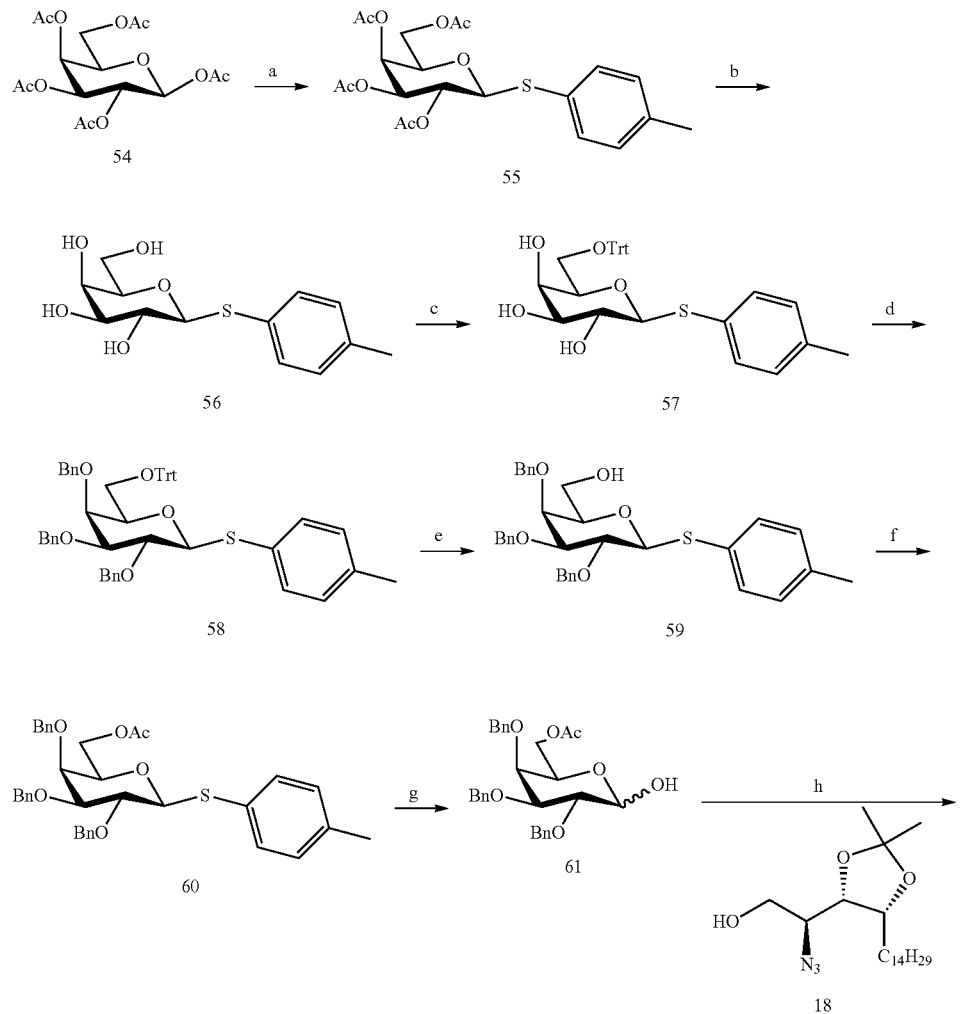

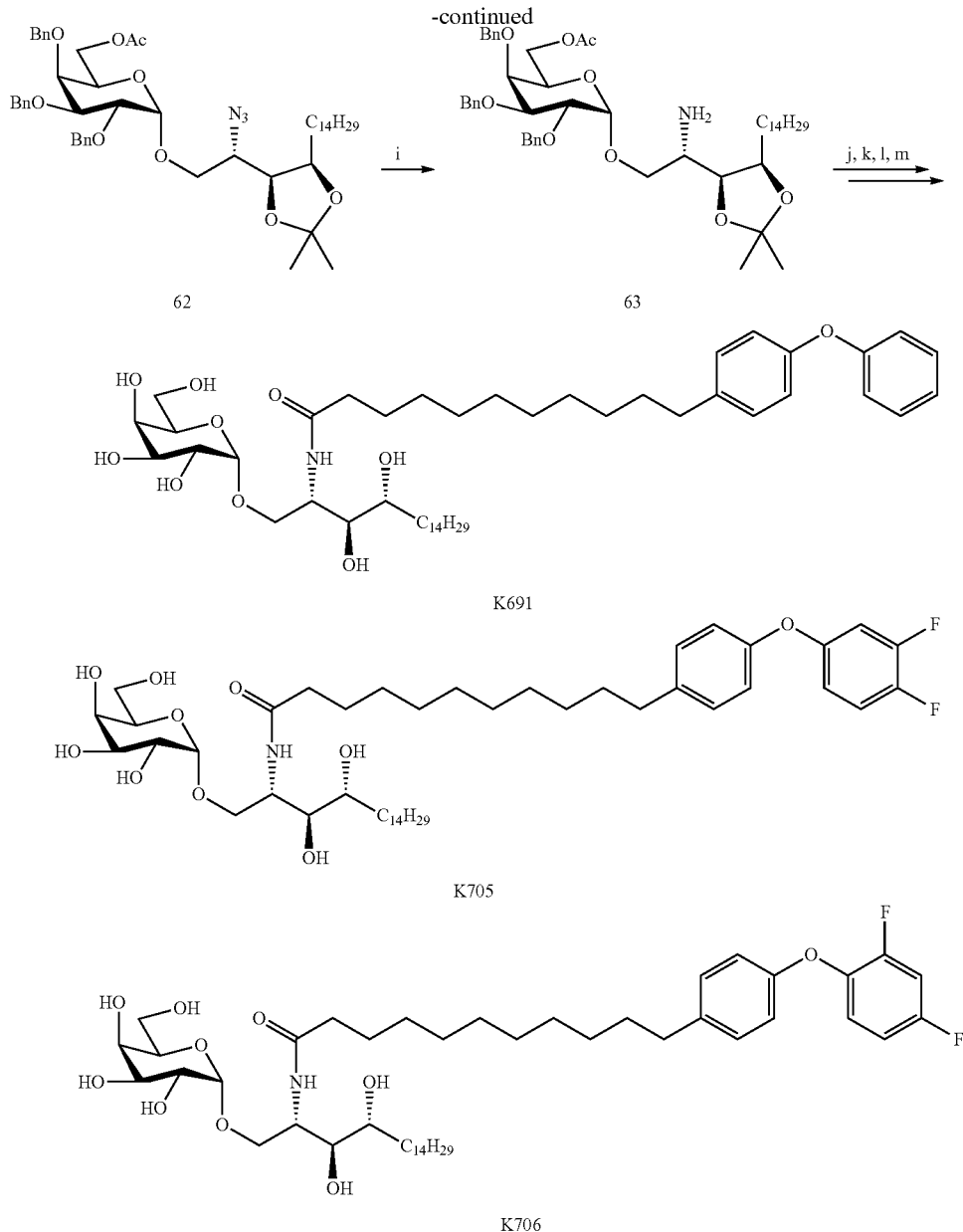

Synthesis of α-galactosylceramide analogues, reagents and conditions were as follows. a, thiocresol, BF$_3$OEt$_2$, CH$_2$Cl$_2$, 0° C., 16 h. b, NaOMe, MeOH, rt, 3 h, two steps 90%. c, triphenylmethyl chloride, pyridine, 60° C., 16 h, 64%. d, BnBr, NaH, DMF, 0° C., 16 h, 75%. e, 80% AcOH, 70° C., 3 h, 92%. f, Ac$_2$O, pyridine, 0° C., 5 h, 99%. g, NBS, 80% acetone, rt, 1 h, 70%. h, Tf$_2$O, 2-cl-pyr., Me$_2$S, CH$_2$Cl$_2$, −45° C., 16 h, 60%. i, PPh$_3$, pyr/H$_2$O, 50° C. j, EDC, HBTu, Et$_3$N, CH$_2$Cl$_2$, rt., 16 h, 80%. k, NaOMe, MeOH/CH$_2$Cl$_2$, 90%. l, 80% AcOH, 70° C., 16 h, 50%. m, H$_2$, Pd(OH)$_2$, MeOH/CH$_2$Cl$_2$, 70%.

Compound 55

To a solution of 1,2,3,4,6-Penta-O-acetyl-β-D-galactopyranose 54 (40 g, 102.5 mmol) in 200 mL of dry CH$_2$Cl$_2$ was added p-toluenethiol (15.4 g, 123 mmol) and BF$_3$OEt$_2$ (15.4 mL, 123 mmol) at 0° C., the reaction was stirred for 16 h at ambient temperature under argon. The resulting solution was directly extracted with saturated NaHCO$_3$ solution, brine, dried over MgSO$_4$ and evaporated. Followed by recrystallization in a solution of AcOEt-hexanes to give 55 as white solid. $^1$H NMR (CDCl$_3$, 600 MHz): δ 7.39 (d, 2H, J=8.0 Hz), 7.10 (d, 2H, J=8.0 Hz), 5.38 (d, 1H, J=3.3 Hz), 5.19 (t, 1H, J=10.0, 10.0 Hz), 5.11 (dd, 1H, J=10.0, 3.3 Hz), 4.62 (d, 1H, J=10.0 Hz), 4.16 (dd, 1H, J=11.3, 6.6 Hz), 4.09 (dd, 1H, J=11.3, 6.6 Hz), 3.88 (t, 1H, J=6.6, 6.6 Hz), 2.32 (s, 3H), 2.09 (s, 3H), 2.08 (s, 3H), 2.02 (s, 3H), 1.95 (s, 3H). $^{13}$C NMR (CDCl$_3$, 150 MHz): δ 170.62, 170.45, 170.32, 169.68, 138.70, 133.36, 129.86, 128.83, 87.20, 74.55, 72.24, 67.48, 67.41, 61.79, 21.38, 21.09, 20.90, 20.86, 20.82. HRMS (ESI-TOF) for C$_{21}$H$_{26}$O$_9$SNa$^+$ [M+Na]$^+$ calcd 477.1190. found 477.1236.

Compound 56

To a solution of 55 in 500 mL of dry MeOH was added catalytic amount of sodium methoxide (NaOMe) and stirred for 3 h at ambient temperature. The reaction was neutralized by adding Amberlite IR-120 and filtered, the resulting solution was concentrated to dryness to give 56 (26.3 g, two steps 90%) as white solid, which was directly used for next reaction without further purification. $^1$H NMR (MeOD, 600 MHz): δ 7.45 (d, 2H, J=8.1 Hz), 7.12 (d, 2H, J=8.1 Hz), 4.50 (d, 1H, J=9.6 Hz), 3.89 (d, 1H, J=3.3 Hz), 3.75 (dd, 1H, J=11.4, 6.0 Hz), 3.70 (dd, 1H, J=11.4, 6.0 Hz), 3.57 (t, 1H, J=9.6 Hz), 3.53 (t, 1H, J=6.0 Hz), 3.48 (dd, 1H, J=9.6, 3.3 Hz), 2.31 (s, 3H). $^{13}$C NMR (MeOD, 150 MHz): δ 138.55, 133.03, 132.26, 130.67, 90.83, 80.72, 76.49, 71.15, 70.55, 62.73, 21.22. HRMS (ESI-TOF) for $C_{13}H_{18}O_5SNa^+$ [M+Na]$^+$ calcd 309.0767. found 309.0748.

Compound 57

To a solution of 56 (26.3 g, 91.9 mmole) in 113 mL of dry pyridine was added triphenylmethyl chloride (32 g, 116 mmole). The reaction was stirred for 16 h at 60° C. under argon. After removal of the solvent, the mixture was purified by flash column chromatography on silica gel (hexanes:AcOEt:MeOH 1:1:0.1) to give 57 (31.1 g, 64%) as white powder. $^1$H NMR (MeOD, 600 MHz): δ 7.53 (d, 2H, J=7.5 Hz), 7.45 (m, 6H), 7.27 (m, 6H), 7.22 (m, 6H), 7.04 (d, 2H, J=7.5 Hz), 4.57 (d, 1H, J=9.5 Hz), 3.69 (d, 1H, J=3.3 Hz), 3.53-3.59 (m, 3H, J=9.5, 8.4, 1.2 Hz), 3.42 (dd, 1H, J=9.5, 3.3 Hz), 3.12 (dd, 1H, J=8.4, 1.2 Hz), 2.26 (s, 3H). $^{13}$C NMR (MeOD, 150 MHz): δ 145.62, 138.26, 132.69, 132.62, 130.78, 130.10, 128.92, 128.18, 90.62, 88.14, 79.78, 76.43, 71.38, 71.30, 65.81, 21.29. HRMS (ESI-TOF) for $C_{32}H_{32}O_5SNa^+$ [M+Na]$^+$ calcd 551.1863. found 551.1840.

Compound 58

To a solution of 57 (31.1 g, 58.7 mmole) in 300 mL of dry N,N-dimethylformamide (DMF) was added sodium hydride (60% in mineral oil) (8.5 g, 211.3 mmole) at 4° C. The reaction was stirred for 1 h, followed by the addition of benzyl bromide (25.3 mL, 211.3 mmole) then stirred for 16 h under argon at ambient temperature. The reaction was quenched by MeOH and evaporated to dryness. The residue was diluted with AcOEt, extracted with H$_2$O and brine then dried over MgSO$_4$. After removal of the solvent, the mixture was purified by flash column chromatography on silica gel (hexanes:AcOEt 10:1) to give 58 (35 g, 75%) as white powder. $^1$H NMR (CDCl$_3$, 600 MHz): δ 7.42 (d, 2H, J=7.8 Hz), 7.37 (d, 8H, J=7.8 Hz), 7.18-7.34 (m, 20H, J=7.8 Hz), 7.11 (m, 2H), 6.92 (d, 2H, J=7.8 Hz), 4.83 (d, 1H, J=11.4 Hz), 4.71-4.76 (m, 2H), 4.66-4.70 (m, 2H), 4.51 (d, 1H, J=9.6 Hz), 4.48 (d, 1H, J=11.4 Hz), 3.88 (d, 1H, J=2.4 Hz), 3.83 (t, 1H, J=9.6 Hz), 3.54 (dd, 1H, J=9.6, 6.3 Hz), 3.51 (dd, 1H, J=9.6, 2.4 Hz), 3.30 (t, 1H, J=6.3 Hz), 3.21 (dd, 1H, J=9.6, 6.3 Hz), 2.25 (s, 3H). $^{13}$C NMR (CDCl$_3$, 150 MHz): δ 144.07, 138.89, 138.58, 138.56, 137.14, 131.92, 130.65, 129.73, 128.83, 128.61, 128.57, 128.53, 128.22, 128.04, 127.91, 127.89, 127.82, 127.43, 127.23, 88.13, 87.13, 84.38, 77.71, 77.50, 75.79, 74.32, 74.15, 73.07, 63.00, 21.29. HRMS (ESI-TOF) for $C_{53}H_{50}O_5SNa^+$ [M+Na]$^+$ calcd 821.3271. found 821.3228.

Compound 59

To a solution of 58 (31.5 g, 39.4 mmol) in 1000 mL of aqueous acetic acid solution (AcOH: H$_2$O 4:1) was stirred for 2 h at 75° C. After removal of the solvent, the residue was purified by flash column chromatography on silica gel (hexanes:AcOEt 2:1) to give 59 (20.2 g, 92%) as colorless oil. $^1$H NMR (CDCl$_3$, 600 MHz): δ 7.43 (d, 2H, J=7.8 Hz), 7.38 (d, 2H, J=7.2 Hz), 7.26-7.35 (m, 13H), 7.02 (d, 2H, J=7.8 Hz), 4.95 (d, 1H, J=12.0 Hz), 4.82 (d, 1H, J=12.0 Hz), 4.75 (d, 1H, J=12.0 Hz), 4.74 (d, 1H, J=9.6 Hz), 4.72 (d, 1H, J=12.0 Hz), 4.62 (d, 1H, J=12.0 Hz), 4.57 (d, 1H, J=12.0 Hz), 3.90 (t, 1H, J=9.6 Hz), 3.82 (d, 1H, J=3.0 Hz), 3.81 (dd, 1H, J=11.1, 6.6 Hz), 3.58 (dd, 1H, J=9.6, 3.0 Hz), 3.50 (dd, 1H, J=11.1, 6.6 Hz), 3.40 (t, 1H, J=6.6 Hz), 2.87 (s, 3H). $^{13}$C NMR (CDCl$_3$, 150 MHz): δ 138.53, 138.49, 138.35, 137.63, 132.43, 130.20, 129.85, 128.72, 128.61, 128.57, 128.55, 128.43, 128.04, 128.02, 127.99, 127.86, 88.24, 84.49, 78.94, 77.74, 75.89, 74.33, 73.45, 73.26, 62.50, 21.32. HRMS (ESI-TOF) for $C_{34}H_{36}O_5SNa^+$ [M+Na]$^+$ calcd 579.2176. found 579.2193.

Compound 60

To a solution of 59 (3.1 g, 5.6 mmol) in 10 mL of dry pyridine was added acetic anhydride (0.7 mL, 6.7 mmol). The reaction was stirred for 16 h at ambient temperature under argon. After removal of the solvent, the residue was diluted with AcOEt, extracted with H$_2$O, brine then dried over MgSO$_4$. The mixture was purified by flash column chromatography on silica gel (hexanes:AcOEt 5:1) to give 60 (3.3 g, 99%) as white solid. $^1$H NMR (CDCl$_3$, 600 MHz): δ 7.45 (d, 2H, J=8.0 Hz), 7.37 (d, 2H, J=7.0 Hz), 7.26-7.35 (m, 13H), 7.00 (d, 2H, J=8.0 Hz), 4.96 (d, 1H, J=11.0 Hz), 4.81 (d, 1H, J=11.0 Hz), 4.75 (d, 1H, J=11.0 Hz), 4.74 (d, 1H, J=9.3 Hz), 4.72 (d, 1H, J=11.0 Hz), 4.61 (d, 1H, J=11.0 Hz), 4.54 (d, 1H, J=11.0 Hz), 4.24 (dd, 1H, J=11.2, 6.5 Hz), 4.09 (dd, 1H, J=11.2, 6.5 Hz), 3.89 (t, 1H, J=9.3 Hz), 3.81 (d, 1H, J=2.5 Hz), 3.57 (dd, 1H, J=9.3, 2.5 Hz), 3.55 (t, 1H, J=6.5 Hz), 2.28 (s, 3H), 1.97 (s, 3H). $^{13}$C NMR (CDCl$_3$, 150 MHz): δ 170.84, 138.46, 138.33, 137.60, 132.57, 130.31, 129.73, 128.70, 128.57, 128.46, 128.33, 128.00, 127.89, 127.80, 88.32, 84.40, 77.55, 76.14, 75.90, 74.43, 73.47, 73.32, 63.63, 21.32, 21.05. HRMS (ESI-TOF) for $C_{36}H_{38}O_6SNa^+$ [M+Na]$^+$ calcd 621.2281. found 621.2322.

Compound 61

To a solution of 60 (102 mg, 0.17 mmol) in 2 mL of aqueous acetone solution (acetone: H$_2$O 4:1) was added N-bromosuccinimide (30 mg, 0.17 mmol). The reaction was stirred for 1 h at ambient temperature. After removal of the solvent, the residue was diluted with AcOEt, extracted with H$_2$O, aqueous sodium thiosulfate (NaS$_2$O$_3$) solution, brine then dried over MgSO$_4$. The mixture was purified by flash column chromatography on silica gel (hexane: AcOEt 2:1) to give 61 (64 mg, 76%) as white solid.

Compound 62

To a solution of galactosyl donor 61 (5.8 g, 11.8 mmol), dimethylsulfide (1.1 mL, 15.6 mmol), 4 Å molecular sieve (1 g) and 2-chloropyridine (3.6 mL, 39 mmol) in anhydrous CH$_2$Cl$_2$ (30 mL) was added trifluoromethanesulfonic anhydride (2 mL, 11.9 mmol) at −45° C. under argon. The reaction was stirred for 20 min at −45° C., 20 min at 0° C. and another 20 min at ambient temperature, followed by the addition of galactosyl acceptor 18 in 10 mL of CH$_2$Cl$_2$. The reaction was stirred for 16 h at ambient temperature under argon. The solution was filtered through Celite 545 to remove molecular sieve. After removal of the solvent, the residue was diluted with AcOEt, extracted with H$_2$O, brine and dried over MgSO$_4$ then evaporated to dryness. The mixture was purified by flash column chromatography on silica gel (hexanes:AcOEt 15:1) to give 62 as colorless oil (4 g, 60%). $^1$H NMR (CDCl$_3$, 600 MHz) δ: 7.37-7.24 (m, 15H), 4.95 (d, J=11.5 Hz, 1H), 4.91 (d, J=3.6 Hz, 1H), 4.86 (d, J=11.5 Hz, 1H), 4.77 (d, J=11.5 Hz, 1H), 4.71 (d, J=11.5 Hz, 1H), 4.67 (d, J=11.5 Hz, 1H), 4.59 (d, J=11.5 Hz, 1H), 4.11 (dd, J=10.7 Hz, 7.6 Hz, 1H), 4.08 (m, J=4.4 Hz, 1H), 4.05 (dd, J=10.1 Hz, 3.6 Hz, 1H), 4.02 (dd, J=10.7 Hz, 3.5 Hz, 1H), 4.01 (dd, J=10.5 Hz, 2.4 Hz, 1H), 4.00 (dd, J=9.2 Hz, 4.4 Hz, 1H), 3.95 (dd, J=10.1 Hz, 2.7 Hz, 1H), 3.92 (dd, J=7.6 Hz, 3.5 Hz, 1H), 3.83 (d, J=2.7 Hz, 1H), 3.69 (dd, J=10.5 Hz, 6.6 Hz, 1H), 3.40 (ddd, J=9.2 Hz, 6.6 Hz, 2.4 Hz, 1H), 1.95 (s, 3H), 1.60 (s, 3H), 1.50 (m, 2H), 1.35 (s, 3H), 1.34-1.20 (m, 32H), 0.85 (t, J=6.8 Hz, 3H). $^{13}$C NMR (CDCl$_3$, 150 MHz) δ: 170.79, 138.95, 138.37, 128.67, 128.58, 128.55, 128.47, 128.00, 127.83, 127.80, 127.74, 127.70, 108.39, 98.96, 78.77, 77.93, 76.71, 75.46, 75.02, 74.73, 73.83, 73.15, 69.83, 69.13, 63.91, 59.93, 32.13, 29.90, 29.87, 29.83, 29.81, 29.77, 29.57, 29.52, 28.40, 26.73, 25.91, 22.90, 21.03, 14.34. HRMS (ESI-TOF) for C$_{50}$H$_{77}$FN$_3$O$_9$Na$^+$ [M+Na]$^+$ calcd 880.5083. found 880.5050.

Compound K691

$^1$H NMR (MeOD-CDCl$_3$ 1:1, 600 MHz): δ 7.26 (t, 2H, J=8.4 Hz), 7.09 (d, 2H, J=8.4 Hz), 7.02 (t, 1H, J=7.2 Hz), 6.92 (d, 2H, J=8.4 Hz), 6.86 (d, 2H, J=8.4 Hz), 4.85 (d, 1H, J=3.6 Hz), 4.16 (dd, 1H, J=9.6, 4.8 Hz), 3.88 (d, 1H, J=3.0 Hz), 3.84 (dd, 1H, J=10.8, 4.2 Hz), 3.74-3.78 (m, 2H), 3.63-3.73 (m, 4H), 3.48-3.54 (m, 2H), 2.54 (t, 2H, J=7.8 Hz), 2.17 (t, 2H, J=7.8 Hz), 1.49-1.64 (m, 6H), 1.19-1.35 (m, 39H). 0.83 (t, 3H, J=7.2 Hz). $^{13}$C NMR (MeOD-CDCl$_3$ 1:1, 150 MHz): δ 175.53, 158.77, 155.96, 138.90, 130.48, 130.42, 123.71, 119.74, 119.18, 100.77, 75.32, 72.74, 72.06, 71.22, 70.70, 69.91, 68.09, 62.59, 51.48, 37.19, 36.04, 32.99, 32.81, 32.57, 30.63, 30.57, 30.52, 30.47, 30.40, 30.37, 30.30, 30.23, 30.12, 26.82, 26.76, 23.50, 14.52. HRMS (MALDI-TOF) for C$_{47}$H$_{77}$NO$_{10}$H$^+$ [M+H]$^+$ calcd 816.5620. found 816.5621.

Compound K705

$^1$H NMR (MeOD-CDCl$_3$ 1:1, 600 MHz): δ 7.55 (d, 1H, J=9.0 Hz), 7.12 (t, 2H, J=8.4 Hz), 7.08 (dd, 1H, J=19.2, 9.0 Hz), 6.87 (d, 2H, J=8.4 Hz), 6.75-6.78 (m, 1H), 6.67-6.68 (m, 1H), 4.86 (d, 1H, J=3.6 Hz), 4.14-4.18 (m, 1H), 3.88 (d, 1H, J=3.0 Hz), 3.84 (dd, 1H, J=10.8, 4.2 Hz), 3.74-3.79 (m, 2H), 3.64-3.74 (m, 4H), 3.48-3.54 (m, 2H), 2.55 (t, 2H, J=7.2 Hz), 2.17 (t, 2H, J=7.8 Hz), 1.49-1.64 (m, 6H), 1.19-1.38 (m, 38H). 0.83 (t, 3H, J=6.6 Hz). $^{13}$C NMR (MeOD-CDCl$_3$ 1:1, 150 MHz): δ 175.40, 155.21, 155.07, 155.05, 154.99, 152.17, 152.08, 150.53, 150.44, 147.91, 147.82, 146.30, 146.22, 139.64, 130.55, 119.83, 118.26, 118.13, 114.55, 114.52, 114.51, 114.49, 108.40, 108.27, 100.63, 75.27, 72.65, 71.87, 71.10, 70.57, 69.78, 67.99, 62.49, 51.34, 37.12, 35.94, 32.98, 32.69, 32.40, 30.53, 30.51, 30.47, 30.40, 30.35, 30.28, 30.25, 30.18, 30.11, 30.00, 26.69, 26.64, 23.39, 14.47. HRMS (MALDI-TOF) for C$_{47}$H$_{75}$F$_2$NO$_{10}$H$^+$ [M+H]$^+$ calcd 852.5432. found 852.5443.

Compound K706

$^1$H NMR (MeOD-CDCl$_3$ 1:1, 600 MHz): δ 7.08 (d, 2H, J=8.4 Hz), 6.99-7.03 (m, 1H), 6.93-6.97 (m, 1H), 6.79-6.85 (m, 3H), 4.86 (d, 1H, J=4.2 Hz), 4.17 (dd, 1H, J=10.2, 4.2 Hz), 3.88 (d, 1H, J=3.6 Hz), 3.85 (dd, 1H, J=10.8, 4.8 Hz), 3.75-3.79 (m, 2H), 3.64-3.74 (m, 4H), 3.49-3.55 (m, 2H), 2.53 (t, 2H, J=7.8 Hz), 2.17 (t, 2H, J=7.2 Hz), 1.50-1.65 (m, 6H), 1.20-1.38 (m, 38H). 0.84 (t, 3H, J=7.2 Hz). $^{13}$C NMR (MeOD-CDCl$_3$ 1:1, 150 MHz): δ 175.36, 160.26, 160.19, 158.64, 158.57, 156.27, 155.90, 155.82, 154.24, 154.16, 141.26, 141.24, 141.18, 141.16, 138.59, 130.27, 123.22, 123.15, 117.51, 112.03, 112.01, 111.88, 111.86, 106.07, 105.92, 105.89, 105.74, 100.57, 75.27, 72.63, 71.78, 71.05, 70.52, 69.73, 67.97, 62.48, 51.28, 37.09, 35.81, 33.01, 32.64, 32.38, 30.49, 30.47, 30.42, 30.36, 30.31, 30.24, 30.21, 30.13, 30.07, 29.95, 26.65, 26.59, 23.36, 14.46. HRMS (MALDI-TOF) for C$_{47}$H$_{75}$F$_2$NO$_{10}$H$^+$ [M+H]$^+$ calcd 852.5432. found 852.5446.

Biological Studies

Injection of Glycolipid Analogs in Mice

All the glycolipids were dissolved in 100% DMSO at a concentration of 1-2 mg/ml. For in vivo experiments, all compounds were diluted to 10 μg/ml in saline just before injection of 100 μl diluted glycolipid or 100 μl 1% DMSO into mice. Pathogen-free C57BL/6 female mice aged 6-12 weeks were obtained from the National Laboratory Animal Center (Taipei, Taiwan). Jα18 knockout (KO) B6 mice were the gifts from Dr. Masaru Taniguchi (RIKEN Research Center for Allergy and Immunology, Yokohama, Japan). All the mice were maintained in pathogen free vivarium of Institute of Cellular and Organismic Biology, Academia Sinica (Taipei, Taiwan).

Determination of Murine Cytokine/Chemokine Secretions

B6 WT or Jα18 KO mice were intravenously injected with vehicle or glycolipids at 0.1 or 1 μg/mouse. Serum was collected at 2 and 18 h after injection for measurement of cytokines/chemokines by Beadlyte® Mouse Cytokine kit (Millipore, N.Y.) and read by a Luminex® 200™ system (Luminex, Austin, Tex.).

FACS Analyses of Mouse Immune Cells after the Specific Glycolipid Stimulation

B6 WT or Jα18 KO mice treated with specific glycolipid (1 μg/mouse) or vehicle (1% DMSO in PBS) were sacrificed at 72 hr post-injection and their spleens were harvested. After pressing spleens through 70 um strainer and lysis of erythrocytes, the nucleated cells were resuspended in PBS buffer containing azide (0.05%) and stained with antibodies recognizing the indicated cell surface antigens for 30 min at 4° C. After washing, the splenocytes were subjected to FACS analysis. The antibodies against CD3, CD4, CD8α, CD11c, CD80, and CD86 were obtained from BD Bioscience-Pharmingen.

Binding Strengths of the Binary Complex Between mCD1d and Glycolipid

Different concentrations of mCD1d$^{di}$-glycolipid complexes coated on the ELISA plate were incubated with the saturated amounts of L363 antibody (BioLegend) conjugated with biotin, followed by streptavidin-HRP detection and ELISA measurement. The KD between L363 antibody and the indicated mCD1d$^{di}$-glycolipid complex was calculated from the linear regression of the Scatchard transformation of the L363 antibody binding curve using GraphPad Prism software. L363 was found to recognize the mCD1d$^{di}$-7DW8-5-Glc complex and mCD1d$^{di}$-7DW8-5 complex with similar binding strength. Next, the KD of the binary complex was determined as follows. Different concentrations of glycolipids were incubated with fixed amounts of mCD1d dimer at 37° C. overnight, and then mCD1d$^{di}$-glycolipid complexes were coated on the 96 well ELISA plate at 4° C.

overnight. After washing and blocking with BSA at room temperature (RT) for 1 hr, L363 antibody conjugated with biotin was added for 30 min at RT, followed by incubation with streptavidin-HRP for 30 min at RT and detection with an ELSIA reader. KD values of the binary complex were calculated from the linear regression of the Scatchard transformation of the L363 antibody binding curve.

Expansion of Human iNKT Cells

Human naïve Vα24+ iNKT cells were cultured with autologous immature CD14+ DCs pulsed with the indicated glycolipid at 100 ng/ml or DMSO on day 2 for 18 h. On day 3, the suspension cells were transferred to a new dish, cultured in the presence of 50 U/ml IL-2 (R & D Systems), and replenished with fresh medium every 3 days. The percentage of Vα24+/Vβ11+ cells was determined by flow cytometry on day 9. The total cell number after expansion was calculated with the Guava ViaCount reagent (Millipore, USA) and detected by the Guava system with CytoSoft™ software containing the ViaCount module (Millipore, USA).

Binding Avidity of Various CD1d-Loaded Glycolipids to Vα14+ iNKT Cells

Briefly, murine CD1d:Ig dimer (BD Biosciences PharMingen, San Diego, Calif.) was loaded with glycolipids at a molar ratio of 1:10 or vehicle for overnight at 37° C. Murine 1.2 Vα14+ iNKT cells were incubated with various doses of dimer-glycolipid complex in buffer containing azide (0.05%) for 30 min at 4° C. These cells were then stained with anti-mouse IgG1-PE mAb (A85-1) for another 30 min at 4° C., followed by washing, fixation with 4% paraformaldehyde (PFA), and the bound mCD1d dimer complexes were detected by flow cytometry. The binding curve and linear fit of the Scatchard transformation were plotted by Graphpad Prism software.

Binding Avidity of CD1d-Loaded Glycolipids with Vα24+ iNKT Cells

Binding avidity of human CD1d-glycolipid complexes to Vα24+ iNKT cells expanded by 7DW8-5 at 100 ng/ml was determined as described previously.[19]

Isolation and Generation of Human Vα24+ iNKT Cell Lines and Immature Monocyte-Derived Dendritic Cells Vα24+ iNKT cells and CD14+ cells were isolated from peripheral blood cells as described previously.[19] Immature DCs were generated from the CD14+ cells after 2-day incubation in the presence of 300 U/ml GM-CSF (R & D Systems) and 100 U/ml IL-4 (R& D Systems).

Vα24+ iNKT cell lines expanded with 7DW8-5 or C1 were generated as follows. After irradiation with 2,000 rad, the immature DCs were cocultured with syngenic Vα24+ iNKT cells in the presence of 7DW8-5 or C1 at 100 ng/ml for 1 day. The cells were expanded in the presence of 50 U/ml IL-2 for 10-14 days after lipid removal. The same procedures were repeated once for further stimulation and expansion of iNKT cells. The 7DW8-5 or C1-expanded iNKT cell line was shown to express Vα24 T cell antigen receptor (>95% purity).

mCD1d Vs. hCD1d Swapping Assay

Murine DN3A4-1.2 Vα14+ iNKT hybridoma cells or C1-expanded Vα24+ iNKT cells were pulsed with the indicated glycolipid antigen presented either by mCD1d (A20-CD1d cells) or hCD1d (HeLa-CD1d cells) at 1, 0.1, and 0.01 µg/ml. After 18 hr, the supernatants were harvested for the measurement of cytokine secretion(s). IL-2 released from Vα14+ iNKT cells was determined by ELISA assay. IFN-γ, IL-4 and IL-2 secreted from Vα24+ iNKT cells were detected using Beadlyte® Human Cytokine kit (Millipore, N.Y., USA) and Luminex® 200 reading system.

Computer Modeling and Simulation

The crystal structures of both human and mouse CD1d (hCD1d and mCD1d) presenting α-GalCer to their respective iNKT TCRs were retrieved from the RCSB Protein Data Bank (www.rcsb.org; PDB coded 3HUJ, 3QUX, 3QUY, 3QUZ, and 3HE6). These crystal structures were superimposed by referencing to the backbone atoms of 3QUX. The two α-GalCer ternary structures obtained from 3HE6 and 3HUJ were used to create the other ternary complexes composed of different GSLs. The ternary structure containing C34 was derived from that containing C1 by modifying the acyl chain on Meastro (Schrödinger LLC, USA). The ternary structures bearing C1-Glc and C34-Glc were created by a inverting the 04 chirality of C1 and C34, respectively. The modeling for the remaining new ternary complexes were built using these GSLs and CD1d-iNKT TCR structures from 3QUX and 3HUJ for mice and humans, respectively. All structures were processed using Protein Preparation wizard (Schrödinger LLC, USA) and the lipid tails were further refined to minimize the steric collision using MacroModel's conformation search and energy minimization with the default methods and OPLS2005 force field in a solvent of water. The binding modes of GSLs to iNKT TCRs were recomputed by Autodock4.2 using a semi-empirical free energy force field to evaluate conformations during simulations. The estimated free energy of binding in solvent was computed by the equation built in the Autodock4.2:

$$\Delta G = \Delta V^L(\text{bound-undound}) + \Delta V^P(\text{bound-undound}) + \Delta V^{PL}(\text{bound-undound}) + \Delta S_{conf})$$

where L refers to the "ligand"; P refers to the "protein"; V refers to the pair-wise energetic terms including evaluations for dispersion/repulsion, hydrogen bonding, and electrostatics; $\Delta S_{conf}$ is an estimate of the conformational entropy lost upon binding. All required input files for running Autodock4 were prepared on MGLTools. A grid box of 60×60×60 Å$^3$ and various atom-typed energy maps were generated. In each molecular docking run, all hydroxyl groups were set to free rotation and the two lipid tails were assigned to their prior refined poses. The Lamarckian genetic algorithm (maximum number of 5.0×10$^7$ energy evaluations and 27,000 generations and a mutation rate of 0.02 with a crossover rate of 0.8) was employed for search. The results were visualized in MGLTools and the contribution of hydrogen bonding to individual residue was obtained by the built in function. Graphic representation was finished on Maestro.

Example

Demonstration of Efficacy

Figure 2A:
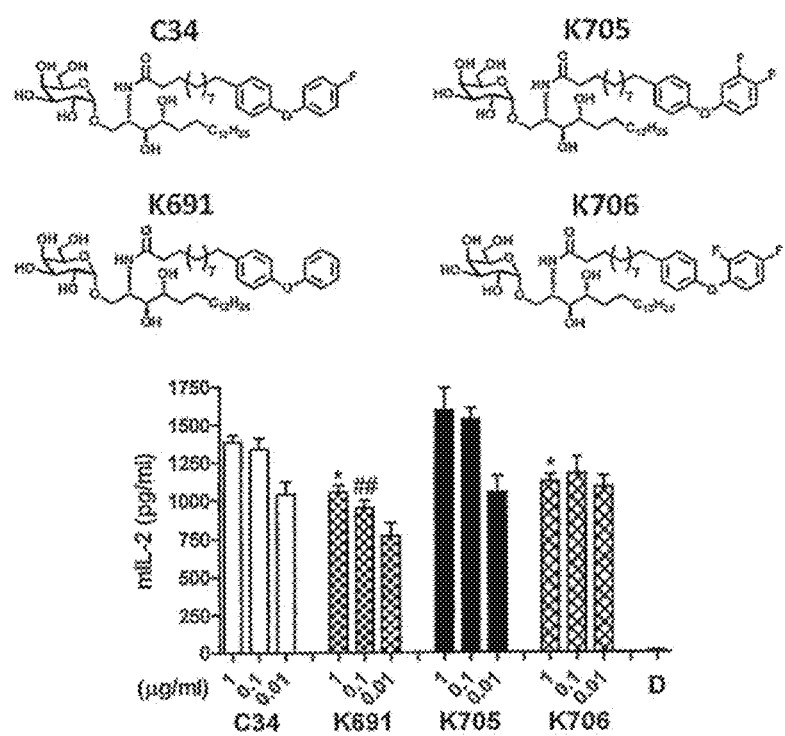
FIG. 2A. Exemplary representative C34 GSL derivatives (C34, K691, K705, K706) with galactose linkage. CD1d-reactive T cell hybridoma cells with a Vα14 T cell antigen receptor, DN3A4-1.2, were cultured with mouse CD1d presenting cells, A20-CD1d, in 96 wells and stimulated with different glycolipids at 1, 0.1, 0.01 μg/mL. After incubation for 18 h, IL-2 released into the medium as the readout of the iNKT cells activation was measured by an ELISA assay. K691 secreted significantly less amounts of IL-2 than C34 at 1 and 0.1 μg/mL, suggesting the importance of the presence of F on the 2$^{nd}$ phenyl ring of C34. K706 was significantly less potent than C34 to stimulate iNKT IL-2 secretion at 1 μg/mL. In the induction of mouse IL-2 secretion, K705 was similar to C34 at all concentrations and better than K706 at 1 and 0.1 μg/mL, indicating that the 2$^{nd}$ F at the meta position was better than at the ortho position to activate mouse iNKT cells. Taken together, the number and position of F atom on the 2$^{nd}$ phenyl ring can greatly modulate the mouse iNKT activation.
Figures 1, 2B:
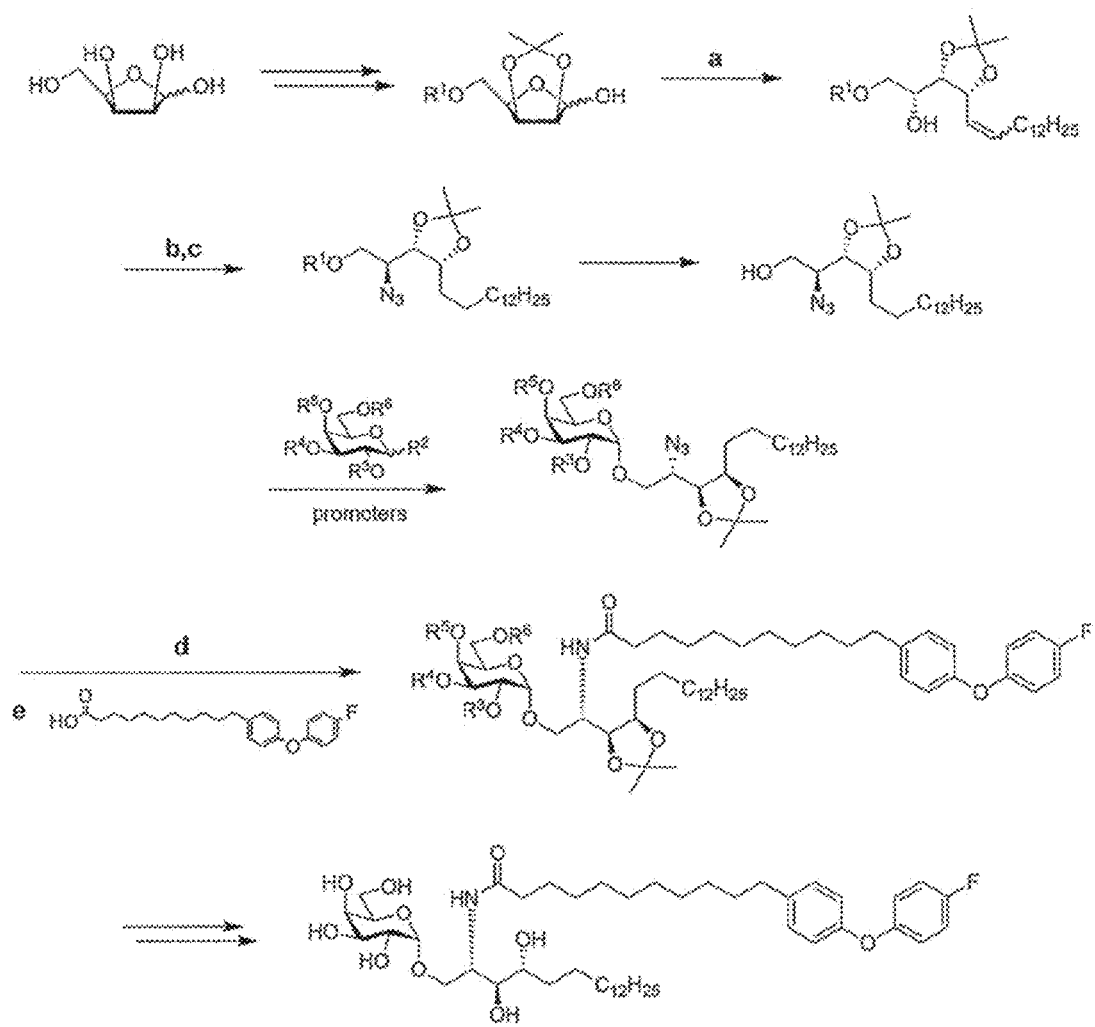
Figures 2, 2B:
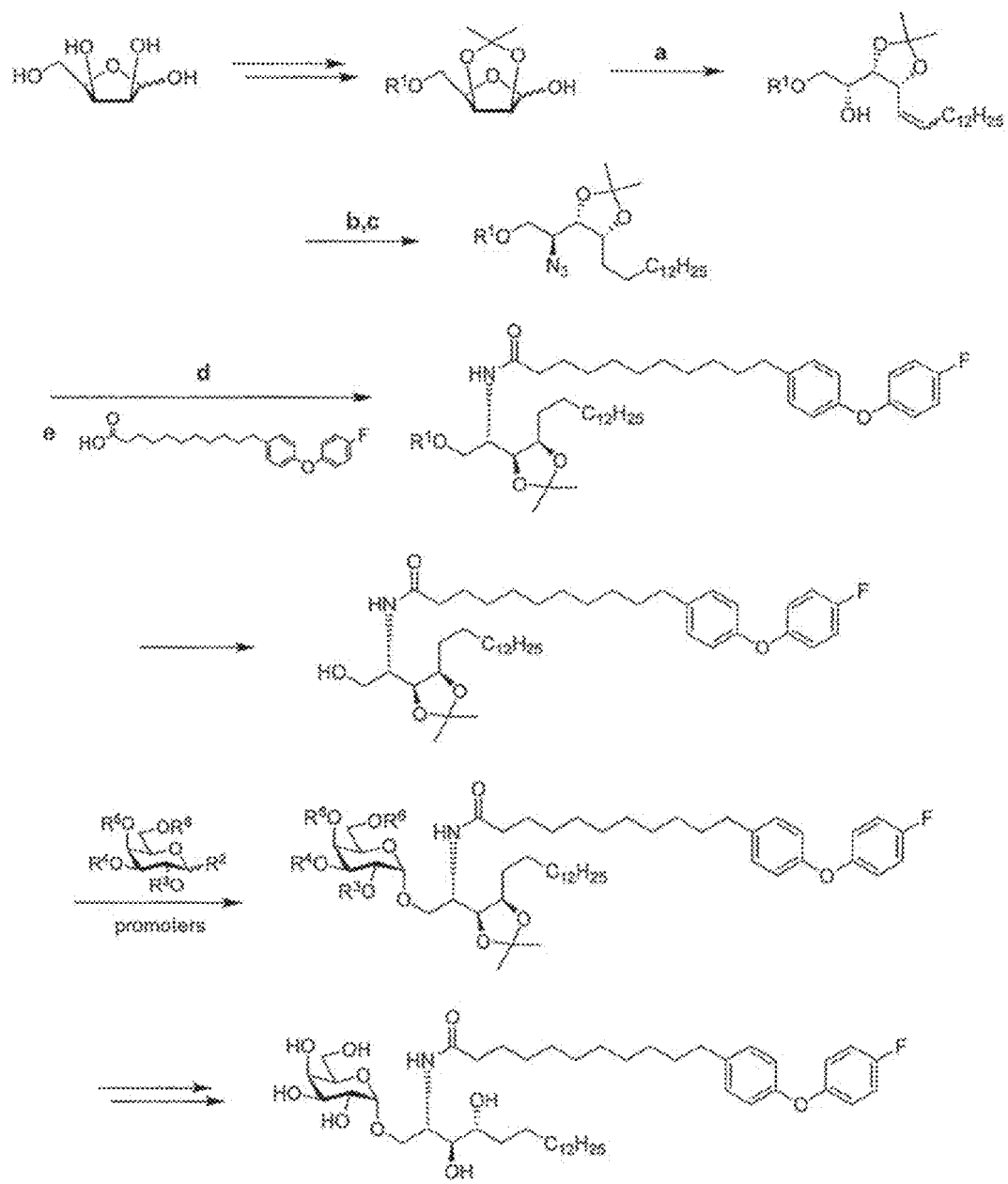
Figures 2, 2B, 3:
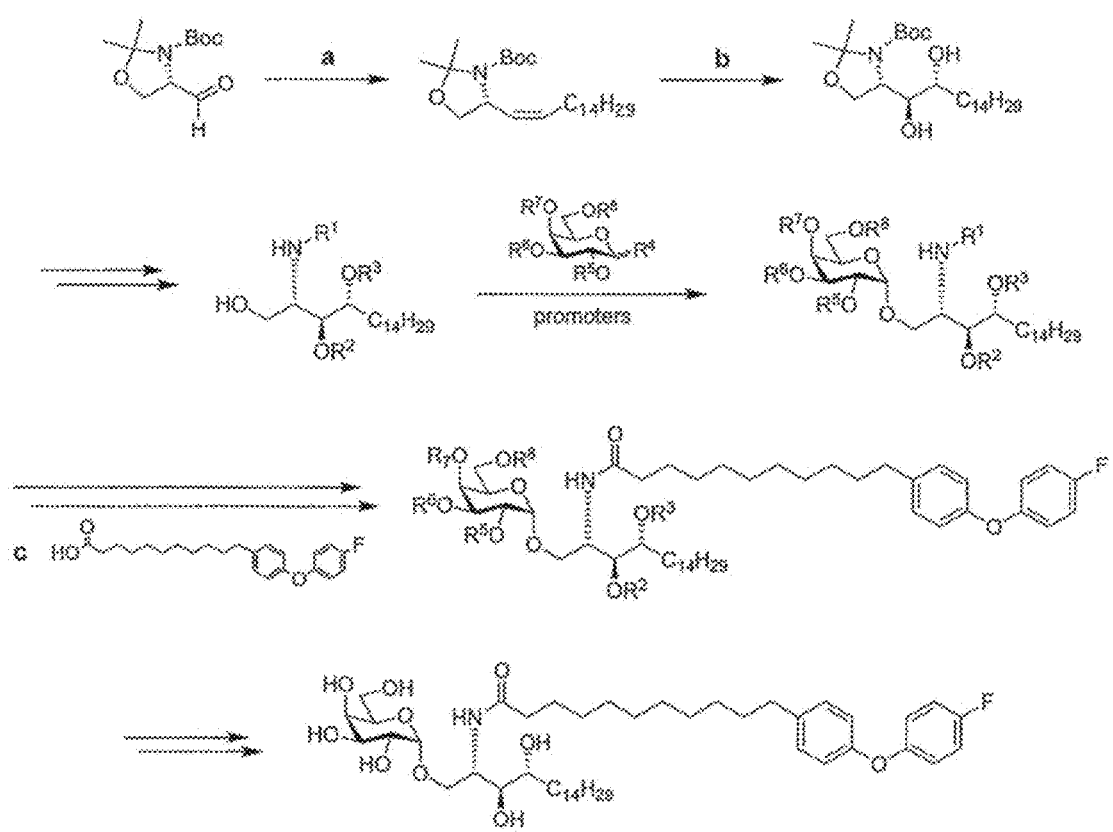
Figures 2, 2B, 3, 4:
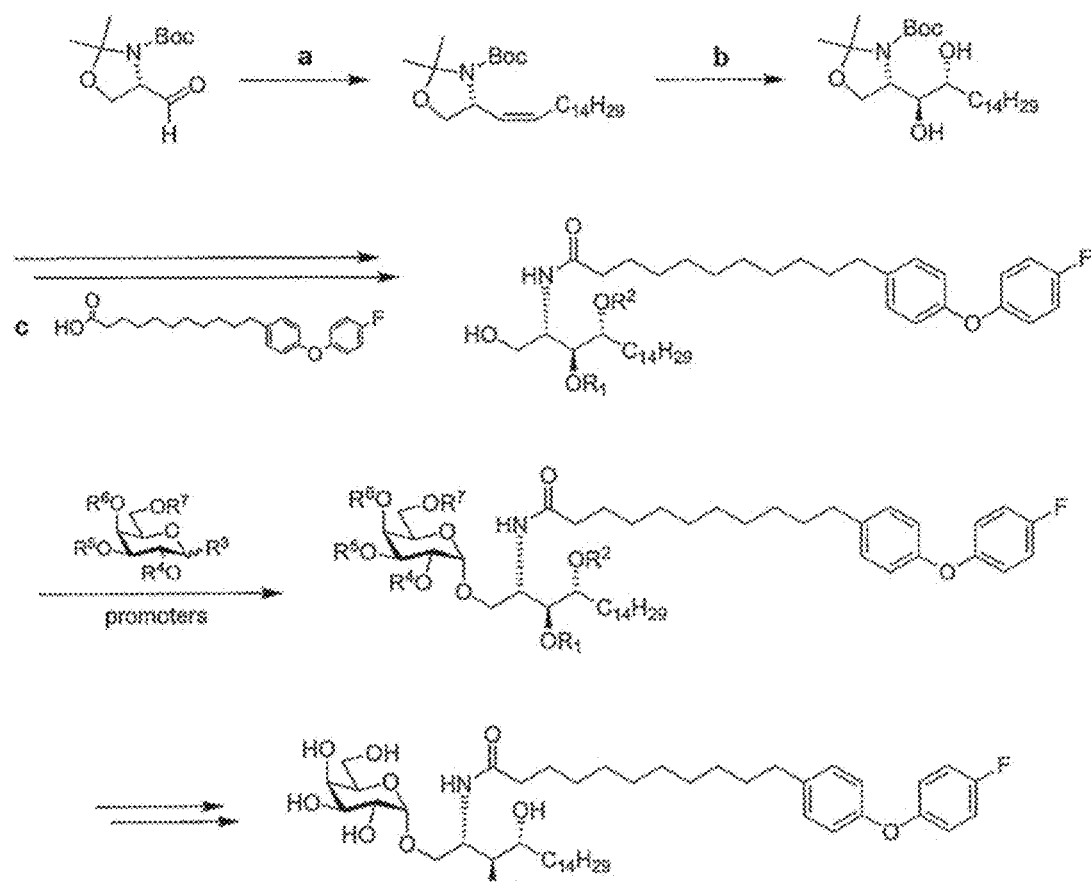
Figures 2, 2B, 3, 4, 5:
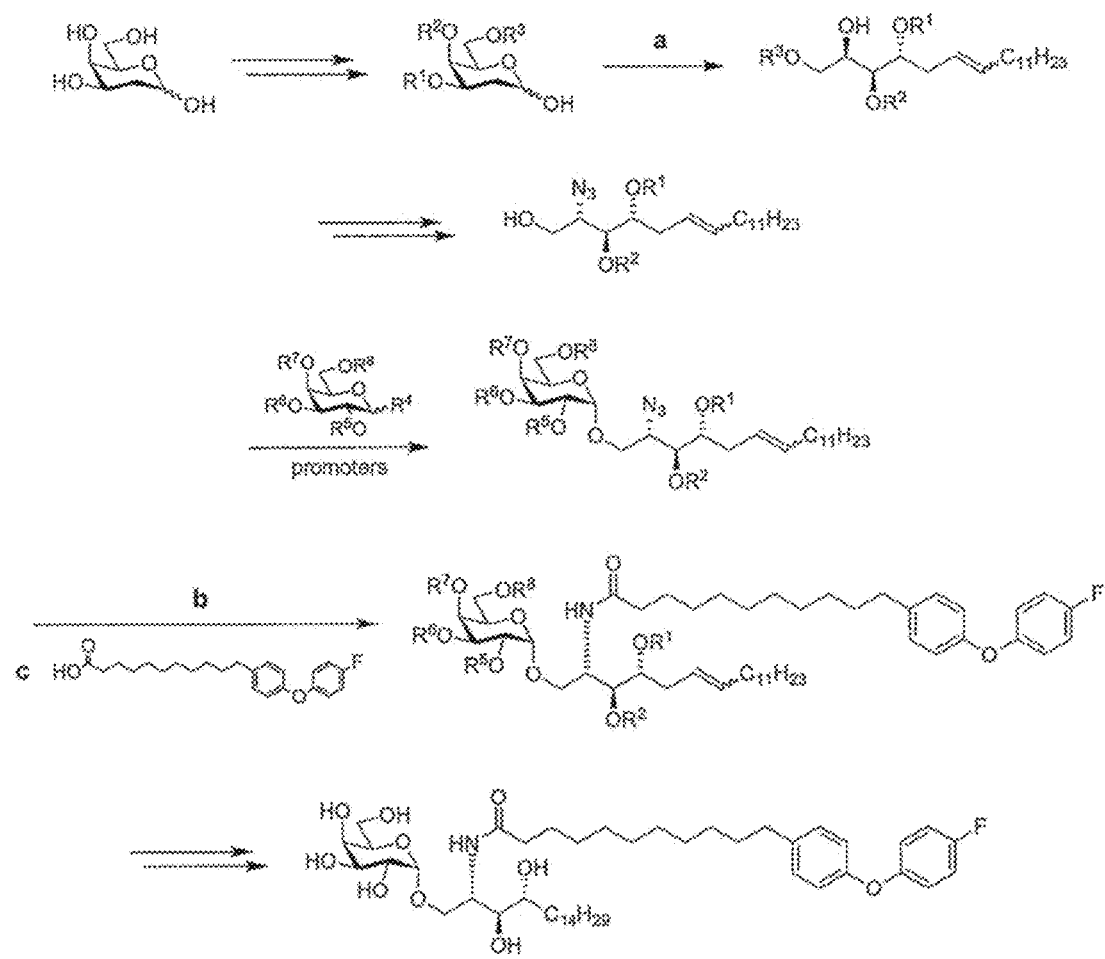
Figures 2, 2B, 3, 4, 5, 6:
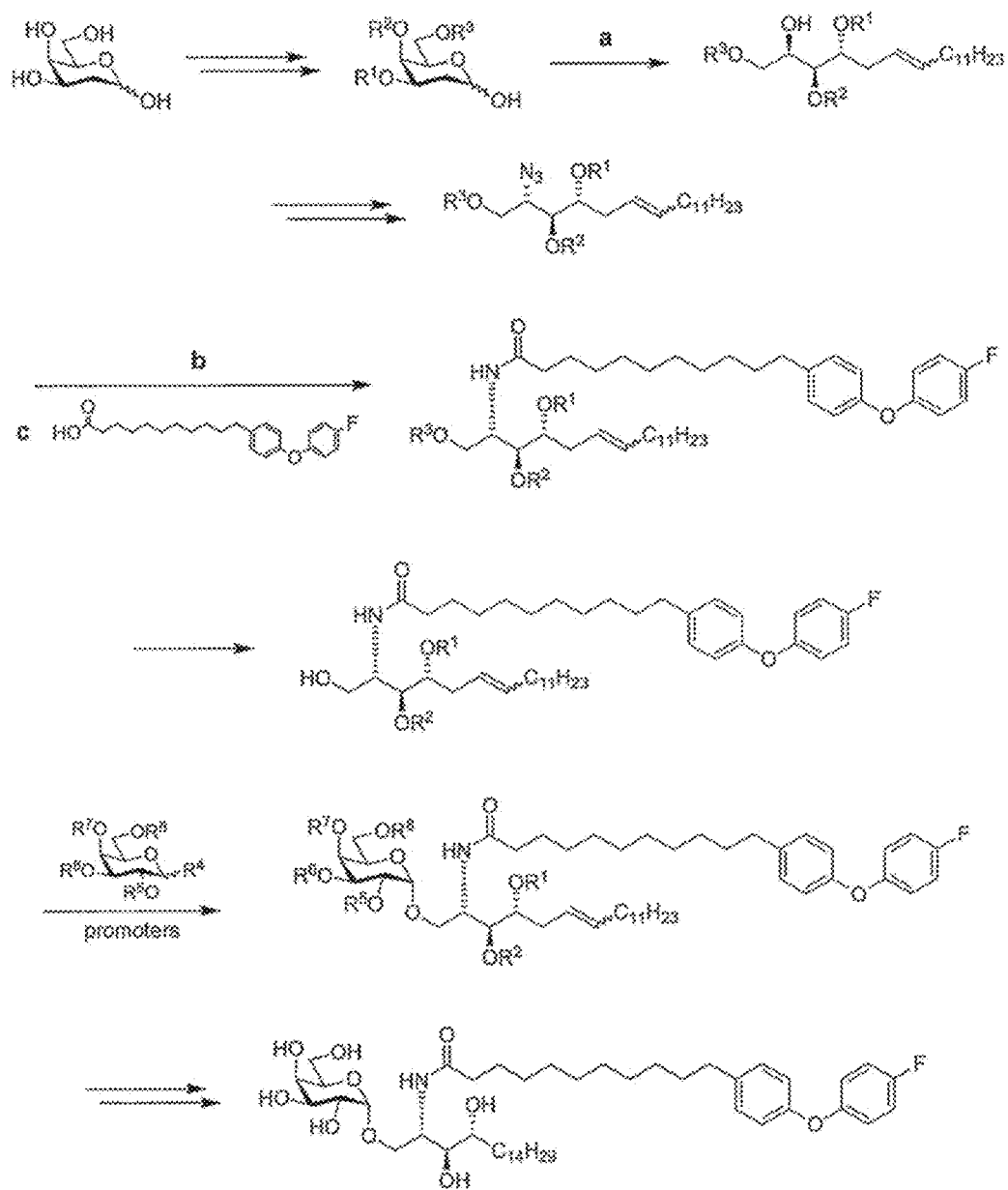
Figures 2, 2B, 3, 4, 5, 6, 7:
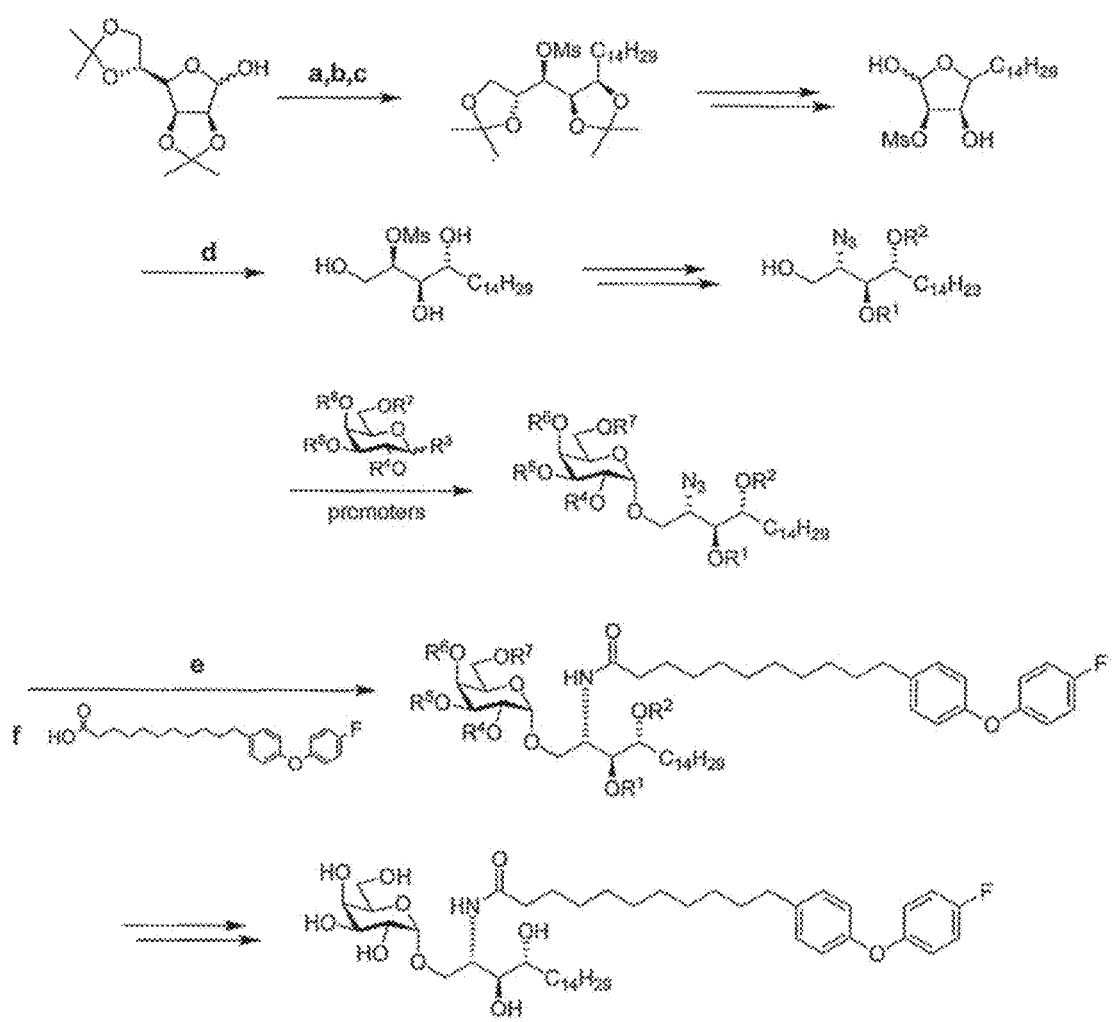

To compare the capacities of C1, C34, K691, K705 and K706 in activating human iNKT cells, human Vα24-restricted NKT cells were isolated from PBMC by magnetic beads, and incubated with recombinant human IL-2 (50 µg/mL). Two days later, iNKT cells were co-cultured with autologous monocyte-derived DCs loaded with different glycolipids (1 µg/mL), including C1, C34, K691, K705 and K706, in 96 wells for three days. The supernatants were collected to determine cytokines/chemokines by Luminex assay. As shown in Figure A, the level of IFN-γ and IL-4 secretion was shown for the different glycolipids. The ratio of IFN-γ/IL-4 was significantly higher for C34, K691, and K706 than C1 (Figure B), suggesting that the C34, K691, and K706 are more TH1 polarized than C1 to in the human immune system, and K706 is even more so than C34. Additionally, all glycolipids induced GM-CSF secretion at some level, demonstrating that these glycolipids can promote the activation of myeloid cells. These glycolipids also induced the production of IL-10 and IL-13. Taken together, K706 induced cytokines with the highest IFN-g/IL-4 ratio and comparable levels of IFN-g, GM-CSF, IL-10 and IL-13 as C1, and C34, demonstrating that K706 might be more potent than C1 and C34 in inducing TH1 polarized immune responses of human iNKT cells. (Statistical evaluation was performed using one-way ANOVA. * P<0.05 compared with C1. #, P=0.002 compared with C34, using Student's T test). Glycosphingolipids (GSLs) with a Glc Head are Immune Modulators Previously, 0.1 μg/mouse of 7DW8-5 was sufficient for immune stimulation,[19] but higher dosage (1 μg/mouse) was required for the glucose analog 7DW8-5-Glc to induce immune responses (FIG. 6). Thus, the biological activities of newly synthesized glycolipids were tested in B6 mice 2 and 18 hr after i.v. injection of glycolipids at 1 μg/mouse. As shown in FIG. 2 and FIG. 7, the mannose analog 7DW8-5-Man failed to induce any cytokines/chemokines. As compared to GSLs with αGlc, GSLs with αGal induced higher levels of cytokines and chemokines, including IFN-γ, IL-2, IL-4, IL-6, GM-CSF, TNFα and IP-10. A similar trend was noted for αGalCer and C34 analogs with different glycosyl groups (FIG. 2A, 2B and FIG. 7).

Although C1-Glc and C34-Glc triggered both cytokines and chemokines, 7DW8-5-Glc induced very low levels of Th1 and Th2 cytokines but relatively high levels of KC, MCP-1, IP-10 and MIG chemokines. To probe the possibility that other immune cells than iNKT cells might contribute to the chemokine induction by 7DW8-5-Glc, Jα18 KO mice which harbored no iNKT cells were injected with 7DW8-5-Glc or 7DW8-5 at 1 μg/mouse.[25] Mouse sera collected 2 and 18 hr after injection showed no induction of cytokines by either 7DW8-5 or 7DW8-5-Glc (FIG. 2A, 2B and FIG. 7). Surprisingly, 7DW8-5-Glc but not 7DW8-5 triggered the secretion of several chemokines including KC, MCP-1, IP-10 and MIG in Jα18 KO mice. These findings suggested that immune cells other than iNKT cells in Jα18 KO mice must have contributed to the production of chemokines in WT mice and Jα18 KO mice treated with 7DW8-5-Glc.

Figures 2, 2B, 3, 4, 5, 6, 7, 8:
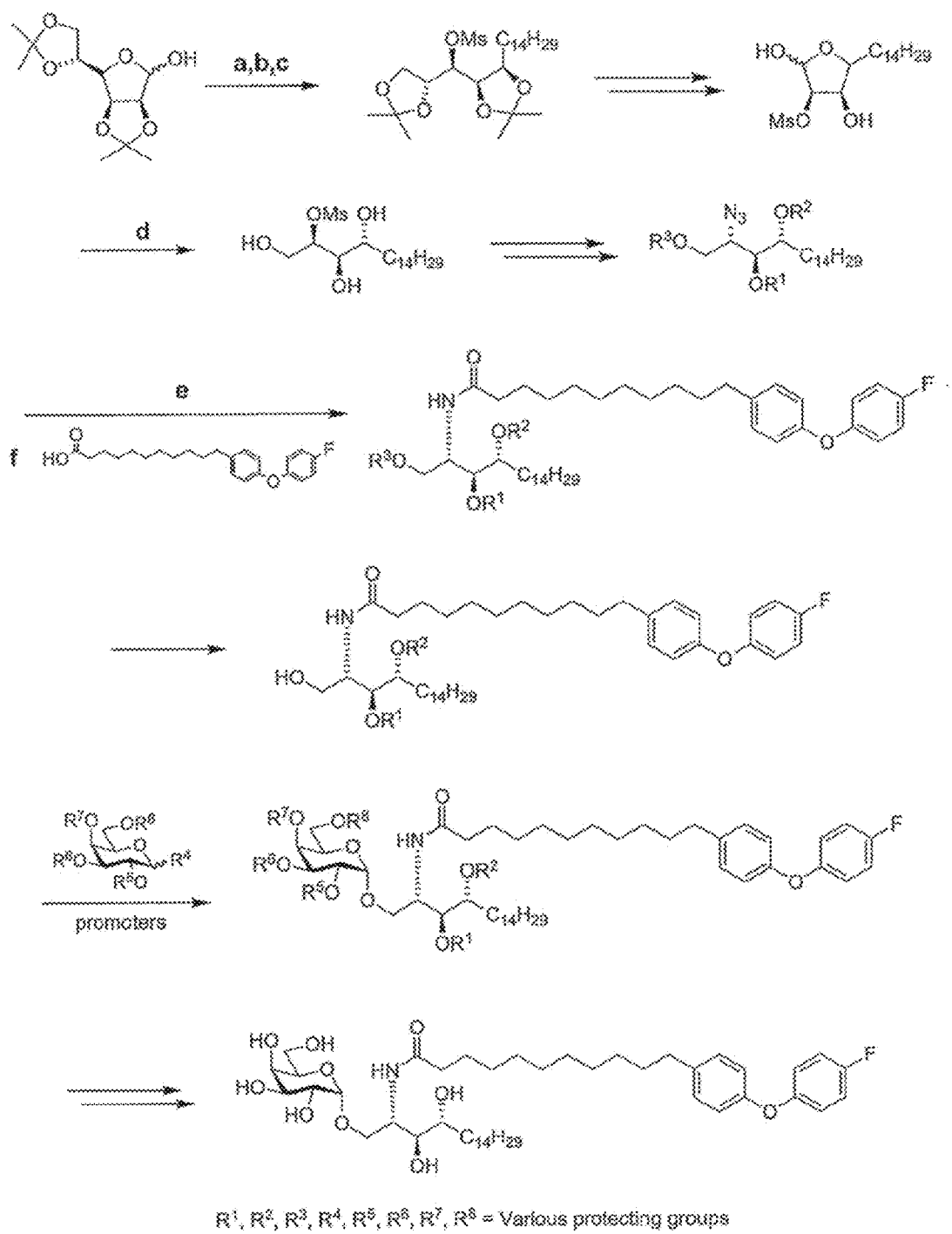

Next, we analyzed the expansion/activation of immune cells in WT mice 3 days after glycolipid stimulation. The numbers of total T cells, CD4$^+$ T and CD8$^+$ T cells were higher in mice treated by GSLs with αGal head than those treated by GSLs with αGlc (FIGS. 2C, 8E and 8F). This was in line with the observation that more cytokines/chemokines were induced by GSLs with αGal than GSLs with αGlc in mice (FIGS. 2A, 2B and 7). Further comparison of immunostimulatory activities among GSLs with αGlc revealed that both C1-Glc and C34-Glc were better than 7DW8-5-Glc in the induction of cytokines/chemokines (FIGS. 2A, 2B and 7) and the expansion/activation of DCs (FIG. 8B-8D). C34-Glc activated 2 fold more CD80$^+$ or CD86$^+$ DCs than 7DW8-5-Glc (FIGS. 8C and 8D) although they induced similar numbers of total splenocytes and DCs (FIGS. 8A and 8B). As compared to 7DW8-5-Glc, C1-Glc not only expanded 1.3 fold more splenocytes and DCs (FIGS. 8A and 8B) but also activated 3.5 fold more CD80$^+$ DCs as well as 3 fold more CD86$^+$ DCs (FIGS. 8C and 8D). The increased expansion/activation of DCs may contribute to the stronger immunogenicity triggered by C1-Glc and C34-Glc as compared to 7DW8-5-Glc in vivo. In contrast, 7DW8-5-Man did not expand any types of immune cells (FIGS. 2C and 8), consistent with the lack of induction of cytokines/chemokines (FIGS. 2A, 2B and 7).

Figures 2, 2B, 3, 4, 5, 6, 7, 8, 9:
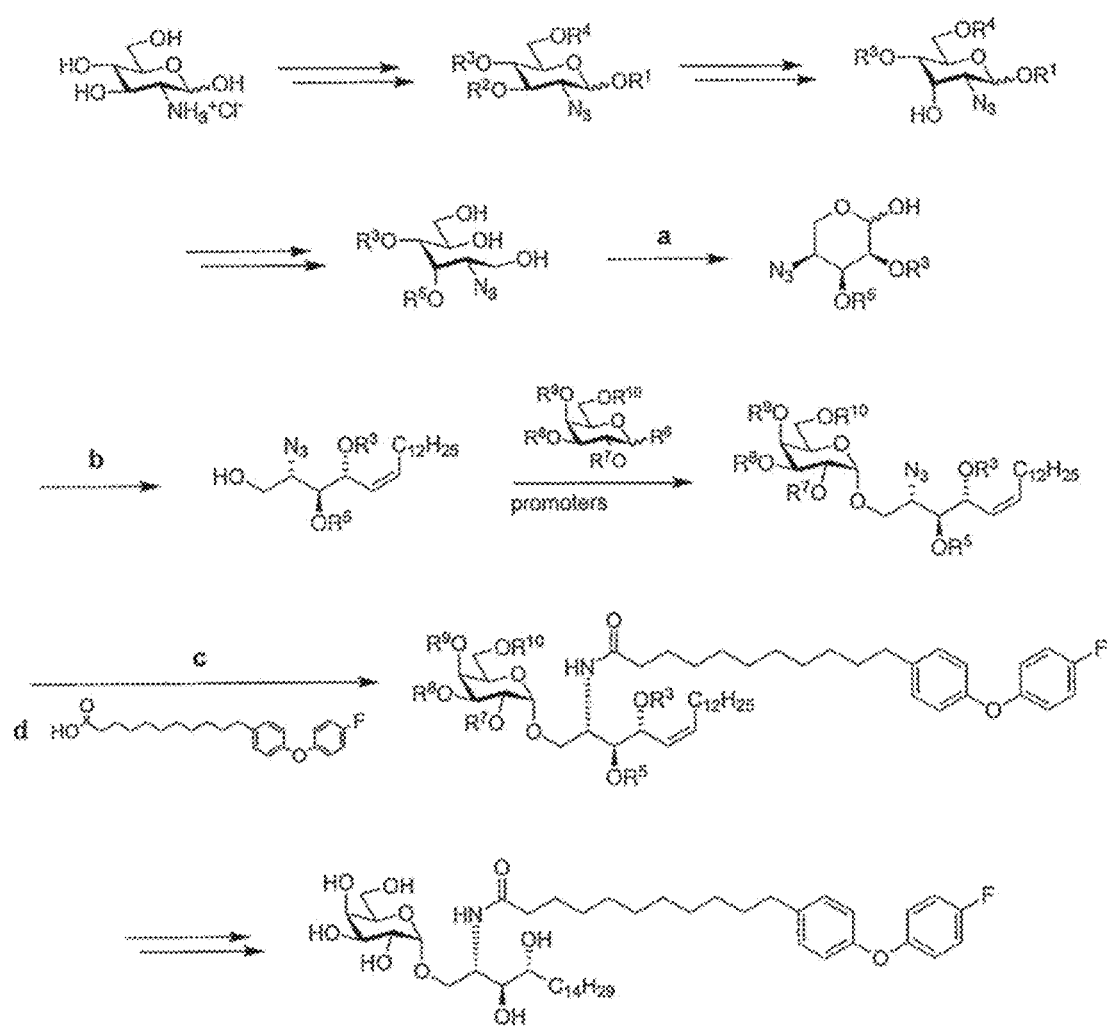

Unexpectedly, we also observed that 7DW8-5-Glc induced chemokines in Jα18 KO mice (FIG. 7). FACS analyses of Jα18 KO mouse splenocytes 3 days after i.v. injection of 7DW8-5-Glc or 7DW8-5 revealed that CD11c$^{hi}$ monocyte-derived DCs were significantly expanded and activated by 7DW8-5-Glc but not 7DW8-5 (FIG. 9B-9D). No significant differences in the total splenocytes, CD4$^+$ T and CD8$^+$ T cells were noted after stimulation with either 7DW8-5 or 7DW8-5-Glc (FIGS. 9A, 9E and 9F). These findings indicated that monocytes might be responsible for the induction of chemokines such as KC, MCP-1, IP-10 and MIG in Jα18 KO mice treated with 7DW8-5-Glc.

Figures 2, 2B, 3, 4, 5, 6, 7, 8, 9, 10:
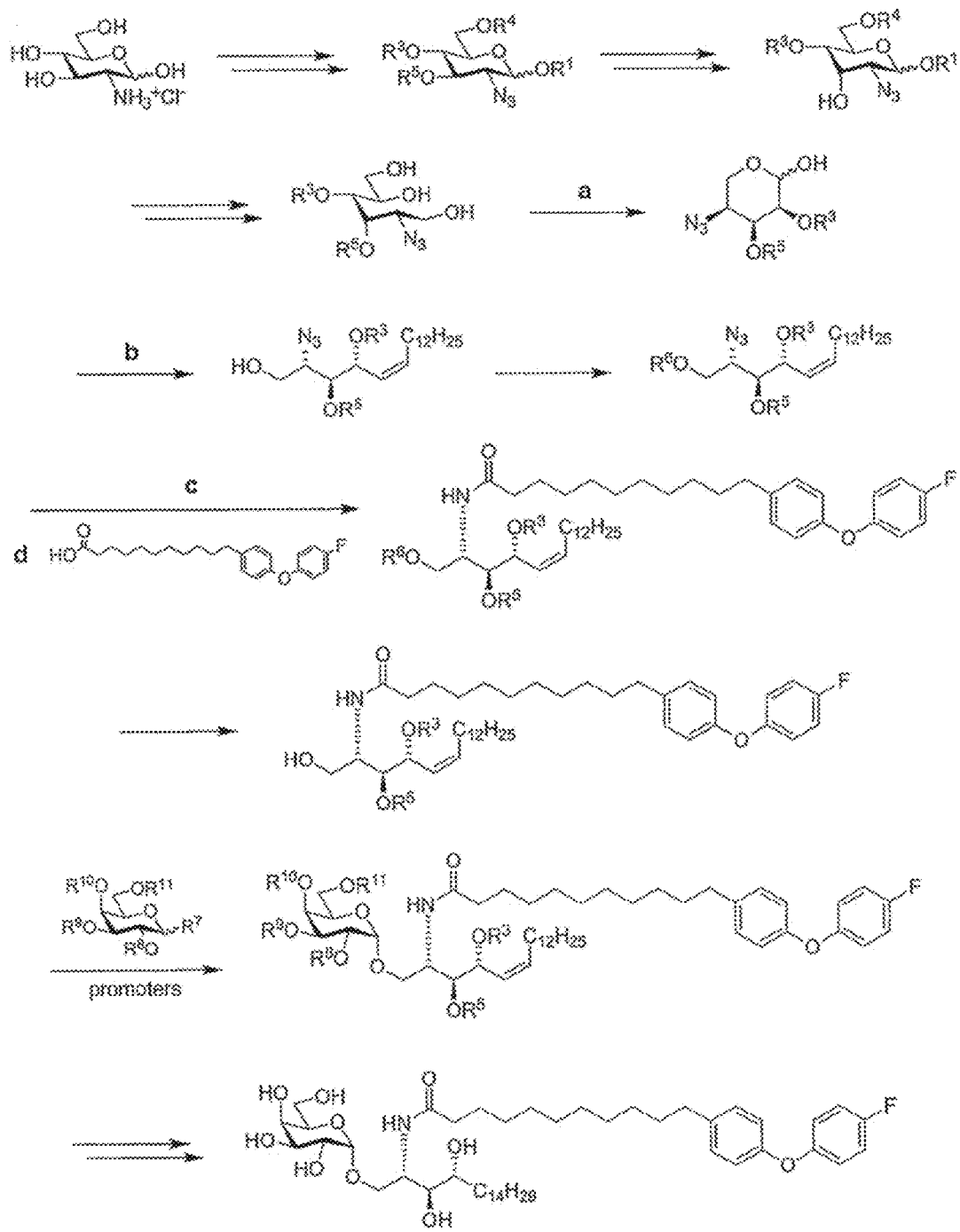
Figures 2, 2B, 3, 4, 5, 6, 7, 8, 9, 10, 11:
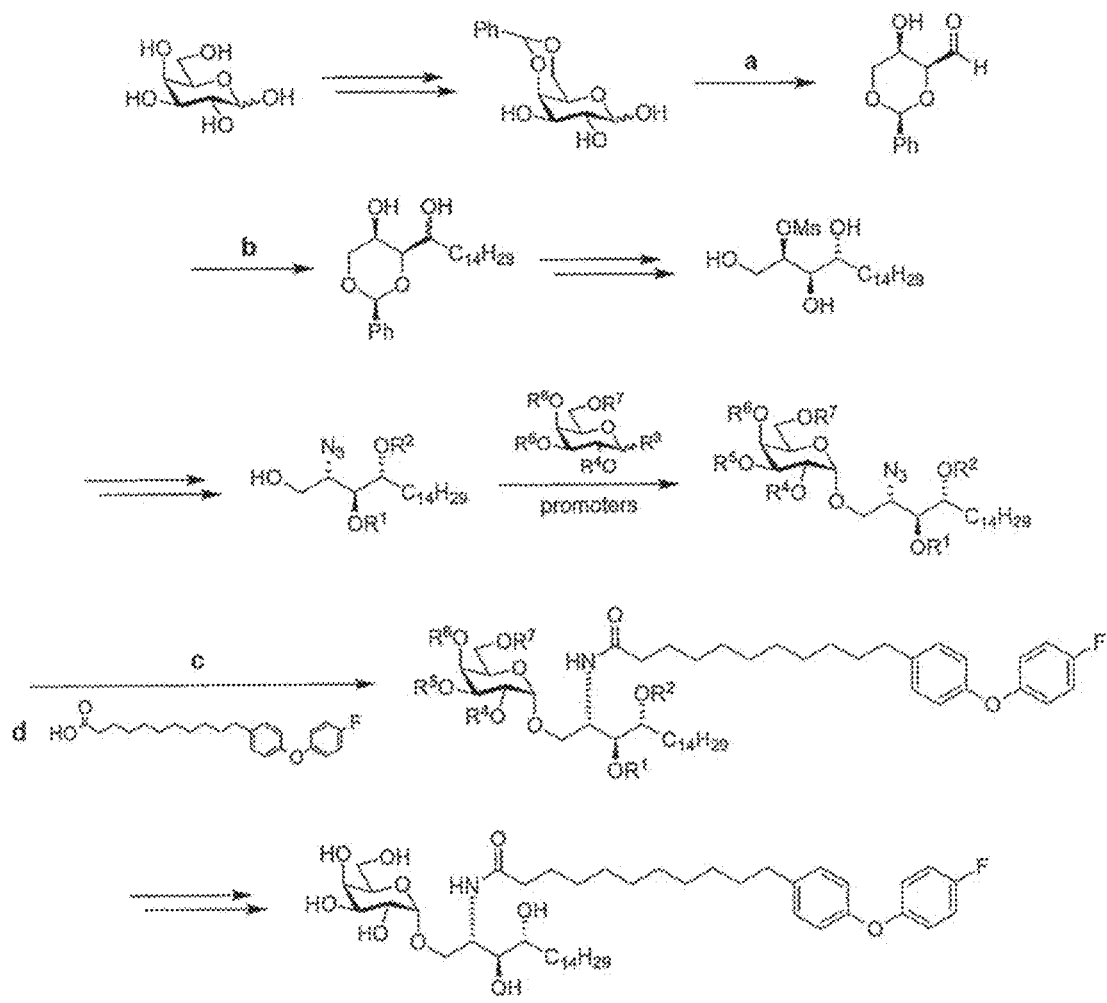

As described above, glycolipid analogs with αGal were stronger immune modulators than those with αGlc in mice, especially for the comparison between 7DW8-5 and 7DW8-5-Glc. To investigate if similar trends also applied to human iNKT cells, Vα24$^+$ iNKT cells isolated from the peripheral blood were incubated with immature DCs pulsed with the indicated glycolipid at 100 ng/ml on day 2. After antigen removal on day 3, human iNKT cells were cultured in the presence of IL-2. The number of expanded iNKT cells was counted using the Guava ViaCount reagent on day 9. Surprisingly, 7DW8-5-Glc was significantly (p=0.0009) better than 7DW8-5 in expanding human iNKT cells in vitro (FIG. 2D). Taken together, these findings suggested that the bioactivities of GSLs with αGal were more potent in mice but less in humans as compared to GSLs with αGlc.
Binary Interaction Between mCD1d and Glycolipids To understand the basis for the differences in the immune modulating activities of 7DW8-5 and 7DW8-5-Glc, we measured the binding strength of the binary interaction between mCD1d and specific glycolipid using L363 mAb which could bind to mCD1d complexed with glycolipids.[26] Various concentrations of mCD1d$^{di}$-glycolipid complexes at fixed ratio were incubated with saturated amounts of L363-biotin antibody, followed by streptavidin-HRP detection and ELISA measurement (FIG. 10A). The dissociation constant (KD) between L363 and the indicated mCD1d$^{di}$-glycolipid complexes was calculated from the linear regression of the Scatchard transformation of the plot (FIG. 10A) using GraphPad Prism software. L363 was found to recognize mCD1d$^{di}$-7DW8-5-Glc complex with similar binding strength as with mCD1d$^{di}$-7DW8-5 complex (FIG. 10B). Next, we determined the KD of the binary complex by incubating different concentrations of glycolipids with fixed amounts of mCD1d dimer and L363-biotin antibody, followed by streptavidin-HRP detection and ELISA measurement (FIG. 10C). The KD was calculated from the Scatchard transformation of the binding curve drawn from the L363 detection readout (FIG. 10D). Not surprisingly, 7DW8-5-Glc having identical lipid tails as 7DW8-5 bound to mCD1d dimer with similar strength, but their binding avidities were 20 fold greater than αGalCer. This indicated that the strength of the binary interaction could not account for the differential immune activating capacities between 7DW8-5 and 7DW8-5-Glc.
Ternary Interaction Between CD1d-GSL Complexes and iNKT Cells Next, we measured the ternary interaction between CD1d-glcolipid complex and the iNKT TCR in mice and humans. Different concentrations of mCD1d$^{th}$-glycolipid and hCD1d$^{th}$-glycolipid complexes were incubated with fixed amounts of DN3A4-1.2 murine iNKT hybridoma cells and human Vα24$^+$/Vβ11$^+$ iNKT cells, respectively. The level of bound complexes at the indicated concentration was detected by anti-mIgG1 secondary antibody and analyzed by flow cytometry (FIGS. 3A and 3B). The KD of the ternary complex was calculated from the Scatchard transformation of the plots in FIGS. 3A and 3B using GraphPad Prism software. As shown in FIG. 3C, mCD1d-7DW8-5 complex displayed 10 fold stronger interaction with iNKT TCR than mCD1d-7DW8-5-Glc complex. This was consistent with the observation that higher percentages of C1-pulsed splenocytes were stained by the mCD1d-7DW8-5 complex (36.2±5.0%) than mCD1d-7DW8-5-Glc complex (17.1±0.8%) (FIG. 11). When complexed with mCD1d, both C1 (KD: 1.240±0.003 nM) and C34 (KD: 0.735±0.010 nM) exhibited stronger ternary interactions toward iNKT TCR than C1-Glc (KD: 5.137±0.110 nM) and C34-Glc (KD: 7.960±1.269 nM), respectively (FIG. 3C).

In humans, GSLs with αGlc (KD of C1-Glc: 8.550±0.617; C34-Glc: 0.378±0.019; 7DW8-5-Glc: 0.481±0.008 nM) exhibited stronger ternary interactions toward Vα24+/Vβ11+ iNKT TCR than GSLs with αGal (KD of C1: 16.410±4.200; C34: 0.498±0.005; 7DW8-5: 0.777±0.022 nM) in complex with hCD1d (FIG. 3D). Thus, irrespective of the types of lipid tails, GSLs with αGal exhibited stronger ternary interaction with mouse iNKT TCR but weaker ternary interaction with human iNKT TCR than GSLs with αGlc (FIGS. 3C and 3D). This may account for the observation that GSLs with αGal triggered higher levels of cytokines/chemokines and greater expansions of immune cells in mice (FIGS. 2A-2C, 7 and 8) while less iNKT cell expansion in humans (FIG. 2D) Taken together, the ternary interaction among iNKT TCR, CD1d and GSL seems to be more relevant for the bioactivities of glycolipids than the binary interaction between CD1d and GSL.

Effects of Swapping Human Vs. Mouse CD1d Molecules Against iNKT Cells

Figures 2, 2B, 3, 4, 5, 6, 7, 8, 9, 10, 11, 12:
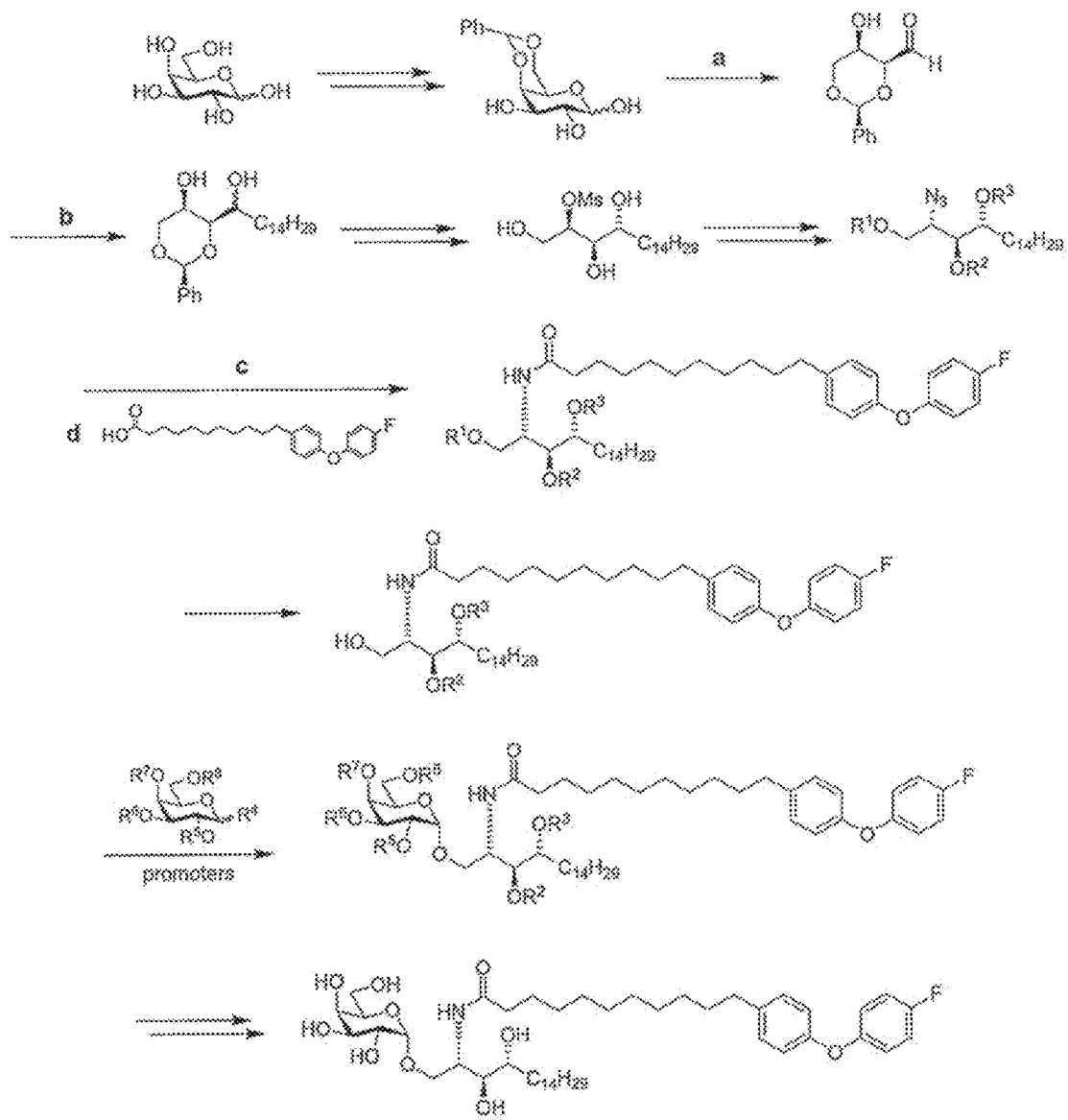
Figures 2, 2B, 3, 4, 5, 6, 7, 8, 9, 10, 11, 12, 13:
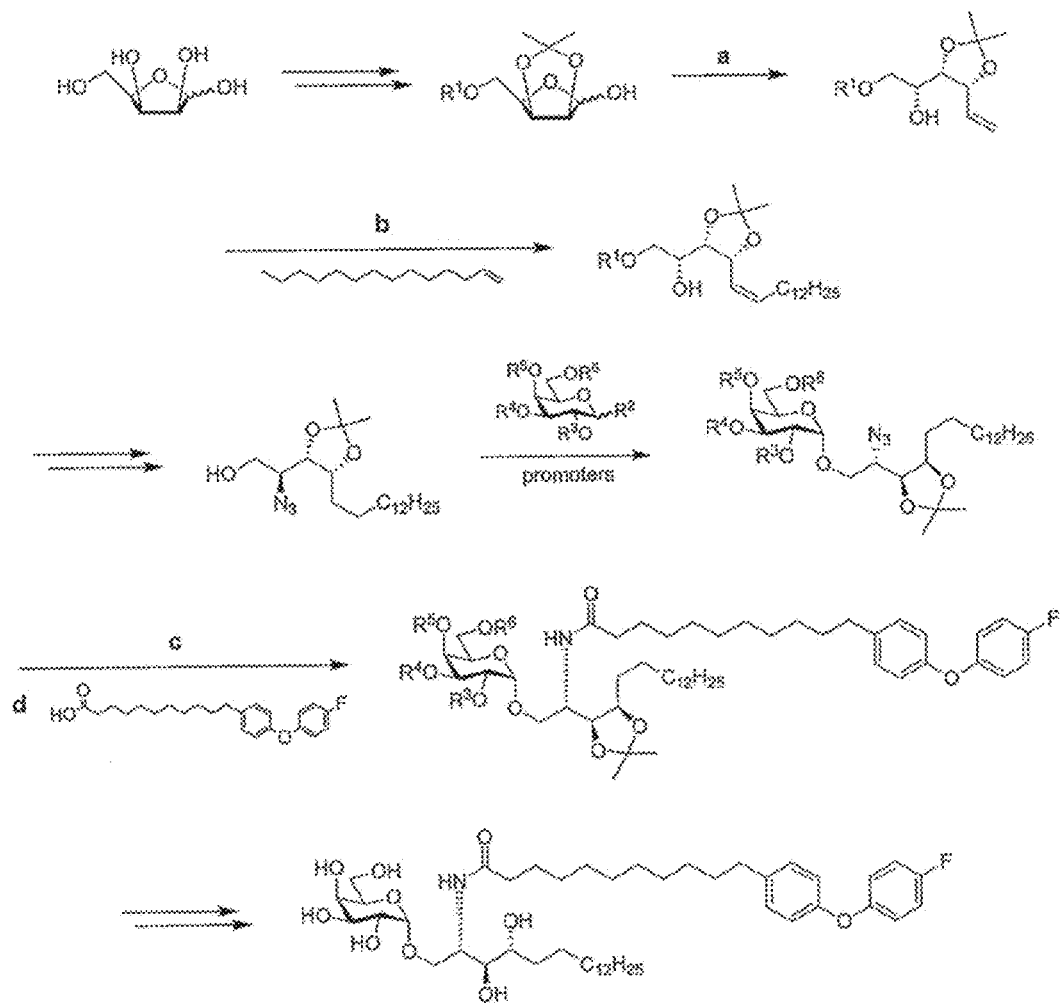
Figures 2, 2B, 3, 4, 5, 6, 7, 8, 9, 10, 11, 12, 13, 14:
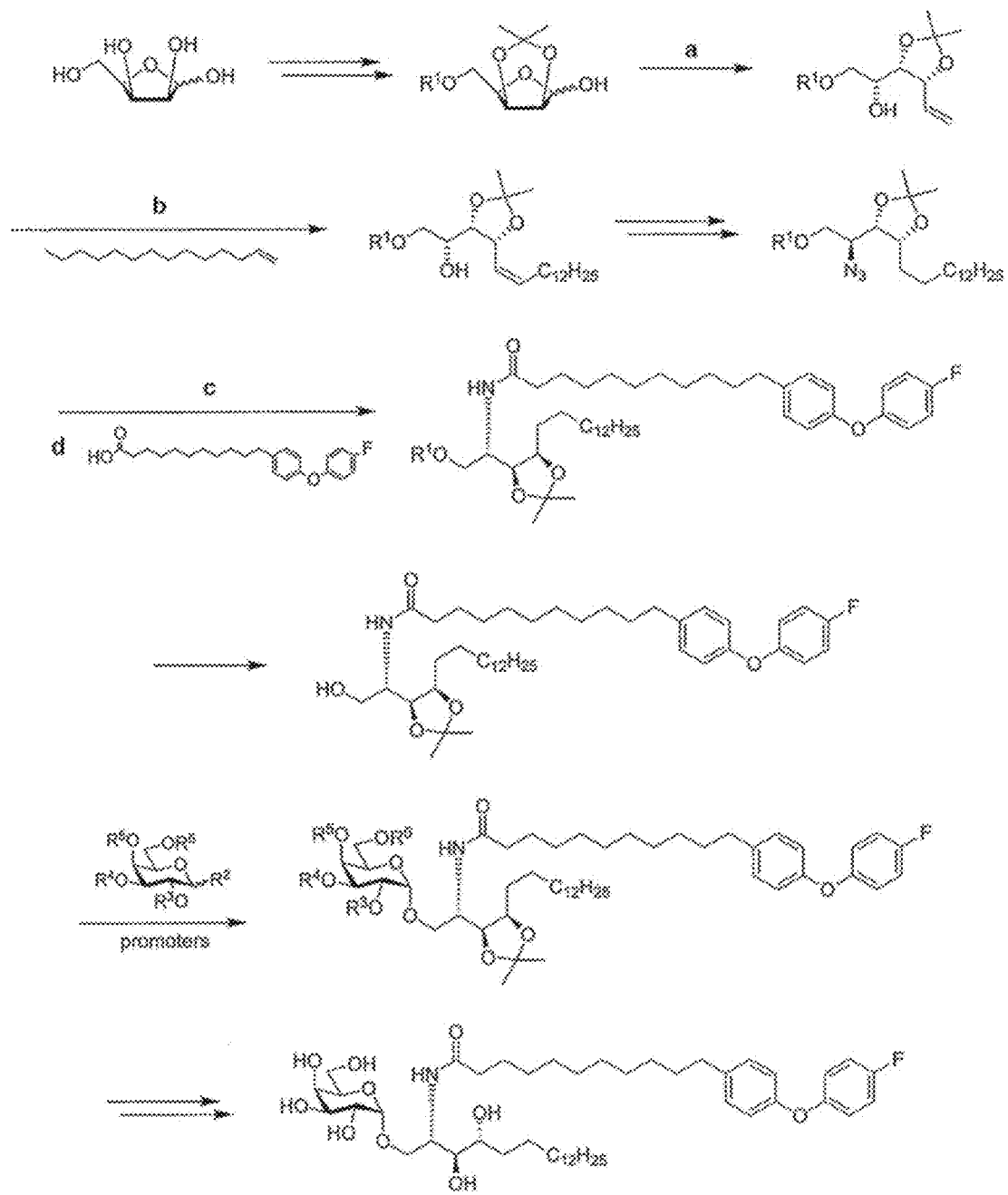
Figures 2, 2B, 3, 4, 5, 6, 7, 8, 9, 10, 11, 12, 13, 14, 15:
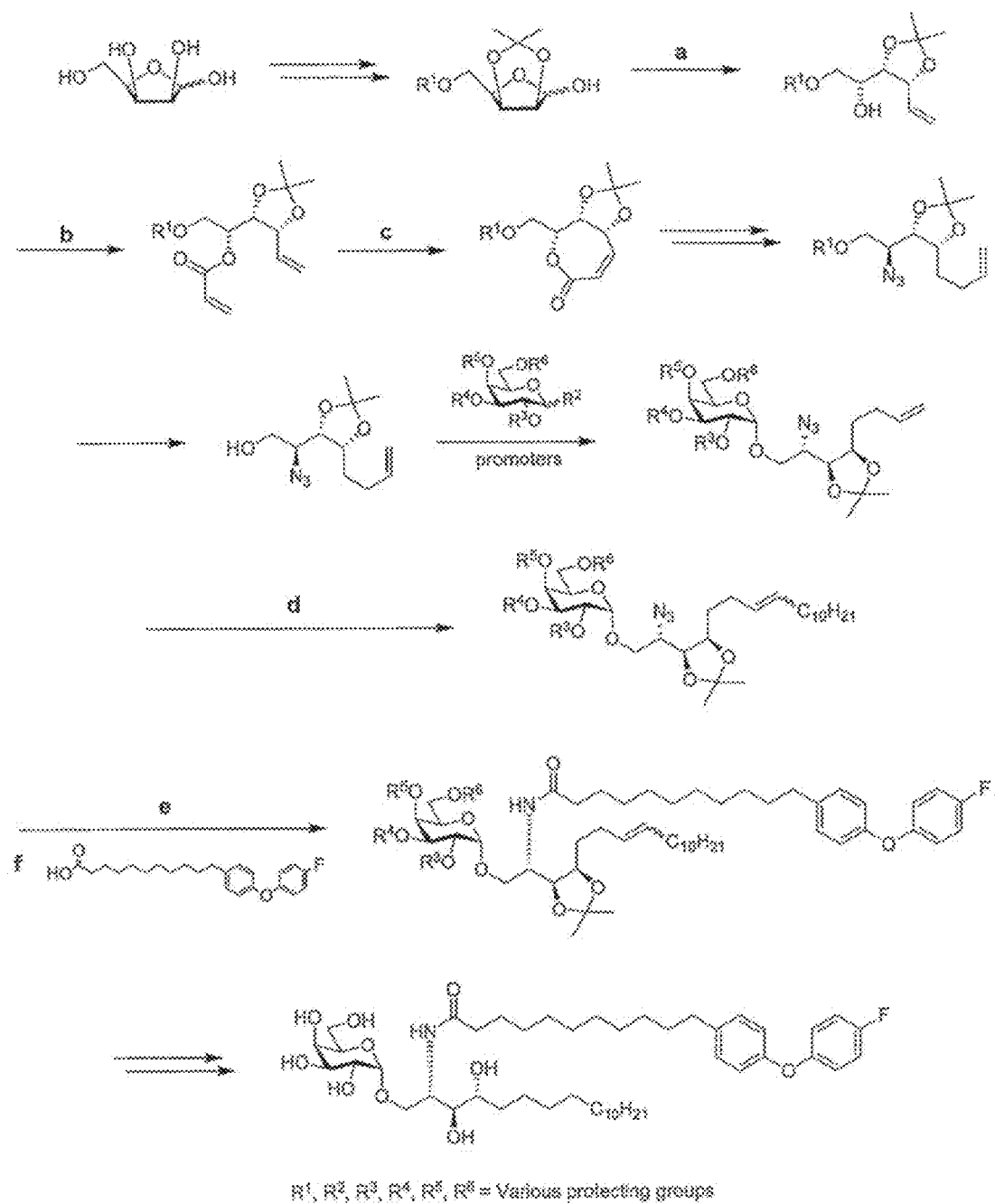
Figures 2, 2B, 3, 4, 5, 6, 7, 8, 9, 10, 11, 12, 13, 14, 15, 16:
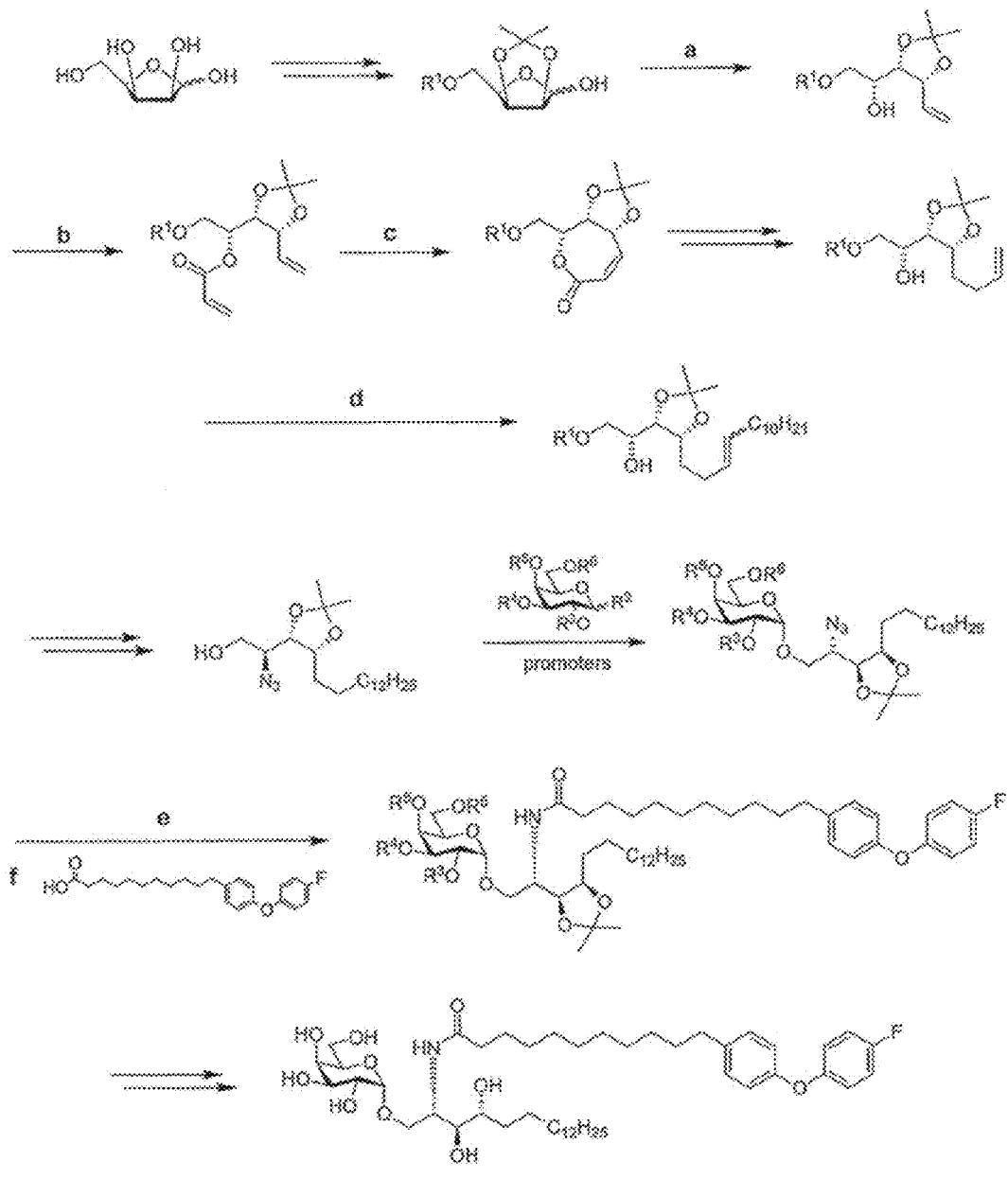
Figures 2, 2B, 3, 4, 5, 6, 7, 8, 9, 10, 11, 12, 13, 14, 15, 16, 17:
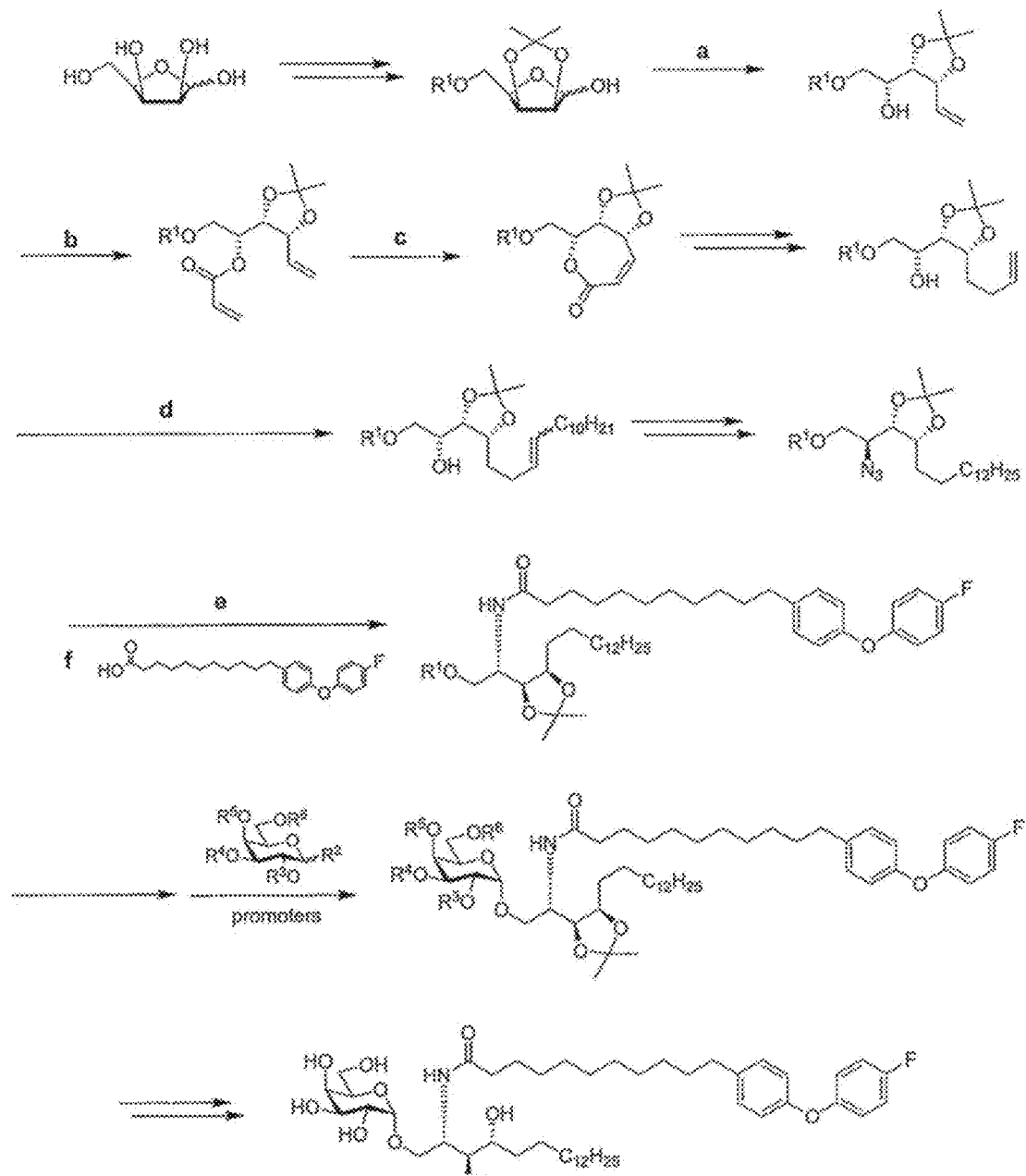
Figures 2, 2B, 3, 4, 5, 6, 7, 8, 9, 10, 11, 12, 13, 14, 15, 16, 17, 18:
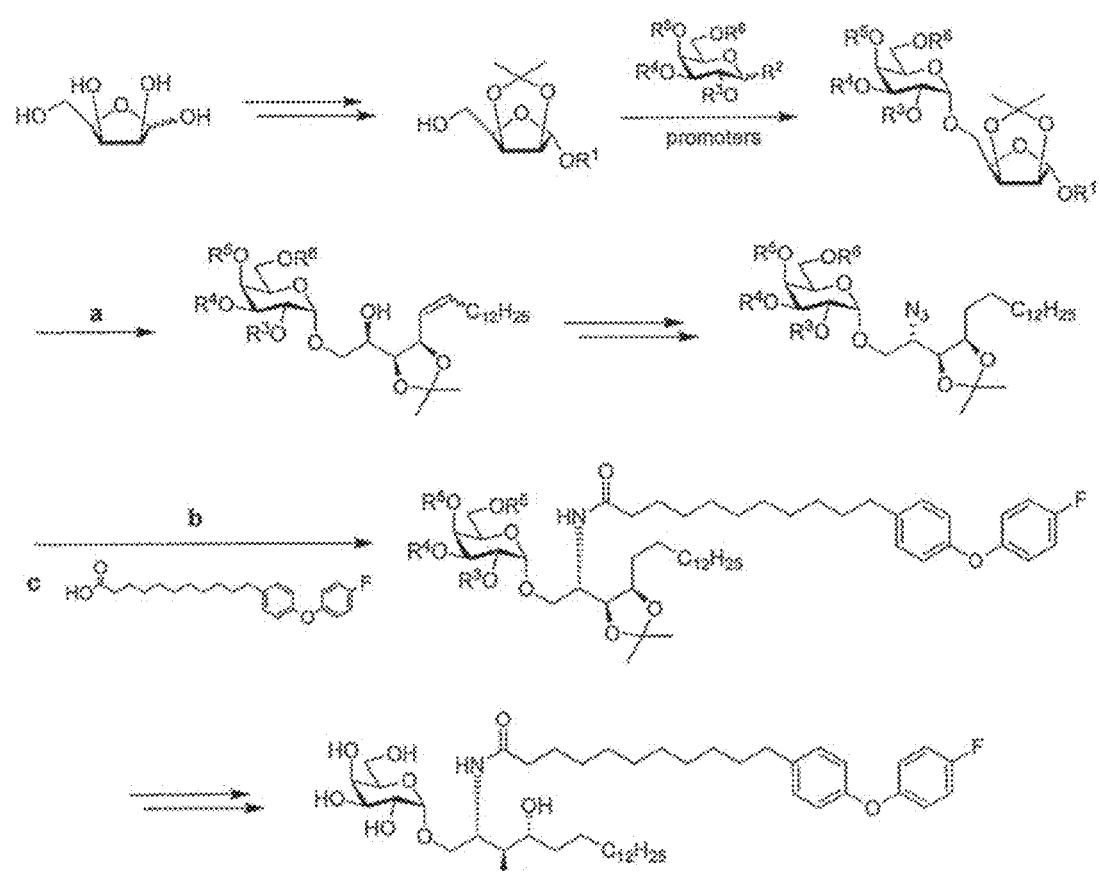
Figures 2, 2B, 3, 4, 5, 6, 7, 8, 9, 10, 11, 12, 13, 14, 15, 16, 17, 18, 19:
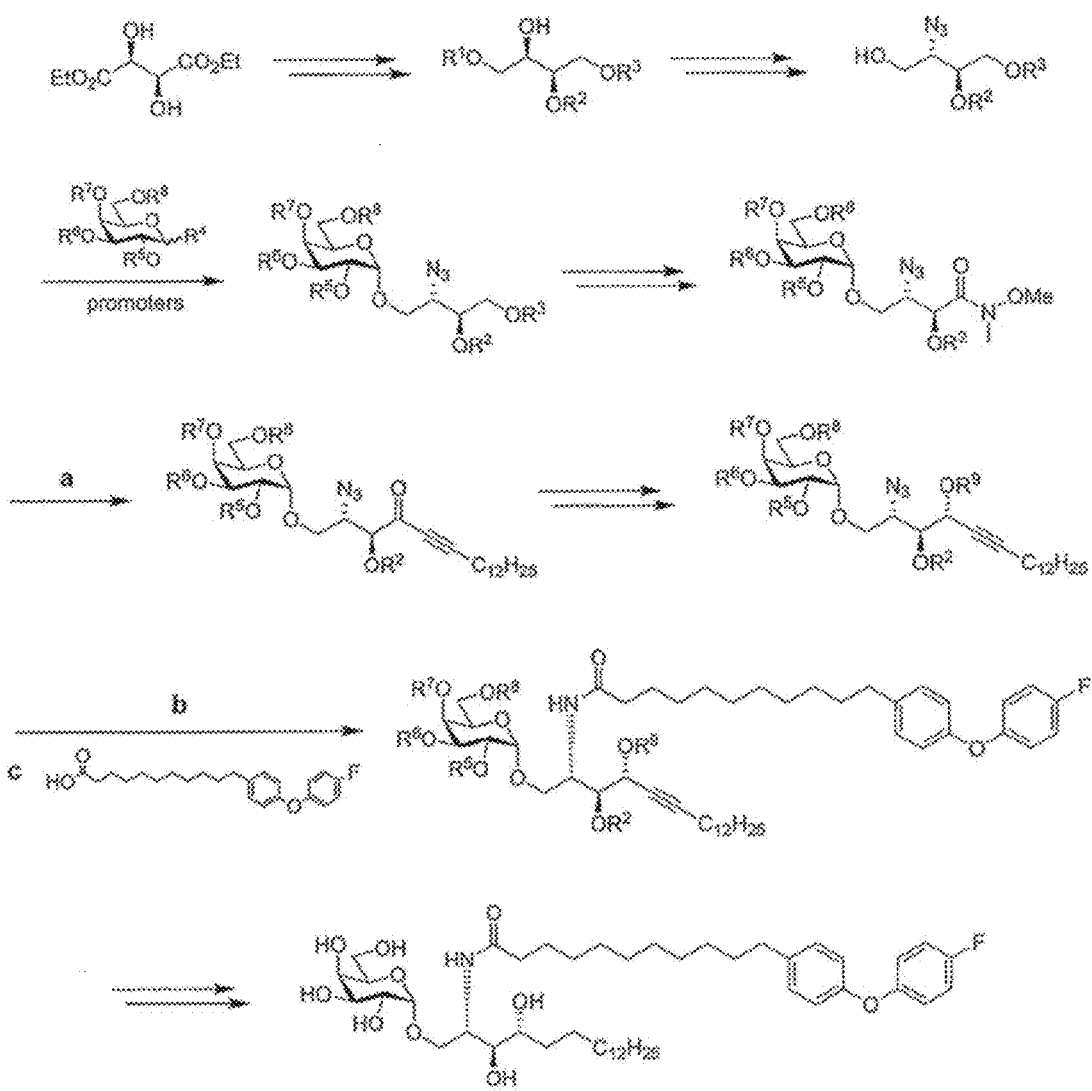
Figure 3:
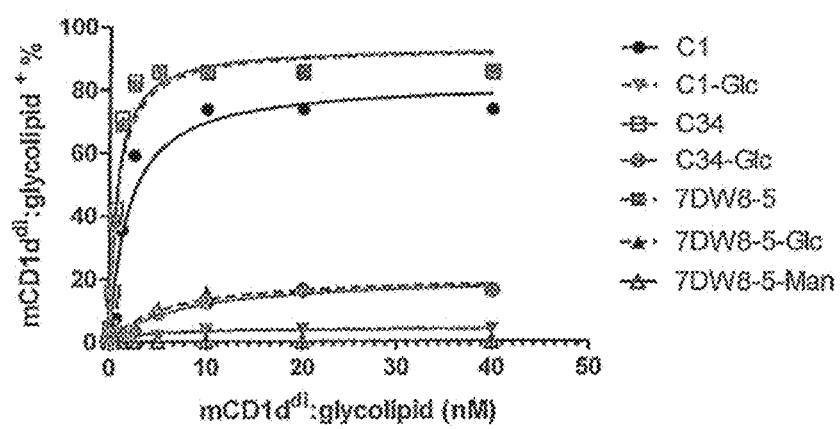
Figure 3:
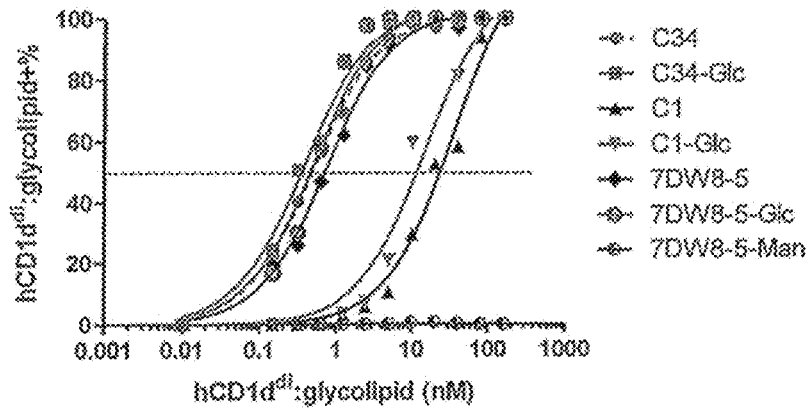
Figure 4:
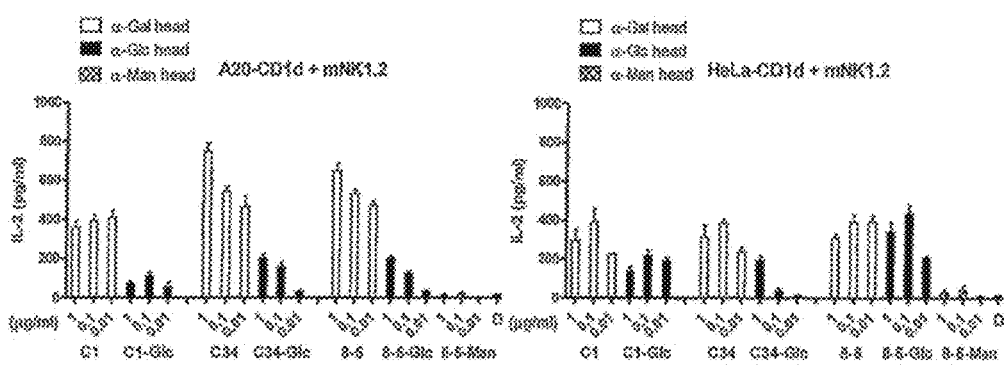
Figure 4:
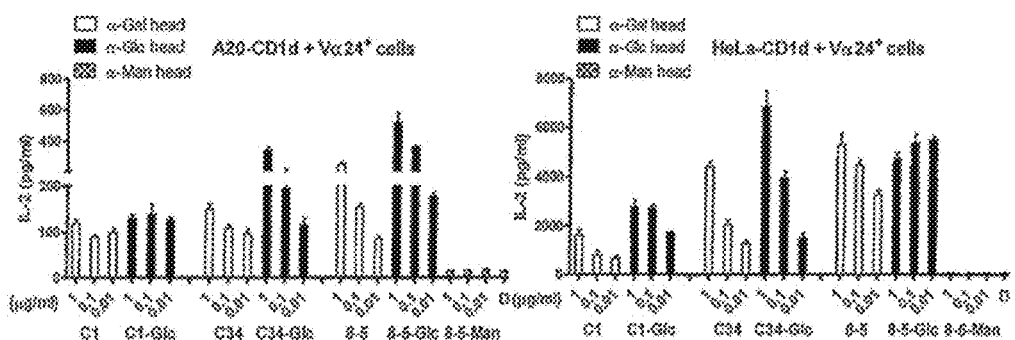
Figure 5:
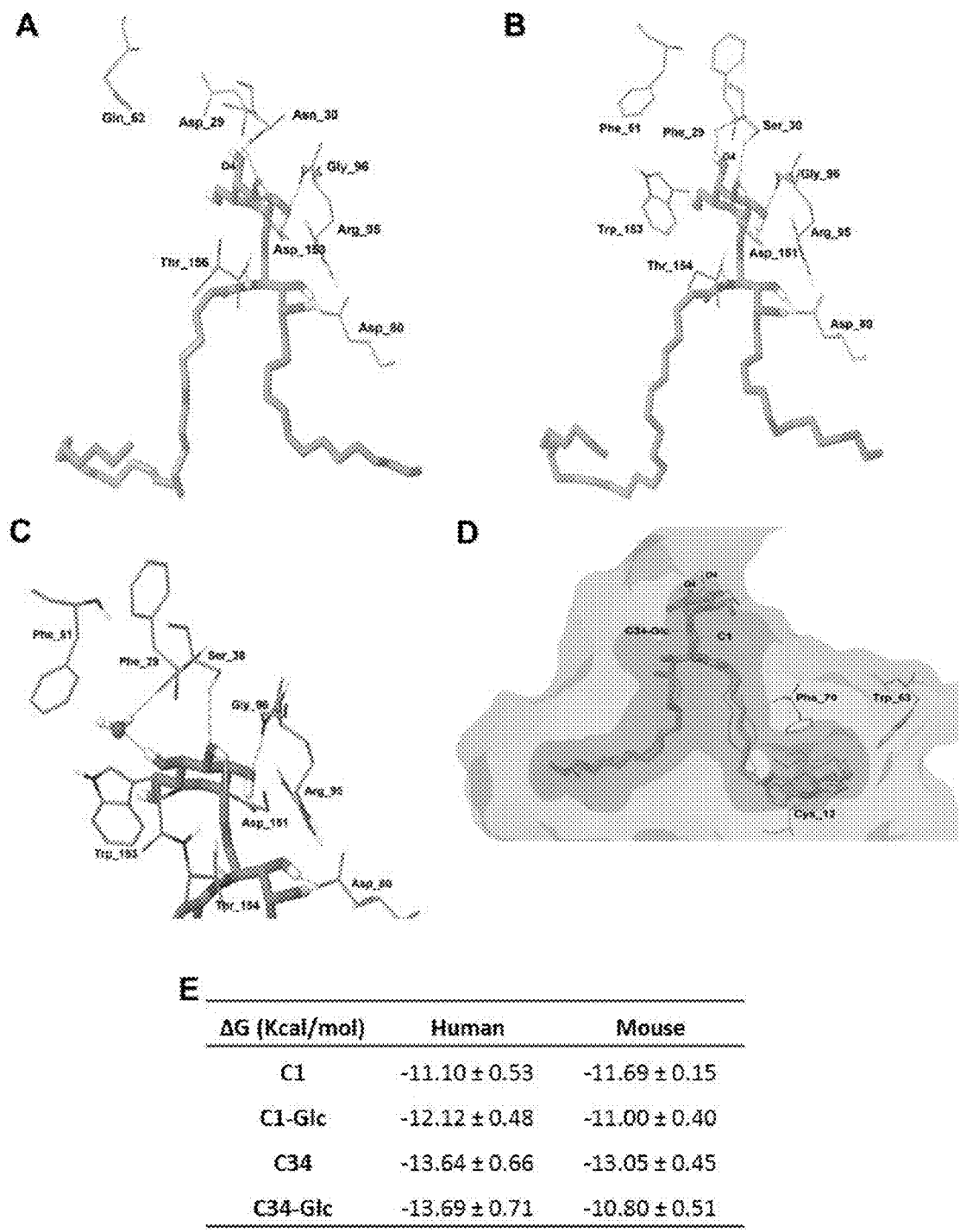
Figure 6:
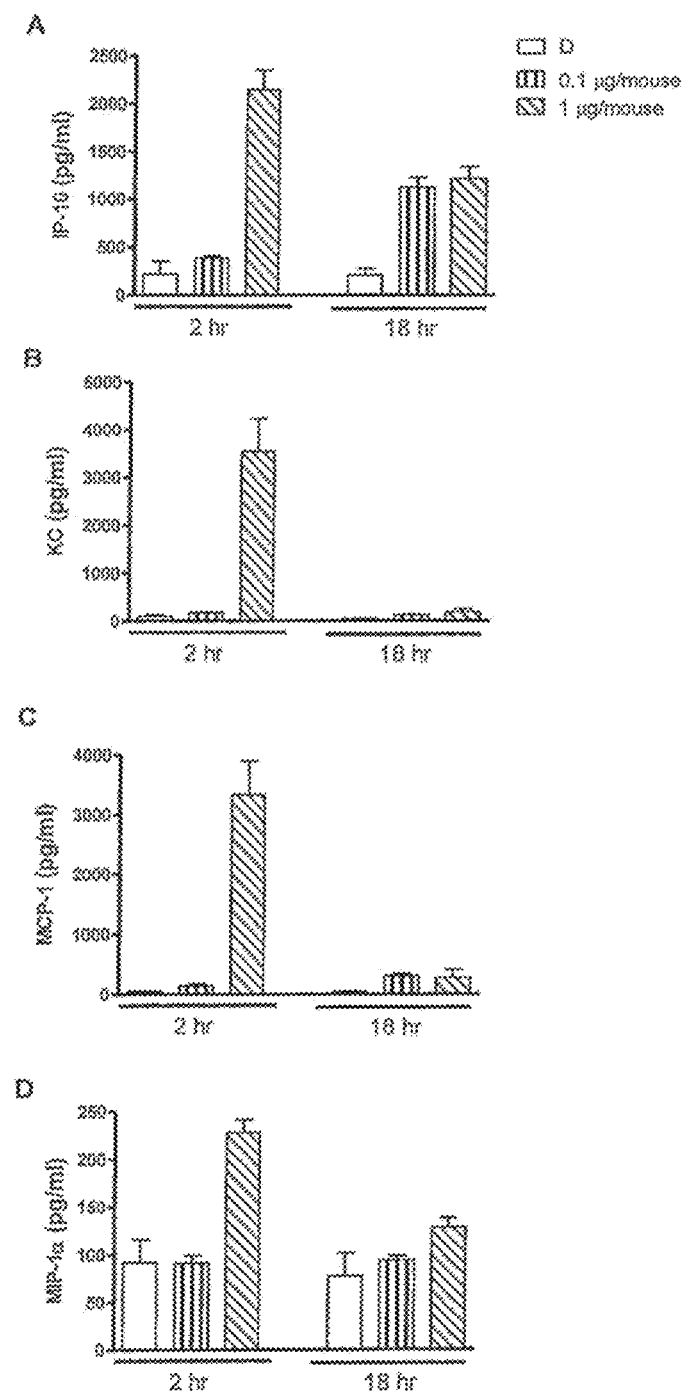
Figure 7:
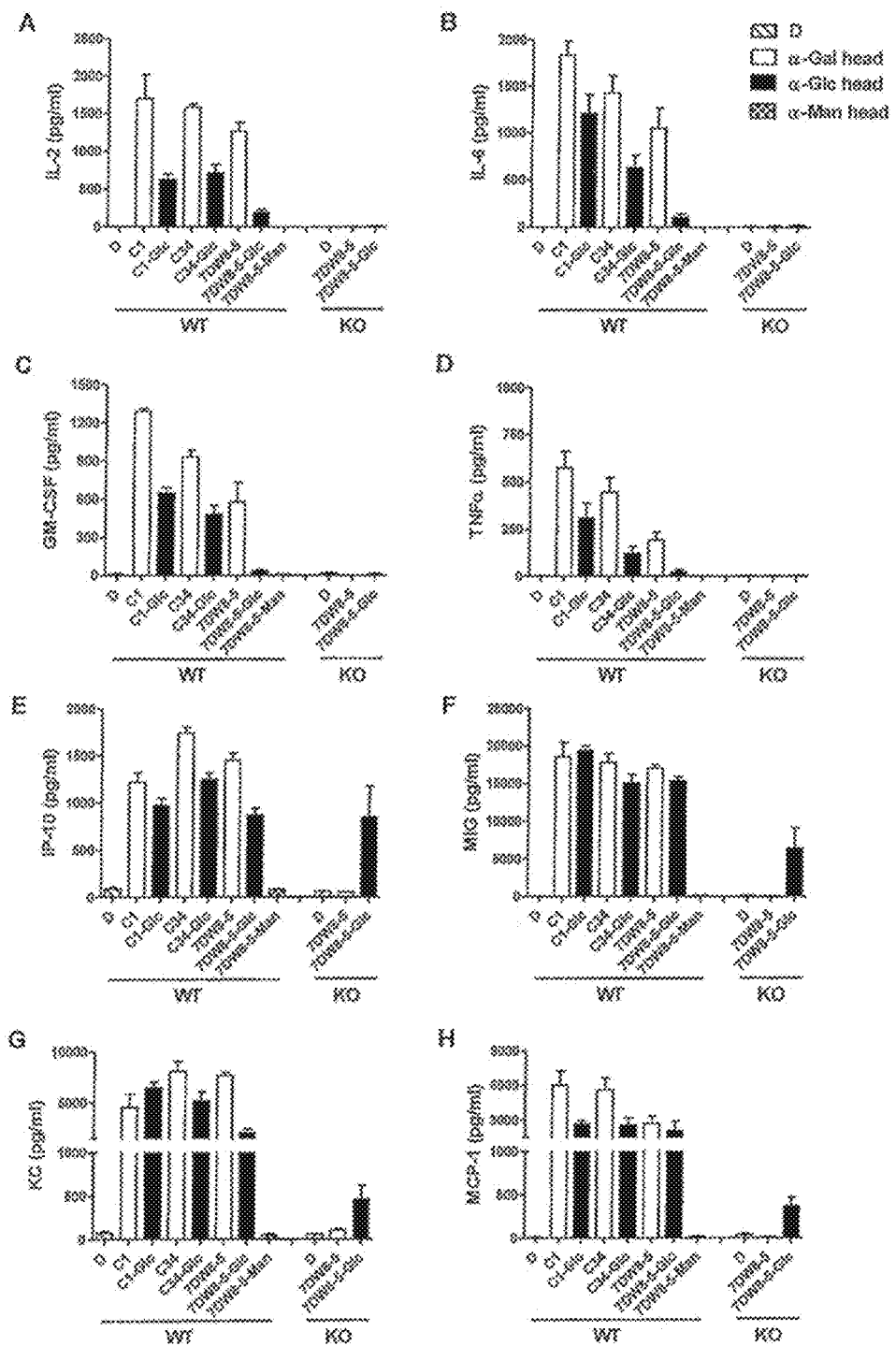
Figure 8:
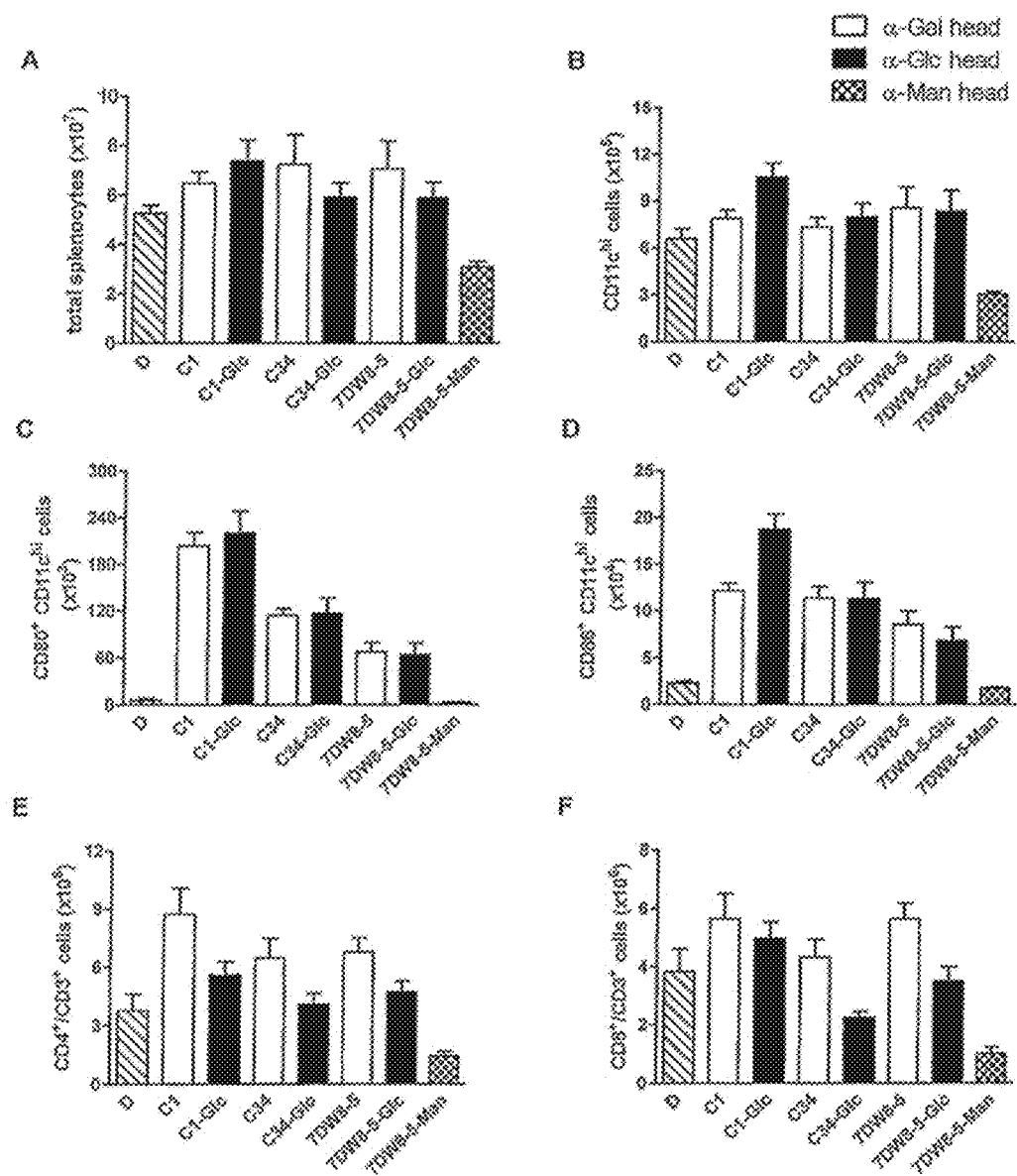
Figure 9:
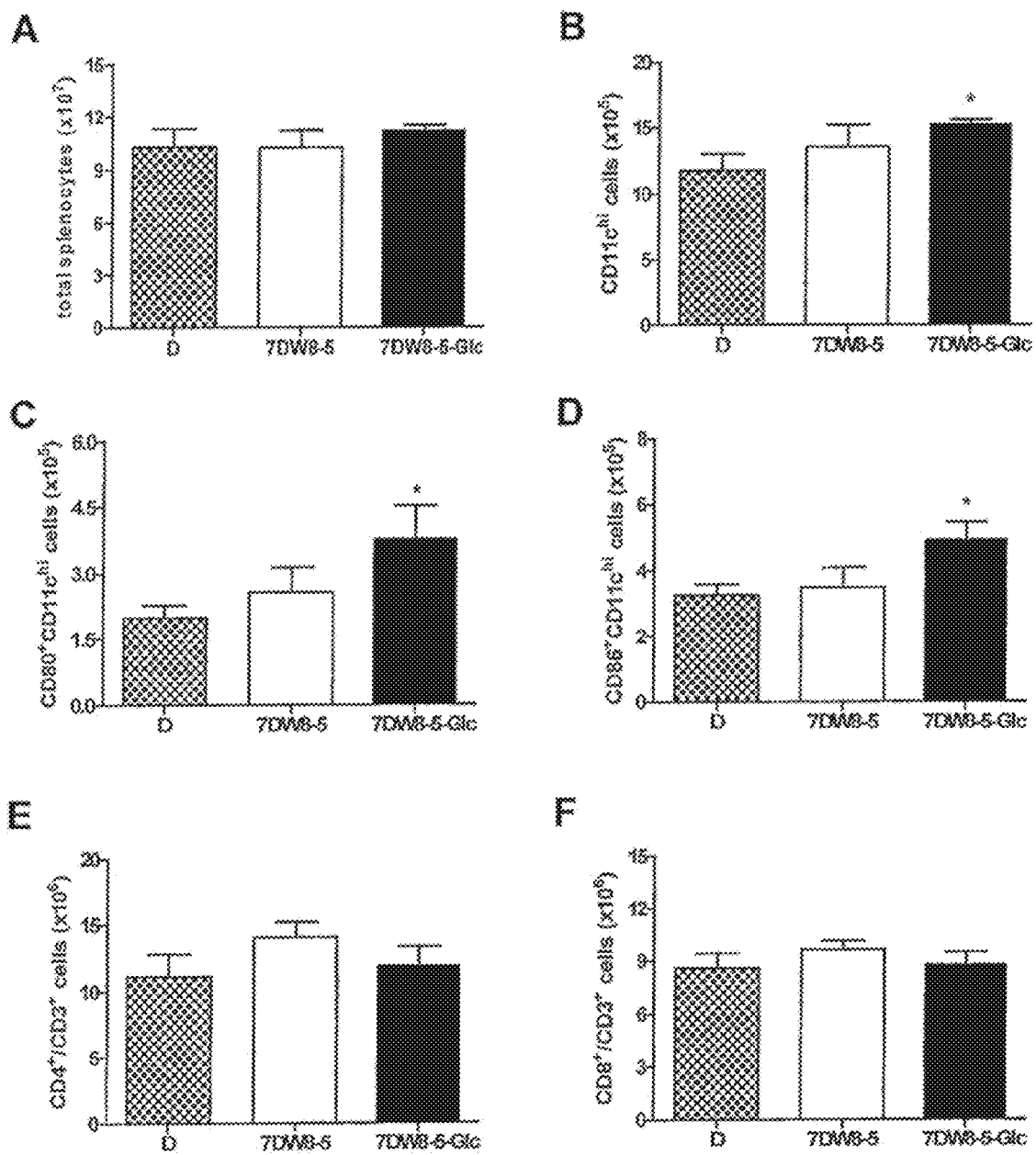
Figure 10:
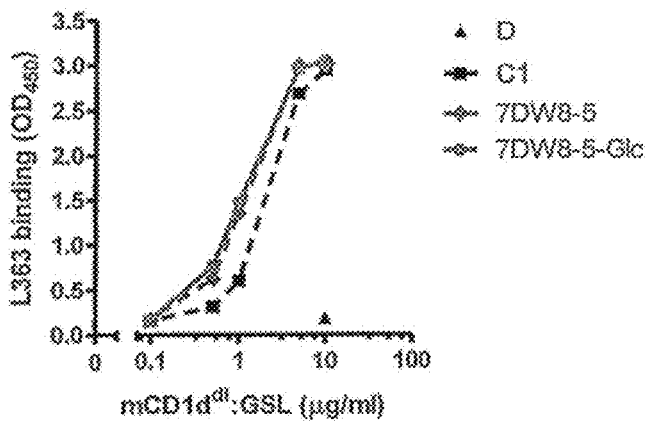
Figure 10:
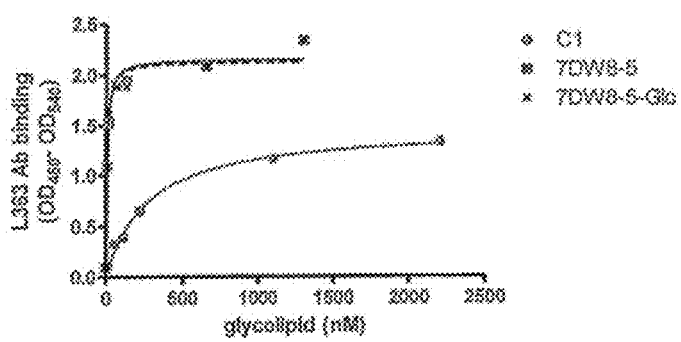
Figure 11:
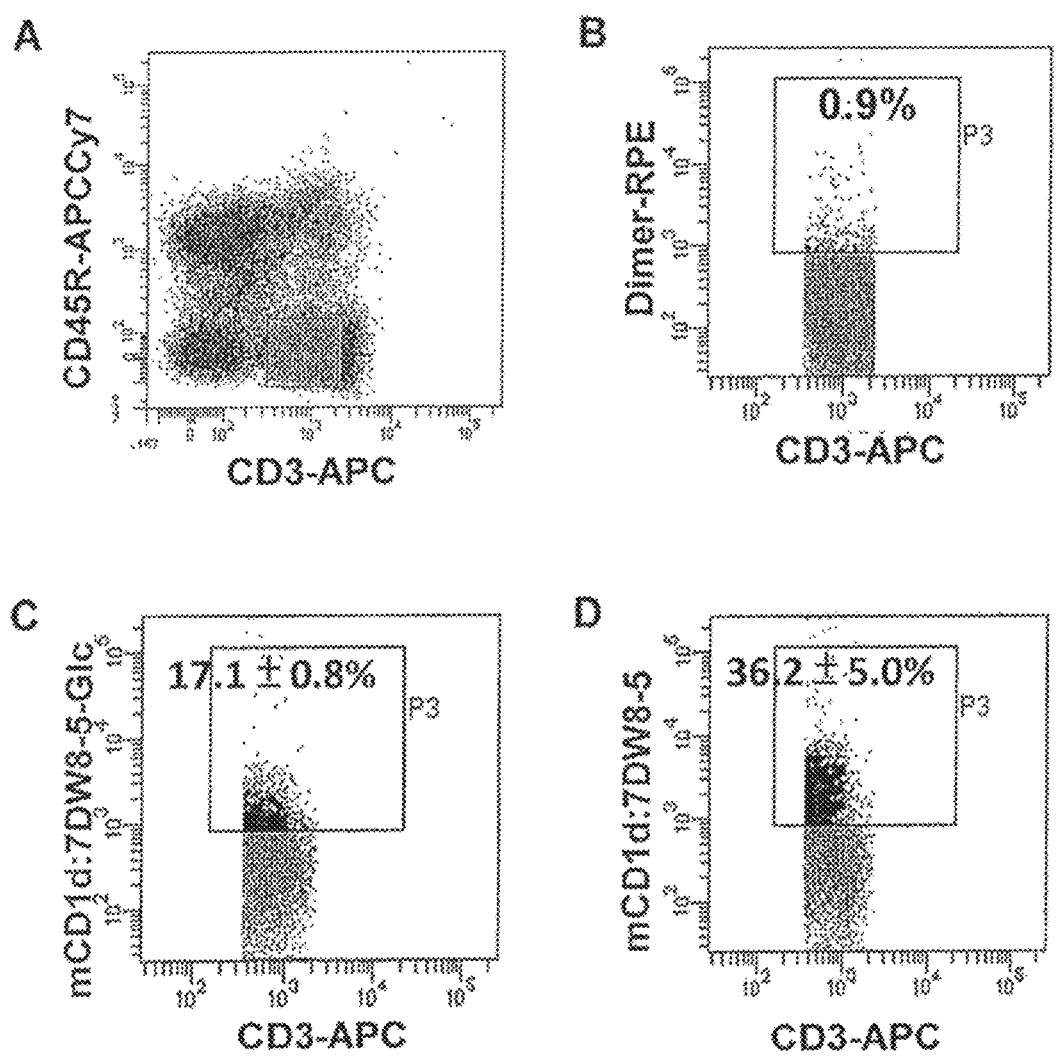
Figure 12:
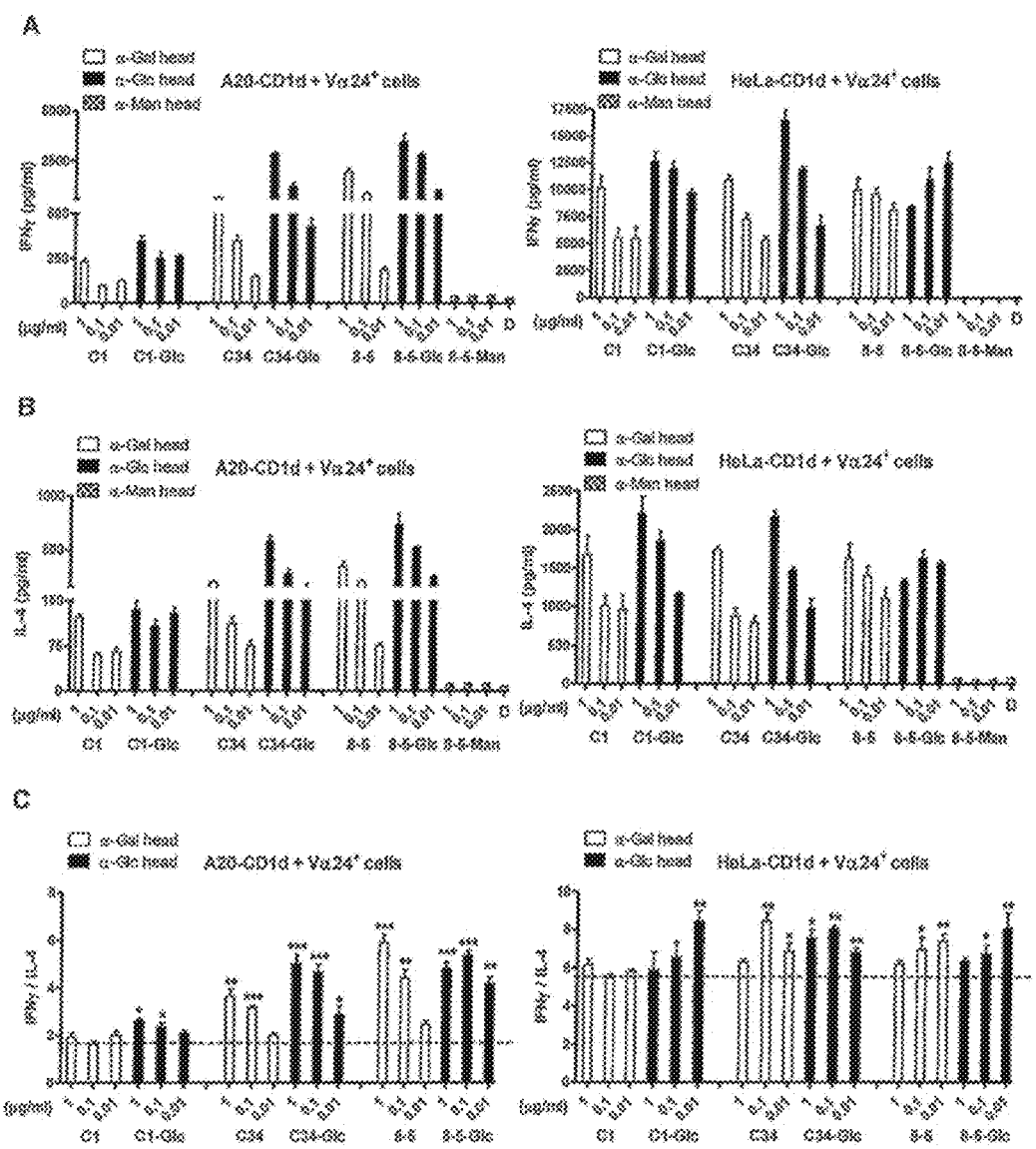
Figure 13:
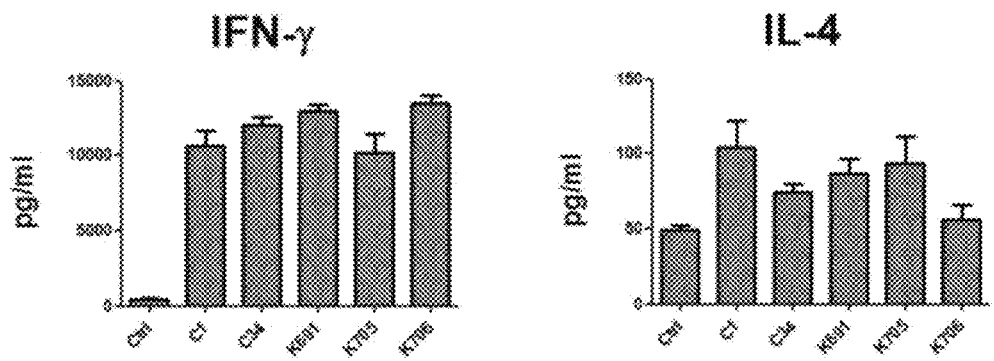
Figure 13:
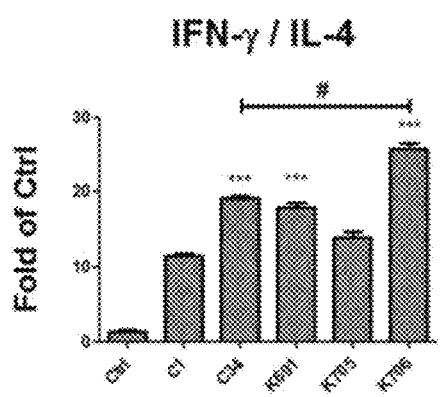
Figure 13:
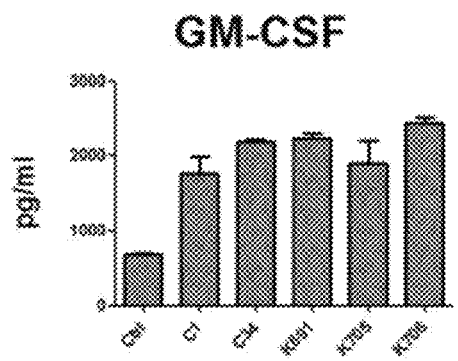
Figure 13:
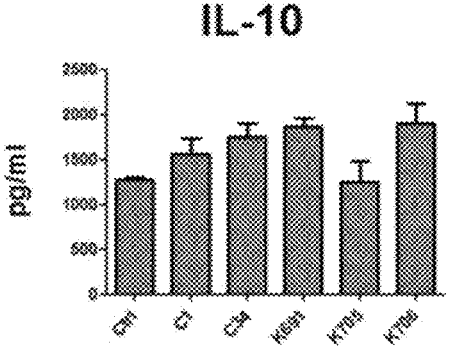
Figure 13:
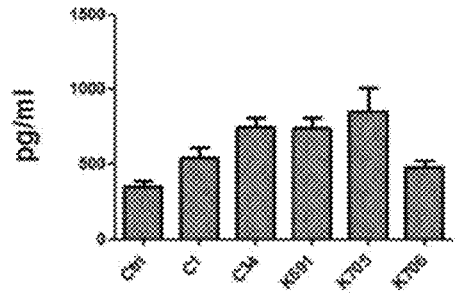

To explain the species-specific responses, we examined the effects of swapping human vs. mouse CD1d molecules against human vs. murine iNKT cells on the stimulatory activities of GSLs with different glycosyl groups. Murine iNKT hybridoma cells (FIG. 4A) or C1-expanded human Vα24+ iNKT cells (FIG. 4B) were pulsed with the indicated glycolipid presented by either mCD1d (A20-CD1d) or hCD1d (HeLa-CD1d). The supernatants were harvested 24 hr later to measure the cytokine secretions. Whether presented by mCD1d or hCD1d, GSLs with αGal induced more IL-2 secretion than GSLs with αGlc from murine iNKT cells (FIG. 4A). This was consistent with the in vivo findings that GSLs with αGal were more potent than GSLs with αGlc to induce serum cytokine secretion (FIGS. 2 and 7). In contrast, when presented by either mCD1d or hCD1d, GSLs with αGlc triggered more IL-2 secretion than GSLs with αGal from human iNKT cells (FIG. 4B). Similar trends were also observed on IFN-γ and IL-4 secretions from human iNKT cells (FIG. 12A and FIG. 12B). The species-specific stimulatory activities of GSLs with different glycosyl groups were dictated by the murine vs. human iNKT TCR, rather than CD1d. In comparison, 7DW8-5-Man could not stimulate mouse and human iNKT cells to secret any cytokines regardless of its presentation by mCD1d or hCD1d. Notably, all GSLs with αGlc triggered significantly more Th1-skewed responses than C1 based on the ratio of IFN-γ over IL-4 (FIG. 12C). Besides, irrespective of lipid tails, GSLs with αGlc seemed more Th1-biased than GSLs with αGal in humans (FIG. 12C). These findings indicated that modification at the 4'-OH of the glycosyl group could selectively induce the responses of human iNKT cells toward Th1 direction.

Structural Modeling of the Ternary Complex of CD1d-GSL-iNKT TCR

To further explain differential binding avidities of the ternary complex in mice and men, computer modeling was performed based on the x-ray structures of murine and human CD1d-αGalCer-iNKT TCR complexes, respectively (PDB access code 3HUJ, 3QUX, 3QUY, 3QUZ, and 3HE6).

(1) Interactions of the Sugar Head Groups

As shown in FIGS. 3A and 3B, the GSL with Man could not bind to the mouse and human iNKT cells when complexed with CD1d. A vertical 2'OH in mannose created a steric hindrance against iNKT TCR (Ser30 in men and Asn30 in mice) and lost two hydrogen bonds originally formed by the 2'OH of galactose toward the iNKT TCR (Gly96 and Asp151 in men as well as Gly96 and Asp153 in mice). As for GSLs with Gal, the binding of C1 to CD1d and iNKT TCR for mice and humans was shown in FIGS. 5A and 5B, respectively. Formations of hydrogen bond (H-bond) interactions were observed in most conserved residues, including human Asp80 (mouse Asp80), human Thr154 (mouse Thr156), human Asp151 (mouse Asp 153) of CD1d and human Gly96 (mouse Gly96) of iNKT TCR. On the other hand, the H-bond interactions of the 3'OH/4'OH of C1 with human and mouse iNKT TCR were quite different. The residue Asn30 of mouse iNKT TCR was crucial for binding to the 3'- and 4'-OHs of C1. The free energy contribution of Asn30 was estimated to be −2.27~−3.38 Kcal/mol using MGLTools. In comparison, Ser30 of human iNKT TCR was more distant from the 4'-OH of C1, resulting in a weaker H-bond interaction with the 3'-OH only, while a H-bond could be formed between 4'-OH of C1 and the backbone C=O group of Phe29 (FIG. 5B). The free energy contribution of Ser30 with the 3'-OH and Phe29 with the 4'-OH of C1 was computed to be about −1.23~−1.63 Kcal/mol. Thus, a change from axial (Gal) to equatorial (Glc) direction of 4' OH would lose the H-bond interaction with mouse Asn30 and human Phe29 of iNKT TCRs. As compared to C1 and C34, respectively, C1-Glc and C34-Glc lacked the H-bond interaction with murine Asn30, leading to a decreased free energy (−0.7~−0.9 Kcal/mol calculated by MGLTools). This was in line with the drops in the murine ternary interaction in the KD measurement (FIG. 3C) when galactose was changed to the glucose head. On the contrary, human ternary interactions were greater for GSLs with glucose (FIG. 3D). Based on the computer modeling, we found that the equatorial 4'-OH of glucose could compensate for the loss of Phe29 interaction (−0.4 Kcal/mol) by a stronger interaction (~−1.84 Kcal/mol) with a crystal water, which was trapped by human iNKT TCR-Phe51 and hCDld-Trp153 (FIG. 5C). Without the formation of hydrophobic space and the trapped water molecule in mice, the ternary interaction would be weaker for GSLs with Glc than those with Gal.

(2) Interactions of the Lipid Tails

The two aromatic rings at the acyl tail of C34 could form aromatic interactions with Phe70 and Trp63 of CD1d. Thus, the change of the acyl tail from C1 to C34 could increase the interaction (−1.8~−2.4 Kcal/mol by modeling) with CD1d. In addition, the higher energy from aromatic interactions could drive the acyl chain of C34 or C34-Glc to a lower position (near Cys12) of the A' channel within CD1d, leading to a subtle perturbation to the orientation of the head group (FIG. 5D). Therefore, without a congenial force between mouse iNKT TCR and the equatorial 4'-OH of the glucose head, the binding of mCD1d-C34-Glc to iNKT TCR was a little weaker than mCD1d-C1-Glc (FIG. 3C). This may explain why C34-Glc was less potent than C1-Glc while C34 was superior to C1 in mice.

(3) Computed Free Energy Using AUTODOCK4

The free energy of each GSL bound to human and mouse CD1d-iNKT TCRs was computed in triplicate. In each round, the GSLs were docked to the human and mouse CD1d-C1-iNKT TCRs and the topmost ranked free energies were selected. As shown in FIG. 5E, the computed free energy in general correlated with the trends of the KD values measured for mice (FIG. 3C) and humans (FIG. 3D).

A variety of means can be used to formulate the compositions of the invention. Techniques for formulation and administration may be found in "Remington: The Science and Practice of Pharmacy," Twentieth Edition, Lippincott Williams & Wilkins, Philadelphia, Pa. (1995). For human or animal administration, preparations should meet sterility, pyrogenicity, and general safety and purity standards comparable to those required by the FDA. Administration of the pharmaceutical formulation can be performed in a variety of ways, as described herein.

Cytokine Induction and Ternary Interactions Among GSLs, CD1d and iNKT TCR

As compared to αGalCer, αGlcCer has been reported to be less stimulatory on the murine iNKT cell proliferation but appeared more potent to stimulate human iNKT cell proliferation. In our studies, the differential activities between αGalCer and αGlcCer in mice and humans were also observed on the cytokine induction and ternary interaction among GSLs, CD1d and iNKT TCR. Furthermore, phenyl GSLs bearing αGal or αGlc head showed similar species-specific activities. Thus, irrespective of lipid tails, GSLs with αGal were better than GSLs with αGlc in mice but worse in men. This indicated that the bioactivity of glycolipids in mice cannot be translated to that in humans despite the highly homologous sequences of CD1d and iNKT TCR between mice and humans.[30]

The species-specific responses were most likely attributed to the differences in iNKT TCR between mice and men, as demonstrated by mCD1d vs. hCD1d swapping assay. GSLs with αGal, either presented by mCD1d or hCD1d, were more potent than GSLs with αGlc to stimulate murine iNKT cells but less stimulatory for human iNKT cells. According to the crystal structures of CD1d-αGalCer-iNKT TCR, the residues in contact with the 4'-OH of the galactose head in the CDR1α region of iNKT TCR were not conserved between mice (Asn30) and humans (Phe29). Our computer modeling revealed that the change of 4'-OH from the axial to equatorial direction could result in the loss of hydrogen bond between the 4'OH and iNKT TCR-Asn30 in mice. On the contrary, the equatorial 4'-OH of glucose could compensate for the loss of Phe29 interaction by a stronger interaction with a crystal water, which was trapped by human iNKT TCR-Phe51 and hCD1d-Trp153. Thus, the ternary interaction composed of GSLs with αGlc was stronger than GSLs with αGal in humans but weaker in mice. Taken together, the structural modeling of murine and human CD1d-GSL-iNKT TCR complexes provided a good explanation for species-specific biological activities, and the computed free energy changes correlated well with the trends of measured binding avidities of the ternary complex.

In contrast to our paired analogues with the same tail but different glycosyl groups, the species-specific immune responses were also seen in other cases with the same glycosyl group but different lipid tails. Similarly, it was the iNKT TCR, instead of CD1d, that shaped the preferential activities of two C-glycoside analogs between mice and men, which correlated well with the binding strengths of the ternary complex. For our glycolipids, ternary interaction was also more important than binary interaction in predicting the biological responses in mice and men. Both 7DW8-5 and 7DW8-5-Glc bound with mCD1d much stronger than C1, probably due to the increased contacts of the phenyl ring and the fluoride atom with the CD1d A' pocket. Even though the two glycolipids with the same lipid tails exhibited similar binging strengths toward CD1d, they showed different immune stimulatory potencies. 7DW8-5-Glc was better than 7DW8-5 in men but worse in mice, which had a good relationship with the binding avidities of ternary complexes. In addition to 7DW8-5 and 7DW8-5-Glc, the bioactivities of the other two paired analogues (C1 vs. C1-Glc and C34 vs. C34-Glc) also correlated well with the strengths of the ternary interaction in mice and men. That is, GSLs with αGal showed stronger ternary interaction and immune stimulatory activities than GSLs with αGlc in mice, but the trend was opposite in men. Hence, the measurement of the ternary interaction in vitro could be used to predict the immune-stimulatory potency of our new glycolipids in vivo.

Further comparison among GSLs with αGlc revealed that both C1-Glc and C34-Glc were better than 7DW8-5-Glc in cytokine induction in mice. However, the binding avidities of the murine ternary complex were comparable for C34-Glc and 7DW8-5-Glc. These findings suggested that factors other than KD may also modulate immune responses in vivo. In fact, both C1-Glc and C34-Glc activated more CD80$^+$ or CD86$^+$ DCs than 7DW8-5-Glc, which may contribute to the stronger bioactivities of C1-Glc and C34-Glc in mice. Taken together, several factors, including the strength of the ternary interaction and the expansion/activation of immune cells, could regulate immune stimulation in vivo.

In contrast to GSLs with αGal or αGlc, αManCer and 7DW8-5-Man failed to induce iNKT cell proliferation, cytokines/chemokines, and/or the expansion/activation of immune cells in both mice and humans. This may be attributed to the fact that neither murine nor human iNKT TCR could recognize the αMan head, as demonstrated by the lack of staining with CD1d-7DW8-5-Man dimer in iNKT cells. As compared to 7DW8-5-Man, 7DW8-5-Glc was able to induce Th1 and Th2 cytokines albeit at very low levels in mice. In comparison, large amounts of KC, MCP-1, IP-10 and MIG chemokines were triggered by 7DW8-5-Glc in WT and Jα18 KO mice, indicating that certain types of immune cells other than iNKT cells may contribute to these chemokine secretions. Indeed, monocytes were significantly expanded/activated in Jα18 KO mice by 7DW8-5-Glc. It had been reported that monocytes could produce these chemokines in response to stimulations, suggesting that monocytes may be responsible for chemokine secretions in 7DW8-5-Glc-treated mice. Nevertheless, we could not exclude that other possible sources existing in Jα18 KO mice may also play a role. Vα10 NKT cells could produce IFN-γ and IL-4 in response to αGalCer and αGlcCer in vitro,[38] but IFN-γ was not secreted in the sera of Jα18 KO mice treated with αGalCer.[39] We could not detect any cytokine productions from Jα18 KO mice treated with 7DW8-5 or 7DW8-5-Glc. These findings implied that Vα10 NKT cells contributed little to the chemokines triggered by 7DW8-5-Glc in mice.

However, most of the cytokines and chemokines, including IFN-γ, IL-2, IL-4, IL-6, GM-CSF and TNFα were not produced in Jα18 KO mice stimulated with either 7DW8-5 or 7DW8-5-Glc. Immune cells like CD4$^+$ T and CD8$^+$ T cells were not expanded in Jα18 KO mice either. Thus, iNKT cells remained to be the key player in the above-mentioned cytokine/chemokine induction and immune cell expansion by 7DW8-5 or 7DW8-5-Glc.

In summary, GSLs with αGlc bore stronger ternary interaction and triggered more Th1-biased immunity as compared to GSLs with αGal in humans. However, GSLs with αGlc were less stimulatory than GSLs with αGal in mice. The species-specific responses were attributed to the differential binding avidities of ternary complexes between species, reflecting the differences between murine and human iNKT TCR as supported by mCD1d vs. hCD1d swapping assay. This was in line with the prediction by the computer modeling based on the crystal structures of the CD1d-αGalCer-iNKT TCR complex in mice and men.[27-29] In addition to the ternary interaction between CD1d-glycolipid complex and iNKT TCR, expanded/activated monocytes could also modulate immune responses in vivo, especially for GSLs with αGlc.

From our studies, the change of the 4'OH direction on the glycosyl group led to different bioactivities in mice and humans. This was consistent with the report that the aromatic group introduced to 4'OH of the αGalCer head could affect iNKT cell cytokine production in mice, but their effects in humans were not investigated. Alterations at the 6 position of the glycosyl group also showed variable effects on the biological responses.[29,41] These findings together with our work provided a new direction for the future design and synthesis of new GSLs.

Throughout this application, various publications, patents and published patent applications are cited. The inventions of these publications, patents and published patent applications referenced in this application are hereby incorporated by reference in their entireties into the present invention. Citation herein of a publication, patent, or published patent application is not an admission the publication, patent, or published patent application is prior art.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. An immune adjuvant compound having the structure of Formula (I):

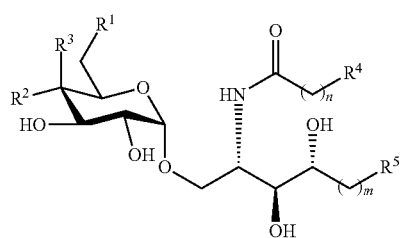

or a pharmaceutically acceptable salt thereof;
wherein:
$R^1$ is —OH or halogen;
$R^2$ is -hydrogen or halogen;
$R^3$ is —OH, hydrogen or halogen;

$R^4$ has the structure of Formula (III):

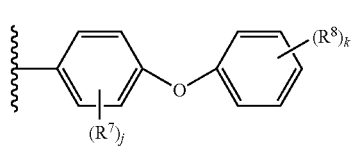

wherein:
j is 0, 1, 2, 3, or 4;
k is 0, 1, 2, 3, 4, or 5;
wherein the summation of j and k is greater than or equal to 1;
each instance of $R^7$ and $R^8$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkoxy, an optionally substituted amino group, and optionally substituted acyl;
$R^5$ is selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkoxy, an optionally substituted amino group, and optionally substituted acyl;
n is an integer of 5 to 15, inclusive;
m is an integer of 1 to 20, inclusive;
with the proviso that the compound is not any one of:

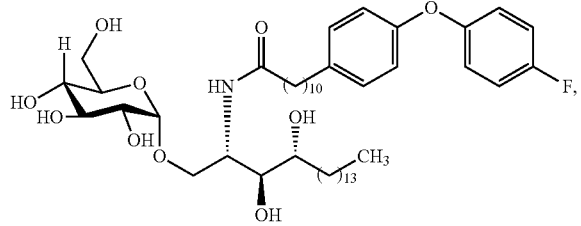

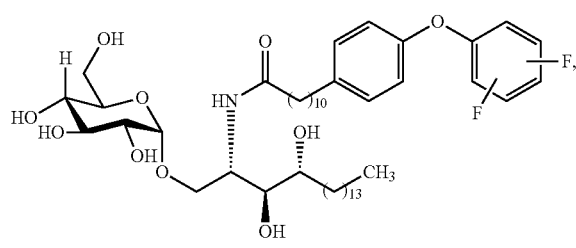

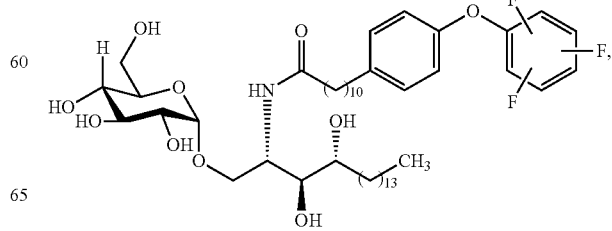

III-4
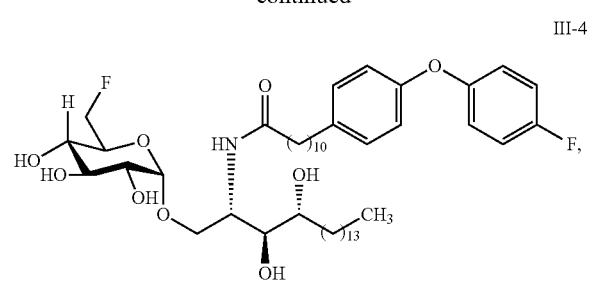
III-10
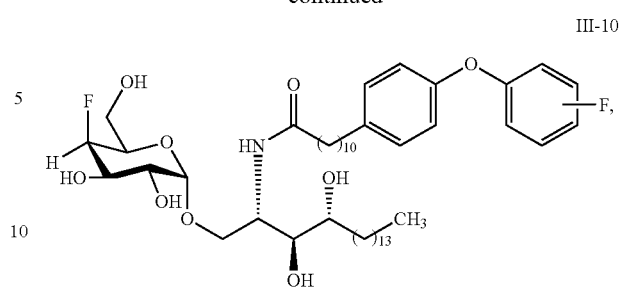
III-5
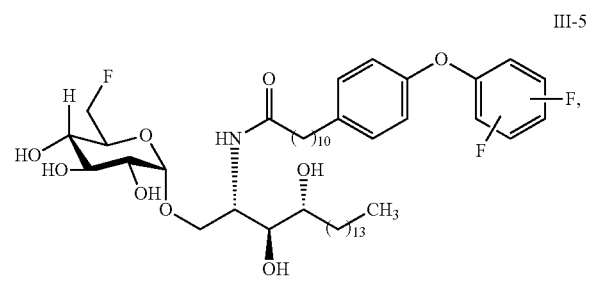
III-11
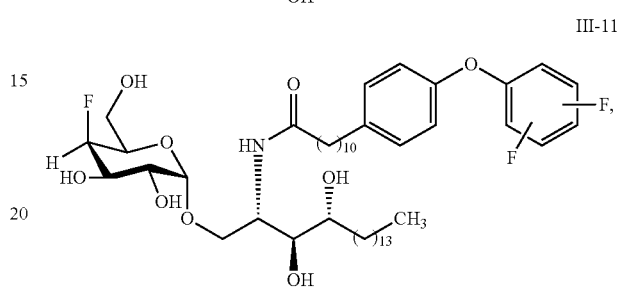
III-6
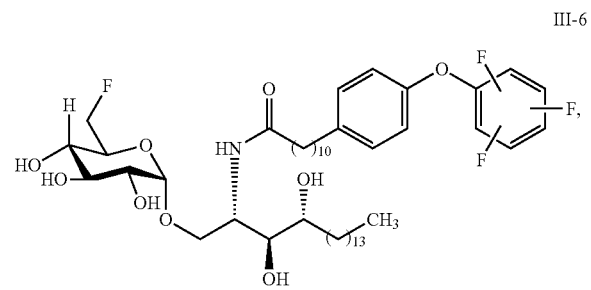
III-12
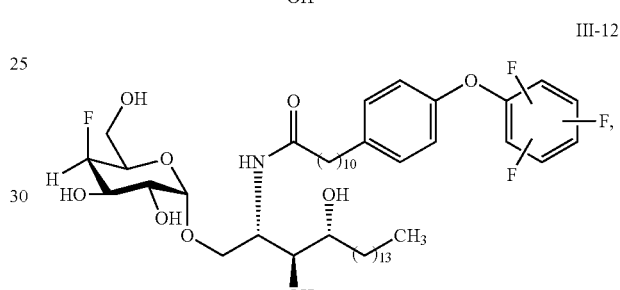
III-7
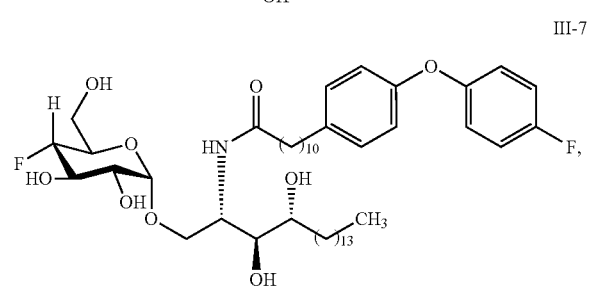
III-13
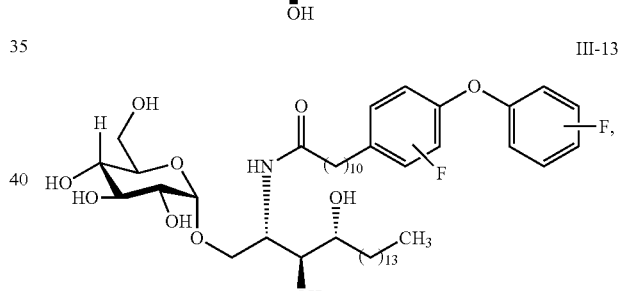
III-8
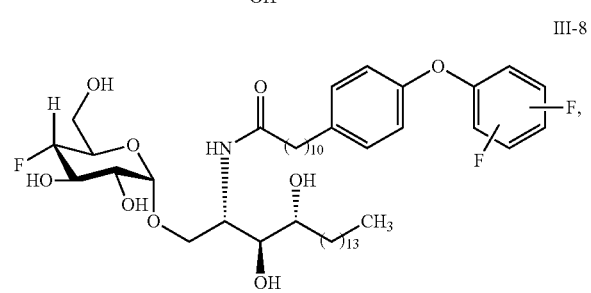
III-14
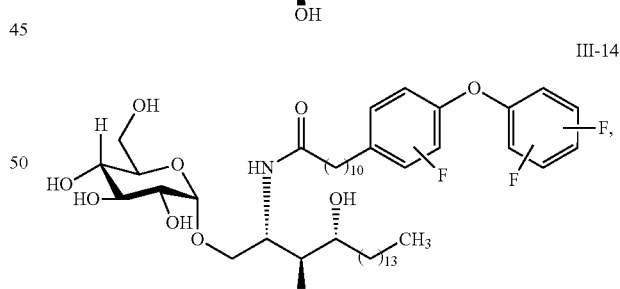
III-9
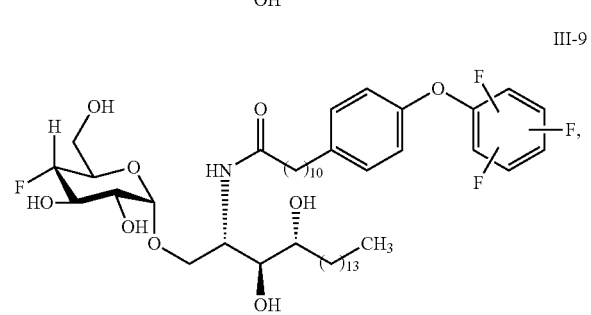
III-15
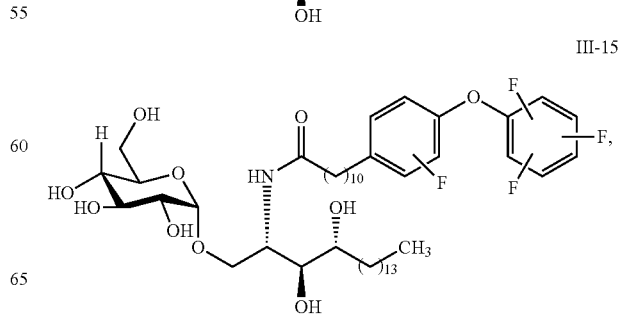

III-16
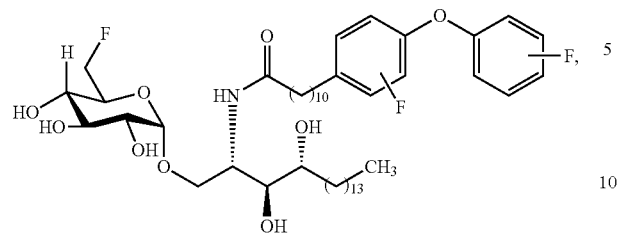

III-17
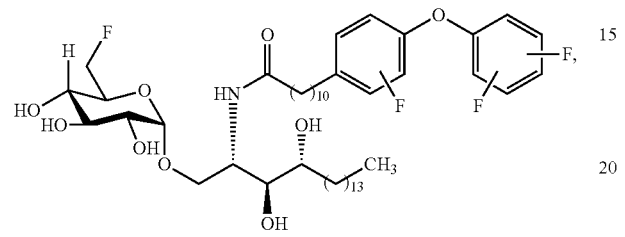

III-18
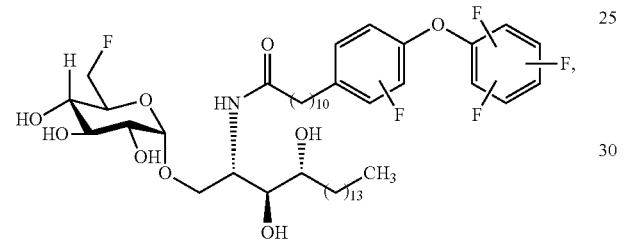

III-19
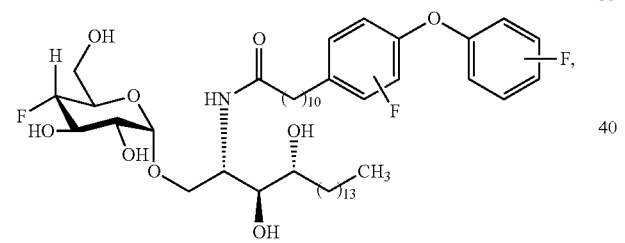

III-20
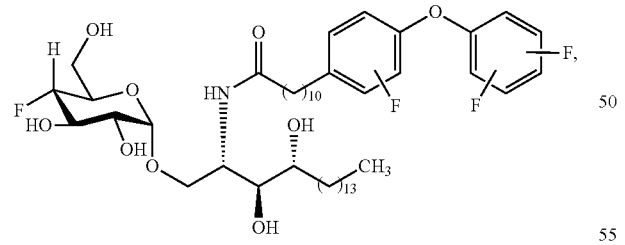

III-21
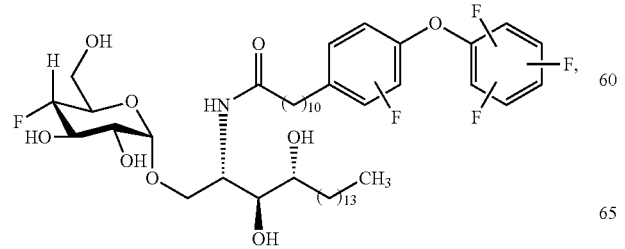

III-22
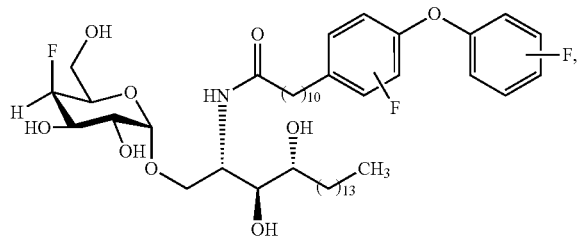

III-23
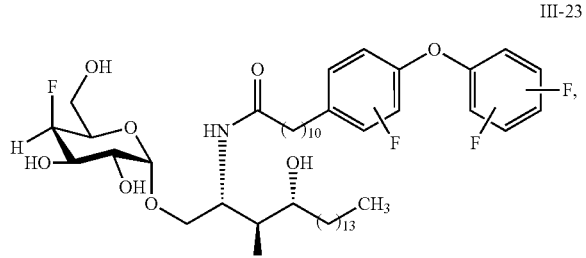

III-24
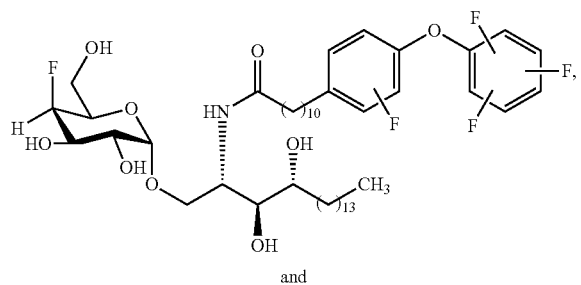

and

C34
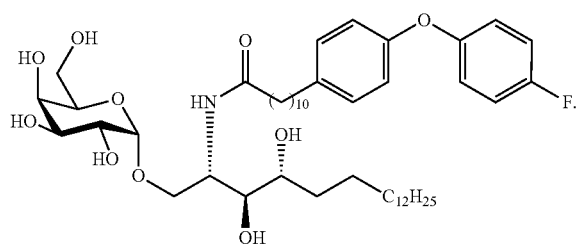

2. The compound of claim 1, wherein $R^3$ is —OH.

3. The compound of claim 1, wherein $R^3$ is halogen.

4. The compound of claim 1 or claim 2, wherein $R^1$ is —OH.

5. The compound of any one of claims 1, 3, or 3, wherein $R^1$ is halogen.

6. The compound of claim 1, wherein each instance of $R^7$ and $R^8$ is halogen.

7. The compound of claim 1, wherein $R^8$ is the halogen F; and k is 2 or 3.

8. The compound of claim 1, wherein $R^7$ is F; and j is 2 or 3.

9. The compound of claim 1, wherein $R^7$ and $R^8$ both are the halogen F; k is 1, 2 or 3; and j is 1, 2 or 3.

10. A compound selected from one of the following:

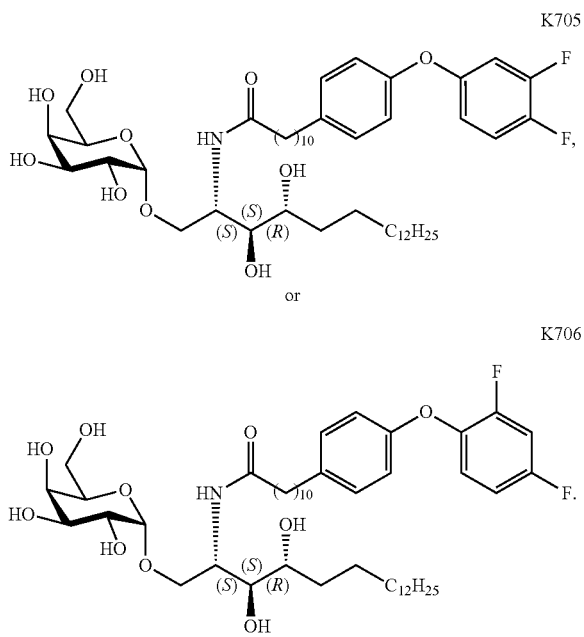

11. A pharmaceutical composition comprising: (i) a therapeutically effective amount of a compound according to any of claims 1, 2, 6, 7, or 10 in an amount sufficient to stimulate an immune response when co-administered with an antigen to a human subject, and (ii) a pharmaceutically acceptable excipient.

12. A method for augmenting an immunogenicity of an antigen in a subject in need thereof, comprising co-administering a pharmaceutically effective amount of said antigen with an adjuvant composition comprising a GSLs compound of claim 1.

13. A method for stimulating an immune response in a human subject in need thereof, the method comprising: administering to the subject a therapeutically effective amount of an immune adjuvant composition in a pharmaceutically acceptable carrier, wherein the composition comprises a compound according to any of claims 1, 2, 6, 7, or 10.

14. The method of claim 12, wherein the adjuvant composition is a vaccine adjuvant.

15. The method of claim 12, wherein the adjuvant composition is administered in an amount capable of elevating invariant Natural Killer T (iNKT) cells in humans.

16. The method of claim 13, wherein administration of the adjuvant composition increases cytokine and/or chemokine production in humans.

17. The method of claim 16, wherein the cytokine production is sufficient to transactivate downstream immune cells.

18. The method of claim 17, wherein the downstream immune cells comprise one or more of dendritic cells (DC), natural killer cells (NK), B cells, CD4$^+$ T and CD8$^+$ T cells.

19. The method of claim 16, wherein the cytokines comprise Th1 cytokines.

20. The method of claim 19, wherein the Th1 cytokines is selected from at least one of the group comprising: interferon-gamma (IFN-γ), GM-CSF, TNFα, interleukin 2, and interleukin 12.

21. The method of claim 16, wherein the chemokine is selected from at least one of the group comprising RANTES, MIP-1α, KC, MCP-1, IP-10 and MIG.

22. The method of claim 12, wherein administration of the antigen/adjuvant composition has anti-cancer effect.

23. The method of claim 22, wherein the anti-cancer effect is directed at a cancer from the group consisting of lung cancer, breast cancer, hepatoma, leukemia, solid tumor and carcinoma.

24. A method for elevating invariant Natural Killer T (iNKT) cells production in a human subject in need thereof, the method comprising: administering to the subject a therapeutically effective amount of a pharmaceutical composition, wherein the composition comprises a compound according to any of claims 1 or 10.

25. A method for stimulating cytokine and/or chemokine production in a human subject in need thereof, the method comprising: administering to the subject a therapeutically effective amount of a pharmaceutical composition, wherein the composition comprises a compound according to any of claims 1 or 10 in an amount sufficient to increase cytokine/chemokine production.

26. The method of claim 25, wherein the cytokine production is sufficient to transactivate downstream immune cells.

27. The method of claim 26, wherein the downstream immune cells comprise one or more of dendritic cells (DC), natural killer cells (NK), B cells, CD4$^+$ T and CD8$^+$ T cells.

28. The method of claim 25, wherein the cytokines comprise Th1 cytokines.

29. The method of claim 28, wherein the cytokines are selected from: interferon-gamma (IFN-γ), GM-CSF, TNFα, interleukin 2, and interleukin 12.

30. The method of claim 25, wherein the chemokines are selected from: RANTES, MIP-1α, KC, MCP-1, IP-10 and MIG.

31. A method for augmenting the immune response in a subject, the method comprising administering to the subject an effective amount of a vaccine comprising one or more antigens and an immunogenically effective amount of an adjuvant composition of claim 11.

32. The method of claim 31, wherein the one or more antigens are selected from the group consisting of bacterial antigen, viral antigen, fungal antigen, protozoal antigen, prion antigen, neoantigen, tumor antigen and self-antigen.

33. The method of claim 31, wherein the vaccine is selected from the group consisting of a nucleic acid, protein, peptide, glycoprotein, carbohydrate, fusion protein, lipid, glycolipid, carbohydrate-protein conjugate; cells or extracts thereof; dead or attenuated cells, or extracts thereof; tumor cells or extracts thereof; viral particles; and allergens or mixtures thereof.

34. The method of claim 31 wherein the antigen is a tumor antigen.

35. The method of claim 31, wherein the amount of antigen is administered in the range of 0.1 μg-100 mg per kg of body weight.

36. The method of claim 31, wherein the amount of adjuvant is in the range of 10-100 μg per kg of body weight.

37. The method of claim 31 wherein the adjuvant composition is a coformulated pharmaceutically acceptable composition comprising the GSLs of Formula I and a pharmaceutically acceptable carrier.

38. An article of manufacture comprising a compound of claim 1.

* * * * *